US009095614B2

(12) United States Patent
McKenna et al.

(10) Patent No.: US 9,095,614 B2
(45) Date of Patent: *Aug. 4, 2015

(54) TAMPER RESISTANT DOSAGE FORMS

(71) Applicant: Purdue Pharma L.P., Stamford, CT (US)

(72) Inventors: William H. McKenna, Yonkers, NY (US); Richard O. Mannion, Furlong, PA (US); Edward P. O'Donnell, Basking Ridge, NJ (US); Haiyong H. Huang, Princeton, NJ (US)

(73) Assignees: PURDUE PHARMA L.P., Stamford, CT (US); PURDUE PHARMACEUTICALS L.P., Wilson, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/515,855

(22) Filed: Oct. 16, 2014

(65) Prior Publication Data

US 2015/0037411 A1 Feb. 5, 2015

Related U.S. Application Data

(60) Continuation of application No. 13/803,132, filed on Mar. 14, 2013, now abandoned, which is a division of application No. 11/844,872, filed on Aug. 24, 2007, now Pat. No. 8,894,987.

(60) Provisional application No. 60/840,244, filed on Aug. 25, 2006.

(51) Int. Cl.
| | |
|---|---|
| *A61K 9/00* | (2006.01) |
| *A61K 9/28* | (2006.01) |
| *A61K 9/20* | (2006.01) |
| *A61K 31/485* | (2006.01) |
| *A61K 47/34* | (2006.01) |
| *A61K 47/10* | (2006.01) |
| *A61K 9/16* | (2006.01) |
| *A61J 3/06* | (2006.01) |
| *A61K 9/24* | (2006.01) |
| *A61K 45/06* | (2006.01) |
| *A61J 3/10* | (2006.01) |
| *B29C 43/00* | (2006.01) |

(52) U.S. Cl.
CPC . *A61K 47/10* (2013.01); *A61J 3/06* (2013.01); *A61J 3/10* (2013.01); *A61K 9/0002* (2013.01); *A61K 9/1641* (2013.01); *A61K 9/209* (2013.01); *A61K 9/2031* (2013.01); *A61K 9/2077* (2013.01); *A61K 9/2095* (2013.01); *A61K 9/2853* (2013.01); *A61K 9/2866* (2013.01); *A61K 31/485* (2013.01); *A61K 45/06* (2013.01); *A61K 47/34* (2013.01); *B29C 43/003* (2013.01); *A61K 9/2072* (2013.01)

(58) Field of Classification Search
None
See application file for complete search history.

(56) References Cited

U.S. PATENT DOCUMENTS

| | | | |
|---|---|---|---|
| 1,468,805 | A | 9/1923 | Freund |
| 1,485,673 | A | 3/1924 | Freund |
| 2,772,270 | A | 11/1956 | Weiss |
| 3,096,248 | A | 7/1963 | Rudzki |
| 3,806,603 | A | 4/1974 | Gaunt et al. |
| 3,941,865 | A | 3/1976 | Miller et al. |
| 3,966,747 | A | 6/1976 | Monkovic et al. |
| 3,980,766 | A | 9/1976 | Shaw et al. |
| 4,070,494 | A | 1/1978 | Hoffmeister et al. |
| 4,175,119 | A | 11/1979 | Porter |
| 4,404,183 | A | 9/1983 | Kawata et al. |
| 4,501,828 | A | 2/1985 | Hadermann et al. |
| 4,612,008 | A | 9/1986 | Wong et al. |
| 4,616,644 | A | 10/1986 | Saferstein et al. |
| 4,619,988 | A | 10/1986 | Leung et al. |
| 4,629,621 | A | 12/1986 | Snipes |
| 4,629,624 | A | 12/1986 | Grouiller et al. |
| 4,690,822 | A | 9/1987 | Uemura et al. |
| 4,713,243 | A | 12/1987 | Schiraldi et al. |
| 4,744,976 | A | 5/1988 | Snipes et al. |
| 4,764,378 | A | 8/1988 | Keith et al. |
| 4,765,989 | A | 8/1988 | Wong et al. |
| 4,774,074 | A | 9/1988 | Snipes |
| 4,783,337 | A | 11/1988 | Wong et al. |
| 4,806,337 | A | 2/1989 | Snipes et al. |
| 4,861,598 | A | 8/1989 | Oshlack |
| RE33,093 | E | 10/1989 | Schiraldi et al. |
| 4,892,778 | A | 1/1990 | Theeuwes et al. |
| 4,960,814 | A | 10/1990 | Wu et al. |
| 4,970,075 | A | 11/1990 | Oshlack |
| 5,004,601 | A | 4/1991 | Snipes |
| 5,019,397 | A | 5/1991 | Wong et al. |

(Continued)

FOREIGN PATENT DOCUMENTS

| | | |
|---|---|---|
| CA | 1110972 | 10/1981 |
| CA | 2352874 | 6/2000 |

(Continued)

OTHER PUBLICATIONS

Mai et al. (Materiaux et Constructions 1982. 15(2); pp. 99-106).*
AlKhatib et al. (AAPS PharmSciTech, 2010. 11(1); pp. 253-266).*
Mpofu et al. (Journal of Colloid and Interface Science. 2004, 271; pp. 145-156).*
"2.9.8. Resistance to Crushing of Tablets," Pharmaceutical Technical Procedures, European Pharmacopoeia, p. 135 (1997).
2002 Label for Oxycontin®, PDR, 56ed. (2002).
2013 Guidelines for Authors, Organic Letters, (Apr. 2013).
A. Apicella et al., "Poly(ethylene oxide) (PEO) and different molecular weight PEO blends monolithic devices for drug release," Biomaterials 1993, vol. 14, No. 2, pp. 83-90.
Abe et al. "Studies on Morphine Alkaloids-VIII: Some Reactions of 14β-Bromocodeine and Related Compounds," Tetrahedron, 27, p. 4495 (1971).

(Continued)

*Primary Examiner* — Misook Yu
*Assistant Examiner* — Kauser M Akhoon
(74) *Attorney, Agent, or Firm* — Troutman Sanders LLP

(57) ABSTRACT

The present invention relates to pharmaceutical dosage forms, for example to a tamper resistant dosage form including an opioid analgesic, and processes of manufacture, uses, and methods of treatment thereof.

30 Claims, 27 Drawing Sheets

(56) References Cited

U.S. PATENT DOCUMENTS

| | | |
|---|---|---|
| 5,051,222 A | 9/1991 | Marten |
| 5,139,790 A | 8/1992 | Snipes |
| 5,169,645 A | 12/1992 | Shukla |
| 5,200,197 A | 4/1993 | Wright et al. |
| 5,211,892 A | 5/1993 | Gueret |
| 5,266,331 A | 11/1993 | Oshlack et al. |
| 5,273,758 A * | 12/1993 | Royce ........................ 424/465 |
| 5,273,760 A | 12/1993 | Oshlack et al. |
| 5,286,493 A | 2/1994 | Oshlack et al. |
| 5,350,741 A | 9/1994 | Takada |
| 5,356,467 A | 10/1994 | Oshlack et al. |
| 5,393,528 A | 2/1995 | Staab |
| 5,405,366 A | 4/1995 | Fox et al. |
| 5,458,887 A | 10/1995 | Chen et al. |
| 5,472,712 A | 12/1995 | Oshlack et al. |
| 5,478,577 A | 12/1995 | Sackler et al. |
| 5,508,042 A | 4/1996 | Oshlack et al. |
| 5,549,912 A | 8/1996 | Oshlack et al. |
| 5,656,295 A | 8/1997 | Oshlack et al. |
| 5,672,360 A | 9/1997 | Sackler et al. |
| 5,695,781 A | 12/1997 | Zhang |
| 5,801,201 A | 9/1998 | Graudums et al. |
| 5,849,240 A | 12/1998 | Miller |
| 5,866,164 A | 2/1999 | Kuczynski |
| 5,914,131 A | 6/1999 | Merrill |
| 5,945,125 A | 8/1999 | Kim |
| 5,948,787 A | 9/1999 | Merrill et al. |
| 5,958,452 A | 9/1999 | Oshlack |
| 5,968,551 A | 10/1999 | Oshlack |
| 6,008,355 A | 12/1999 | Huang et al. |
| 6,009,690 A | 1/2000 | Rosenberg et al. |
| 6,096,339 A | 8/2000 | Ayer et al. |
| 6,117,453 A | 9/2000 | Seth et al. |
| 6,177,567 B1 | 1/2001 | Chiu et al. |
| 6,228,863 B1 | 5/2001 | Palermo et al. |
| 6,238,697 B1 | 5/2001 | Kumar |
| 6,251,430 B1 | 6/2001 | Zhang |
| 6,261,599 B1 | 7/2001 | Oshlack |
| 6,277,409 B1 | 8/2001 | Luber et al. |
| 6,306,438 B1 | 10/2001 | Oshlack et al. |
| 6,309,668 B1 | 10/2001 | Bastin et al. |
| 6,340,475 B2 | 1/2002 | Shell et al. |
| 6,357,957 B1 | 3/2002 | Champlin |
| 6,375,957 B1 | 4/2002 | Kaiko et al. |
| 6,436,441 B1 | 8/2002 | Sako et al. |
| 6,461,644 B1 | 10/2002 | Jackson et al. |
| 6,488,962 B1 | 12/2002 | Berner et al. |
| 6,488,963 B1 | 12/2002 | McGinity et al. |
| 6,491,683 B1 | 12/2002 | Dong |
| 6,534,089 B1 | 3/2003 | Ayer et al. |
| 6,547,997 B1 | 4/2003 | Breitenbach et al. |
| 6,635,280 B2 | 10/2003 | Shell et al. |
| 6,699,503 B1 | 3/2004 | Sako et al. |
| 6,723,340 B2 | 4/2004 | Gusler et al. |
| 6,733,783 B2 | 5/2004 | Oshlack |
| 6,864,370 B1 | 3/2005 | Lin et al. |
| 6,919,373 B1 | 7/2005 | Lam et al. |
| 6,930,129 B2 | 8/2005 | Lam et al. |
| 7,129,248 B2 | 10/2006 | Chapman et al. |
| 7,141,250 B2 | 11/2006 | Oshlack et al. |
| 7,153,966 B2 | 12/2006 | Casner et al. |
| 7,157,103 B2 | 1/2007 | Sackler |
| 7,201,920 B2 | 4/2007 | Kumar |
| 7,399,488 B2 | 7/2008 | Hirsh |
| 7,674,799 B2 | 3/2010 | Chapman |
| 7,674,800 B2 | 3/2010 | Chapman |
| 7,683,072 B2 | 3/2010 | Chapman |
| 7,776,314 B2 | 8/2010 | Bartholomaus et al. |
| 7,842,307 B2 | 11/2010 | Oshlack |
| 8,114,383 B2 | 2/2012 | Bartholomaus |
| 8,163,798 B2 | 4/2012 | Gupta et al. |
| 8,309,060 B2 | 11/2012 | Bartholomaus |
| 8,337,888 B2 | 12/2012 | Wright |
| 8,808,741 B2 | 8/2014 | McKenna et al. |
| 8,815,289 B2 | 8/2014 | McKenna et al. |
| 8,821,929 B2 | 9/2014 | McKenna et al. |
| 8,834,925 B2 | 9/2014 | McKenna et al. |
| 8,846,086 B2 | 9/2014 | McKenna et al. |
| 8,894,987 B2 | 11/2014 | McKenna et al. |
| 8,894,988 B2 | 11/2014 | McKenna et al. |
| 8,911,719 B2 | 12/2014 | McKenna et al. |
| 2001/0031278 A1 | 10/2001 | Oshlack et al. |
| 2001/0038852 A1 | 11/2001 | Kolter et al. |
| 2002/0051820 A1 | 5/2002 | Shell et al. |
| 2002/0114838 A1 | 8/2002 | Ayer et al. |
| 2002/0187192 A1 | 12/2002 | Joshi et al. |
| 2002/0192277 A1 | 12/2002 | Oshlack |
| 2003/0004177 A1 | 1/2003 | Kao |
| 2003/0015814 A1 | 1/2003 | Krull et al. |
| 2003/0044464 A1 | 3/2003 | Ziegler et al. |
| 2003/0064099 A1 | 4/2003 | Oshlack et al. |
| 2003/0065002 A1 | 4/2003 | Caruso et al. |
| 2003/0068375 A1 * | 4/2003 | Wright et al. .................. 424/468 |
| 2003/0068392 A1 | 4/2003 | Sackler |
| 2003/0069318 A1 | 4/2003 | Dang et al. |
| 2003/0091630 A1 | 5/2003 | Louie-Helm et al. |
| 2003/0092724 A1 | 5/2003 | Kao et al. |
| 2003/0104052 A1 | 6/2003 | Berner et al. |
| 2003/0104053 A1 | 6/2003 | Gusler |
| 2003/0118641 A1 | 6/2003 | Maloney et al. |
| 2003/0124185 A1 | 7/2003 | Oshlack et al. |
| 2003/0129234 A1 | 7/2003 | Baichwal et al. |
| 2003/0133985 A1 | 7/2003 | Louie-Helm et al. |
| 2003/0152622 A1 | 8/2003 | Louie-Helm et al. |
| 2003/0161882 A1 | 8/2003 | Waterman |
| 2003/0203024 A1 | 10/2003 | Sako et al. |
| 2003/0224051 A1 | 12/2003 | Fink et al. |
| 2003/0229158 A1 | 12/2003 | Chen et al. |
| 2004/0010000 A1 | 1/2004 | Ayer et al. |
| 2004/0011806 A1 | 1/2004 | Luciano et al. |
| 2004/0024006 A1 | 2/2004 | Simon |
| 2004/0126428 A1 | 7/2004 | Hughes |
| 2004/0156899 A1 | 8/2004 | Louie-Helm et al. |
| 2004/0170680 A1 | 9/2004 | Oshlack et al. |
| 2004/0185105 A1 | 9/2004 | Berner et al. |
| 2004/0213848 A1 | 10/2004 | Li et al. |
| 2005/0031546 A1 * | 2/2005 | Bartholomaus et al. ...... 424/10.1 |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaus |
| 2005/0222188 A1 | 10/2005 | Chapman |
| 2005/0236741 A1 | 10/2005 | Arkenau et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0173029 A1 | 8/2006 | Chapman et al. |
| 2006/0193914 A1 | 8/2006 | Ashworth et al. |
| 2006/0240110 A1 | 10/2006 | Klicki et al. |
| 2006/0251724 A1 | 11/2006 | Farrell et al. |
| 2006/0269603 A1 | 11/2006 | Miller et al. |
| 2007/0003616 A1 | 1/2007 | Arkenau-Marie et al. |
| 2007/0020335 A1 | 1/2007 | Chen et al. |
| 2007/0048228 A1 | 3/2007 | Arkenau-Maric et al. |
| 2007/0092573 A1 | 4/2007 | Joshi et al. |
| 2007/0117826 A1 | 5/2007 | Janjikhel et al. |
| 2007/0117829 A1 | 5/2007 | Chapman |
| 2007/0117831 A1 | 5/2007 | Chapman |
| 2007/0183979 A1 | 8/2007 | Arkenau-Maric et al. |
| 2007/0183980 A1 | 8/2007 | Arkenau-Maric et al. |
| 2007/0196396 A1 | 8/2007 | Pilgaonkar et al. |
| 2008/0248113 A1 | 10/2008 | Bartholomaus et al. |
| 2008/0274183 A1 | 11/2008 | Cook |
| 2008/0317854 A1 | 12/2008 | Arkenau et al. |
| 2009/0005408 A1 | 1/2009 | Arkenau-Marie et al. |
| 2009/0081290 A1 | 3/2009 | McKenna et al. |
| 2010/0168148 A1 | 7/2010 | Wright |
| 2011/0038930 A1 | 2/2011 | Barnscheid et al. |
| 2013/0251796 A1 | 9/2013 | McKenna et al. |
| 2013/0251797 A1 | 9/2013 | McKenna et al. |
| 2013/0251800 A1 | 9/2013 | McKenna et al. |
| 2013/0251801 A1 | 9/2013 | McKenna et al. |
| 2013/0259938 A1 | 10/2013 | McKenna et al. |
| 2014/0024669 A1 | 1/2014 | McKenna et al. |

(56) References Cited

U.S. PATENT DOCUMENTS

| | | | |
|---|---|---|---|
| 2014/0030327 A1 | 1/2014 | McKenna et al. |
| 2015/0028512 A1 | 1/2015 | McKenna et al. |
| 2015/0037411 A1 | 2/2015 | McKenna et al. |
| 2015/0037412 A1 | 2/2015 | McKenna et al. |
| 2015/0037413 A1 | 2/2015 | McKenna et al. |

FOREIGN PATENT DOCUMENTS

| | | |
|---|---|---|
| CA | 2502965 | 5/2004 |
| CA | 2534925 | 2/2005 |
| CA | 2551231 | 7/2005 |
| CA | 2572491 | 1/2006 |
| CH | 689109 | 10/1998 |
| CN | 1130352 | 9/1996 |
| CN | 1514721 | 7/2004 |
| DE | 4309528 | 9/1994 |
| DE | 19753534 | 6/1999 |
| DE | 19800698 | 7/1999 |
| DE | 19822979 | 12/1999 |
| DE | 19855440 | 6/2000 |
| DE | 10036400 | 6/2002 |
| DE | 10227077 | 6/2002 |
| DE | 69429710 T | 8/2002 |
| DE | 10336400 | 8/2003 |
| DE | 10250083 | 12/2003 |
| DE | 10250084 | 5/2004 |
| EP | 0 008 131 B1 | 2/1980 |
| EP | 0 177 893 A2 | 4/1986 |
| EP | 0 216 453 B1 | 4/1987 |
| EP | 0 226 061 B1 | 6/1987 |
| EP | 0 228 417 B1 | 7/1987 |
| EP | 0 232 877 A2 | 8/1987 |
| EP | 0 277 289 B1 | 8/1988 |
| EP | 0 293 066 B1 | 11/1988 |
| EP | 0 328 775 B1 | 8/1989 |
| EP | 0 583 726 B1 | 2/1994 |
| EP | 0 598 606 A1 | 5/1994 |
| EP | 0 661 045 B1 | 7/1995 |
| EP | 0 682 945 | 11/1995 |
| EP | 0 693 475 | 1/1996 |
| EP | 0 696 598 B1 | 2/1996 |
| EP | 0 780 369 | 6/1997 |
| EP | 0 820 698 | 1/1998 |
| EP | 0 889 045 A1 | 1/1999 |
| EP | 0 974 343 | 1/2000 |
| EP | 0 980 894 | 2/2000 |
| EP | 1 250 045 | 10/2002 |
| EP | 1 293 127 | 3/2003 |
| EP | 1 658 055 | 2/2005 |
| EP | 0 998 271 | 8/2005 |
| EP | 1 859 789 A1 | 11/2007 |
| EP | 1897545 B1 | 9/2009 |
| EP | 2070538 B1 | 12/2010 |
| EP | 2082742 B1 | 12/2010 |
| EP | 2080514 B1 | 2/2011 |
| EP | 2292229 B1 | 5/2012 |
| EP | 2292230 B1 | 5/2012 |
| EP | 2311459 B1 | 6/2012 |
| EP | 2343071 B1 | 3/2013 |
| EP | 2384754 B1 | 3/2013 |
| EP | 2399579 B1 | 4/2013 |
| EP | 2399580 B1 | 4/2013 |
| GB | 2450691 A | 1/2009 |
| WO | WO/90/03776 | 4/1990 |
| WO | WO/91/07950 | 6/1991 |
| WO | WO/93/06723 | 4/1993 |
| WO | WO/93/10758 | 6/1993 |
| WO | WO/93/11749 | 6/1993 |
| WO | WO/94/06414 | 3/1994 |
| WO | WO/94/08567 | 4/1994 |
| WO | WO/95/14460 | 6/1995 |
| WO | WO/95/20947 | 8/1995 |
| WO | WO/95/22319 | 8/1995 |
| WO | WO/95/30422 | 11/1995 |
| WO | WO/96/00066 | 1/1996 |
| WO | WO/96/14058 | 5/1996 |
| WO | WO/96/32097 | 10/1996 |
| WO | WO/97/33566 | 9/1997 |
| WO | WO/97/37689 | 10/1997 |
| WO | WO/97/49384 | 12/1997 |
| WO | WO/97/49385 | 12/1997 |
| WO | WO/98/20073 | 5/1998 |
| WO | WO/98/44911 | 10/1998 |
| WO | WO/98/56354 | 12/1998 |
| WO | WO/98/56359 | 12/1998 |
| WO | WO/99/32119 | 7/1999 |
| WO | WO/99/32120 | 7/1999 |
| WO | WO/99/44591 | 9/1999 |
| WO | WO/00/09639 | 2/2000 |
| WO | WO/00/33835 | 6/2000 |
| WO | WO/01/15667 | 3/2001 |
| WO | WO/01/45644 | 6/2001 |
| WO | WO/02/26928 A1 | 4/2002 |
| WO | WO/02/087512 | 11/2002 |
| WO | WO/03/013476 | 2/2003 |
| WO | WO/03/013479 | 2/2003 |
| WO | WO/03/015531 | 2/2003 |
| WO | WO/03/024429 | 3/2003 |
| WO | WO/03/024430 A1 | 3/2003 |
| WO | WO/03/026624 | 4/2003 |
| WO | WO/03/028620 | 4/2003 |
| WO | WO/03/028698 | 4/2003 |
| WO | WO/03/035029 A1 | 5/2003 |
| WO | WO/03/035053 | 5/2003 |
| WO | WO/03/035054 | 5/2003 |
| WO | WO/03/035177 | 5/2003 |
| WO | WO/03/053417 | 7/2003 |
| WO | WO/03/072086 | 9/2003 |
| WO | WO/03/094812 | 11/2003 |
| WO | WO/03/105808 A1 | 12/2003 |
| WO | WO/2004/026262 | 4/2004 |
| WO | WO/2004/026263 | 4/2004 |
| WO | WO/2004/037230 | 5/2004 |
| WO | WO/2004/037259 | 5/2004 |
| WO | WO/2004/037260 | 5/2004 |
| WO | WO/2004/093819 | 11/2004 |
| WO | WO/2005/016313 A1 | 2/2005 |
| WO | WO/2005/016314 A1 | 2/2005 |
| WO | WO/2005/041968 A2 | 5/2005 |
| WO | WO/2005/063214 A1 | 7/2005 |
| WO | WO/2005/079760 | 9/2005 |
| WO | WO/2005/097801 | 10/2005 |
| WO | WO/2005/102286 A1 | 11/2005 |
| WO | WO/2006/002883 A1 | 1/2006 |
| WO | WO/2006/002884 A1 | 1/2006 |
| WO | WO/2006/002886 | 1/2006 |
| WO | WO/2006/082097 A1 | 8/2006 |
| WO | WO/2006/082099 A1 | 8/2006 |
| WO | WO/2006/084211 | 8/2006 |
| WO | WO/2007/008752 A2 | 1/2007 |
| WO | WO/2007/048233 A1 | 5/2007 |
| WO | WO/2007/053698 A2 | 5/2007 |
| WO | WO/2008/086804 | 7/2008 |

OTHER PUBLICATIONS

Aitken-Nichol, C., et al., "Controlled Release Pellets and Granulations Manufactured Via Hot Melt Extrusion, Pharmaceutical Research," 12(9), p. S154 (1995).

Aitken-Nichol, C., et al., "Hot melt extrusion of acrylic films," Pharmaceutical Research, 13(5), pp. 804-808 (1996).

A.J. Hartley et al., "Raman scattering from mixtures of poly(ethylene oxide) 2000 with poly(ethylene oxide) 200", Polymer 1977, 18, 336-340.

A. Moroni et al., "Application of Poly(Oxyethylene) Homopolymers in Sustained Release Solid Formulations," Drug Development and Industrial Pharmacy, 21 (12), 1411-1428 (1995).

Apicella et al., "Poly(ethylene oxide) (PEO) Constant Release Monolithic Devices" Polymers in Medicine: Biomedical and Pharmaceutical Applications, Chapter 3 (1993).

Armbruster and Pry, "Limit of Blank, Limit of Detection and Limit of Quantitation," Clin. Biochem. Rev. vol. 29, Suppl. (i), p. S49 (2008).

Ary and Rona, "LC Determination of Morphine and Morphine

(56) References Cited

OTHER PUBLICATIONS

Glucuronides in Human Plasma by Coulometric and UV Detection," J Pharm. Biomed. Anal. 26, pp. 179-187 (2001).
Barradas et al., "Direct Stereocontrolled Synthesis of Polyoxygenated Hydrobenzofurans and Hydrobenzopyrans from p-Peroxy Quinols," Organic Letters, vol. 9, No. 24, pp. 5019-5022 (2007).
Bartlett and Woods, "Some Reactions of Δ2-Cyclyhexenone, Including the Synthesis of Bicyclo(2,2,2)-octanedione-2,6," J. Am. Chem. Soc., 62, pp. 2933-2938 (1940).
Barton, D.H.R., "The Conformation of the Steroid Nucleus", Experientia, vol. VI/8:316-320 (1950).
Bauer et al., Coated Pharmaceutical Dosage Forms: Fundamentals, ManufactUring Techniques, Biopharrnaceutical Aspects, Test Methods and Raw Materials, Scientific Publishers Stuttgart 1998, CRC Press, 8 pp.
Bentley, KW., The Chemistry of the Morphine Alkaloids, Chapters XVII and XVIII (pp. 251-262), Oxford at the Clarendon Press, (1954).
Berlin et al. "α-Aminoarylmethylphosphonic Acids and Diethyl α-Aminoarylmethylphosphonate Hydrochlorides: Aluminum-Amalgam Reduction of Oximes of Deithyl Aroylphosphonates," J. Org. Chem. vol. 33, No. 8, pp. 3090-3095 (1968).
Bighley, "Salt Forms of Drugs and Absorption," 13 Encyclopedia Pharm. Tech., pp. 453-499 (1996).
Bluelight Message Board: Mechanisms for Time Released Ritalin, www.bluelight.ru/vb/archive/index.php/t-36856.htm (Last visited Aug. 28, 2013).
Bohumil Proska, 10-Hydroxythebaine, 332 Arch. Phatm. Pharm. Med. Chem., pp. 369-370 (1999).
Braga et al, "Crystal polymorphism and multiple crystal forms," Struct. Bond, 2009, 132, pp. 25-50.
Breitenbach, J., "Melt Extrusion from Process to Drug Delivery Technology," 54 Eur. J. Pharm. Biopharm., pp. 107-117 (2002).
Bruan, David B.,"Poly(Ethylene Oxide)," Published by Union Carbide Corporation, at p. 19-20 (1980).
Carey et al., Advanced Organic Chemistry, pp. 102-105, 3rd ed. (1990).
Carreno, et al., "Enantioselective Synthesis of (+)- and (−)-Dihydroepiepoformin and (+)Epiepoformin," Organic Letters, vol. 7, No. 7, pp. 1419-1422 (2005).
Carreno, et al., "Enantioselective Synthesis of Natural Polyoxygenated Cyclohexanes and Cyclohexenes from [p-Tolylfulfinyl)Methyl]-p-quinols," Chem. Eur. J. 12, pp. 1064-1077 (2007).
C. D. Hanning et al., "The Morphine Hydrogel Suppository ," British Journal of Anaesthesia, 1988, 61, 221-227.
Chapman, Robert, U.S. Appl. No. 60/557,492, "Process for preparing oxycodone substantially free of 14-hydroxycodeinone and compositions thereof," (filed Mar. 30, 2004).
Chapman, Robert, U.S. Appl. No. 60/620,072 "Process for preparing oxycodone hydrochloride having less than 25 PPM 14-hydroxycodeinone and compositions thereof," (filed Oct. 18, 2004).
Chapman, Robert, U.S. Appl. No. 60/648,625 "Process for preparing oxycodone hydrochloride having less than 25 PPM 14-hydroxycodeinone and compositions thereof, " (filed Jan. 31, 2005).
Chapman, Robert, U.S. Appl. No. 60/651,778, "Process for preparing oxycodone hydrochloride having less than 25 PPM 14-hydroxycodeinone (filed Feb. 10, 2005).
Cherng-Ju Kim, "Drug Release from Compressed Hydrophilic POLYOX-WSR Tablets," Journal of Pharmaceutical Sciences, vol. 84, No. 3, Mar. 1995.
Chiao et al., "Sustained-Release Drug Delivery Systems." Remington: The Science and Practice of Pharmacy. Chapter 94. Alfonso R. Gennaro. Ed. pp. 1660-1675 (1995).
Chilean Patent Application No. 02485-2007: Office Action, dated Aug. 16, 2011.

Choi et ai, "Development of a directly compressible poly(ethylene oxide) matrix for the sustained-release of dihydrocodeine bitartrate," Drug Dev and Ind. Pharm, 2003, 29(10), 1045-1052.
Ciccone Patrick, "Attempted Abuse of Concerta," Letters to the Editor, J. Am. Acad. Child Adolesc. Psychiatry, 41:7, (Jul. 2002).
Citizen Petition filed by Purdue Pharma L.P. and Rohodes Technologies on Oct. 10, 2007.
Coluzzi F., Mattia C., "Oxycodone; Pharmacological profile and clinical data in chronic pain management," Minerva Anestesiol. 2005, 71(7-8):451-460.
Commonwealth of Australia, In the matter of Australian Patent Application No. 2002305559 in the name of Endo Pharmaceuticals, Inc. and Opposition thereto by Mundipharma Pty Limited, apmm A0111098466v3 2060308791.10., pp. 1-4.
Compilation of Monographs from Physicians' Desk Reference, 54th ed (2000).
Cone, E.J., "Ephemeral profiles of prescription drug and forumlation tampering: Evolving pseudoscience on the Internet," Drug and Alcohol Dependence 83S S31-S39 (2006).
Coppens et al., "Hypromellose, Ethylcellulose, and Polyethylene Oxide Use in Hot Melt Extrusion," Pharmaceutical Technology, 5 pp. (2005/2006).
CNN, "States Work to Control OxyContin Abuse," (2001) http://archives.cnn.com/2001/HEALTH/07/20/hillbilly.heroin/index.html (Last Visited Aug. 28, 2013).
Crowley et al., "Physicochemical properties and mechanism of drug release from ethyl cellulose matrix tablets prepared by direct compression and hot-melt extrusion," Int. J. Pharmaceutics 269, 509-522 (2004).
Currie, A.C., Some Reactions of 14-Hydroxycodeine, J. chemical Soc'y 773 (1960).
Davis M.P., Varga J., Dickerson D., Walsh D., LeGrand S.B., Lagman R., "Normal-release and controlled-release oxycodone: pharmacokinetics, pharmacodynamics and controversy," Support Care in Cancer 2003 , 11(2): 84-92.
Dawson, et al., "A Rapid and Sensitive High-Performance Liquid Chromatography-Electrospray Ionization-Triple Quadrupole Mass Spectrometry Method for the Quantitation of Oxycodone in Human Plasma," 40 J. Chrom. Sci., pp. 40-44 (2002).
Deighan, et al., "Rhabdomyolysis and Acute Renal Failure Resulting from Alcohol and Drug Abuse," 93 Q. J. Med., pp. 29-33 (1999).
De Jong, Pharmaceutisch Weekblad Scientific Edition, 24-28 (1987).
Deslongchamps, "Stereoelectronic Effects in Organic Chemistry," Ch. 5, pp. 163-208, Pergamon Press: Oxford (1983).
Dipiro, et al., "Pain Management," Pharmacotherapy: A Pathophysiological Approach, Chapter 56, pp. 1014-1026 (4th ed. 1999).
Dolan (ed)., "Calibration Curves, Part I: To b or Not to b," LCGC North America, vol. 27, No. 3, (2009).
Donnelly, Craig L, "ADHD medications: past and future," Behavioral Health Management, (May 1, 2002).
Dow Technical Data, POLYOX TM WSR, (Feb. 2003).
Dyson, "Chromatographic Integration Methods," The Royal Society of Chemistry, pp. 71-81 (2nd Ed.) (1998).
Edwards JE, Moor RA, McQuay HJ, "Single dose oxycodone and oxycodone plus paracetamol (acetaminophen) for acute postoperative pain," Cochrane Database Syst. Rev. 2000(4): CD002763. Review. Abstract.
E. G. Rippie et al., "Regulation of Dissolution Rate by Pellet Geometry," Journal of Pharmaceutical Sciences, Vo. 58, No. 4, Apr. 1969, pp. 428-431.
Eliel, et al., "Conformational Analysis," Interscience: New York, pp. 36, 92-109 (1965).
EP1014941: Opposition brief filed by opponent Grunenthal dated Dec. 23, 2009 (includes English-language translation) (24 pages).
EP1658054: Affidavit by Inventor of EP1658054, Prof. Johannes Bartholomaus, dated Oct. 7, 2009, with English translation (28 pages).
EP1658054: Annex to Third party observation—Test Report by Professor McGinity dated Jan. 26, 2009 (4 pages).
EP1658054: English translation of Patentee's response dated Jan. 15, 2009 (8 pages).
EP1658054: Opposition brief filed on Mar. 27, 2008 (15 pages).

(56) References Cited

OTHER PUBLICATIONS

EP1658054: Patentee's Response to Opposition dated Jan. 15, 2009 (12 pages).
EP1658054: Third party observation dated Feb. 2, 2009 (4 pages).
EP1658054: Third party observation dated Mar. 27, 2009 (3 pages).
EP1658054: Wolfgang, Ritschel, Die Tablette: Handbuch der Entwicklung, Herstellung and Qualitatssicherung (extract), with English translation (2002) (5 pages).
EP1658055: Annex to Third Party Observation—Test Report by Prof. McGinity dated Jan. 26, 2009 (4 pages).
EP1658055: Berger et al., Water-Soluble Resins, pp. 169-201 (1962) (34 pages).
EP1658055: Ethylene Oxide Polymers, Union Carbide Corporation, Technical Booklet (reprinted from Encyclopedia of Polymer Science and Technology, vol. 6, pp. 103-145 (1967).
EP1658055: European Pharmacopoeia, 3rd Ed ., chapter 2.9.8, 3 pages. (1997).
EP1658055: Experimental Report—Breaking strength tests on calibrated Instron tester dated Mar. 12, 2008 (4 pages).
EP1658055: Experimental Report—Breaking strength tests on uncalibrated Instron tester dated Dec. 6, 2007 (10 pages).
EP1658055: IP Search. Summary of prior art search for EP1658055 provided by Swiss Intellectual Property Office dated Dec. 3, 2007 (117 pages).
EP1658055: Opposition brief filed on Dec. 14, 2007 (14 pages).
EP1658055: Patentee's Response to Opposition dated Oct. 31, 2008, with English translation (23 pages).
EP1658055: Third Party Observation dated Feb. 2, 2009 (4 pages).
EP1658055: Third Party Observation dated Mar. 27, 2009 (3 pages).
EP1897545: Communicated dated Dec. 20, 2007 from the European Patent Office containing the European Search Report (6 pages).
EP1897545: Response to Office Communication dated May 21, 2008 (15 pages).
EP2070538: Annex 2 of the Report: Photos from Second Hydration Rate dated Mar. 5, 2010 (9 pages).
EP2070538: Annex1 of the Report: Photos from First Hydration Rate (9 pages).
EP2070538: Communication dated Jun. 25, 2009 from the European Patent Office (4 pages).
EP2070538: Communication dated May 18, 2009 from the European Patent Office including the European Search Report (3 pages).
EP2070538: Report—Comparison of Cured and Heat-Compressed PEO Tablets dated Mar. 5, 2010 (11 pages).
EP2070538: Response to Office Communicated dated Mar. 5, 2010 (23 pages).
EP2080514: Communication dated Jun. 15, 2009 from the European Patent Office containing the European Search Report (3 pages).
EP2080514: Office Action from EPO dated Jul. 14, 2009 (4 pages).
EP2080514: Response to Office Communicated dated Mar. 19, 2010 (14 pages).
EP2082742: Communication dated Jul. 9, 2009 from the European. Patent Office (4 pages).
EP2082742: Communication dated Jun. 15, 2009 from the European Patent Office containing the European Search Report (3 pages).
EP2082742: Response to Office Communication dated Mar. 19, 2010 (21 pages).
Falbe et al. (Eds.), Rompp Chemie Lexikon: with English translation (1992) (9 pages).
EP2399580: European Search Report issued Nov. 29, 2011.
EP2399579: European Search Report issued Nov. 30, 2011.
EP2384754: Submission to European Patent Office dated May 3, 2012.
EP2399579: Submission to the European Patent Office dated Jun. 28, 2012, including new claims.
EP2399580: Submission to European Patent Office Dated Jun. 28, 2012, including new claims.
EP2343071: Submission to the European Patent Office dated Jan. 11, 2012, including new claims.
EP2343071: Third Party Observation dated Nov. 17, 2012.

Excerpts from Handbook of Plastics Technologies 3.2.1.1 (Charles A. Harper ed.,2006).
Excerpts from Handbook of Pharmaceutical Excipients (6th ed. 2009), Polyethylene Glycol.
Excerpts from Remington: The Science and Practice of Pharmacy, 19th ed. 1995, pp. 1487-1494, 1615-49.
Excerpts from Remington: The Science and Practice of Pharmacy, 21st ed. 2006, pp. 889-928.
Excerpt from Sigma-Aldrich Catalog, Online Version in pdf format, Available: http://www.sigmaaldrich.com/, Accessed: Apr. 11, 2012.
FDA's Guidance for Industry SUPAC-MR: Modified Release Solid Oral Dosage Forms, (Sep. 1997).
FDA-approved drugs containing PEO, including the OROS formulations Procardia XL, Glucotrol XL, DynaCirc CR, Covera HS, Ditropan XL, Concerta (FDA Advisory Committee Briefing Document on NDA 22-272) (2009).
F. E. Bailey et al., "Some Properties of Poly(ethylene oxide) in Aqueous Solution," Journal of Applied Polymer Science, vol. 1, Issue No. 1, pp. 56-62 (1959).
Feldman, et ai, "Obtaining of Dihydroxycodeinone Hydrochloride From Thebaine," Journal of Applied Chemistry, vol. XVIII, No. 11-12 (1945).
Fell, J.T. et al., "Determination of Tablet Strength by the Diametral Compression Test," J. Pharm. Sci. vol. 59, No. 5, pp. 688-691 (1970).
Fiese, et al., "Comparison of the acid stability of azithromycin and erythromycin A," 25(a) J. Antimic. Chemother., pp. 39-47 (1990).
Fieser, et al., "Selective Oxidation with N-Bromosuccinimde," 71 J. Am. Chem. Soc., pp. 3938-3941 (1949).
Final Draft Labeling for Concerta Extended Release Tablets, (dated Jul. 2000), http://www.accessdata.fda.gov/drugsatfda_docs/label/2000/211211b1.pdf.
Findlay, et al., "The Acid-catalyzed Conversion of Codeinone to 8-Hydroxydihydrocodeinone" 73 J. Am. Chem. Soc., pp. 4001-4004 (1951).
Freund and Speyer. J. Prakt. Chem. 135-178 (1916).
Fuchs and VanderWerf. "Direction of Ring Opening in the Reduction of p-Substituted Styrene Oxides With Lithium Borohydride," J. Am. Chem. Soc., vol. 76, pp. 1631-1634 (1954).
Fürst and Plattner, "The Steric Course of the Reactions of Steroid Epoxides," Abstracts of Papers, 12th International Congress of Pure and Applied Chemistry (1951).
F. Zhang et al., "Properties of Sustained-Release Tablets Prepared by Hot-Melt Extrusion," Pharmaceutical Development and Technology, 4(2),241-250 (1999) pp. 241-250.
GAO Report to Congressional Requesters Prescription Drugs—Oxycontin Abuse and Diversion and Efforts to Address the Problem (GAO-04-110) (2003).
Gaskell H, Derry S, Moor RA, McQuay HJ, Update in Cochrane Database Syst. Rev. 2009(3): CD002763: "Single dose oral oxycodone and oxycodone plus paracetamol (acetaminophen) for acute postoperative pain in adults". Review. Abstract and full text.
Gates and Tschudi, "The Synthesis of Morphine," J Am. Chem. Soc., No. 7, vol. 78, pp. 1380-1393 (1956).
Gates and Tschudi, "The Synthesis of Morphine," J. Am. Chem. Soc., Communications to the Editor, 74, pp. 1109-1110 (1952).
G. Bechmann: "Ueber die verzogerte Wirkstoff-Freigabe aus peroral en, festen Arzneiformen" Ph.D. Thesis, University of Frankfort 1964.
Goodman & Gilman's The Pharmacological Basis of Therapeutics (7th ed. 1985).
Graham, et al., "Hydrogels for Controlled Drug Delivery," Biomaterials, 5(1), p. 27 (1984).
Graham, et al., "Hydrogels for the Controlled Release of Prostaglandin E2," Polym. Preprints 21(1), p. 104 (1980).
Graham, et al., "The release of prostaglandin E2 from a novel Crystalline-Rubbery Poly(ethylene oxide) Network Crosslinked by 3 ,4-dihydm-2H-pyranyl-2-methyl-(3 ,4-dihydro-2Hpyran-2-carboxylate)," Advances in Drug Delivery Systems (Eds. J.M. Anderson and S.W. Kim), Elsevier, Amsterdam, The Netherlands, pp. 231-244 (1986).
Griffith, Dorsey, "Potential new ADHD drug creating lots of big hopes," Sacramento Bee (California), (Oct. 30, 2002).
Grigoreva, The Stereochemistry and Mechanism of Dehydration of Cyclohexane Derivatives, Russ. Chem. Rev., 31(1): 18-35 (1962).

(56) References Cited

OTHER PUBLICATIONS

Guidance for Industry: Bioanalytical Method Validation, May 2001.
Guidelines for Authors, J. Org. Chem., vol. 69, No. 1, pp. 13A-21A, (2004).
Guidelines for Authors: Critical Manuscript Submission Requirements, J. Org. Chem., Jan. 2013.
Gulland and Robinson, "The Constitution of Codeine and Thebaine," Mem. Proc. Manchester Lit. Phil. Soc. 69, p. 79 (1925).
Gulland and Robinson, "The Morphine Group: A Discussion of the Constitutional Problem," J. Chem. Soc., pp. 980-998 (1923).
Gulyas, et al., "Morphine Alkaloids, 104: Synthesis and Conversions of New Epoxy Derivatives," 125(2) Acta Chimica Hungarica, pp. 255-265 (1988).
Hall and Dolan, "Performance Qualification of LC Systems," LCGC North America, vol. 20, No. 9, pp. 842-848 (2002).
Handbook of Pharmaceutical Excipients, Arthur H. Kibbe, ed. at 399 (3rd ed. 2000).
Handbook of Pharmaceutical Excipients 280, (Ainley Wade & Paul J. Wellers eds. 2d. 1994).
Handbook of Pharmaceutical Excipients 454, 460 (Raymond C. Rowe et al. eds., 4th ed. 2003).
Harano,Teruo et al., 3a-Jydroxy-5β,14β-chol-8-en-24-oic Acid and its Isomer, Dehydration Products of Chenodeoxycholic Acid Obtained by Treatment with Concentrated HCl, 30 Steroids 393 (1977).
Harris, Daniel C., Quantitative Chemical Analysis 646-49 (5th ed. 1999).
Hauser, et al. "14-Hydroxycodeinone: An Improved Synthesis," J. Med. Chem., vol. 17, No. 10, pp. 1117 (1974).
Honzumi and Ogasawara. "A Synthesis of Cyclohexanoid Butenolides Isolated from Sinomenium Acutum," Tetrahedron Letters, 43, pp. 1047-1049 (2002).
H. Tada et al., "Ketalisation of ab-unsaturated Ketones. Part I: 3-methoxy-N-methylmorphinan derivatives and 14-hydroxycodeineone", Tetrahedron Leiters No. 22, pp. 1805-1808 (1969).
http://www.accessdata.fda.gov/sripts/cder/drugsatfda/index.cfm?fuseaction-Search.DrugDetails (accessed Aug. 21, 2013).
http://www.bluelight.ru/vb/archive/index.php/t-36856.html (accessed Apr. 26, 2013).
http://www.bluelight.ru/vb/archive/index.php/t-39723.html (accessed Apr. 26, 2013).
Huang, et al., Preparation of Controlled Release Oral Dosage Forms by Low Temperature Melt Extrusion (Poster presented at the American Association of Pharmaceutical Sciences Annual Meeting in 2000).
Huang, H., et al., "Preparation of Controlled Release Oral Dosage Froms by Low Temperature Melt Extrusion," American Association of Pharmaceutical Scientists, (Nov. 2000), Annual Meeting Extracts, Union Carbide Corporation.
Huang, Hugh, Poster and Abstract on extruded POLYOX tablets presented at the poster session of 2000 MPS Annual Meeting, 4 pp.
Hudlicky and Reed, The Way of Synthesis: Evolution of Design and Methods for Natural Products, Wiley-Vch: Verlag GmbH & Co., Weinheim Germany, Part 1.2 (2007).
Hughes, et al., "Determiantin of Carryover and Contamination for Mass Spectrometry-Based Chromatographic Assays," The AAPS Journal, 9(3) Article 42, pp. E353-E360, (2007).
Huttenrauch et al. "Spritzgiessverfahren zur Herstellung peroraler Retardpraparate" Pharmazie vol. 30, No. 4, pp. 229-233; PMID: 1153488, 1975.
ICH Harmonised Tripartite Guideline: Validation of Analytical Procedures: Text and Methodology Q2(R1), International Conference on Harmonisation of Technical Requirements for Registration of Pharmaceuticals for Human Use (1996).
Ikuo Iijima et al., "The Oxidation of Thebaine with m-Chloroperbenzoic Acid Studies in the (+)-Morphinan Series. III", 60 Helvetica Chimica Acta, pp. 2135-2137 (1977).

Ikuo Iijima et al., Studies in the (+)-Morphinan Series, 5, Synthesis and Biological Properties of (+) Naloxone, 21 J. Medicinal Chemistry 398 (1978).
Jaffe, Steven L., M.D., "Failed Attempts at Intranasal Abuse of concerta," Letters to the Editor, J. AM. Acad. Child Adolesc, Psychiatry, 41:1, (Jan. 2002).
J.B. Ashworth. et al., "Effect of Tablet mechanical Stability on Drug Preference and Relative Street Value of Oxycodone Controlled-Release (CR) Tablets in Experienced Oxycodone CR Abusers" (Abstract) Presented at the 69th Annual Scientific Meeting of the College on Problems of Drug Dependence (Quebec City. Canada, Jun. 16, 2007).
J. Bartholomaeus, et al., "A New Technology to Increase the Mechanical Stability of Matrix Tablets to Prevent Abuse by Crushing or Chewing" (Abstract) Presented at the Drug Formulations and Abuse Liability Conference "Impact of Drug Formulation on Abuse Liability, Safety and Regulatory Decisions" (North Bethesda, Maryland, Apr. 19-20, 2005), pp. 12-13.
J.L. Stringer et al., "Diffusion of small molecular weight drugs in radiation-crosslinked poly(ethylene oxide) hydrogels," Journal of Controlled Release 42 (1996) 195-202.
J. Scheirs et al., "Characterizing the solid-state thermal oxidation of poly(ethylene oxide) powder," Polymer, 1991, vol. 32, No. 11.
Kadam, Granulation Technology for Bioproducts, CRC Press, Ch. 5, pp. 101-117 (1991).
Kalant, et al., "Death in Amphetamine Users: Causes and Rates," 112 CMA Journal, pp. 299-304 (1975).
Kalso E., "Oxycodone", J. Pain Symptom Manage. 2005, 29(5 Suppl):S47-S56.
Kim, "Drug Release from Compressed Hydrophilic POLYOX-WSR Tablets," 84(3) J. Pharm. Sci., pp. 303-306 (1995).
Kim et al., "Preparation and Evaluation of Eudragit Gels V. Rectal Gel Preparations for Sustained Release and Avoidance of First-Pass Metabolism of Lidocaine," Chern. Pharm. Bull. 40(10) 2800-2804 (1992).
Kirby, "Stereoelectronic Effects," New York: Oxford Science Publications, Ch. 6, pp. 51-75 (1996).
K.S. Chan et al., "Internal pressure of solid poly(ethylene oxide) 6000 swollen with liquid poly(ethylene oxide) 200", European Polymer Journal 1979, 15, 721-722.
Lee and Warner, "The System Biphenyl-Bibenzyl-Naphthalene: Nearly Ideal Binary and Ternary Systems," J. Am. Chem. Soc., 57(2), pp. 318-321 (1935).
Letter from FDA to Purdue Pharma L.P. dated Jan. 2, 2004.
Letter from Janet Woodcock, M.D., Director, Center for Drug Evaluation and Research, FDA to Philip C. Strassburger, Purdue Pharma L.P. and Edward B. Mahony, Rhodes Technologies Inc., Responding to Citizen Petition and Petition for Stay of Action (Mar. 24, 2008).
Lever Jr., et al., "Opioid Receptor Interactions and Conformations of the 6α and 6β Epimers of Oxymorphamine—Solid-State Conformation of 6α-Oxymorphamine," J. Med. Chem., 28, pp. 1652-1656 (1985).
LF Small. RE Lutz, Chemistry of the Opium Alkaloids, Suppl. No. 103 to Publich Health Reports, pp. 250-261, Washington (1932).
Lopez, et al., "The [4+2] Addition of Singlet Oxygen to Thebaine: New Access to Highly Functionalized Morphine Derivatives via Opioid Endoperoxides," J. Org. Chem. 65, pp. 4671-4678 (2000).
Lugo R.A., Kern S.E., "The pharmacokinetics of oxycodone", J. Pain Palliat. Care Pharmacother. 2004, 18(4): 17-30.
L. Yang et al., "Characterization of Compressibility and Compatibility of Poly(ethylene oxide) Polymers for Modified Release Application by Compaction Simulator," Journal of Pharmaceutical Sciences, vol. 85, No. 10, Oct. 1996.
Lyons, et al., "Twitch Interpolation in the Assessment of the Maximum Force-Generating Capacity of the Jaw-Closing Muscles in Man," 41:12 Arch. Oral. Biol., pp. 1161-1168 (1996).
M. Adel El-Egakey et al., "Hot extruded dosage forms Part 1," Pharmaceutica Acta Helvetiae, vol. 46, Mar. 19, 1970.
Maggi et al., "Dissolution behaviour of hydrophilic matrix tablets containing two different polyethylene oxides (PEOs) for the controlled release of a water-soluble drug. Dimensionality study," Biomaterials, vol. 23, QQ, 1113-1119 (2002).

(56) References Cited

OTHER PUBLICATIONS

Maniruzzaman, M., et al., "A Review of Hot-Melt Extrusion: Process Technology to Pharmaceutical Products," ISRN Pharmaceutics (2012).
Marshall and Fanta, "The Synthesis of Bicyclic Ketols from Cyclohexanones," J. Org. Chem. 29, pp. 2501-2505 (1964).
Maurer, Peter J. et al., Nitrogen-Bridged Conformationally Constrained Etrophine Analogues. Synthesis and Biological Evaluation, 30 J. Med. Chem. 2016 (1987).
McGinity et al., Hot-Melt Extrusion as a Pharmaceutical Process, V. 4 (2) , 25-36 (2001).
McGinity, James W., U.S. Appl. No. 60/020,623 "Hot-Melt Extrudable Pharmaceutical Formulation" (filed Jun. 26, 1996).
McKelvey, J., "Polymer Processing," John Wiley & Sons, Inc., Ch. 11, pp. 277-298 (1962).
McMurry, John, Organic Chemistry, pp. 249-252, 5th ed. (2002).
M. Efentakis et al., "Evaluation of High Molecular Weight Poly(Oxyethylene) (Poly ox) Polymer: Studies of Flow Properties and Release Rates of Furosemide and Captopril from Controlled-Release Hard Gelatin Capsules," Pharmaceutical Development and Technology, 5(3), 339-346 (2000).
Meier, B., Maker Chose Not to Act to Reduce Abuse of OxyContin, New York Times, Aug. 2001 http://www.nytimes.com/2001/08/13/health/13OXYC.html (Last Visited Aug. 28, 2013).
Merck Index 13th edition, p. 7028 (2001).
Merino, et al., "Stereocontrolled Approach to Phenyl Cyclitols From (SR)-[(p-Tolylsulfinyl)methyl]p-quinol," J. Org. Chem., 74, pp. 2824-2831 (2009).
Merino, et al. "Stereocontrolled Approach to Phenyl Cyclitols From (SR)-[(p-Tolylsulfinyl)methyl]-p-quinol," Supporting Information (2009).
Meyer, "Pitfalls and Errors of HPLC in Pictures," (2nd Rev. Ed.), Wiley-VCH, pp. 128-137 (2006).
Meyer, "Practical High-Performance Liquid Chromatography," John Wiley & Sons, Ltd., pp. 300-302 (5th Ed.) (2010).
Michael M. Crowley et al., "Pharmaceutical Applications of Hot-Melt Extrusion: Part 1"; 33 Drug Development and Industrial Pharmacy 909-926 (2007).
Miura et al., "Comparison of Maximum Bite Force and Dentate Status Between Healthy and Frail Elderly Persons," 28 J. Oral Rehabilitation, pp. 592-595 (2001).
Miyashita, et al. "The Organoselenium-Mediated Reduction of a,β-Epoxy Ketones, a, β-Epoxy Esters, and Their Congeners to β-Hydroxy Carbonyl Compounds: Novel Methodologies for the Synthesis of Aldols and Their Analogues," Tetrahedron, vol. 53, No. 37, pp. 12469-12486 (1997).
M.M. Crowley et al., "Stability of polyethylene oxide in matrix tablets prepared by hot-melt extrusion," Biomaterials 23 (2002) 4241-4248.
Molavi and Barron. "Melting Point Analysis," Physical Methods in Chemistry and NanoScience. http://cnx.org/content/m43565/latest/?collection=col10699/latest (Rice University) (2012).
Morrison et al., Organic Chemistry pp. 382-384; 548-549 (Allyn and Bacon, Inc. 4th ed. 1983).
M.S. Mesiha et al., "A Screening Study of Lubricants in Wet Powder Masses Suitable for Extrusion-Spheronization," Drug Development and Industrial Pharmacy, 19(8), 943-959 (1993).
Mueller U, "Polymorphism", Inorganic Structural Chemistry, John Wiley and Sons, 1993, pp. 14-15.
Nagase, et al., "The Facility of Formation of a $\Delta^6$ Bond in Dihydromorphinone and Related Opiates," J. Org. Chem. 54, pp. 4120-4125 (1989).
N.B. Graham, "Poly(Ethylene Glycol) Gels and Drug Delivery," Poly(Ethylene Glycol) Chemistry: Biotechnical and Biomedical Applications, Chapter 17,1992.
N. Follonier et al., "Evaluation of Hot-Melt Extrusion as a New Technique for the Production of Polymer-Based Pellets for Sustained Release Capsules Containing High Loadings of Freely Soluble Drugs," Drug Development and Industrial Pharmacy, 20(8), 1323-1339 (1994).
N. Follonier et al., "Various ways of modulating the release of diltiazem hydrochloride from hot-melt extruded sustained release pellets prepared using polymeric materials," Journal of Controlled Release 36 (1995) 243-250.
N. Ohnishi et al., "Effect of the Molecular Weight of Polyethylene Glycol on the Bioavailability of Indomethacin Sustained-Release SUPPOSitories Prepared with Solid Dispersions," Chern. Pharm. Bull., 35 (8) 3511-3515 (1987).
Notre, et al., "Synthesis of New Terpene Derivatives Via Ruthenium Catalysis: Rearrangement of Silylated Enynes Derived from Terpenoids," Tetrahedron, 59, pp. 9425-9432 (2003).
O.L. Sprockel et al., "Permeability of Cellulose Polymers: Water Vapour Transmission Rates," J. Pharm. Pharmacol. 1990, 42: 152-157.
"Oral Solid Dosage Forms," Remington's Pharmaceutical Sciences, 18th edition, Chapter 89, pp. 1633-1665 (1990).
Ott, "An Introduction to Statistical Methods and Data Analysis," (4th Ed.), Duxbury Press, p. 99 (1993).
Pascual, et al., "Fully automated analytical method for codeine quantification in human plasma using on-line solid-phase extraction and high-performance liquid chromatography with ultraviolet detection," 724 J. Chrom. B., pp. 295-302 (1999).
Pharmaceutical Research, Official Journal of the American Association of Pharmaceutical Scientists, Sep. 1989 (Supplement), vol. 6, No. 9, 6.S-98.
Pharmaceutical Research, Official Journal of the American Association of Pharmaceutical Scientists, Oct. 1991 (Supplement), Vo. 8, No. 10, 8.S-192.
Physicians Desk Reference, p. 2163, 51st etd. (1997).
Plattner and Furst, Hely. Chim, Acta, vol. 32, p. 275(1949).
Podczeck et al., "Investigations into the tensile failure of doubly-convex cylindrical tablets under diametral loading using finite element methodology," International Journal of Pharmaceutics 454 (2013) 412-424.
POLYOX Water-Soluble Resins NF in Pharmaceutical Applications, Dow Chemical Company, Aug. 2002.
POLYOX Water-Soluble Resins NF Patents Related to Pharmaceutical Applications, Dow Chemical Company, May 2004.
POLYOX Water-Soluble Resins, Dow Chemical Company, Mar. 2002.
POLYOX WSR Solid Dosage Formulation via Melt Extrusion, Dow Chemical Company, Feb. 2003.
Poyhia R., Vainio A., Kalso E., "A review of oxycodone's clinical pharmacokinetics and pharmacodynamics," J. Pain Sympton Manage, 1993, 8(2): 63-67.
"Practice Parameter for the Use of Stimulant Medications in the Treatment of Children, Adolescents, and Adults," J. AM. Acad. Child Adolesc. Psychiatry, 41:2 Supplement, Feb. 2002.
Proeschel et al., "Task-dependence of Activity/Bite-force Relations and its Impact on Estimation of Chewing Force from EMG," J Dent Res, vol. 81, No. 7, pp. 464-468 (20021-.
Proksa, "Separation of Products of Thebaine Rearrangement by Capillary Electrophoresis in the Presence of Cyclodextrins," 55 Chem. Pap., pp. 196-201 (2001).
P. Shivanand et al., "Factors Affecting Release of KCI from Melt Extruded Polyethylene Disks," Pharmaceutical Research, Official Journal of the American Association of Pharmaceutical Scientists; Oct. 1991, vol. 8, No. 10.
*Purdue v. Teva*, Trial Decision (Case 04-MD-01603-SHS 568) (# 149 Jan. 14, 2014).
Ramanathan, et al., "Dihydrocodeine, Dihydrocodeinone, 1 4-Hydroxydihydrocodeinone & Their Derivatives," 2(10) Indian J. Tech., pp. 350-351 (1964).
Ramanathan et al., Indian J Technol, pp. 350-351 (1964).
Reich/Nelsen, Oxidation State of Organic Molecules; Redox Agents; Reagents by Redox and Acid/Base Classes. Chem. 343/345, http://www.chem.wisc.edu/areas/reich/handouts/chem343-345/redox.pdf (last accessed Aug. 28, 2013).
Bruckner, "Oxidations and Reductions: 1.1—Oxidation Numbers in Organic Chemical Compounds, and Organic Chemical Redox Reactions," Organic Mechanisms, Springer-Verlag, Berlin, 737-741, (2010).

(56) References Cited

OTHER PUBLICATIONS

Remington's Pharmaceutical Sciences, "Analgesics and Antipyretics," Mack Printing Company, Ch. 60, pp. 1099-1123 (1985).
Remington's Pharmaceutical Sciences, "Coating of Pharmaceutical Dosage Forms," Ch. 90, pp. 1666-1675 and, "Sustained-Release Drug Delivery Systems," Ch. 91, pp. 1676-1693, Mack Publishing Company, 18$^{th}$ Ed., (1990).
Remington's Pharmaceutical Sciences 17$^{th}$ ed., Mack Publishing Co., (1985) 1418.
Report: Cured v. Heat-Compressed PEO Tablets (Mar. 2010); submitted in EP 2 070 538 (Application No. 09156832.9) and other EP and foreign applications.
Reynolds, et al., "Selective Reduction of a,β-epoxyketones to β-hydroxyketones Using Silyllithium Reagents," Tetrahedron Letters, 48, pp. 6751-6753 (2007).
R. Mank et al., "Darstellung wirkstoffhaltiger Extrusionsformlinge auf der Basis von Thermoplasten," Pharmazie 44 (1989) H. 11; pp. 773-776.
R. Mank et al., "Darstellung wirkstoffhaltiger Extrusionsformlinge auf der Basis von Thermoplasten," Pharmazie 45 (1990), H. 8; pp. 592-593.
Robinson and Henderson. "Reduction of a, β-Oxido Ketones with Chromous Acetate: Synthesis of 3β,5β,17β, 19-Tetrahydroxy-5β-Androstane, A Degradation Product of Strophanthidian," J. Org. Chem., vol. 37, No. 4, pp. 565-568 (1972).
Roland Krassnig, et al., "Optimization of the sythesis of oxycodone and 5-methyloxycodone,"Arch. Pharm. Med. Chem., vol. 329, pp. 325-326 (1996).
Rubin, R., New Form of OxyContin would thwart abusers, USA Today, Aug. 8, 2001 http://usatoday30.usatoday.com/news/healthscience/health/2001-08-08-oxycontin.htm (Last visited Aug. 29, 2013).
Salvador, et al., "Hydrazine Hydrate Induced Reductive Cleavage of a, β-epoxy ketones: An Efficient Procedure for the Preparation of β-hydroxy ketones," Tetrahedron Letters, 46, pp. 1067-1070 (2005).
Schroeder et al., "Granulierung hydrophober Wirkstoffe im Planetwalzenextruder" (Summary in English), Wissenschaft and Technik, Pharm. Ind., vol. 65, No. 4, 367-372 (2003).
Seki, "An Improved Preparation of 14-Hydroxycodeinone," 12 Tak. Inst. Ann. Rpt., pp. 52-55 (1960).
Seki, Isao, Studies on the Morphine Alkaloids and Its Related Compounds, XV, 17 Chemical & Pharm. Bull, 1549 (1969).
Sentry POLYOX Water-Soluble Resins NF Patents Related to Drug Delivery and Wound Care, Oct. 1997.
Sentry POLYOX Water-Soluble Resins NF Patents Related to Drug Delivery and Wound Care, Union Carbide Corporation, Oct. 1997.
Simonds et al. "Extrusion of Plastics, Rubber and Metals" Reinhold Publishing Corp. New York (1954).
S. Janicki et al., "Slow-Release Microballs: Method of Preparation," Acta Pharm. Technol. 33(3) 154-155 (1987).
Skelly et al., Scaleup of Oral Extended-Release Dosage Forms, Pharmaceutical Research 10(12) 1800-05 (1993).
S.L. Madorsky et al., "Thermal Degradation of Polyethylene Oxide and Polypropylene Oxide," Journal of Polymer Science, vol. XXXVI, pp. 183-194 (1959).
Smith and March, "March's Advanced Organic Chemistry: Reactions, Mechanisms, and Structure," pp. 1048-1051, John Wiley & Sons, Inc. (5th Ed.) (2001).
Smith, et al., "High Molecular Weight Polymers of Ethylene Oxide, Industrial and Engineering Chemistry," Union Carbide Chemicals Co., pp. 12-16 Jan. 1958.
Snyder, et al. "Introduction to Modern Liquid Chromatography," John Wiley & Sons, Inc. Hoboken, New Jersey, John Wiley & Sons, Inc. (3rd Ed.) (2010).
Soloveichik and Krakauer, "Oxidation Stages of Organic Aliphatic Compounds: A Classification Scheme," J. Chem. Education. vol. 43, No. 10, Oct. 1966, pp. 532-535.
Sprockel, O.L., et al., A melt-extrusion process for manufacturing matrix drug delivery systems, International Journal of Pharmaceutics, 155(2): 191-199 (1997).

S. Radko et al., "Molecular sieving by polymer solutions: dependence on particle and polymer size, independence of polymer entanglement," Applied and Theoretical Electrophoresis (1995), 5,79-88.
Stewart, A.W., Heterocyclic Division, 16 Ann. Rep. on Progress Chemistry 104 (1919).
Stoeltje, "Lone Star Living; Ritalin Alternatives: Attention focuses on new ADHD drugs," The Associated Press State & Local Wire, Apr. 4, 2001.
Streitwieser Jr., et al., "Introduction to Organic Chemistry," pp. 135-137 and 259-270, Macmillan Publishing Company (4th Ed.) (1992).
Wenderski, et al., Supporting Information for Publication "Enantioselective Total Synthesis of All of the Known Chiral Cleroindicins (C-F): Clarification Among Optical Rotations and Assignments," S1-S59, J. Org. Chem, 74, pp. 4104-4109 (2009).
Tachihara and Kitahara. "Total Synthesis of (+)-epiepoformin, (+)-epiepoxydon and (+)-bromoxone Employing a Useful Chiral Building Block, Ethyl (1R,2S)-5,5-Ethylenedioxy-2-Hydroxycyclohexanecarboxylate," Tetrahedron, 59, pp. 1773-1780 (2003).
Tadmor Z & Gogos C.G., Principles of Polymer Processing 752, 811, 2nd edition (2006), pp. 753-823.
Billmeyer, Jr., F., Textbook of Polymer Sciences, Second Edition, Ch. 17, pp. 497-498, John Wiley & Sons, Inc. (1991).
The Merck Index, Merck & Co., Inc. (11th Ed.) (1989) p. 6907.
Tough, "The Alchemy of OxyContin: From Pain Relief to Drug Addiction," New York Times, Jul. 29, 2001.
T. Ozeki et al., "Control of medicine release from solid dispersion composed of the poly(ethylene oxide)-carboxyvinylpolymer interpolymer complex by varying molecular weight of poly(ethylene oxide)," Journal of Controlled Release 58 (1999) 87-95.
U.S. Food and Drug Administration ("FDA") Orange Book: Concerta Patent Data Aug. 28, 2013.
U.S. Pharmacopeia: National Formulary Supplement. USP 23, Supplement 8, NF 18 (1998).
1995 U. S. Pharmacopoeia & the National Formulary: USP 23-NF18; vol. 23, No. 18, pp. 1791-1793; ISBN: 0913595764; General Chapters on General Tests and Assays, Section 711, Dissolution.
Varian, Inc.'s Liquid Chromatography Backgrounder Mar. 2002.
Vavon, et al., "Contribution à l'étude des cholestanols (a)," 53 Bull. Soc. Chim. France, pp. 581-588 (1933).
Viebock, F., "Oxydation des Thebians mit Manganiacetate", Chem. Ber. 67, pp. 197-202 (1934).
Vippagunta et al., "Chrystalline solids", Advanced Drug Delivery Reviews, 2001, 48, pp. 3-26.
Viswanathan, et al., "Workshop/Conference Report—Quantitative Bioanalytical Methods Validation and Implementation: Best Practices for Chromatographic and Ligand Binding Assays," The AAPS Journal, 9(1), Article 4, pp. E30-E42 (2007).
V.K. Thoma et al., "Bestimmung der In-vitro-Freigabe von schwach basischen Wirkstoffen aus Retardarzneiformen," Pharm. Ind. 51, Nr. 3 (1989).
Vogel's Textbook of Practical Organic Chemistry, pp. 89-90, and 133-153, 5th ed. (1989).
Walsh D., "Advances in opioid therapy and formulations", Supportive Care in Cancer 2005, 13(3): 138-144.
Water-Soluble Resins Are Unique, Union Carbide Corporation (1973).
Weihe and McMorris, "Stereoselective Synthesis of 23-Deoxyantheridiol," J. Org. Chem., vol. 43, No. 20, pp. 3942-3946 (1978).
Weiss, Ulrich, "Derivatives of Morphine. II. Demethylation of 14-hydroxycodeinone. 14-Hydroxymorphinone and 8, 14-Dihydroxydihydromorphinone," The Journal of Organic Chemistry, vol. 22, No. 11, pp. 1505-1508 (1957).
Wenderski, et al., "Enantioselective Total Synthesis of All of the Known Chiral Cleroindicins (C-F): Clarification Among Optical Rotations and Assignments," J. Org. Chem, 74, pp. 4 104- 4109 (2009).
Whalen, et al., "Effects of Para-Substituents on the Mechanisms of Solvolysis of Styrene Oxides," J. Org. Chem 58, pp. 924-932 (1993).
Wikipedia—Newton (unit) (2014).
Wingert, "No More Afternoon Nasties," Newsweek, Dec. 4, 2000.

(56) References Cited

OTHER PUBLICATIONS

W. Prapaitrakul et al., "Release of Chlorpheniramine Maleate from Fatty Acid Ester Matrix Disks Prepared by Melt-extrusion," J. Pharm. Pharmacol. 1991,43: 377-381.
Wright, Curtis, U.S. Appl. No. 60/310,534 "Pharmaceutical formulation containing gelling agent" (filed Aug. 6, 2001).
Wright, Curtis, U.S. Appl. No. 60/310,537, "Pharmaceutical formulation containing opioid agonist, opioid antagonist and gelling agent" (filed Aug. 6, 2001).
Yu, D. et al., "Viscoelastic Properties of Poly(ethylene oxide) Solution, Journal of Pharmaceutical Sciences," (83) Oct. 10, 1994.
Zhang, "Hot-Melt Extrusion as a Novel Technology to Prepare Sustained-Release Dosage Forms," Ph.D. Dissertation, University of Texas at Austin, Dec. 1999 at Section 1.1, p. 13.
Bjeldanes et al., A Bisulfite Mediated Oxidation of Thebaine. Formation of 6-0-Demethylsalutaridine, J Org. Chem. 37(9):1453-1454 (1972).
Board of Patent Appeals and Interferences Memorandum Opinion and Order regarding Patent Interference No. 105,553 Mar. 13, 2008.
*Chapman v. Casner*, Nos. 2008-1427, -1428, 315 Fed. Appx. 294, 2009 WL 606065 (Fed. Cir. Mar. 11, 2009).
Dec. 1996 PDR Supplement for OxyContin® (OxyContin 1996 Package Insert).
Guidance for Industry-Q3A Impurities in New Drug Substances Feb. 2003: 1-14.
Interference No. 105,553 File History *Johnson Matthey Public Limited co. v. Purdue Pharma L.P.* Declared Apr. 19, 2007.
Li et al., Synthesis of C-7 oxidized abietane diterpenes from racemic ferruginyl methyl ether, Tetrahedron, 59:5737-5741 (2003).
OxyContin® Product Information dated Jul. 30, 2003.
OxyContin® Product Information dated Jun. 5, 1998.
Remington's Pharmaceutical Sciences, Hoover, Mack Publishing Company (15th Ed.) (1975).
Guidance for Industry. S2B Genotoxicity: A Standard Battery for Genotoxicity Testing of Pharmaceuticals, ICH, Jul. 1997.
Response to Citizen Petition on behalf of Purdue Pharma L.P., Jan. 14, 2011.
Josh', Yatrindra, U.S. Appl. No. 60/287,509, "Pharmaceutical composition which reduces or eliminates drug abuse potential" filed Apr. 30, 2001.
Oshlack Benjamin, U.S. Appl. No. 60/288,211, "Once-a-day oxycodone formulations" filed May 2, 2001.
Oshlack Benjamin, U.S. Appl. No. 60/310,514, "Pharmaceutical formulation containing bittering agent" filed Aug. 6, 2001.
Complaint, *Purdue Pharma L.P., et al. v. Varam Inc., et al.*, CA No. 10-cv-04028-PBT (EDPA 2010).
Varam, Inc.'s Answer, Separate Defenses and Counterclaims, *Purdue Pharma L.P., et al. v. Varam Inc., et al.*, C.A. No. 10-cv-04028-PBT (EDPA 2010).
Purdue's Answer to the Counterclaims of Defendant Varam, Inc., *Purdue Pharma L.P., et. al. v. Varam Inc., et al.*, CA No. 10-cv-04028-PBT (EDPA 2010).
Complaint, *Purdue Pharma L.P., et al. v. Varam, Inc., et al.*, CA No. 10 CIV 6038 (SDNY 2010).
Complaint. *Purdue Pharma L.P .. et al. v. Ranbaxy Inc .. et al.*, CA No. 10-03734-SHS (SDNY 2010).
Actavis Elizabeth LLC's Answer and Counterclaims, *Purdue Pharma L.P. et al. v. Ranbaxy Inc., et al.*, CA No. 10-03734-SHS (SDNY 2010).
Defendants Ranbaxy Inc.'s Answer and Counterclaims, *Purdue Pharma L.P., et al. v. Ranbaxy Inc., et al.*, CA No. 10-03734-SHS (SDNY 2010).
Plaintiffs' Answer to the Counterclaims of Defendants Ranbaxy Inc. et al., *Purdue Pharma L.P. et al. v. Ranbaxy Inc. et al.*, CA No. 1-10-cv-03734-SHS (SDNY 2010).
Mylan Pharmaceuticals Inc.'s and Mylan Inc.'s Answer and Counterclaims, *Purdue Pharma L.P., et al. v. Ranbaxy Inc., et al.*, CA No. 10-03734-SHS (SDNY 2010).

Plaintiffs' Answer to the Counterclaims of Defendant Actavis Elizabeth LLC, *Purdue Pharma L.P., et al. v. Ranbaxy Inc., et al.*, CA No. 10-03734-SHS (SDNY 2010).
Plaintiffs' Answer to the Counterclaims of Defendants Mylan Pharmaceuticals Inc. and Mylan inc., *Purdue Pharma L.P., et al. v. Ranbaxy Inc., et al.*, CA No. 10-03734-SHS (SNDY 2010).
Complaint, *Purdue Pharma L.P., et al. v. Ranbaxy Inc., et al.*, C.A No. 1 :11-cv-2401-UA (SDNY 2011).
Defendants Ranbaxy Inc.'s Answer and Counterclaims, *Purdue Pharma L.P., et al. v. Ranbaxy Inc. et al.*, CA No. 1: 11-cv-2401 (SDNY 2011).
Plaintiffs' Answer to the Counterclaims of Defendants Ranbaxy Inc. et al., *Purdue Pharma L.P., et al. v. Ranbaxy Inc. et al.*, CA No. 1 :11-cv-02401 (SDNY 2011).
Complaint, *Purdue Pharma L.P., v. Ranbaxy Inc., et al.*, CA No. 11-cv-7104 (SDNY 2011).
Complaint, *Purdue Pharma L.P .. et al. v. Watson Laboratories, Inc., et al.*, C.A No. 1 :11-cv-02036-UA, (SDNY 2011).
Answer, *Purdue Pharma L.P., et al. v. Watson Laboratories, Inc., et al.*, C.A. No. 1 :11-cv-02036-UA (SDNY 2011).
Complaint, *Purdue Pharma L.P., et al. v. Andrx Labs, LLC*, CA No. 11 CIV 00248 (DDDE 2011).
Complaint, *Purdue Pharma L.P., et al. v. Watson Laboratories, Inc.*, CA No. 0:II-cv-60643-xxxx (SDFL 2011).
Complaint, *Purdue Pharma L.P., et al. v. Actavis Elizabeth LLC*, CA No. 1 :11-cv-02038-UA (SDNY 2011).
Answer of Plaintiffs Purdue and University of Texas System to the Counterclaims of Defendant Actavis Elizabeth LLC, *Purdue Pharma L.P., et al. v. Actavis Elizabeth LLC*, CA No. 1 :11-cv-02038-UA (SDNY 2011).
Plaintiff Purdue's Notice of Motion and Rule 12(b)(6) Motion to Dismiss Actavis's Third Counterclaim, *Purdue Pharma L.P., et al. v. Actavis Elizabeth LLC*, CA No. 1 :11-cv-02038-UA (SDNY 2011).
Memorandum of Law in Support of Plaintiffs' Rule 12(b)(6) Motion to Dismiss Actavis's Third Counterclaim, *Purdue Pharma L.P., et al. v. Actavis Elizabeth LLC*, CA No. 1 :11-cv-02038-UA (SDNY 2011).
Plaintiffs Reply in Support of Plaintiffs Rule 12(b)(6) Motion to Dismiss Actavis's Third Claim, *Purdue Pharma L.P., et al v. Actavis Elizabeth LLC*, CA No. 1 :11-cv-02038-UA (SDNY 2011).
Plaintiffs' Corrected Reply in Support of Plaintiffs Rule 12(b) (6) Motion to Dismiss Actavis's Third Counterclaim, *Purdue Pharma L.P., et al. v. Actavis Elizabeth LLC*, CA No. 1 :11-cv-02038-UA (SDNY 2011).
Complaint, *Purdue Pharma L.P., et al. v. Impax Laboratories Inc*, CA No. 1 :11-cv-02400-UA (SDNY 2011).
Answer, Affirmative Defenses, and Counterclaims of Defendant Impax Laboratories, Inc., *Purdue Pharma L.P., et al. v. Impax Laboratories Inc*, CA No. 1 :11-cv-02400-UA (SDNY 2011).
Answer of Plaintiffs Purdue and University of Texas System to the Counterclaims of Defendant Impax Laboratories, Inc., *Purdue Pharma L.P., et al. v. Impax Laboratories Inc*, CA No. 1 :11-cv-02400-UA (SDNY 2011).
Answer of Plaintiff/Counterclaim-Defendant Grunenthal GmbH to the Counterclaims of Defendant Impax Laboratories, Inc., *Purdue Pharma L.P., et al. v. Impax Laboratories Inc*, CA No. 1 :11-cv-02400-UA (SDNY 2011).
Complaint, *Purdue Pharma L.P., et al. v. Sandoz Inc.*, CA No. 1 :11-cv-04694-UA (SDNY 2011).
Sandoz Inc.'s Answer, Affirmative Defenses and Counterclaims, *Purdue Pharma L.P., et al. v. Sandoz Inc.*, C.A. No. 1: 11-cv-04694-UA (SDNY 2011).
Answer by Plaintiff/Counterclaim-Defendant Grunenthal GmbH to the Counterclaims of Defendant Sandoz Inc. *Purdue Pharma L.P., et al. v. Sandoz Inc.*, CA No. 1 :11-cv-04694-UA (SDNY 2011).
Answer of Plaintiffs Purdue and University of Texas System to the Counterclaims of Defendant Sandoz Inc., *Purdue Pharma L.P., et al. v. Sandoz Inc.*, CA No. 1 :11-cv-04694-UA (SDNY 2011).
Complaint, *Purdue Pharma L.P., et al. v Teva Pharmaceuticals USA, Inc.*, CA No. 1 :11-cv02037-UA (SDNY 2011).
Teva Pharmaceuticals USA, Inc.'s Answer, Affirmative Defenses and Counterclaims to Complaint, *Purdue Pharma L. P., et al. v Teva Pharmaceuticals USA, Inc.*, CA No. 1 :11-cv-02037-UA (SDNY 2011).

(56) References Cited

OTHER PUBLICATIONS

Answer by Plaintiff/Counterclaim-Defendant Grunenthal Gmbh to the Counterclaims of Defendant Teva 36 Pharmaceuticals, Inc., *Purdue Pharma L.P., et al.* v *Teva Pharmaceuticals USA, Inc.*, CA No. 1:11-cv-02037-UA 0 (SDNY 2011).
Answer of Plaintiff Purdue to the Counterclaims of Defendant Teva Pharmaceuticals USA, Inc., *Purdue Pharma L.P., et al.* v *Teva Pharmaceuticals USA, Inc.*, CA No. 1:11-cv-02037-UA (SDNY 2011).
Markman Order dated Aug. 23, 2013, in In re OxyContin Antitrust Litigation, in the Southern District of New York, (SDNY 2004).
Statement of Related Cases dated, Jul. 2, 2013, in the Southern District of New York, Civil Docket No. 1: 13-cv-04606 (SHS) (SDNY 2013).
Docket Sheet dated Aug. 27, 2013 in *Purdue Pharma L.P. et al* v. *Epic Pharma, LLC*, in the Southern District of New York, Civil Docket No. 1: 13-cv-00683 (SHS) (SDNY 2013).
Docket Sheet dated Aug. 27, 2013 in *Purdue Pharma L.P. et al* v. *Mylan Pharmaceuticals Inc. et ai*, in the Southern District of New York, Civil Docket No. 1:12-cv-02959 (SHS) (SDNY 2012).
Docket Sheet dated Aug. 27, 2013 in *Purdue Pharma L.P. et al* v. *PAR Pharmaceuticals, Inc.*, in the Southern District of New York, Civil Docket No. 1: 12-cv-05615 (SHS) (SDNY 2012).
Docket Sheet dated Aug. 27, 2013 in *Purdue Pharma L.P. et al* v. *Impax Laboratories, Inc.*, in the Southern District of New York, Civil Docket No. 1: 11-cv-02400 (SHS) (SDNY 2011).
Docket Sheet dated Aug. 27, 2013 in *Purdue Pharma L.P. et al* v. *Par Pharmaceuticals, Inc.* In the Southern District of New York, Civil Docket No. 1: 13-cv03374 (SHS) (SDNY 2013).
Docket Sheet dated Aug. 27, 2013 in *Purdue Pharma L.P. et al* v. *Amneal Pharmaceuticals, LLC.*, in the Southern District of New York, Civil Docket No. 1: 13cv-03372 (SHS) (SDNY 2013).
Docket Sheet dated Aug. 27, 2013 in *Purdue Pharma L.P. et al* v. *Amneal Pharmaceuticals, LLC.*, in the Southern District of New York, Civil Docket No. 1: 11cv-08153 (SHS) (SDNY 2011).
Docket Sheet dated Aug. 27, 2013 in *Purdue Pharma L.P. et al* v. *Sandoz, Inc.*, in the Southern District of New York, Civil Docket No. 1: 12-cv-07582 (SHS) (SDNY 2012).
Docket Sheet dated Aug. 27, 2013 in *Purdue Pharma L.P. et al* v. *Sandoz, Inc.*, in the Southern District of New York, Civil Docket No. 1: 12-cv-05082 (SHS) (SDNY 2012).
Docket Sheet dated Aug. 27, 2013 in *Purdue Pharma L.P. et al* v. *Sandoz, Inc.*, in the Southern District of New York, Civil Docket No. 1: 12-cv-00897 (SHS) (SDNY 2012).
Docket Sheet dated Aug. 27, 2013 in *Purdue Pharma L.P. et al* v. *Sandoz, Inc.*, in the Southern District of New York, Civil Docket No. 1:11-cv-04694 (SHS) (SDNY 2011).
Docket Sheet dated Jul. 23, 2013 in *Purdue Pharma L.P. et al* v. *Ranbaxy, Inc. et al*, in the Southern District of New York, Civil Docket No. 1:11-cv-07104 (SHS) (SDNY 2011).
Docket Sheet dated Jul. 23, 2013 in *Purdue Pharma L.P. et al* v. *Ranbaxy, Inc. et al*, in the Southern District of New York, Civil Docket No. 1:11-cv-02401 (SHS) (SDNY 2011).
Docket Sheet dated Aug. 27, 2013 in *Purdue Pharma L.P. et al* v. *Impax Laboratories, Inc.*, in the Southern District of New York, Civil Docket No. 1:13-cv-03188 (SHS) (SDNY 2013).
Docket Sheet dated Aug. 27, 2013 in *Purdue Pharma L.P. et al* v. *Impax Laboratories, Inc.*, in the Southern District of New York, Civil Docket No. 1:13-cv-000763 (SHS) (SDNY 2013).
Docket Sheet dated Aug. 27, 2013 in *Purdue Pharma L.P. et al* v. *PAR Pharmaceuticals, Inc.* in the Southern District of New York, Civil Docket No. 1: 11-cv-02038 (SHS) (SDNY 2011).
Docket Sheet dated Aug. 27, 2013 in *Purdue Pharma L.P. et al* v. *Teva Pharmaceuticals, USA, Inc.* in the Southern District of New York, Civil Docket No. 1:13-cv-04606 (SHS) (SDNY 2013).
Docket Sheet dated Aug. 27, 2013 in *Purdue Pharma L.P. et al* v. *Teva Pharmaceuticals, USA, Inc.* in the Southern District of New York, Civil Docket No. 1:12-cv-05083 (SHS) (SDNY 2012).
Docket Sheet dated Aug. 27, 2013 in *Purdue Pharma L.P. et al* v. *Teva Pharmaceuticals, USA, Inc.* in the Southern District of New York, Civil Docket No. 1:11-cv-02037 (SHS) (SDNY 2011).
Docket Sheet dated Jul. 23, 2013 in *Purdue Pharma L.P. et al* v. *Watson Laboratories, Inc.-Florida et al.* in the Southern District of New York, Civil Docket No. 1: 13-cv-01272 (SHS) (SDNY 2013).
Docket Sheet dated Jul. 23, 2013 in *Purdue Pharma L.P. et al* v. *Watson Laboratories, Inc. et al.* in the Southern District of New York, Civil Docket No. 1: 13-cv-0762 (SHS) (SDNY 2013).
Docket Sheet dated Jul. 23, 2013 in *Purdue Pharma L.P. et al* v. *Watson Laboratories, Inc. et al.* in the Southern District of New York, Civil Docket No. 1: 12-cv-03111 (SHS) (SDNY 2012).
Docket Sheet dated Jul. 23, 2013 in *Purdue Pharma L.P. et al* v. *Watson Laboratories, Inc. et al.* in the Southern District of New York, Civil Docket No. 1: 11-cv-02036 (SHS) (SDNY 2011).
Docket Sheet dated Jul. 23, 2013 in *Purdue Pharma L.P. et al* v *Impax Laboratories, Inc.* in the Southern District of New York, Civil Docket No. 1: 13-cv-0684 (SHS) (SONY 2013).
Docket Sheet dated Jul. 23, 2013 in *Purdue Pharma L.P. et al* v. *Varam, Inc. et al.* in the Eastern District of Pennsylvania (Philadelphia), Civil Docket No. 2: 12-cv-01898 (PBT) (ED Pa. 2012).
Docket Sheet dated Jul. 23, 2013 in *Purdue Pharma L.P. et al* v. *Varam, Inc. et al.* in the Southern District of New York, Civil Docket No. 1: 12-cv-02814 (SHS) (SDNY 2012).
Docket Sheet dated Jul. 23, 2013 in *Purdue Pharma L.P. et al* v. *Varam, Inc. et al.* in the Southern District of New York, Civil Docket No. 1:11-cv-00766 (SHS) (SDNY 2011).
Docket Sheet dated Jul. 23, 2013 in *Purdue Pharma L.P. et al* v. *Varam, Inc. et al.* In the Eastern District of Pennsylvania (Philadelphia), Civil Docket No. 2: 10-cv-04028 (PBT) (ED Pa. 2010).
Docket Sheet dated Jul. 23, 2013 in *Purdue Pharma L.P. et al* v. *Varam, Inc. et al.* in the Southern District of New York, Civil Docket No. 1: 10-cv-06038 (SHS) (SDNY 2010).
Docket Sheet dated Jul. 23, 2013 in *Purdue Pharma L.P. et alv. Ranbaxy, Inc. et al*, in the Southern District of New York, Civil Docket No. 1: 10-cv-03734 (SHS) (SDNY 2010).
Docket Sheet dated Aug. 21, 2013 in *Purdue Pharma L.P. et al* v. *Watson Laboratories, Inc. et al.* in the Southern District of Florida, Civil Docket No. 0: 11-cv-60643 (AJ) (SDFL 2011).
Docket Sheet dated Aug. 21, 2013 in *Purdue Pharma L.P. et al* v. *Andrx Labs, LLC* in the District of Delaware, Civil Docket No. 1: 11-cv-00248 (GMS) (DOE 2011).
Docket Sheet dated Aug. 27, 2013 *Purdue Pharma L.P. et al* v. *Boehringer Ingelheim GmbH*, et al. in the Southern District of New York, Civil Docket No. 99-cv-3658 (SHS) (SDNY 1999).
Docket Sheet dated Aug. 27, 2013 *Purdue Pharma L.P. et al* v. *Endo Pharmaceuticals Inc. et al* in the Southern District of New York, Civil Docket No. 00-cv-8029 (SHS) (SDNY 2000).
Docket Sheet dated Aug. 27, 2013 *Purdue Pharma L.P. et al* v. *Endo Pharmaceuticals Inc. et al* in the Southern District of New York, Civil Docket No. 01-cv-2109 (SHS) (SDNY 2001).
Docket Sheet dated Aug. 27, 2013 *Purdue Pharma L.P. et al* v. *Endo Pharmaceuticals Inc. et al* in the Southern District of New York, Civil Docket No. 01-cv-8177 (SHS) (SDNY 2001).
Docket Sheet dated Aug. 27, 2013 *Purdue Pharma L.P. et al* v. *Teva Pharmaceuticals USA, Inc.* in the Southern District of New York, Civil Docket No. 01-cv-8507 (SHS) (SDNY 2001).
Docket Sheet dated Aug. 27, 2013 *Purdue Pharma L.P. et al* v. *Teva Pharmaceuticals USA, Inc.* in the Southern District of New York, Civil Docket No. 01-cv-11212 (SHS) (SDNY 2001).
Docket Sheet dated Aug. 27, 2013 Purdue Pharma L.P. et al v. Teva Pharmaceuticals Usa, Inc. In the Southern District of New York, Civil Docket No. 03-cv-2312 (SHS) (SDNY 2003).
Docket Sheet dated Aug. 27, 2013 *Purdue Pharma L.P. et al* v. *Impax Laboratories, Inc.* in the Southern District of New York, Civil Docket No. 02-cv-2803 (SHS) (SDNY 2002).
Docket Sheet dated Aug. 27, 2013 *Purdue Pharma L.P. et al* v. *Impax Laboratories, Inc.* in the Southern District of New York, Civil Docket No. 02-cv-7569 (SHS) (SDNY 2002).
Docket Sheet dated Aug. 27, 2013 *Purdue Pharma L.P. et al* v. *Impax Laboratories, Inc.* in the Southern District of New York, Civil Docket No. 02-cv-8036 (SHS) (SDNY 2002).
Docket Sheet dated Aug. 27, 2013 *Purdue Pharma L.P. et al* v. *Mallinckrodt Inc.*, in the Southern District of New York, Civil Docket No. 06-cv-13095 (SHS) (SDNY 2006).

(56) References Cited

OTHER PUBLICATIONS

Docket Sheet dated Aug. 27, 2013 *Purdue Pharma L.P. et al v. KV Pharmaceutical Company et al* in the Southern District of New York, Civil Docket No. 07-cv-3972 (SHS) (SDNY 2007).
Docket Sheet dated Aug. 27, 2013 *Purdue Pharma L.P. et al v. KV Pharmaceutical Company* in the Southern District of New York, Civil Docket No. 07-cv-3973 (SHS) (SDNY 2007).
Docket Sheet dated Aug. 27, 2013 *Purdue Pharma L.P. et al v. KV Pharmaceutical Company* in the Southern District of New York, Civil Docket No. 07-cv-4810 (SHS) (SDNY 2007).
Docket Sheet dated Aug. 27, 2013 *Purdue Pharma L.P. et al v. Apotex Inc. et al* in 049 the Southern District of New York, Civil Docket No. 07-cv-8002 (SHS) (SDNY 2007).
Docket Sheet dated Aug. 27, 2013 *Purdue Pharma L.P. et al v. Ranbaxy Inc. et al* in the Southern District of New York, Civil Docket No. 09-cv-8878 (SHS) (SDNY 2009).
Docket Sheet dated Aug. 27, 2013 *Purdue Pharma L.P. et al v. Varam, Inc. et al* in the Southern District of New York, Civil Docket No. 12-cv-6047 (SHS) (SDNY 2012).
Information Disclosure Statement Transmittal Letter, submitted in U.S. Appl. No. 11/844,872, Sep. 16, 2013.
Zezhi J. Shao et al., Effects of Formulation Variables and Postcompression Curing on Drug Release from a New Sustained Release Matrix Material: Polyvinylacetate-Povidone, 6 Pharm. Dev. Tech. 247 (2001).
Marcelo O. Omelczuk & James W. McGinity, The Influence of Thermal Treatment on the Physical Mechanical and Dissolution Properties of Tablets Containing POIY(DL-Lactic Acid), 10 Pharm. Res. 542 (1993).
Docket Sheet dated Feb. 3, 2015 in *Purdue Pharma L.P. et al v. Epic Pharma, LLC*, in the Southern District of New York, Civil Docket No. 1:13-cv-00683 (SHS) (SDNY 2013).
Docket Sheet dated Feb. 3, 2015 in *Purdue Pharma L.P. et al v. Mylan Pharmaceuticals Inc. et al*, in the Southern District of New York, Civil Docket No. 1:12-cv-02959 (SHS) (SDNY 2012).
Docket Sheet dated Feb. 3, 2015 in *Purdue Pharma L.P. et al v. PAR Pharmaceuticals, Inc.*, in the Southern District of New York, Civil Docket No. 1:12-cv-05615 (SHS) (SDNY 2012).
Docket Sheet dated Feb. 3, 2015 in *Purdue Pharma L.P. et al v. Impax Laboratories, Inc.*, in the Southern District of New York, Civil Docket No. 1:11-cv-02400 (SHS) (SDNY 2011).
Docket Sheet dated Feb. 3, 2015 in *Purdue Pharma L.P. et al v. PAR Pharmaceuticals, Inc.* in the Southern District of New York, Civil Docket No. 1:13-cv-03374 (SHS) (SDNY 2013).
Docket Sheet dated Feb. 3, 2015 in *Purdue Pharma L.P. et al v. Amneal Pharmaceuticals, LLC.*, in the Southern District of New York, Civil Docket No. 1:13-cv-03372 (SHS) (SDNY 2013).
Docket Sheet dated Feb. 3, 2015 in *Purdue Pharma L.P. et al v. Amneal Pharmaceuticals, LLC.*, in the Southern District of New York, Civil Docket No. 1:11-cv-08153 (SHS) (SDNY 2011).
Docket Sheet dated Feb. 3, 2015 in *Purdue Pharma L.P. et al v. Sandoz, Inc.*, in the Southern District of New York, Civil Docket No. 1:12-cv-07582 (SHS) (SDNY 2012).
Docket Sheet dated Feb. 3, 2015 in *Purdue Pharma L.P. et al v. Sandoz, Inc.*, in the Southern District of New York, Civil Docket No. 1:12-cv-05082 (SHS) (SDNY 2012).
Docket Sheet dated Feb. 3, 2015 in *Purdue Pharma L.P. et al v. Sandoz, Inc.*, in the Southern District of New York, Civil Docket No. 1:12-cv-00897 (SHS) (SDNY 2012).
Docket Sheet dated Feb. 3, 2015 in *Purdue Pharma L.P. et al v. Sandoz, Inc.*, in the Southern District of New York, Civil Docket No. 1:11-cv-04694 (SHS) (SDNY 2011).
Docket Sheet dated Feb. 3, 2015 in *Purdue Pharma L.P. et al v. Ranbaxy, Inc. et al*, in the Southern District of New York, Civil Docket No. 1:11-cv-07104 (SHS) (SDNY 2011).
Docket Sheet dated Feb. 3, 2015 in *Purdue Pharma L.P. et al v. Ranbaxy, Inc. et al*, in the Southern District of New York, Civil Docket No. 1:11-cv-02401 (SHS) (SDNY 2011).
Docket Sheet dated Feb. 3, 2015 in *Purdue Pharma L.P. et al v. Impax Laboratories, Inc.*, in the Southern District of New York, Civil Docket No. 1:13-cv-03188 (SHS) (SDNY 2013).
Docket Sheet dated Feb. 3, 2015 in *Purdue Pharma L.P. et al v. Impax Laboratories, Inc.*, in the Southern District of New York, Civil Docket No. 1:13-cv-000763 (SHS) (SDNY 2013).
Docket Sheet dated Feb. 3, 2015 in *Purdue Pharma L.P. et al v. PAR Pharmaceuticals, Inc.* in the Southern District of New York, Civil Docket No. 1:11-cv-02038 (SHS) (SDNY 2011).
Docket Sheet dated Feb. 3, 2015 in *Purdue Pharma L.P. et al v. Teva Pharmaceuticals, USA, Inc* in the Southern District of New York, Civil Docket No. 1:13-cv-04606 (SHS) (SDNY 2013).
Docket Sheet dated Feb. 3, 2015 in *Purdue Pharma L.P. et al v. Teva Pharmaceuticals, USA, Inc* in the Southern District of New York, Civil Docket No. 1:12-cv-05083 (SHS) (SDNY 2012).
Docket Sheet dated Feb. 3, 2015 in *Purdue Pharma L.P. et al v. Teva Pharmaceuticals, USA, Inc* in the Southern District of New York, Civil Docket No. 1:11-cv-02037 (SHS) (SDNY 2011).
Docket Sheet dated Feb. 3, 2015 in *Purdue Pharma L.P. et al v. Watson Laboratories, Inc.—Florida et al.* in the Southern District of New York, Civil Docket No. 1:13-cv-01272 (SHS) (SDNY 2013).
Docket Sheet dated Feb. 3, 2015 in *Purdue Pharma L.P. et al v. Watson Laboratories, Inc. et al.* in the Southern District of New York, Civil Docket No. 1:13-cv-0762 (SHS) (SDNY 2013).
Docket Sheet dated Feb. 3, 2015 in *Purdue Pharma L.P. et al v. Watson Laboratories, Inc. et al.* in the Southern District of New York, Civil Docket No. 1:12-cv-03111 (SHS) (SDNY 2012).
Docket Sheet dated Feb. 3, 2015 in *Purdue Pharma L.P. et al v. Watson Laboratories, Inc. et al.* in the Southern District of New York, Civil Docket No. 1:11-cv-02036 (SHS) (SDNY 2011).
Docket Sheet dated Feb. 3, 2015 in *Purdue Pharma L.P. et al v Impax Laboratories, Inc.* in the Southern District of New York, Civil Docket No. 1:13-cv-0684 (SHS) (SDNY 2013).
Docket Sheet dated Feb. 3, 2015 in *Purdue Pharma L.P. et al v. Varam, Inc. et al.* in the Eastern District of Pennsylvania (Philadelphia), Civil Docket No. 2:12-cv-01898 (PBT) (ED Pa. 2012).
Docket Sheet dated Feb. 3, 2015 in *Purdue Pharma L.P. et al v. Varam, Inc. et al.* in the Southern District of New York, Civil Docket No. 1:12-cv-02814 (SHS) (SDNY 2012).
Docket Sheet dated Feb. 3, 2015 in *Purdue Pharma L.P. et al v. Varam, Inc. et al.* in the Southern District of New York, Civil Docket No. 1:11-cv-00766 (SHS) (SDNY 2011).
Docket Sheet dated Feb. 3, 2015 in *Purdue Pharma L.P. et al v. Varam, Inc. et al.* in the Eastern District of Pennsylvania (Philadelphia), Civil Docket No. 2:10-cv-04028 (PBT) (ED Pa. 2010).
Docket Sheet dated Feb. 3, 2015 in *Purdue Pharma L.P. et al v. Varam, Inc. et al.* in the Southern District of New York, Civil Docket No. 1:10-cv-06038 (SHS) (SDNY 2010).
Docket Sheet dated Feb. 3, 2015 in *Purdue Pharma L.P. et al v. Ranbaxy, Inc. et al*, in the Southern District of New York, Civil Docket No. 1:10-cv-03734 (SHS) (SDNY 2010).
Docket Sheet dated Feb. 3, 2015 in *Purdue Pharma L.P. et al v. Watson Laboratories, Inc. et al.* in the Southern District of Florida, Civil Docket No. 0:11-cv-60643 (AJ) (SDFL 2011).
Docket Sheet dated Feb. 3, 2015 in *Purdue Pharma L.P. et al v. Andrx Labs, LLC* in the District of Delaware, Civil Docket No. 1:11-cv-00248 (GMS) (DDE 2011).
Docket Sheet dated Feb. 3, 2015 in *Purdue Pharma L.P., The Purdue Frederick Company, The P.F. Laboratories, Inc., and The Purdue Pharma Company v. Boehringer Ingelheim GmbH, Roxane Laboratories, Inc., and Boehringer Ingelheim Corporation*, 99 Civ. 3658 (SHS).
Docket Sheet dated Feb. 3, 2015 in *Purdue Pharma L.P., The Purdue Frederick Company, The P.F. Laboratories, Inc., and The Purdue Pharma Company v. Endo Pharmaceuticals Inc. and Endo Pharmaceuticals Holdings Inc.*, 00 Civ. 8029.
Docket Sheet dated Feb. 3, 2015 in *Purdue Pharma L.P., The Purdue Frederick Company, The P.F. Laboratories, Inc., and The Purdue Pharma Company v. Endo Pharmaceuticals Inc. and Endo Pharmaceuticals Holdings Inc.* 01 Civ. 2109.
Docket Sheet dated Feb. 3, 2015 in *Purdue Pharma L.P., The Purdue Frederick Company, The P.F. Laboratories, Inc., and The Purdue*

(56) References Cited

OTHER PUBLICATIONS

*Pharma Company* v. *Endo Pharmaceuticals Inc. and Endo Pharmaceuticals Holdings Inc* 01 Civ. 8177.
Docket Sheet dated Feb. 3, 2015 in *Purdue Pharma L.P., The Purdue Frederick Company, The P.F. Laboratories, Inc., and The Purdue Pharma Company* v. *Teva Pharmaceuticals USA, Inc* 01 Civ. 8507.
Docket Sheet dated Feb. 3, 2015 in *Purdue Pharma L.P., The Purdue Frederick Company, The P.F. Laboratories, Inc., and The Purdue Pharma Company* v. *Teva Pharmaceuticals USA, Inc.*, 01 Civ. 11212.
Docket Sheet dated Feb. 3, 2015 in *Purdue Pharma L.P., The Purdue Frederick Company, The P.F. Laboratories, Inc., and the Purdue Pharma Company* v. *Teva Pharmaceuticals USA, Inc.* 03 Civ. 2312.
Docket Sheet dated Feb. 3, 2015 in *Purdue Pharma L.P., The Purdue Frederick Company, The P.F. Laboratories, Inc., and The Purdue Pharma Company* v. *Impax Laboratories, Inc.* 02 Civ. 2803.
Docket Sheet dated Feb. 3, 2015 in *Purdue Pharma L.P., The Purdue Frederick Company, The P.F. Laboratories, Inc., and The Purdue Pharma Company* v. *Impax Laboratories, Inc.* 02 Civ. 7569.
Docket Sheet dated Feb. 3, 2015 in *Purdue Pharma L.P., The Purdue Frederick Company, The P.F. Laboratories, Inc., and The Purdue Pharma Company* v. *Impax Laboratories, Inc.* 02 Civ. 8036.
Docket Sheet dated Feb. 3, 2015 in *Purdue Pharma L.P., The P.F. Laboratories, Inc. and Purdue Pharmaceuticals L.P.* v. *Mallinckrodt Inc.*, 06 Civ. 13095 (SHS) 06 Civ. 13095.
Docket Sheet dated Feb. 3, 2015 in *Purdue Pharma L.P., The P.F. Laboratories, Inc. and Purdue Pharmaceuticals L.P.* v. *KV Pharmaceutical Company and Actavis Totowa LLC*, 07 Civ. 3972 (SHS).
Docket Sheet dated Feb. 3, 2015 in *Purdue Pharma L.P., The P.F. Laboratories, Inc. and Purdue Pharmaceuticals L.P.* v. *KV Pharmaceutical Company*, 07 Civ. 3973.
Docket Sheet dated Feb. 3, 2015 in *Purdue Pharma L.P., The P.F. Laboratories, Inc. and Purdue Pharmaceuticals L.P.* v. *KV Pharmaceutical Company*, 07 Civ. 4810.
Docket Sheet dated Feb. 3, 2015 in *Purdue Pharma L.P., The P.F. Laboratories, Inc. and Purdue Pharmaceuticals L.P.* v. *Apotex Inc. and Apotex Corp.*, 07 Civ. 8002 (SHS).
Docket Sheet dated Feb. 3, 2015 in *Purdue Pharma L.P., The P.F. Laboratories, Inc. and Purdue Pharmaceuticals L.P.* v. *Ranbaxy Inc., Ranbaxy Pharmaceuticals Inc., and Ranbaxy Laboratories Ltd.*, 09 Civ. 8878 (SHS).
Docket Sheet dated Feb. 3, 2015 in *Purdue Pharma L.P., The P.F. Laboratories, Inc., Purdue Pharmaceuticals L.P. and Rhodes Technologies* v. *Varam, Inc. & KVK-Tech, Inc.*, 12 Civ. 2814 (Noted above), 12 Civ. 6047 (SHS).
Brief of Plaintiff-Appellant Grunenthal GmbH, *Purdue Pharma L.P., et al.* v. *Epic Pharma, LLC*, CA No. 1:13-cv-00683-SHS (SDNY 2014).
Information Disclosure Statement Transmittal Letter, submitted in U.S. Appl. No. 11/844,872, Aug. 28, 2013.
Andrx Lab Paragraph IV Letter, Feb. 7, 2011. [Confidential—Filed Under Seal].
Watson Paragraph IV Letter, Feb. 7, 2011. [Confidential—Filed Under Seal].
Teva Paragraph IV Letter, Feb. 9, 2011. [Confidential—Filed Under Seal].
Actavis Paragraph IV Letter, Feb. 15, 2011. [Confidential—Filed Under Seal).
*Purdue* v. *Impax Paragraph IV Letter*, Feb. 23, 2011. [Confidential—Filed Under Seal].
Ranbaxy Paragraph IV Letter, Feb. 24, 2011. (Confidential—Filed Under Seal].
Ranbaxy Paragraph IV Letter, Mar. 23, 2010. [Confidential—Filed Under Seal].
Mylan Paragraph IV Letter, Apr. 1 ,2010. [Confidential—Filed Under Seal].
Actavis Paragraph IV Letter, Apr. 8, 2010. [Confidential—Filed Under Seal].
Ranbaxy Paragraph IV Letter, Apr. 8, 2010. [Confidential—Filed Under Seal].
Mylan Paragraph IV Letter (U.S. Patent 7,683,072), Apr. 9, 2010. [Confidential—Filed Under Seal].
Mylan Paragraph IV Letter (U.S. Patent 7,674,799 and U.S. Patent 7,674,800), Apr. 9, 2010. [Confidential—Filed Under Seal].
Varam, Inc. Paragraph IV Letter, Jun. 28, 2010. [Confidential—Filed Under Seal].
Ranbaxy Paragraph IV Letter (NDA No. 02-2272), Aug. 25, 2011. [Confidential—Filed Under Seal].
Purdue Paragraph IV Letter (Amneal Pharmaceuticals), Sep. 28, 2011. [Confidentialfiled Under Seal].
Sandoz Paragraph IV Letter, May 23,2011. [Confidential—Filed Under Seal].
Transmittal Letter Submitted with Documents Under Seal for U.S. Appl. No. 11/844,872, Mar. 8, 2012.

* cited by examiner

Example 27: Representative Images of Crushed Tablets

Crushed OxyContin™ (10 mg)

Crushed Example 7.2

Example 27: Representative Images of Milled Example 7.2 and OxyContin™ 10 mg Tablets Before and After 45 Minutes of Dissolution

Milled OxyContin™ (10 mg)

Milled Example 7.2

Milled OxyContin™ (10 mg) after 45 min Dissolution

Milled Example 7.2 after 45 min Dissolution

Example 27:

Dissolution Profiles of Milled Example 7.2 and Crushed OxyContin™ 10 mg Tablets

TAMPER RESISTANT DOSAGE FORMS

The present application is a continuation of U.S. application Ser. No. 13/803,132, filed Mar. 14, 2013, which is a divisional application of U.S. application Ser. No. 11/844,872, filed Aug. 24, 2007, which claims priority from U.S. Provisional Application Ser. No. 60/840,244, filed Aug. 25, 2006. The entire contents of those applications are incorporated herein by reference.

TECHNICAL FIELD OF THE INVENTION

The present invention relates to pharmaceutical dosage forms, for example to a tamper resistant dosage form including an opioid analgesic, and processes of manufacture, uses, and methods of treatment thereof.

BACKGROUND OF THE INVENTION

Pharmaceutical products are sometimes the subject of abuse. For example, a particular dose of opioid agonist may be more potent when administered parenterally as compared to the same dose administered orally. Some formulations can be tampered with to provide the opioid agonist contained therein for illicit use. Controlled release opioid agonist formulations are sometimes crushed, or subject to extraction with solvents (e.g., ethanol) by drug abusers to provide the opioid contained therein for immediate release upon oral or parenteral administration.

Controlled release opioid agonist dosage forms which can liberate a portion of the opioid upon exposure to ethanol, can also result in a patient receiving the dose more rapidly than intended if a patient disregards instructions for use and concomitantly uses alcohol with the dosage form.

There continues to exist a need in the art for pharmaceutical oral dosage forms comprising an opioid agonist without significantly changed opioid release properties when in contact with alcohol and/or with resistance to crushing.

OBJECTS AND SUMMARY OF THE INVENTION

It is an object of certain embodiments of the present invention to provide an oral extended release dosage form comprising an active agent such as an opioid analgesic which is tamper resistant.

It is an object of certain embodiments of the present invention to provide an oral extended release dosage form comprising an active agent such as an opioid analgesic which is resistant to crushing.

It is an object of certain embodiments of the present invention to provide an oral extended release dosage form comprising an active agent such as an opioid analgesic which is resistant to alcohol extraction and dose dumping when concomitantly used with or in contact with alcohol.

In certain embodiments, the present invention is directed to a solid oral extended release pharmaceutical dosage form comprising an extended release matrix formulation in the form of a tablet or multi particulates, wherein the tablet or the individual multi particulates can be at least flattened without breaking, characterized by a thickness of the tablet or of the individual multi particulate after the flattening which corresponds to no more than about 60% of the thickness of the tablet or the individual multi particulate before flattening, and wherein said flattened tablet or the flattened multi particulates provide an in-vitro dissolution rate, when measured in a USP Apparatus 1 (basket) at 100 rpm in 900 ml simulated gastric fluid without enzymes (SGF) at 37° C., characterized by the percent amount of active released at 0.5 hours of dissolution that deviates no more than about 20% points from the corresponding in-vitro dissolution rate of a non-flattened reference tablet or reference multi particulates.

In certain embodiments, the present invention is directed to a solid oral extended release pharmaceutical dosage form comprising an extended release matrix formulation in the form of a tablet or multi particulates, wherein the tablet or the individual multi particulates can at least be flattened without breaking, characterized by a thickness of the tablet or the individual multi particulate after the flattening which corresponds to no more than about 60% of the thickness of the tablet or the individual multi particulate before flattening, and wherein the flattened or non flattened tablet or the flattened or non flattened multi particulates provide an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active released at 0.5 hours of dissolution that deviates no more than about 20% points from the corresponding in-vitro dissolution rate measured in a USP Apparatus 1 (basket) at 100 rpm in 900 ml simulated gastric fluid without enzymes (SUE) at 37° C. without ethanol, using a flattened and non flattened reference tablet or flattened and non flattened reference multi particulates, respectively.

In certain embodiments, the present invention is directed to a solid oral extended release pharmaceutical dosage form comprising an extended release matrix formulation, the extended release matrix formulation comprising
a composition comprising at least:
  (1) at least one polyethylene oxide having, based on rheological measurements, an approximate molecular weight of at least 1,000,000; and
  (2) at least one active agent; and
  wherein the composition comprises at least about 80% (by wt) polyethylene oxide.

According to certain such embodiments the active agent is oxycodone hydrochloride and the composition comprises more than about 5% (by wt) of the oxycodone hydrochloride.

In certain embodiments, the present invention is directed to a solid oral extended release pharmaceutical dosage form comprising an extended release matrix formulation, the extended release matrix formulation comprising a composition comprising at least:
  (1) at least one active agent;
  (2) at least one polyethylene oxide having, based on rheological measurements, an approximate molecular weight of at least 1,000,000; and
  (3) at least one polyethylene oxide having, based on rheological measurements, a molecular weight of less than 1,000,000.

In certain embodiments, the present invention is directed to a process of preparing a solid oral extended release pharmaceutical dosage form,
comprising at least the steps of:
  (a) combining at least
    (1) at least one polyethylene oxide having, based on rheological measurements, an approximate molecular weight of at least 1,000,000, and
    (2) at least one active agent, to form a composition;
  (b) shaping the composition to form an extended release matrix formulation; and
  (c) curing said extended release matrix formulation comprising at least a curing step of subjecting the extended release matrix formulation to a temperature which is at least the softening temperature of said polyethylene oxide for a time period of at least about 1 minute.

In certain embodiments, the present invention is directed to a process of preparing a solid oral extended release pharmaceutical dosage form,
comprising at least the steps of:
(a) combining at least
  (1) at least one polyethylene oxide having, based on rheological measurements, an approximate molecular weight of at least 1,000,000, and
  (2) at least one active agent,
to form a composition;
(b) shaping the composition to form an extended release matrix formulation; and
(c) curing said extended release matrix formulation comprising at least a curing step wherein said polyethylene oxide at least partially melts.

In certain embodiments, the present invention is directed to a solid oral extended release pharmaceutical dosage form comprising an extended release matrix formulation comprising an active agent in the form of a tablet or multi particulates,
wherein the tablet or the individual multi particulates can at least be flattened without breaking, characterized by a thickness of the tablet or of the individual multi particulate after the flattening which corresponds to no more than about 60% of the thickness of the tablet or the individual multi particulate before flattening, and wherein said flattened tablet or the flattened multi particulates provide an in-vitro dissolution rate, when measured in a USP Apparatus 1 (basket) at 100 rpm in 900 ml simulated gastric fluid without enzymes (SGF) at 37° C., characterized by the percent amount of active agent released at 0.5 hours of dissolution that deviates no more than about 20% points from the corresponding in-vitro dissolution rate of a non-flattened reference tablet or reference multi particulates.

In certain embodiments, the present invention is directed to a solid oral extended release pharmaceutical dosage form comprising an extended release matrix formulation comprising an active agent in the form of a tablet or multi particulates,
wherein the tablet or the individual multi particulates can at least be flattened without breaking, characterized by a thickness of the tablet or of the individual multi particulate after the flattening which corresponds to no more than about 60% of the thickness of the tablet or the individual multi particulate before flattening, and wherein said flattened tablet or the flattened multi particulates and the non-flattened reference tablet or reference multi particulates provide an in-vitro dissolution rate, which when measured in a USP Apparatus 1 (basket) at 100 rpm in 900 ml simulated gastric fluid without enzymes (SGF) at 37° C., is between about 5 and about 40% (by wt) active agent released after 0.5 hours.

In certain embodiments, the present invention is directed to a solid oral extended release pharmaceutical dosage form comprising an extended release matrix formulation comprising an active agent in the form of a tablet or multi particulates,
wherein the tablet or the individual multi particulates can at least be flattened without breaking, characterized by a thickness of the tablet or the individual multi particulate after the flattening which corresponds to no more than about 60% of the thickness of the tablet or the individual multi particulate before flattening, and wherein the flattened or non flattened tablet or the flattened or non flattened multi particulates provide an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active agent released at 0.5 hours of dissolution that deviates no more than about 20% points from the corresponding in-vitro dissolution rate measured in a USP Apparatus 1 (basket) at 100 rpm in 900 ml simulated gastric fluid without enzymes (SGF) at 37° C. without ethanol, using a flattened and non flattened reference tablet or flattened and non flattened reference multi particulates, respectively.

In certain embodiments, the present invention is directed to a solid oral extended release pharmaceutical dosage form comprising an extended release matrix formulation comprising an active agent in the form of a tablet or multi particulates,
wherein the tablet or the individual multi particulates can at least be flattened without breaking, characterized by a thickness of the tablet or the individual multi particulate after the flattening which corresponds to no more than about 60% of the thickness of the tablet or the individual multi particulate before flattening, and wherein the flattened or non flattened tablet or the flattened or non flattened multi particulates provide an in-vitro dissolution rate, which when measured in a USP Apparatus 1 (basket) at 100 rpm in 900 ml simulated gastric fluid without enzymes (SGF) comprising 40% or 0% ethanol at 37° C., is between about 5 and about 40% (by wt) active agent released after 0.5 hours.

In certain embodiments, the present invention is directed to a solid oral extended release pharmaceutical dosage form comprising an extended release matrix formulation, the extended release matrix formulation comprising
a composition comprising at least:
  (1) at least one polyethylene oxide having, based on rheological measurements, an approximate molecular weight of at least 1,000,000; and
  (2) at least one active agent selected from opioid analgesics; and
wherein the composition comprises at least about 80% (by wt) polyethylene oxide.

In certain embodiments, the present invention is directed to a solid oral extended release pharmaceutical dosage form comprising an extended release matrix formulation, the extended release matrix formulation comprising
a composition comprising at least:
  (1) at least one polyethylene oxide having, based on rheological measurements, an approximate molecular weight of at least 1,000,000; and
  (2) 10 mg oxycodone hydrochloride; and
wherein the composition comprises at least about 85% (by wt) polyethylene oxide.

In certain embodiments, the present invention is directed to a solid oral extended release pharmaceutical dosage form comprising an extended release matrix formulation, the extended release matrix formulation comprising
a composition comprising at least:
  (1) at least one polyethylene oxide having, based on rheological measurements, an approximate molecular weight of at least 1,000,000; and
  (2) 15 mg or 20 mg oxycodone hydrochloride; and
wherein the composition comprises at least about 80% (by wt) polyethylene oxide.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) 40 mg oxycodone hydrochloride; and
- wherein the composition comprises at least about 65% (by wt) polyethylene oxide.

In certain embodiments, the present invention is directed to a solid oral extended release pharmaceutical dosage form comprising an extended release matrix formulation, the extended release matrix formulation comprising
a composition comprising at least:
- (1) at least one polyethylene oxide having, based on rheological measurements, an approximate molecular weight of at least 1,000,000; and
- (2) 60 mg or 80 mg oxycodone hydrochloride; and
- wherein the composition comprises at least about 60% (by wt) polyethylene oxide.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) 8 mg hydromorphone hydrochloride; and
- wherein the composition comprises at least about 94% (by wt) polyethylene oxide.

In certain embodiments, the present invention is directed to a solid oral extended release pharmaceutical dosage form comprising an extended release matrix formulation, the extended release matrix formulation comprising
a composition comprising at least:
- (1) at least one polyethylene oxide having, based on rheological measurements, an approximate molecular weight of at least 1,000,000; and
- (2) 12 mg hydromorphone hydrochloride; and
- wherein the composition comprises at least about 92% (by wt) polyethylene oxide.

In certain embodiments, the present invention is directed to a solid oral extended release pharmaceutical dosage form comprising an extended release matrix formulation, the extended release matrix formulation comprising
a composition comprising at least:
- (1) at least one polyethylene oxide having, based on rheological measurements, an approximate molecular weight of at least 1,000,000; and
- (2) 32 mg hydromorphone hydrochloride; and
- wherein the composition comprises at least about 90% (by wt) polyethylene oxide.

In certain embodiments, the present invention is directed to a solid oral extended release pharmaceutical dosage form comprising an extended release matrix formulation, the extended release matrix formulation comprising a composition comprising at least:
- (1) at least one active agent selected from opioid analgesics;
- (2) at least one polyethylene oxide having, based on rheological measurements, an approximate molecular weight of at least 1,000,000; and
- (3) at least one polyethylene oxide having, based on rheological measurements, an approximate molecular weight of less than 1,000,000.

In certain embodiments, the present invention is directed to a solid oral extended release pharmaceutical dosage form comprising an extended release matrix formulation, the extended release matrix formulation comprising
a composition comprising at least:
- (1) at least one polyethylene oxide having, based on rheological measurements, a molecular weight of at least 800,000; and
- (2) at least one active agent selected from opioid analgesics; and
- wherein the composition comprises at least about 80% (by wt) polyethylene oxide.

In certain embodiments, the present invention is directed to a solid oral extended release pharmaceutical dosage form comprising an extended release matrix formulation, the extended release matrix formulation comprising
a composition comprising at least:
- (1) at least one polyethylene oxide having, based on rheological measurements, an approximate molecular weight of at least 1,000,000; and
- (2) at least one active agent; and
- wherein the extended release matrix formulation when subjected to an indentation test has a cracking force of at least about 110 N.

In certain embodiments, the present invention is directed to a solid oral extended release pharmaceutical dosage form comprising an extended release matrix formulation, the extended release matrix formulation comprising
a composition comprising at least:
- (1) at least one polyethylene oxide having, based on rheological measurements, an approximate molecular weight of at least 1,000.000; and
- (2) at least one active agent; and
- wherein the extended release matrix formulation when subjected to an indentation test has a "penetration depth to crack distance" of at least about 1.0 mm.

In certain embodiments, the present invention is directed to a method of treatment wherein a dosage form according to the invention comprising an opioid analgesic is administered for treatment of pain to a patient in need thereof.

In certain embodiments, the present invention is directed to the use of a dosage form according to the invention comprising an opioid analgesic for the manufacture of a medicament for the treatment of pain.

In certain embodiments, the present invention is directed to the use of high molecular weight polyethylene oxide that has, based on rheological measurements, an approximate molecular weight of at least 1,000,000, as matrix forming material in the manufacture of a solid extended release oral dosage form comprising an active selected from opioids for imparting to the solid extended release oral dosage form resistance to alcohol extraction.

In certain embodiments, the present invention is directed to a process of preparing a solid oral extended release pharmaceutical dosage form, comprising at least the steps of:
- (a) combining at least
  - (1) at least one polyethylene oxide having, based on rheological measurements, a molecular weight of at least 1,000,000, and
  - (2) at least one active agent,
  - to form a composition;
- (b) shaping the composition to form an extended release matrix formulation; and
- (c) curing said extended release matrix formulation comprising at least a curing step of subjecting the extended release matrix formulation to a temperature which is at least the softening temperature of said polyethylene oxide for a time period of at least 5 minutes.

According to certain embodiments of the invention the solid extended release pharmaceutical dosage form is for use as a suppository.

The term "extended release" is defined for purposes of the present invention as to refer to products which are formulated to make the drug available over an extended period after ingestion thereby allowing a reduction in dosing frequency compared to a drug presented as a conventional dosage form (e.g. as a solution or an immediate release dosage form).

The term "immediate release" is defined for the purposes of the present invention as to refer to products which are formulated to allow the drug to dissolve in the gastrointestinal contents with no intention of delaying or prolonging the dissolution or absorption of the drug.

The term "solid oral extended release pharmaceutical dosage form" refers to the administration form comprising a unit dose of active agent in extended release form such as an "extended release matrix formulation" and optionally other adjuvants and additives conventional in the art, such as a protective coating or a capsule and the like, and optionally any other additional features or components that are used in the dosage form. Unless specifically indicated the term "solid oral extended release pharmaceutical dosage form" refers to said dosage form in intact form i.e. prior to any tampering. The extended release pharmaceutical dosage form can e.g. be a tablet comprising the extended release matrix formulation or a capsule comprising the extended release matrix formulation in the form of multi particulates. The "extended release pharmaceutical dosage form" may comprise a portion of active agent in extended release form and another portion of active agent in immediate release form, e.g. as an immediate release layer of active agent surrounding the dosage form or an immediate release component included within the dosage form.

The term "extended release matrix formulation" is defined for purposes of the present invention as shaped solid form of a composition comprising at least one active agent and at least one extended release feature such as an extended release matrix material such as e.g. high molecular weight polyethylene oxide. The composition can optionally comprise more than these two compounds namely further active agents and additional retardants and/or other materials, including but not limited to low molecular weight polyethylene oxides and other adjuvants and additives conventional in the art.

The term "bioequivalent/bioequivalence" is defined for the purposes of the present invention to refer to a dosage form that provides geometric mean values of $C_{max}$, $AUC_t$, and $AUC_{inf}$ for an active agent, wherein the 90% confidence intervals estimated for the ratio (test/reference) fall within the range of 80.00% to 125.00%. Preferably, the mean values $C_{max}$, $AUC_t$, and $AUC_{inf}$ fall within the range of 80.00% to 125.00% as determined in both the fed and the fasting states.

The term "polyethylene oxide" is defined for purposes of the present invention as having a molecular weight of at least 25,000, measured as is conventional in the art, and preferably having a molecular weight of at least 100,000. Compositions with lower molecular weight are usually referred to as polyethylene glycols.

The term "high molecular weight polyethylene oxide" is defined for proposes of the present invention as having an approximate molecular weight of at least 1,000,000. For the purpose of this invention the approximate molecular weight is based on rheological measurements. Polyethylene oxide is considered to have an approximate molecular weight of 1,000,000 when a 2% (by wt) aqueous solution of said polyethylene oxide using a Brookfield viscometer Model RVF, spindle No. 1, at 10 rpm, at 25° C. shows a viscosity range of 400 to 800 mPa s (cP). Polyethylene oxide is considered to have an approximate molecular weight of 2,000,000 when a 2% (by wt) aqueous solution of said polyethylene oxide using a Brookfield viscometer Model RVF, spindle No. 3, at 10 rpm, at 25° C. shows a viscosity range of 2000 to 4000 mPa s (cP). Polyethylene oxide is considered to have an approximate molecular weight of 4,000,000 when a 1% (by wt) aqueous solution of said polyethylene oxide using a Brookfield viscometer Model RVF, spindle No. 2, at 2 rpm, at 25° C. shows a viscosity range of 1650 to 5500 mPa s (cP). Polyethylene oxide is considered to have an approximate molecular weight of 5,000,000 when a 1% (by wt) aqueous solution of said polyethylene oxide using a Brookfield viscometer Model RVF, spindle No. 2, at 2 rpm, at 25° C. shows a viscosity range of 5500 to 7500 mPa s (cP). Polyethylene oxide is considered to have an approximate molecular weight of 7,000,000 when a 1% (by wt) aqueous solution of said polyethylene oxide using a Brookfield viscometer Model RVF, spindle No. 2, at 2 rpm, at 25° C. shows a viscosity range of 7500 to 10,000 mPa s (cP). Polyethylene oxide is considered to have an approximate molecular weight of 8,000,000 when a 1% (by wt) aqueous solution of said polyethylene oxide using a Brookfield viscometer Model RVF, spindle No. 2, at 2 rpm, at 25° C. shows a viscosity range of 10,000 to 15,000 mPa s (cP). Regarding the lower molecular weight polyethylene oxides; Polyethylene oxide is considered to have an approximate molecular weight of 100,000 when a 5% (by wt) aqueous solution of said polyethylene oxide using a Brookfield viscometer Model RVT, spindle No. 1, at 50 rpm, at 25° C. shows a viscosity range of 30 to 50 mPa s (cP) and polyethylene oxide is considered to have an approximate molecular weight of 900,000 when a 5% (by wt) aqueous solution of said polyethylene oxide using a Brookfield viscometer Model RVF, spindle No. 2, at 2 rpm, at 25° C. shows a viscosity range of 8800 to 17,600 mPa s (cP).

The term "low molecular weight polyethylene oxide" is defined for purposes of the present invention as having, based on the rheological measurements outlined above, an approximate molecular weight of less than 1,000,000.

The term "direct compression" is defined for purposes of the present invention as referring to a tableting process wherein the tablet or any other compressed dosage form is made by a process comprising the steps of dry blending the compounds and compressing the dry blend to form the dosage form, e.g. by using a diffusion blend and/or convection mixing process (e.g. Guidance for Industry, SUPAC-IR/MR: Immediate Release and Modified Release Solid Oral Dosage Forms, Manufacturing Equipment Addendum).

The term "bed of free flowing tablets" is defined for the purposes of the present invention as referring to a batch of tablets that are kept in motion with respect to each other as e.g. in a coating pan set at a suitable rotation speed or in a fluidized bed of tablets. The bed of free flowing tablets preferably reduces or prevents the sticking of tablets to one another.

The term "flattening" and related terms as used in the context of flattening tablets or other dosage forms in accordance with the present invention means that a tablet is subjected to force applied from a direction substantially perpendicular to the diameter and substantially inline with the thickness of e.g. a tablet. The force may be applied with a carver style bench press (unless expressly mentioned otherwise) to the extent necessary to achieve the target flatness/reduced thickness. According to certain embodiments of the invention the flattening does not result in breaking the tablet in pieces, however, edge spits and cracks may occur. The flatness is described in terms of the thickness of the flattened tablet compared to the thickness of the non-flattened tablet expressed in % thickness, based on the thickness of the non flattened tablet. Apart from tablets, the flattening can be applied to any shape of a dosage form, wherein the force is applied from a direction substantially in line with the smallest diameter (i.e. the thickness) of the shape when the shape is other than spherical and from any direction when the shape is spherical. The flatness is then described in terms of the thickness/smallest diameter of the flattened shape compared to the thickness/smallest diameter of the non-flattened shape expressed in % thickness, based on the thickness/smallest diameter of the non flattened shape, when the initial shape is non spherical, or the % thickness, based on the non flattened diameter when the initial shape is spherical. The thickness is measured using a thickness gauge (e.g., digital thickness gauge or digital caliper) In FIGS. 4 to 6 tablets are shown that where flattened using a carver bench press. The initial shape of the tablets is shown in FIGS. 1 to 3 on the left hand side of the photograph.

In certain embodiments of the invention, apart from using a bench press a hammer can be used for flattening tablets/dosage forms. In such a flattening process hammer strikes are manually applied from a direction substantially inline with the thickness of e.g. the tablet. The flatness is then also described in terms of the thickness/smallest diameter of the flattened shape compared to the non-flattened shape expressed in % thickness, based on the thickness/smallest diameter of the non-flattened shape when the initial shape is non spherical, or the % thickness, based on the non flattened diameter when the initial shape is spherical. The thickness is measured using a thickness gauge (e.g., digital thickness gauge or digital caliper).

By contrast, when conducting the breaking strength or tablet hardness test as described in Remington's Pharmaceutical Sciences, 18$^{th}$ edition, 1990, Chapter 89 "Oral Solid Dosage Forms", pages 1633-1665, which is incorporated herein by reference, using the Schleuniger Apparatus the tablet/dosage form is put between a pair of flat plates arranged in parallel, and pressed by means of the flat plates, such that the force is applied substantially perpendicular to the thickness and substantially in line with the diameter of the tablet, thereby reducing the diameter in that direction. This reduced diameter is described in terms of % diameter, based on the diameter of the tablet before conducting the breaking strength test. The breaking strength or tablet hardness is defined as the force at which the tested tablet/dosage form breaks. Tablets/dosage forms that do not break, but which are deformed due to the force applied are considered to be break-resistant at that particular force.

A further test to quantify the strength of tablets/dosage forms is the indentation test using a Texture Analyzer, such as the TA-XT2 Texture Analyzer (Texture Technologies Corp., 18 Fairview Road, Scarsdale, N.Y. 10583). In this method, the tablets/dosage forms are placed on top of a stainless stand with slightly concaved surface and subsequently penetrated by the descending probe of the Texture Analyzer, such as a TA-8A ⅛ inch diameter stainless steel ball probe. Before starting the measurement, the tablets are aligned directly under the probe, such that the descending probe will penetrate the tablet pivotally, i.e. in the center of the tablet, and such that the force of the descending probe is applied substantially perpendicular to the diameter and substantially in line with the thickness of the tablet. First, the probe of the Texture Analyzer starts to move towards the tablet sample at the pre-test speed. When the probe contacts the tablet surface and the trigger force set is reached, the probe continues its movement with the test speed and penetrates the tablet. For each penetration depth of the probe, which will hereinafter be referred to as "distance", the corresponding force is measured, and the data are collected. When the probe has reached the desired maximum penetration depth, it changes direction and moves back at the post-test speed, while further data can be collected. The cracking force is defined to be the force of the first local maximum that is reached in the corresponding force/distance diagram and is calculated using for example the Texture Analyzer software "Texture Expert Exceed, Version 2.64 English". Without wanting to be bound by any theory, it is believed that at this point, some structural damage to the tablet/dosage form occurs in form of cracking. However, the cracked tablets/dosage forms according to certain embodiments of the present invention remain cohesive, as evidenced by the continued resistance to the descending probe. The corresponding distance at the first local maximum is hereinafter referred to as the "penetration depth to crack" distance.

For the purposes of certain embodiments of the present invention, the term "breaking strength" refers to the hardness of the tablets/dosage forms that is preferably measured using the Schleuniger apparatus, whereas the term "cracking force" reflects the strength of the tablets/dosage forms that is preferably measured in the indentation test using a Texture Analyzer.

A further parameter of the extended release matrix formulations that can be derived from the indentation test as described above is the work the extended release matrix formulation is subjected to in an indentation test as described above. The work value corresponds to the integral of the force over the distance.

The term "resistant to crushing" is defined for the purposes of certain embodiments of the present invention as referring to dosage forms that can at least be flattened with a bench press as described above without breaking to no more than about 60% thickness, preferably no more than about 50% thickness, more preferred no more than about 40% thickness, even more preferred no more than about 30% thickness and most preferred no more than about 20% thickness, 10% thickness or 5% thickness.

For the purpose of certain embodiments of the present invention dosage forms are regarded as "resistant to alcohol extraction" when the respective dosage form provides an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active released at 0.5 hours, preferably at 0.5 and 0.75 hours, more preferred at 0.5, 0.75 and 1 hour, even more preferred at 0.5, 0.75, 1 and 1.5 hours and most preferred at 0.75, 1, 1.5 and 2 hours of dissolution that deviates no more than about 20% points or preferably no more than about 15% points at each of said time points from the corresponding in-vitro dissolution rate measured in a USP Apparatus 1 (basket) at 100 rpm in 900 ml simulated gastric fluid without enzymes (SGF) at 37° C. without ethanol.

The term "tamper resistant" for the purposes of the present invention refers to dosage forms which at least provide resistance to crushing or resistance to alcohol extraction, preferably both, as defined above and may have further tamper resistant characteristics.

For the purpose of the present invention the term "active agent" is defined as a pharmaceutically active substance which includes without limitation opioid analgesics.

For purposes of the present invention, the term "opioid analgesic" includes single compounds and compositions of compounds selected from the group of opioids and which provide an analgesic effect such as one single opioid agonist or a combination of opioid agonists, one single mixed opioid agonist-antagonist or a combination of mixed opioid agonist-antagonists, or one single partial opioid agonist or a combination of partial opioid agonists and combinations of an opioid agonists, mixed opioid agonist-antagonists and partial opioid agonists with one or more opioid antagonists, stereoisomers, ether or ester, salts, hydrates and solvates thereof, compositions of any of the foregoing, and the like.

The present invention disclosed herein is specifically meant to encompass the use of the opioid analgesic in form of any pharmaceutically acceptable salt thereof.

Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

The opioids used according to the present invention may contain one or more asymmetric centers and may give rise to enantiomers, diastereomers, or other stereoisomeric forms. The present invention is also meant to encompass the use of all such possible forms as well as their racemic and resolved forms and compositions thereof. When the compounds described herein contain olefinic double bonds or other centers of geometric asymmetry, it is intended to include both E and Z geometric isomers. All tautomers are intended to be encompassed by the present invention as well.

As used herein, the term "stereoisomers" is a general term for all isomers of individual molecules that differ only in the orientation of their atoms is space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

Opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts, hydrates and solvates thereof, mixtures of any of the foregoing, and the like.

Opioid antagonists useful in combination with opioid agonists as described above are e.g. naloxone, naltrexone and nalmephene or pharmaceutically acceptable salts, hydrates and solvates thereof, mixtures of any of the foregoing, and the like.

In certain embodiments e.g. a combination of oxycodone HCl and naloxone HCl in a ratio of 2:1 is used.

In certain embodiments, the opioid analgesic is selected from codeine, morphine, oxycodone, hydrocodone, hydromorphone, or oxymorphone or pharmaceutically acceptable salts, hydrates and solvates thereof, mixtures of any of the foregoing, and the like.

In certain embodiments, the opioid analgesic is oxycodone, hydromorphone or oxymorphone or a salt thereof such as e.g. the hydrochloride. The dosage form comprises from about 5 mg to about 500 mg oxycodone hydrochloride, from about 1 mg to about 100 mg hydromorphone hydrochloride or from about 5 mg to about 500 mg oxymorphone hydrochloride. If other salts, derivatives or forms are used, equimolar amounts of any other pharmaceutically acceptable salt or derivative or form including but not limited to hydrates and solvates or the free base may be used. The dosage form comprises e.g. 5 mg, 7.5 mg, 10 mg, 15 mg, 20 mg, 30 mg, 40 mg, 45 mg, 60 mg, or 80 mg, 90 mg, 120 mg or 160 mg oxycodone hydrochloride or equimolar amounts of any other pharmaceutically acceptable salt, derivative or form including but not limited to hydrates and solvates or of the free base. The dosage form comprises e.g. 5 mg, 7.5 mg, 10 mg, 15 mg, 20 mg, 30, mg, 40 mg, 45 mg, 60 mg, or 80 mg, 90 mg, 120 mg or 160 mg oxymorphone hydrochloride or equimolar amounts of any other pharmaceutically acceptable salt, derivative or form including but not limited to hydrates and solvates or of the free base. The dosage form comprises e.g. 2 mg, 4 mg, 8 mg, 12 mg, 16 mg, 24 mg, 32 mg, 48 mg or 64 mg hydromorphone hydrochloride or equimolar amounts of any other pharmaceutically acceptable salt, derivative or form including but not limited to hydrates and solvates or of the free base.

WO 2005/097801 A1, U.S. Pat. No. 7,129,248 B2 and US 2006/0173029 A1, all of which are hereby incorporated by reference, describe a process for preparing oxycodone hydrochloride having a 14-hydroxycodeinone level of less than about 25 ppm, preferably of less than about 15 ppm, less than about 10 ppm, or less than about 5 ppm, more preferably of less than about 2 ppm, less than about 1 ppm, less than about 0.5 ppm or less than about 0.25 ppm.

The term "ppm" as used herein means "parts per million". Regarding 14-hydroxycodeinone, "ppm" means parts per million of 14-hydroxycodeinone in a particular sample product. The 14-hydroxycodeinone level can be determined by any method known in the art, preferably by HPLC analysis using UV detection.

In certain embodiments of the present invention, wherein the active agent is oxycodone hydrochloride, oxycodone hydrochloride is used having a 14-hydroxycodeinone level of less than about 25 ppm, preferably of less than about 15 ppm, less than about 10 ppm, or less than about 5 ppm, more preferably of less than about 2 ppm, less than about 1 ppm, less than about 0.5 ppm or less than about 0.25 ppm.

In certain other embodiments other therapeutically active agents may be used in accordance with the present invention, either in combination with opioids or instead of opioids. Examples of such therapeutically active agents include antihistamines (e.g., dimenhydrinate, diphenhydramine, chlorpheniramine and dexchlorpheniramine maleate), non-steroidal anti-inflammatory agents (e.g., naproxen, diclofenac, indomethacin, ibuprofen, sulindac, Cox-2 inhibitors) and acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilatiors (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants (e.g. pseudoephedrine), laxatives, vitamins, stimulants (including appetite suppressants such as phenylpropanolamine) and cannabinoids, as well as pharmaceutically acceptable salts, hydrates, and solvates of the same.

In certain embodiments, the invention is directed to the use of Cox-2 inhibitors as active agents, in combination with opioid analgesics or instead of opioid analgesics, for example the use of Cox-2 inhibitors such as meloxicam (4-hydroxy-2-methyl-N-(5-methyl-2-thiazolyl)-2H-1,2-benzothiazine-3-carboxamide-1,1-dioxide), as disclosed in U.S. Ser. Nos. 10/056,347 and 11/825,938, which are hereby incorporated by reference, nabumetone (4-(6-methoxy-2-naphthyl)-2-butanone), as disclosed in U.S. Ser. No. 10/056,348, which is hereby incorporated by reference, celecoxib (4-[5-(4-methylphenyl)-3-(trifluoromethyl)-1H-pyrazol-1-yl]benzenesulfonamide), as disclosed in U.S. Ser. No. 11/698,394, which is hereby incorporated by reference, nimesulide (N-(4-Nitro-2-phenoxyphenyl)methanesulfonamide), as disclosed in U.S. Ser. No. 10/057,630, which is hereby incorporated by reference, and N-[3-(formylamino)-4-oxo-6-phenoxy-4H-1-benzopyran-7-yl]methanesulfonamide (T-614), as disclosed in U.S. Ser. No. 10/057,632, which is hereby incorporated by reference.

The present invention is also directed to the dosage forms utilizing active agents such as for example, benzodiazepines, barbiturates or amphetamines. These may be combined with the respective antagonists.

The term "benzodiazepines" refers to benzodiazepines and drugs that are derivatives of benzodiazepine that are able to depress the central nervous system. Benzodiazepines include, but are not limited to, alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, methylphenidate as well as pharmaceutically acceptable salts, hydrates, and solvates and mixtures thereof. Benzodiazepine antagonists that can be used in the present invention include, but are not limited to, flumazenil as well as pharmaceutically acceptable salts, hydrates, and solvates.

Barbiturates refer to sedative-hypnotic drugs derived from barbituric acid (2,4,6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital and as well as pharmaceutically acceptable salts, hydrates, and solvates mixtures thereof. Barbiturate antagonists that can be used in the present invention include, but are not limited to, amphetamines as well as pharmaceutically acceptable salts, hydrates, and solvates.

Stimulants refer to drugs that stimulate the central nervous system. Stimulants include, but are not limited to, amphetamines, such as amphetamine, dextroamphetamine resin complex, dextroamphetamine, methamphetamine, methylphenidate as well as pharmaceutically acceptable salts, hydrates, and solvates and mixtures thereof. Stimulant antagonists that can be used in the present invention include, but are not limited to, benzodiazepines, as well as pharmaceutically acceptable salts, hydrates, and solvates as described herein.

DETAILED DESCRIPTION

Figure 1:
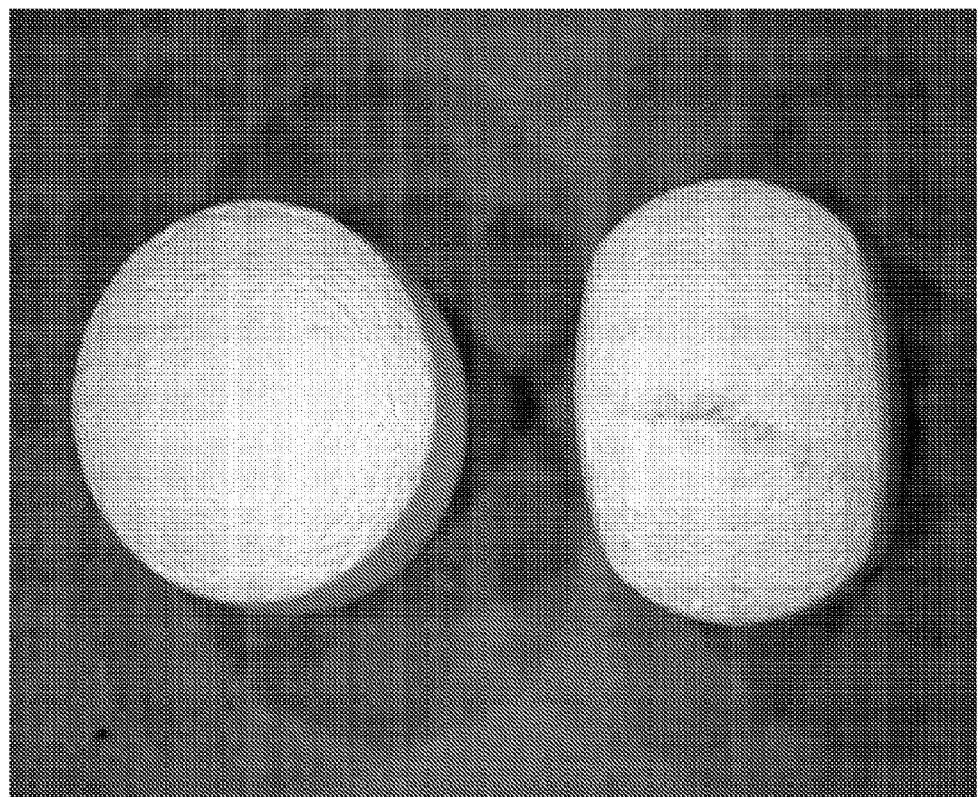
FIG. 1 is a photograph that depicts a top view (view is in line with the thickness of the tablet) of tablets of Example 7.1 before (left side) and after (right side) the breaking strength test using the Schleuniger Model 6D apparatus.
Figure 2:
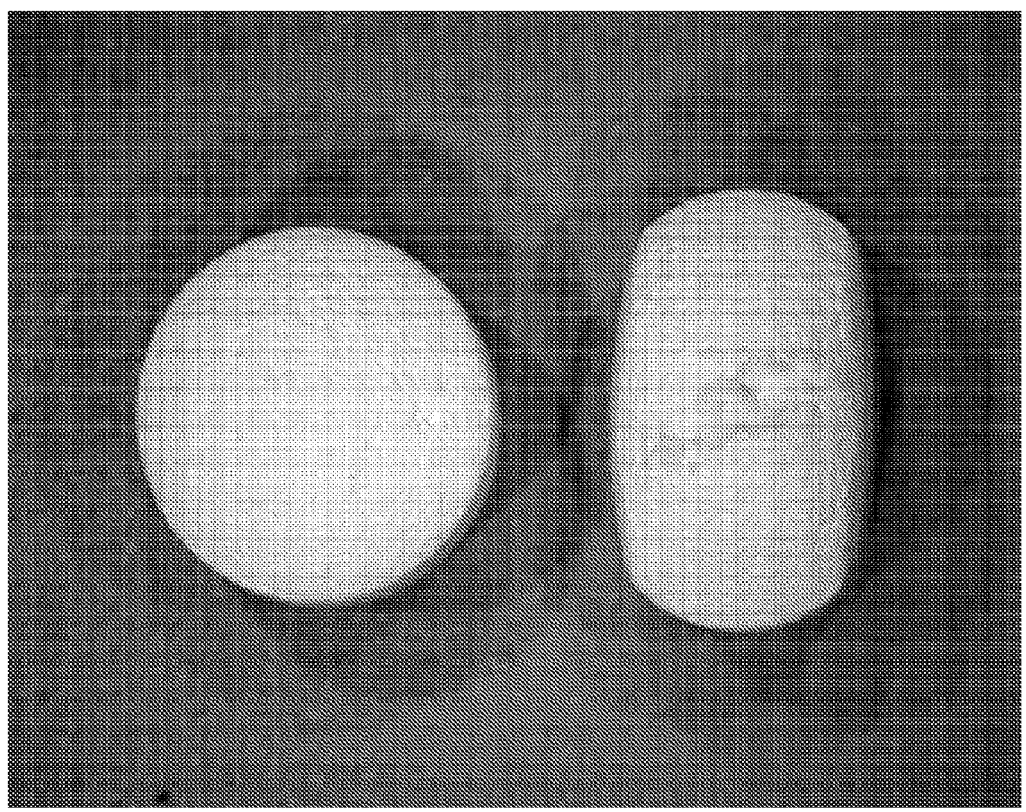
FIG. 2 is a photograph that depicts a top view (view is in line with the thickness of the tablet) of tablets of Example 7.2 before (left side) and after (right side) the breaking strength test using the Schleuniger Model 6D apparatus.
Figure 3:
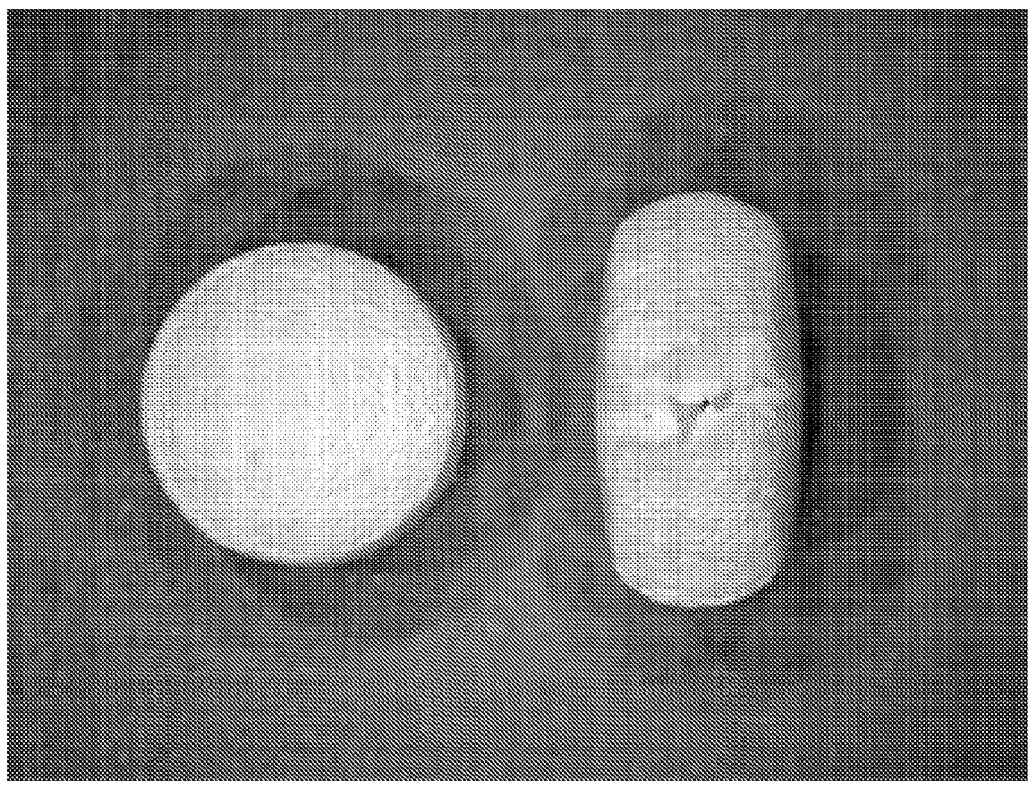
FIG. 3 is a photograph that depicts a top view (view is in line with the thickness of the tablet) of tablets of Example 7.3 before (left side) and after (right side) the breaking strength test using the Schleuniger Model 6D apparatus.
Figure 4:
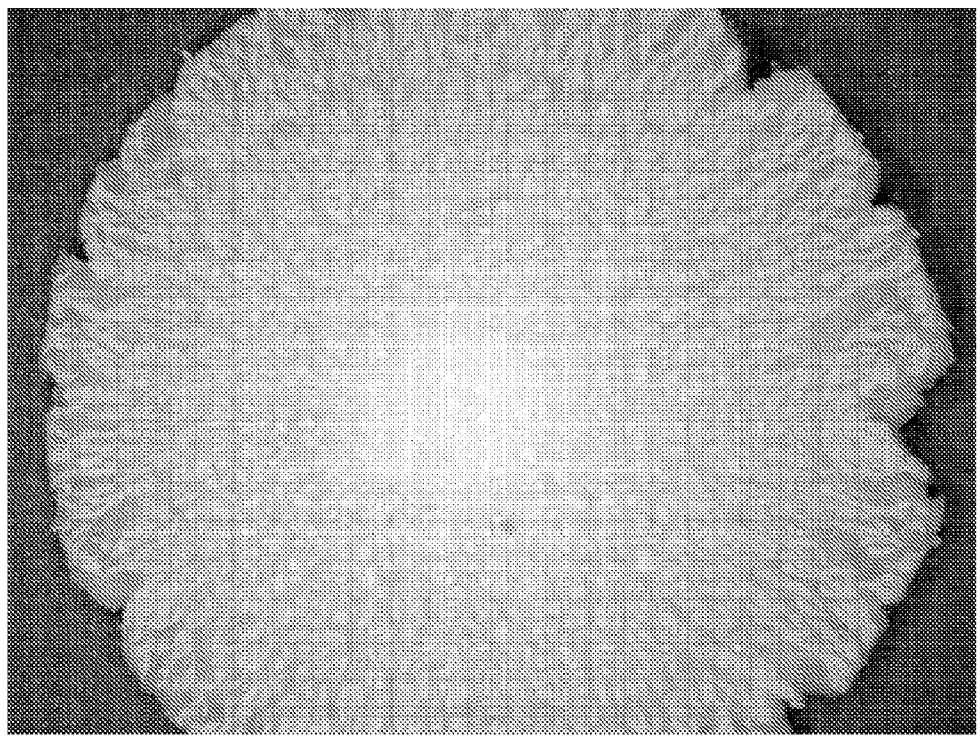
FIG. 4 is a photograph that depicts a top view (view is in line with the thickness of the tablet) of a tablet of Example 7.1 after flattening with a Carver manual bench press (hydraulic unit model #3912).
Figure 5:
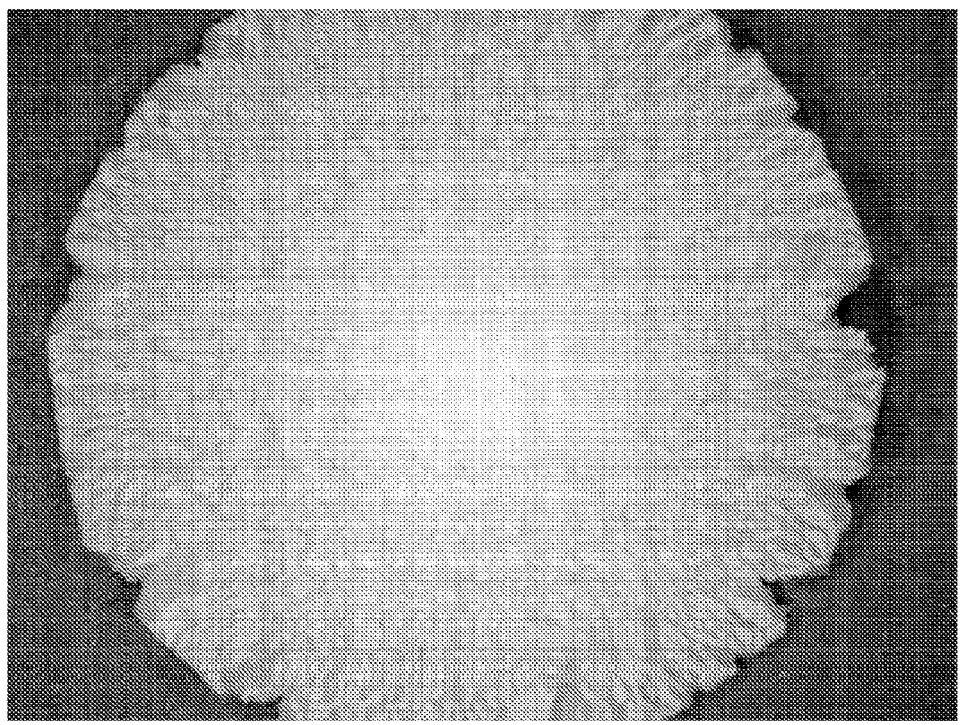
FIG. 5 is a photograph that depicts a top view (view is in line with the thickness of the tablet) of a tablet of Example 7.2 after flattening with a Carver manual bench press (hydraulic unit model #3912).
Figure 6:
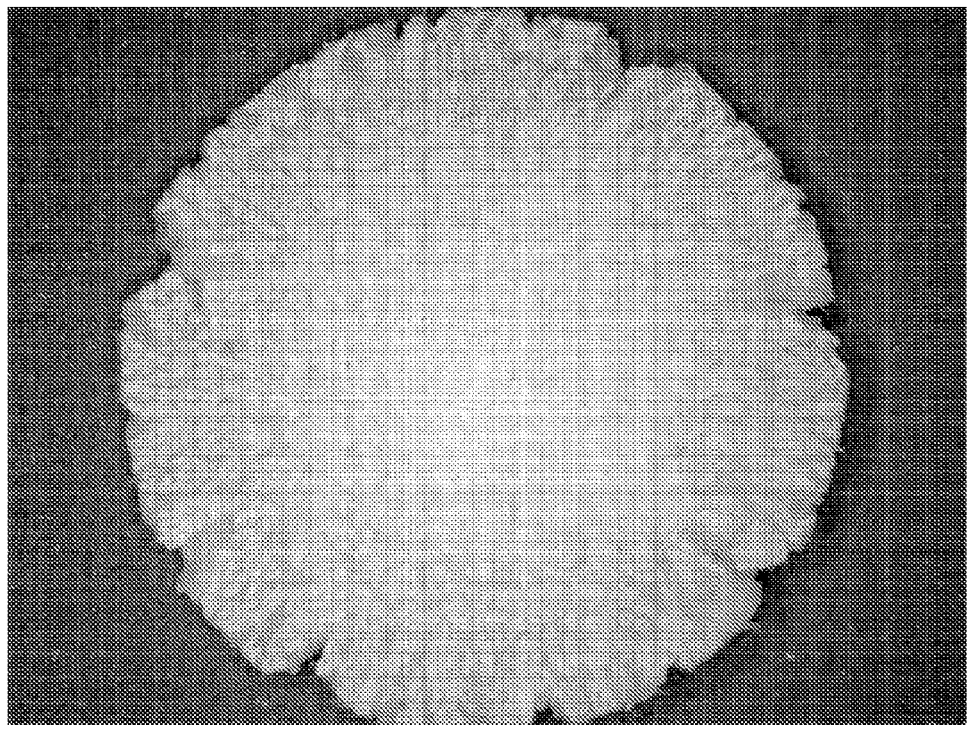
FIG. 6 is a photograph that depicts a top view (view is in line with the thickness of the tablet) of a tablet of Example 7.3 after flattening with a Carver manual bench press (hydraulic unit model #3912).
Figure 7:
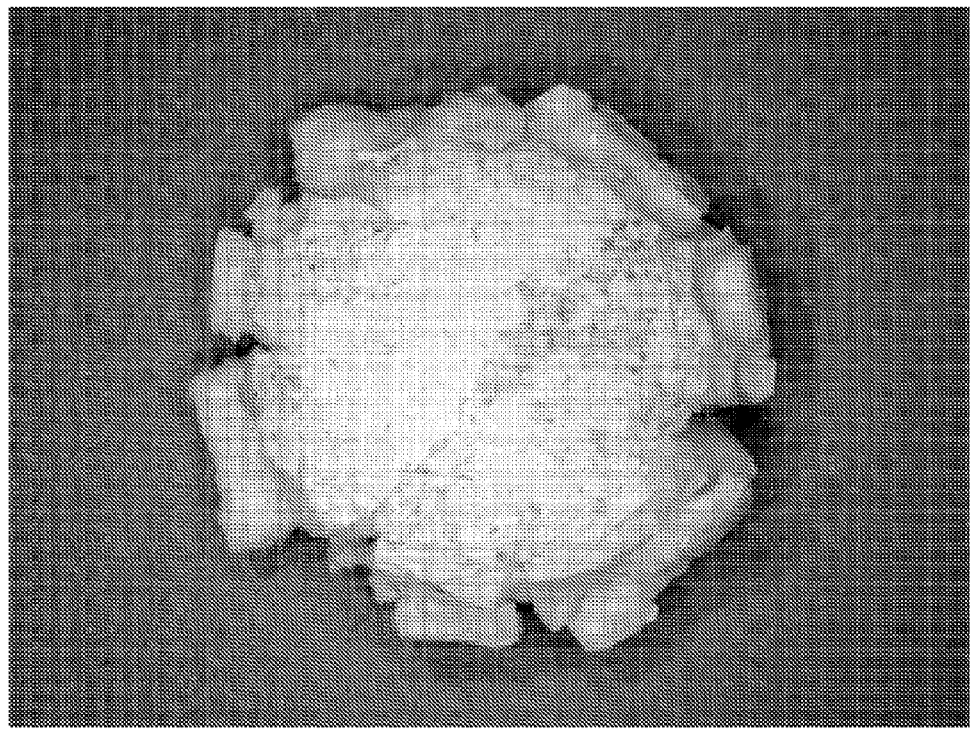
FIG. 7 is a photograph that depicts a top view (view is in line with the thickness of the tablet) of a tablet of Example 7.1 after 10 manually conducted hammer strikes.
Figure 8:
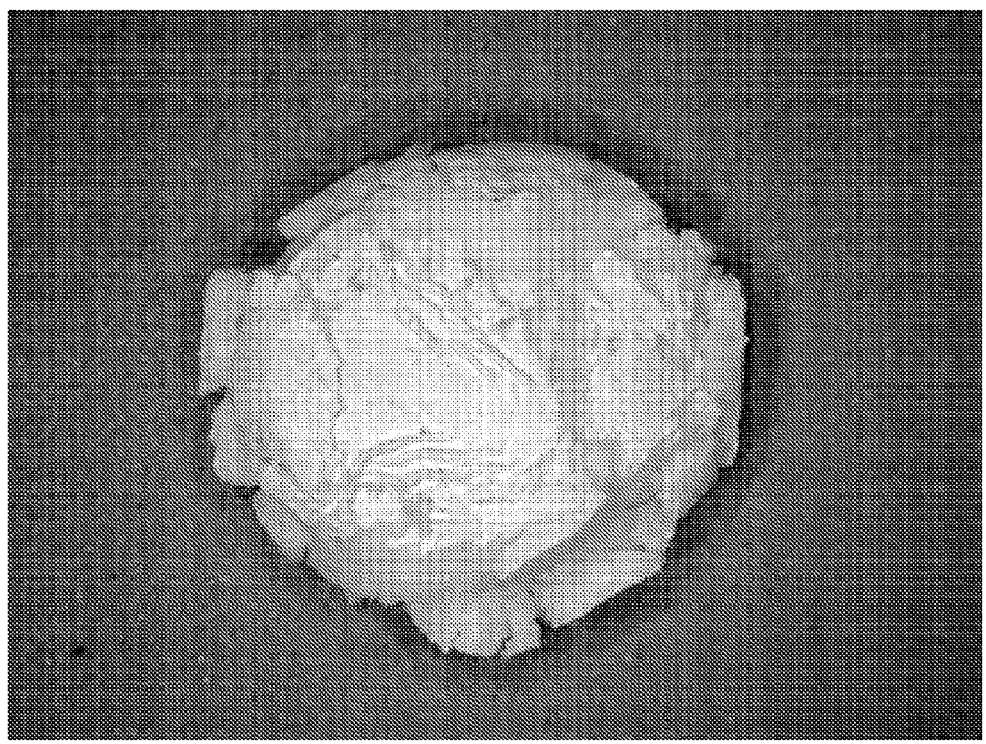
FIG. 8 is a photograph that depicts a top view (view is in line with the thickness of the tablet) of a tablet of Example 7.2 after 10 manually conducted hammer strikes.
Figure 9:
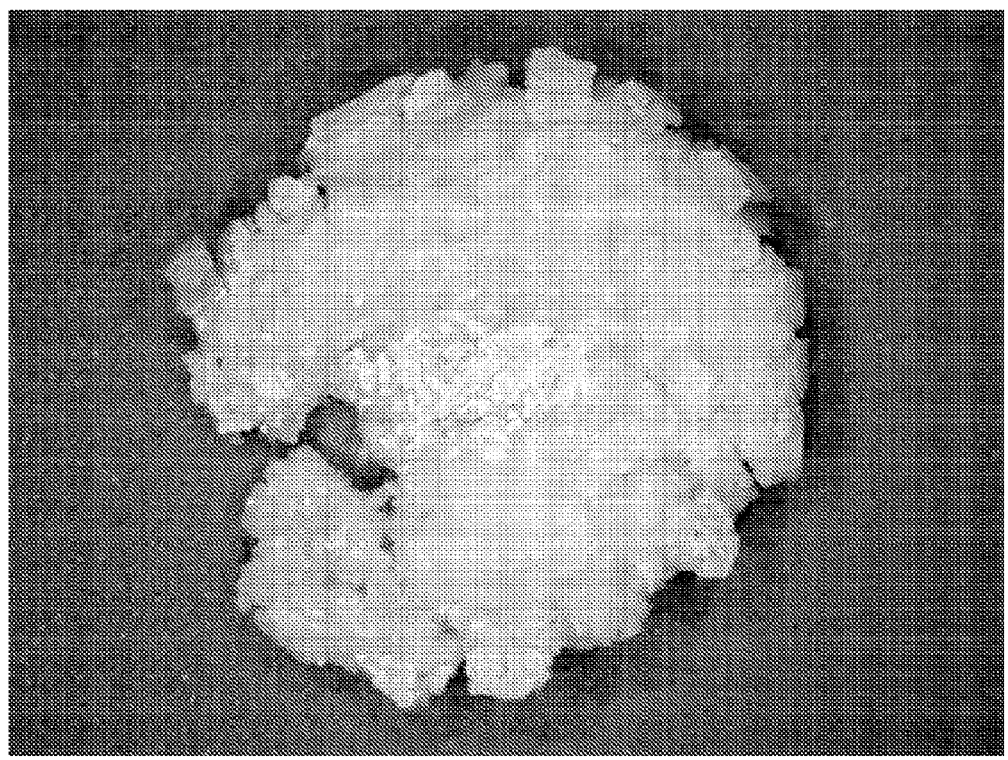
FIG. 9 is a photograph that depicts a top view (view is in line with the thickness of the tablet) of a tablet of Example 7.3 after 10 manually conducted hammer strikes.
Figure 10:
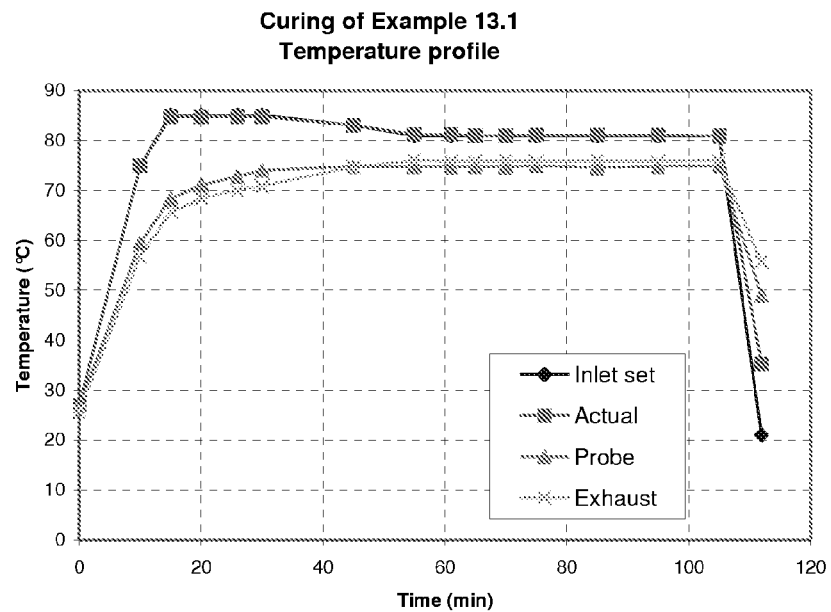
FIG. 10 is a diagram that depicts the temperature profile of the curing process of Example 13.1.
Figure 11:
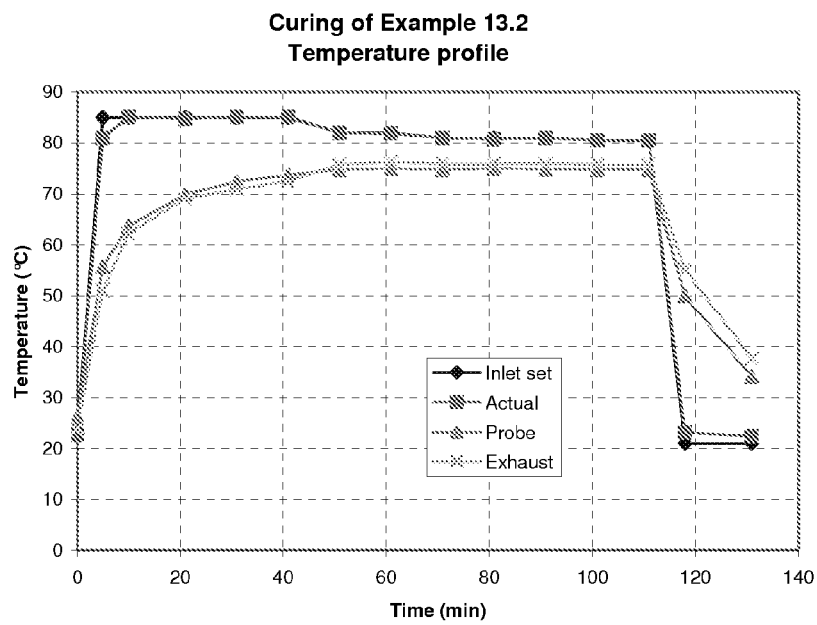
FIG. 11 is a diagram that depicts the temperature profile of the curing process of Example 13.2.
Figure 12:
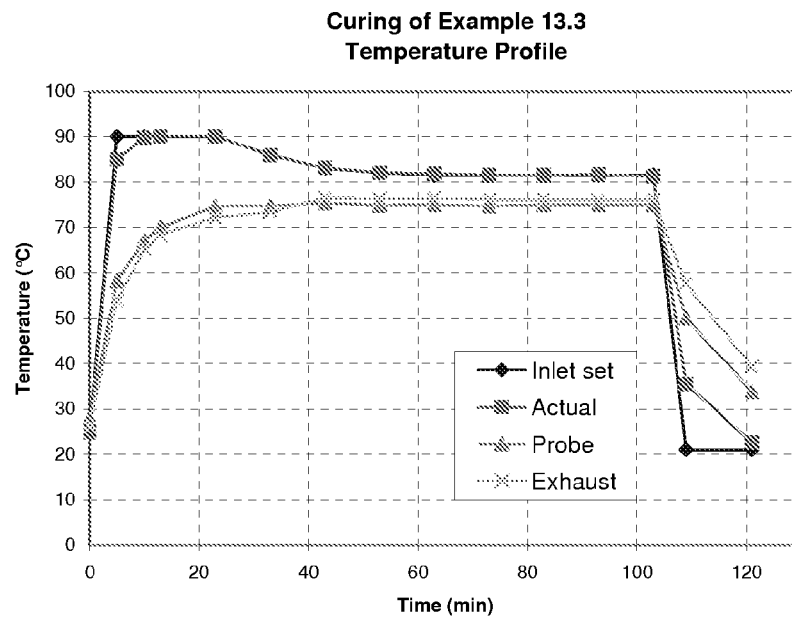
FIG. 12 is a diagram that depicts the temperature profile of the curing process of Example 13.3.
Figure 13:
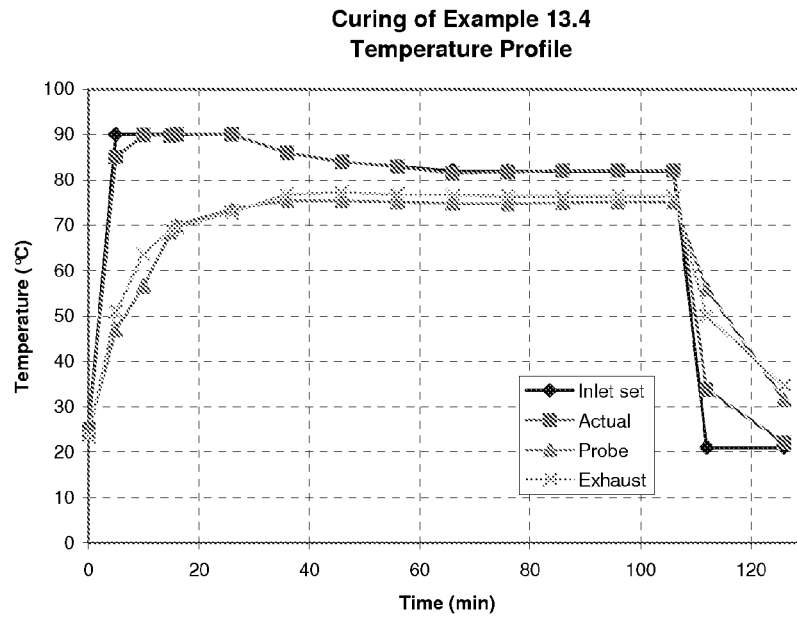
FIG. 13 is a diagram that depicts the temperature profile of the curing process of Example 13.4.
Figure 14:
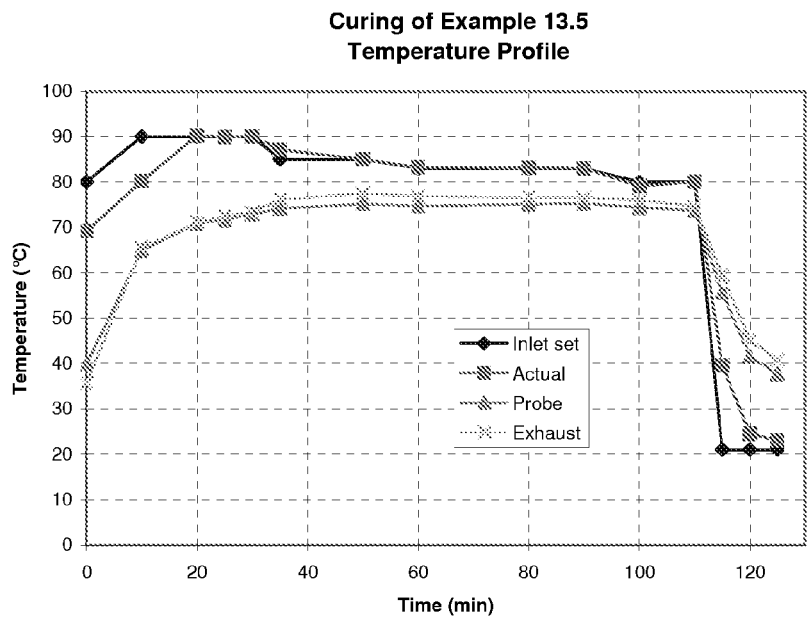
FIG. 14 is a diagram that depicts the temperature profile of the curing process of Example 13.5.
Figure 15:
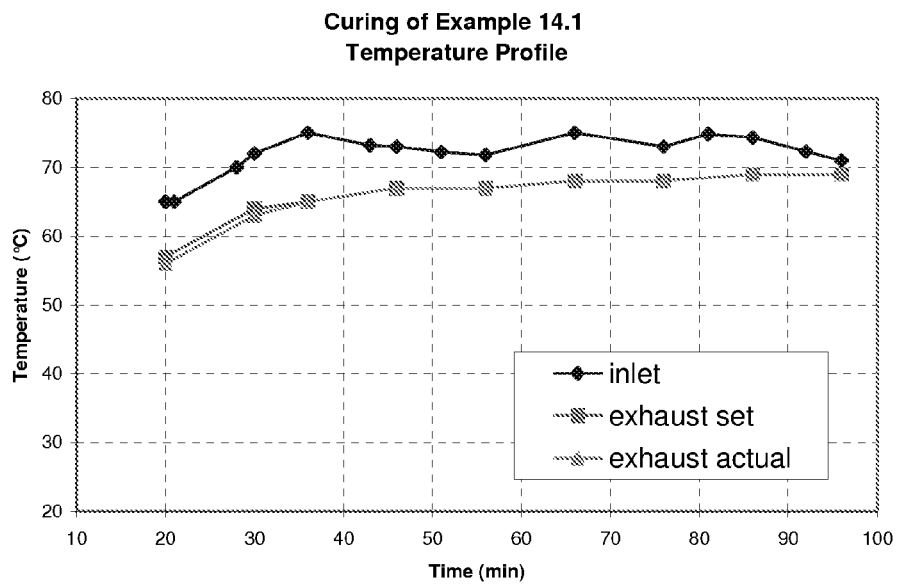
FIG. 15 is a diagram that depicts the temperature profile of the curing process of Example 14.1.
Figure 16:
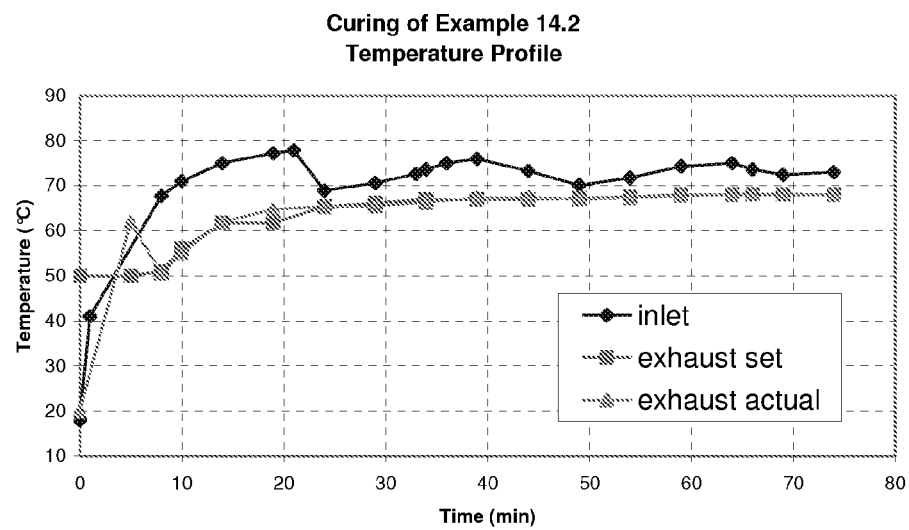
FIG. 16 is a diagram that depicts the temperature profile of the curing process of Example 14.2.
Figure 17:
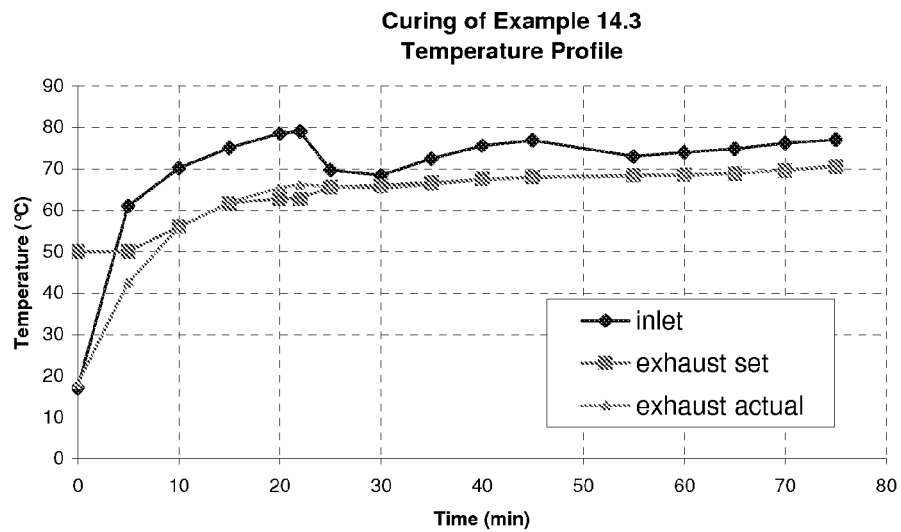
FIG. 17 is a diagram that depicts the temperature profile of the curing process of Example 14.3.
Figure 18:
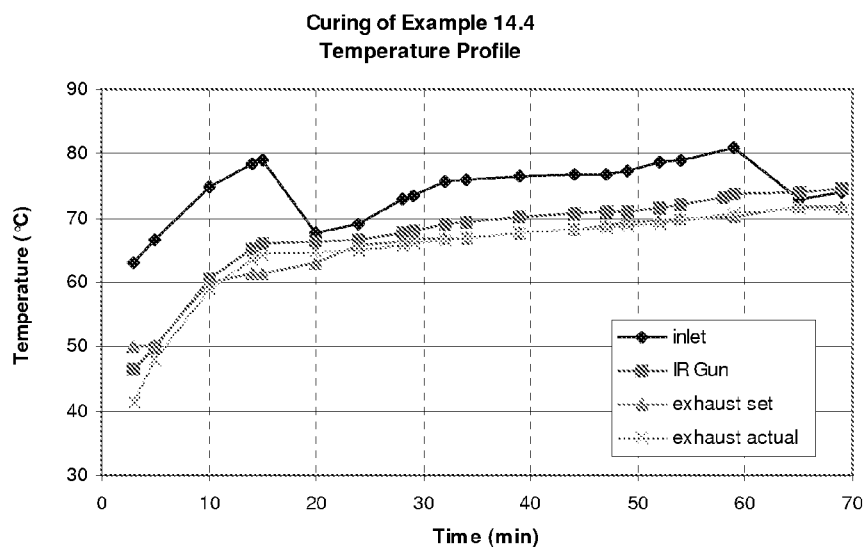
FIG. 18 is a diagram that depicts the temperature profile of the curing process of Example 14.4.
Figure 19:
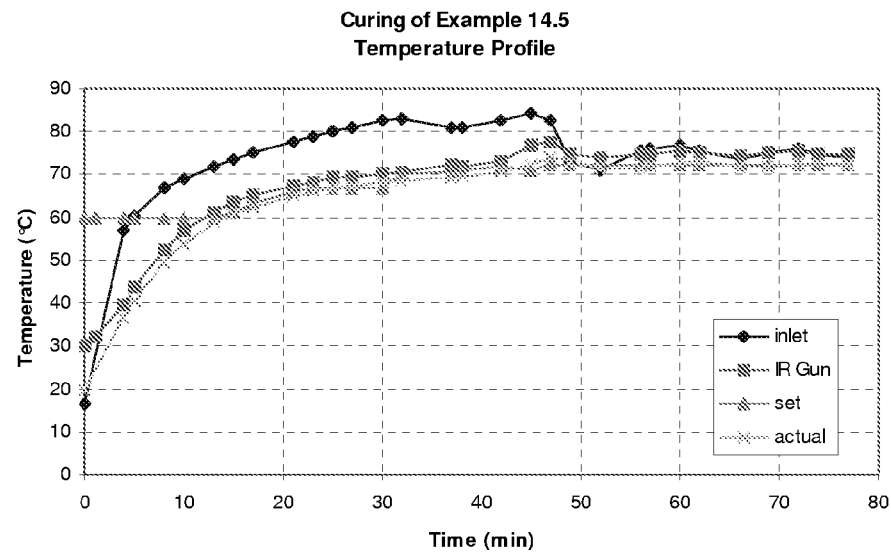
FIG. 19 is a diagram that depicts the temperature profile of the curing process of Example 14.5.
Figure 20:
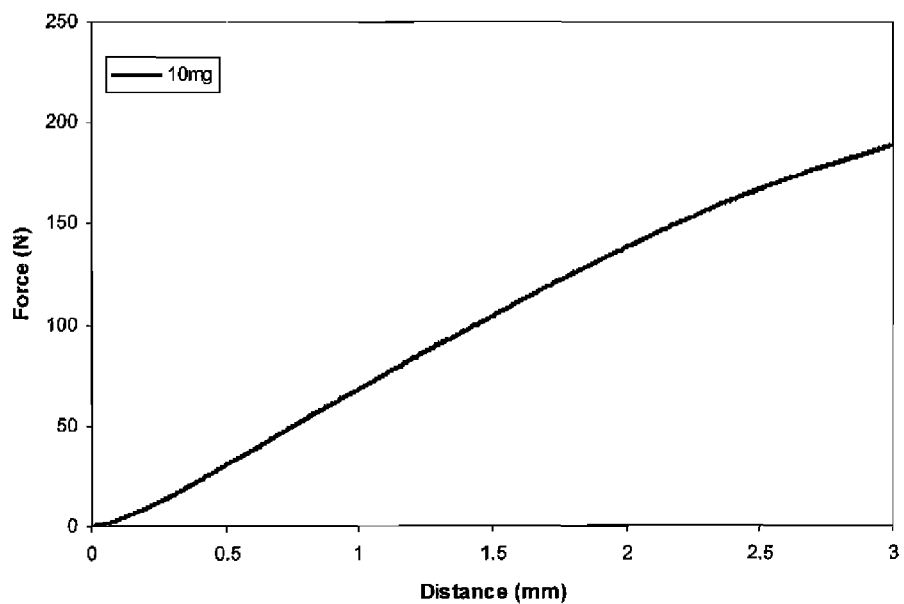
FIG. 20 is a diagram of Example 20 indentation test performed with an Example 13.1 tablet (cured for 30 minutes, uncoated).
Figure 21:
FIG. 21 is a diagram of Example 20 indentation test performed with an Example 13.2 tablet (cured for 30 minutes, uncoated).
Figure 22:
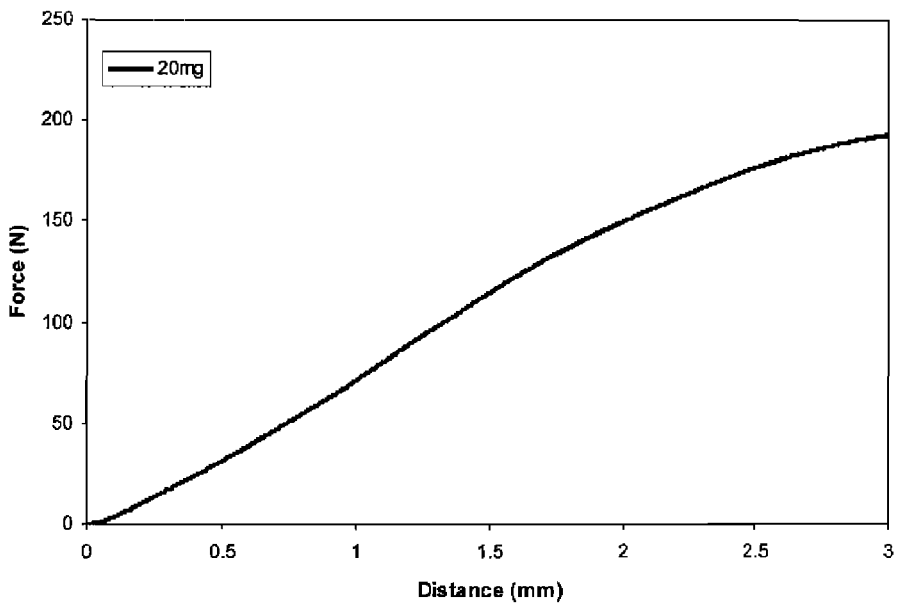
FIG. 22 is a diagram of Example 20 indentation test performed with an Example 13.3 tablet (cured for 30 minutes, uncoated).
Figure 23:
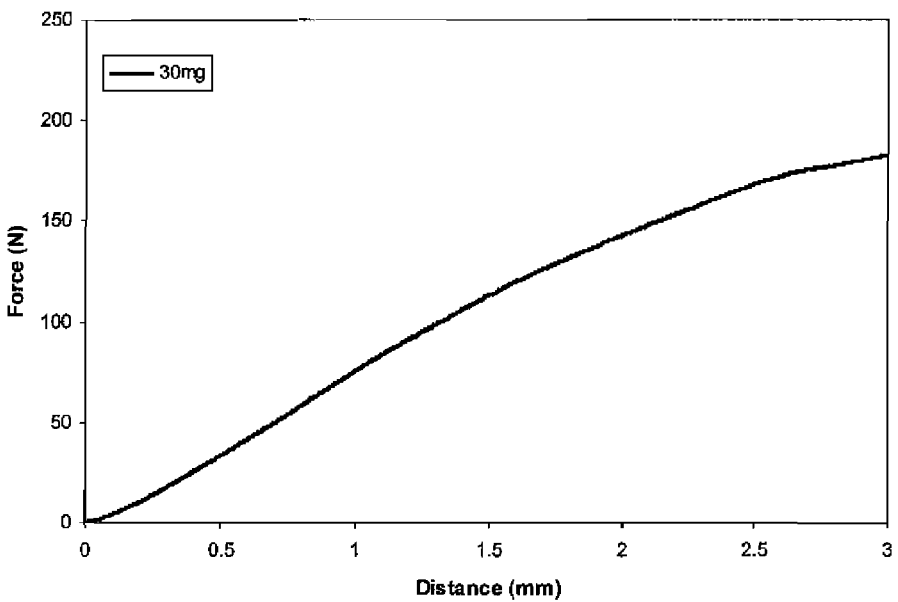
FIG. 23 is a diagram of Example 20 indentation test performed with an Example 13.4 tablet (cured for 30 minutes, uncoated).
Figure 24:
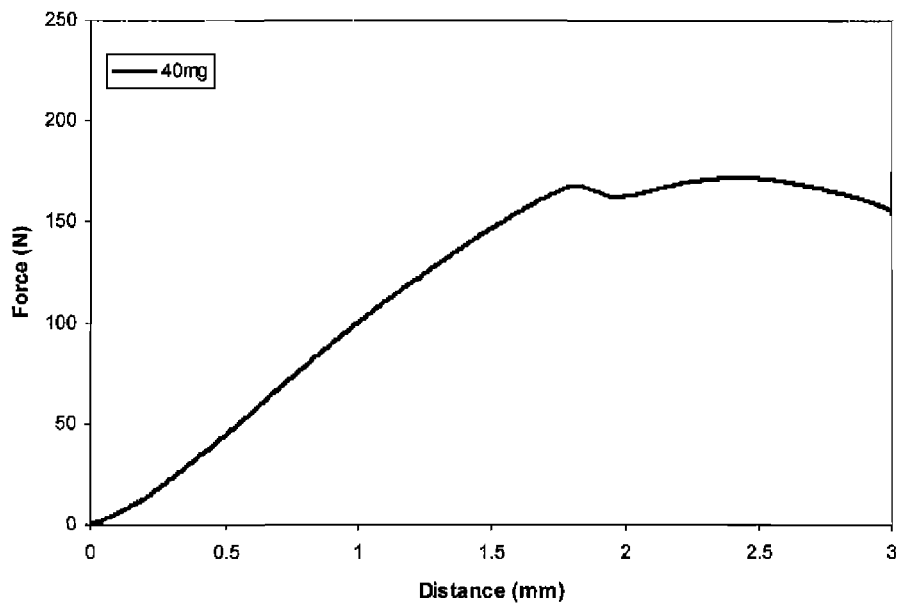
FIG. 24 is a diagram of Example 20 indentation test performed with an Example 13.5 tablet (cured for 30 minutes, uncoated).
Figure 25:
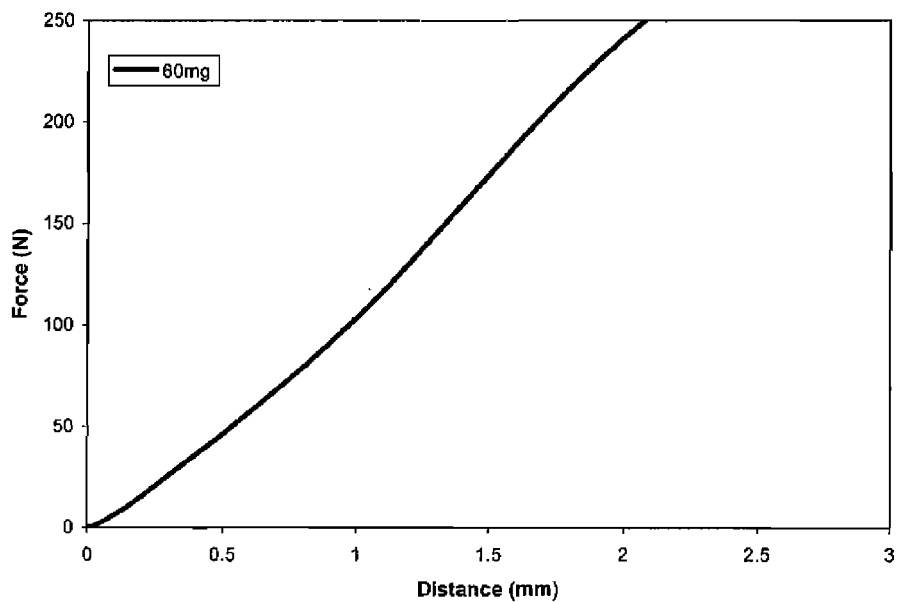
FIG. 25 is a diagram of Example 20 indentation test performed with an Example 17.1 tablet (cured for 15 minutes at 72° C., coated).
Figure 26:
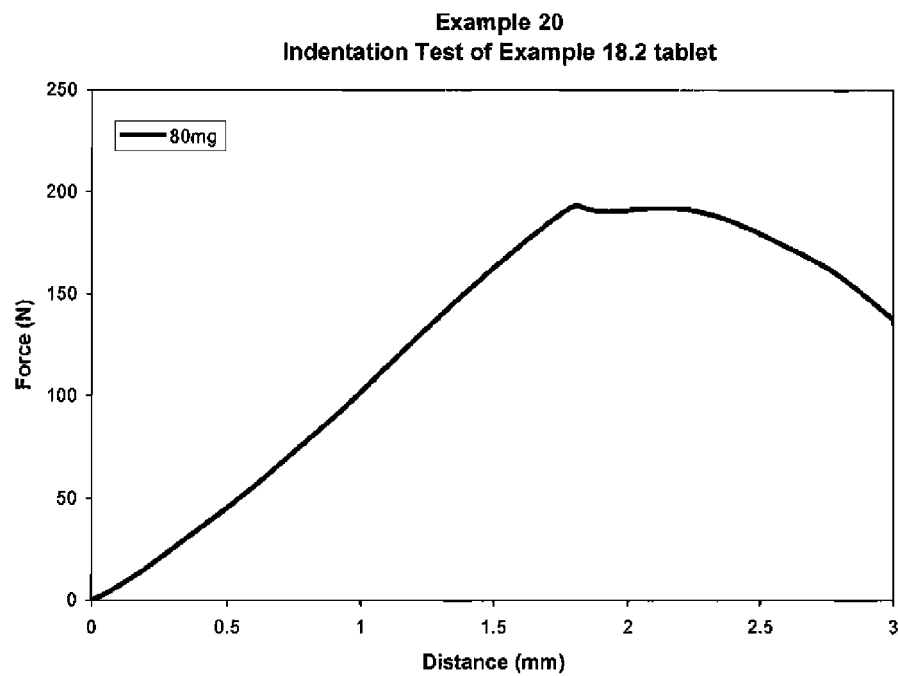
FIG. 26 is a diagram of Example 20 indentation test performed with an Example 18.2 tablet (cured for 15 minutes at 72° C., coated).
Figure 27:
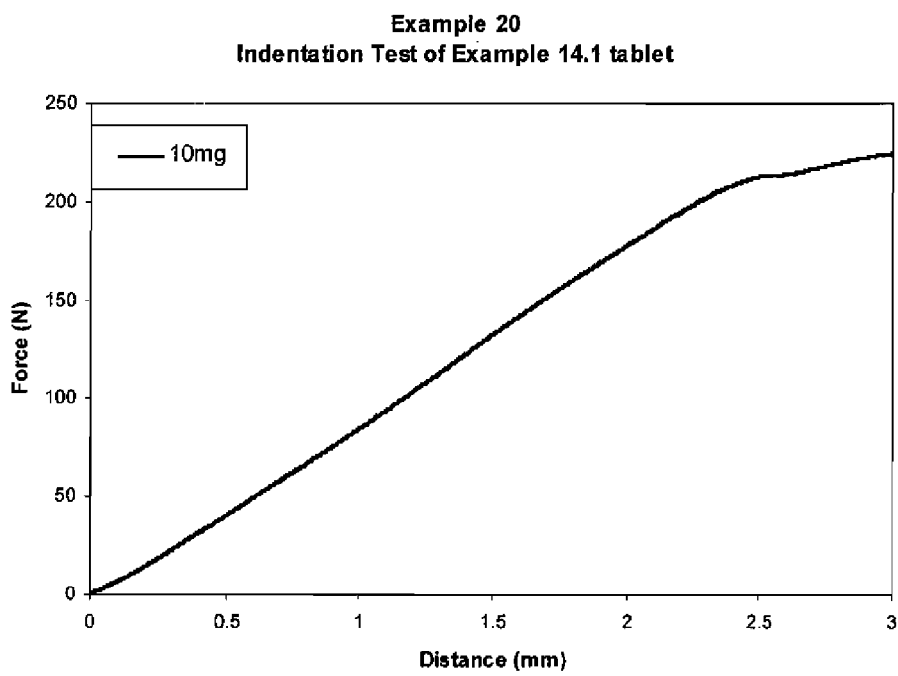
FIG. 27 is a diagram of Example 20 indentation test performed with an Example 14.1 tablet (cured for 1 hour, coated).
Figure 28:
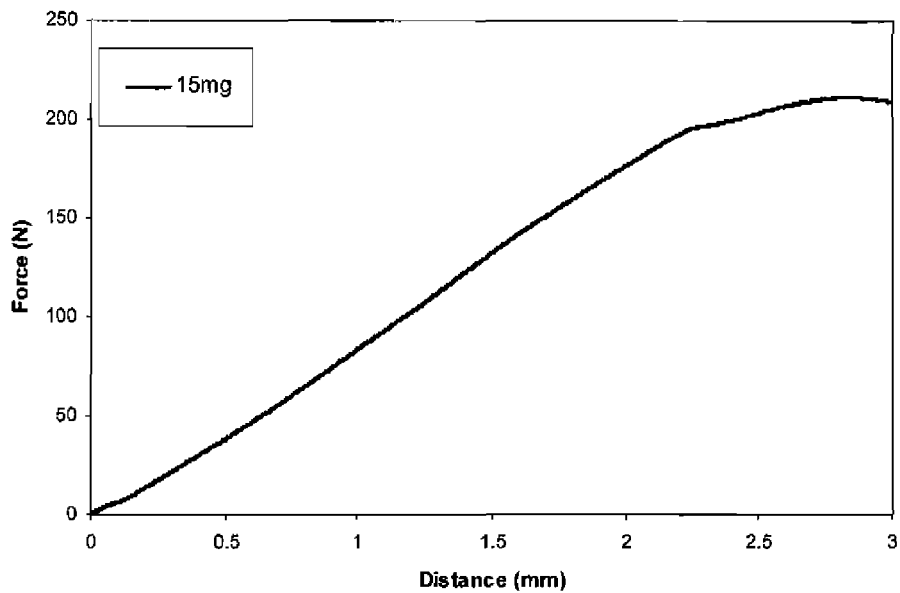
FIG. 28 is a diagram of Example 20 indentation test performed with an Example 14.2 tablet (cured for 1 hour, coated).
Figure 29:
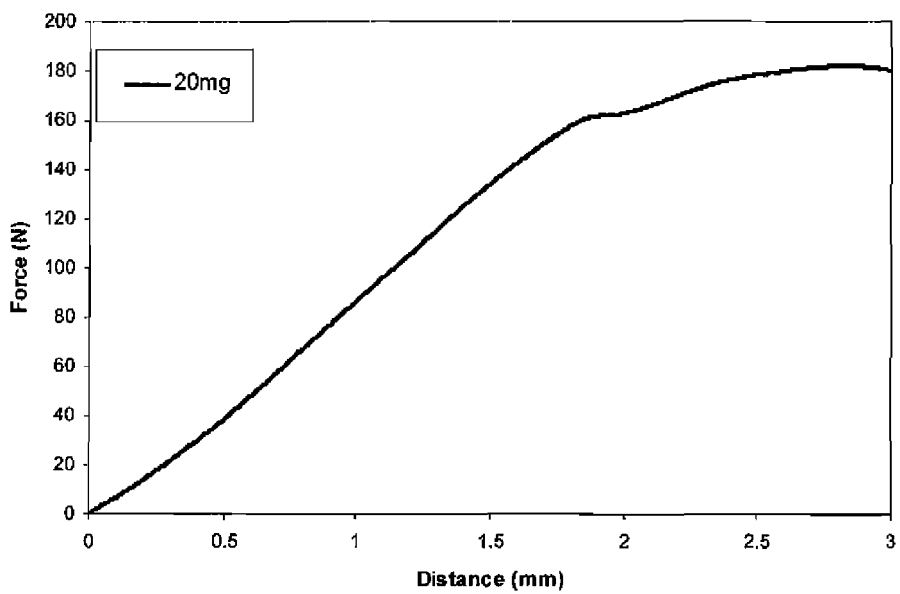
FIG. 29 is a diagram of Example 20 indentation test performed with an Example 14.3 tablet (cured for 1 hour, coated).
Figure 30:
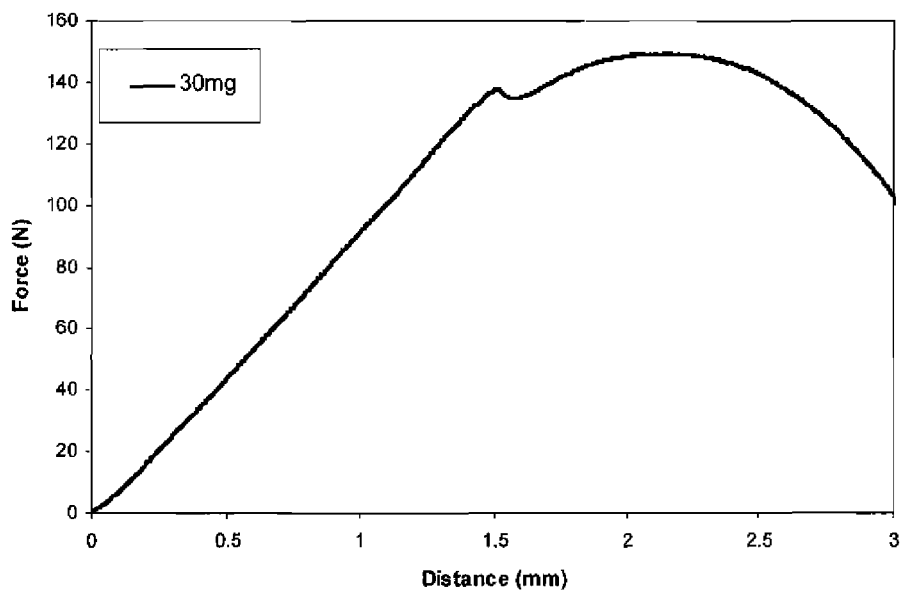
FIG. 30 is a diagram of Example 20 indentation test performed with an Example 14.4 tablet (cured for 1 hour, coated).
Figure 31:
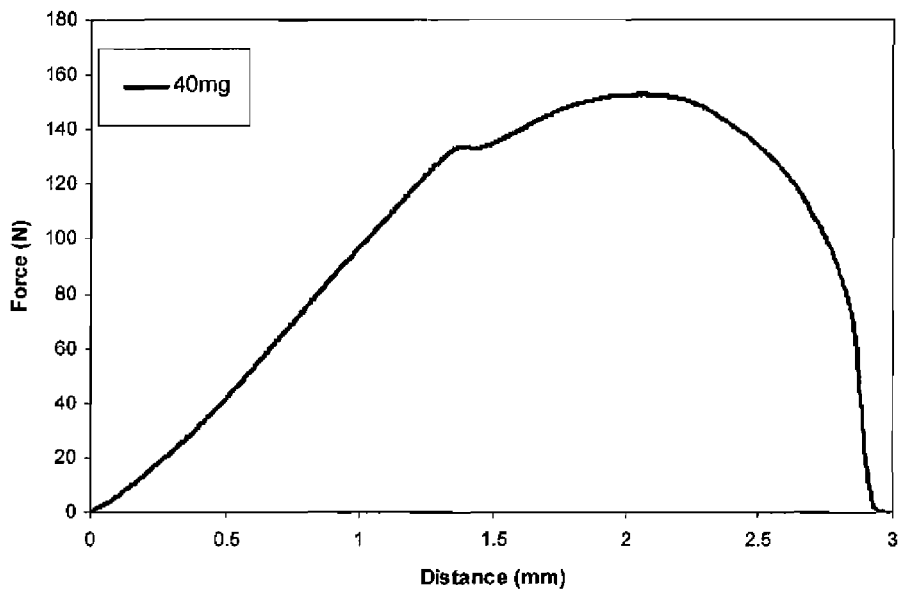
FIG. 31 is a diagram of Example 20 indentation test performed with an Example 14.5 tablet (cured for 1 hour, coated).
Figure 32:
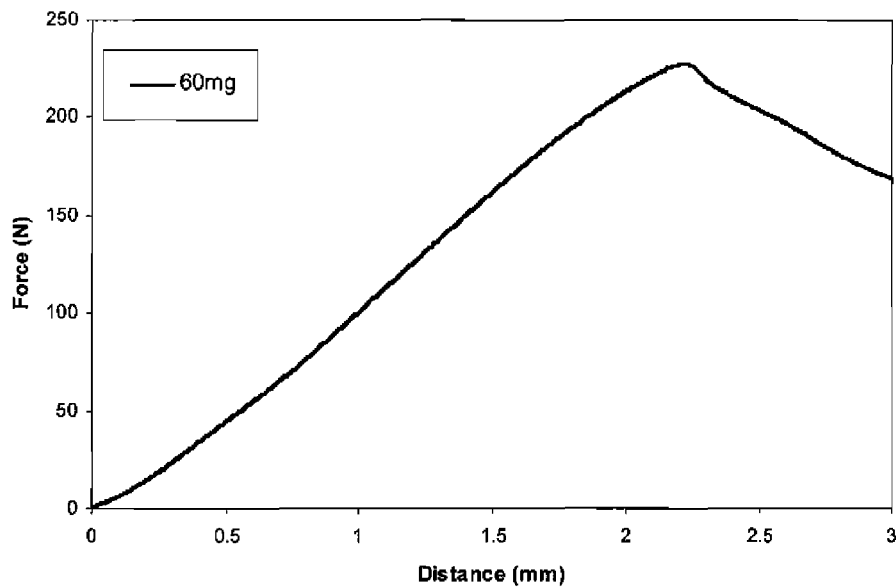
FIG. 32 is a diagram of Example 20 indentation test performed with an Example 16.1 tablet (cured for 15 minutes, coated).
Figure 33:
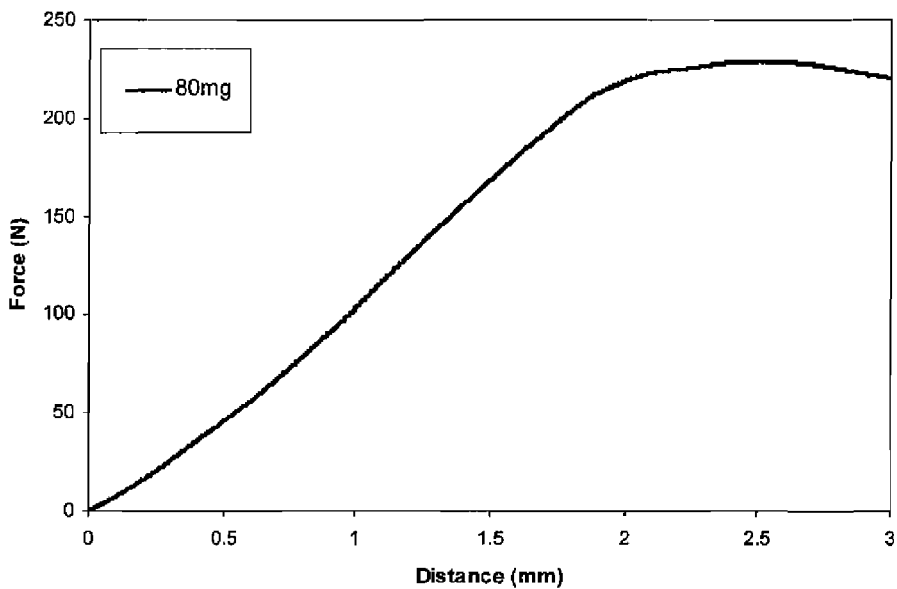
FIG. 33 is a diagram of Example 20 indentation test performed with an Example 16.2 tablet (cured for 15 minutes, coated).

In certain embodiments, the present invention is directed to a process of preparing a solid oral extended release pharmaceutical dosage form,
comprising at least the steps of:
  (a) combining at least
    (1) at least one polyethylene oxide having, based on rheological measurements, an approximate molecular weight of at least 1,000,000, and
    (2) at least one active agent,
    to form a composition;
  (b) shaping the composition to form an extended release matrix formulation; and
  (c) curing said extended release matrix formulation comprising at least a curing step of subjecting the extended release matrix formulation to a temperature which is at least the softening temperature of said polyethylene oxide for a time period of at least about 1 minute.
Preferably, the curing is conducted at atmospheric pressure.

In a certain embodiment the present invention concerns a process of preparing a solid oral extended release pharmaceutical dosage form, comprising at least the steps of:
  (a) combining at least
    (1) at least one polyethylene oxide having, based on rheological measurements, an molecular weight of at least 1,000,000; and
    (2) at least one active agent, to form a composition;
  (b) shaping the composition to form an extended release matrix formulation; and
  (c) curing said extended release matrix formulation comprising at least a curing step of subjecting the extended release matrix formulation to a temperature which is at least the softening temperature of said polyethylene oxide for a time period of at least 5 minutes. Preferably, the curing is conducted at atmospheric pressure.

In certain embodiments, the present invention is directed to a process of preparing a solid oral extended release pharmaceutical dosage form,
comprising at least the steps of:
  (a) combining at least
    (1) at least one polyethylene oxide having, based on rheological measurements, an approximate molecular weight of at least 1,000,000, and
    (2) at least one active agent,
    to form a composition;
  (b) shaping the composition to form an extended release matrix formulation; and
  (c) curing said extended release matrix formulation comprising at least a curing step wherein said polyethylene oxide at least partially melts.
Preferably, the curing is conducted at atmospheric pressure.

In certain embodiments the composition is shaped in step b) to form an extended release matrix formulation in the form of tablet. For shaping the extended release matrix formulation in the form of tablet a direct compression process can be used. Direct compression is an efficient and simple process for shaping tablets by avoiding process steps like wet granulation. However, any other process for manufacturing tablets as known in the art may be used, such as wet granulation and subsequent compression of the granules to form tablets.

In one embodiment, the curing of the extended release matrix formulation in step c) comprises at least a curing step wherein the high molecular weight polyethylene oxide in the extended release matrix formulation at least partially melts. For example, at least about 20% or at least about 30% of the high molecular weight polyethylene oxide in the extended release matrix formulation melts. Preferably, at least about 40% or at least about 50%, more preferably at least about 60%, at least about 75% or at least about 90% of the high molecular weight polyethylene oxide in the extended release matrix formulation melts. In a preferred embodiment, about 100% of the high molecular weight polyethylene oxide melts.

In other embodiments, the curing of the extended release matrix formulation in step c) comprises at least a curing step wherein the extended release matrix formulation is subjected to an elevated temperature for a certain period of time. In such embodiments, the temperature employed in step c), i.e. the curing temperature, is at least as high as the softening temperature of the high molecular weight polyethylene oxide. Without wanting to be bound to any theory it is believed that the curing at a temperature that is at least as high as the softening temperature of the high molecular weight polyethylene oxide causes the polyethylene oxide particles to at least adhere to each other or even to fuse. According to some embodiments the curing temperature is at least about 60° C. or at least about 62° C. or ranges from about 62° C. to about 90° C. or from about 62° C. to about 85° C. or from about 62° C. to about 80° C. or from about 65° C. to about 90° C. or from about 65° C. to about 85° C. or from about 65° C. to about 80° C. The curing temperature preferably ranges from about 68° C. to about 90° C. or from about 68° C. to about 85° C. or from about 68° C. to about 80° C. more preferably from about 70° C. to about 90° C. or from about 70° C. to about 85° C. or from about 70° C. to about 80° C., most preferably from about 72° C. to about 90° C. or from about 72° C. to about 85° C. or from about 72° C. to about 80° C. The curing temperature may be at least about 60° C. or at least about 62° C., but less than about 90° C. or less than about 80° C. Preferably, it is in the range of from about 62° C. to about 72° C., in particular from about 68° C. to about 72° C. Preferably, the curing temperature is at least as high as the lower limit of the softening temperature range of the high molecular weight polyethylene oxide or at least about 62° C. or at least about 68° C. More preferably, the curing temperature is within the softening temperature range of the high molecular weight polyethylene oxide or at least about 70° C. Even more preferably, the curing temperature is at least as high as the upper limit of the softening temperature range of the high molecular weight polyethylene oxide or at least about 72° C. In an alternative embodiment, the curing temperature is higher than the upper limit of the softening temperature range of the high molecular weight polyethylene oxide, for example the curing temperature is at least about 75° C. or at least about 80° C.

In those embodiments where the curing of the extended release matrix formulation in step c) comprises at least a curing step wherein the extended release matrix formulation is subjected to an elevated temperature for a certain period of time, this period of time is hereinafter referred to as the curing time. For the measurement of the curing time a starting point and an end point of the curing step is defined. For the purposes of the present invention, the starting point of the curing step is defined to be the point in time when the curing temperature is reached.

In certain embodiments, the temperature profile during the curing step shows a plateau-like form between the starting point and the end point of the curing. In such embodiments the end point of the curing step is defined to be the point in time when the heating is stopped or at least reduced, e.g. by terminating or reducing the heating and/or by starting a subsequent cooling step, and the temperature subsequently drops below the curing temperature by more than about 10° C. and/or below the lower limit of the softening temperature range of high molecular weight polyethylene oxide, for example below about 62° C. When the curing temperature is reached and the curing step is thus started, deviations from the curing temperature in the course of the curing step can occur. Such deviations are tolerated as long as they do not exceed a value of about ±10° C., preferably about ±6° C., and more preferably about ±3° C. For example, if a curing temperature of at least about 75° C. is to be maintained, the measured temperature may temporarily increase to a value of about 85° C., preferably about 81° C. and more preferably about 78° C., and the measured temperature may also temporarily drop down to a value of about 65° C., preferably about 69° C. and more preferably about 72° C. In the cases of a larger decrease of the temperature and/or in the case that the temperature drops below the lower limit of the softening temperature range of high molecular weight polyethylene oxide, for example below about 62° C., the curing step is discontinued, i.e. an end point is reached. Curing can be restarted by again reaching the curing temperature.

In other embodiments, the temperature profile during the curing step shows a parabolic or triangular form between the starting point and the end point of the curing. This means that after the starting point, i.e. the point in time when the curing temperature is reached, the temperature further increases to reach a maximum, and then decreases. In such embodiments, the end point of the curing step is defined to be the point in time when the temperature drops below the curing temperature.

In this context, it has to be noted that depending on the apparatus used for the curing, which will hereinafter be called curing device, different kinds of temperatures within the curing device can be measured to characterize the curing temperature.

In certain embodiments, the curing step may take place in an oven. In such embodiments, the temperature inside the oven is measured. Based thereon, when the curing step takes place in an oven, the curing temperature is defined to be the target inside temperature of the oven and the starting point of the curing step is defined to be the point in time when the inside temperature of the oven reaches the curing temperature. The end point of the curing step is defined to be (1) the point in time when the heating is stopped or at least reduced and the temperature inside the oven subsequently drops below the curing temperature by more than about 10° C. and/or below the lower limit of the softening temperature range of high molecular weight polyethylene oxide, for example below about 62° C., in a plateau-like temperature profile or (2) the point in time when the temperature inside the oven drops below the curing temperature in a parabolic or triangular temperature profile. Preferably, the curing step starts when the temperature inside the oven reaches a curing temperature of at least about 62° C., at least about 68° C. or at least about 70° C., more preferably of at least about 72° C. or at least about 75° C. In preferred embodiments, the temperature profile during the curing step shows a plateau-like form, wherein the curing temperature, i.e. the inside temperature of the oven, is preferably at least about 68° C., for example about 70° C. or about 72° C. or about 73° C., or lies within a range of from about 70° C. to about 75° C., and the curing time is preferably in the range of from about 30 minutes to about 20 hours, more preferably from about 30 minutes to about 15 hours, or from about 30 minutes to about 4 hours or about 30 minutes to about 2 hours. Most preferably, the curing time is in the range of from about 30 minutes to about 90 minutes.

In certain other embodiments, the curing takes place in curing devices that are heated by an air flow and comprise a heated air supply (inlet) and an exhaust, like for example a coating pan or fluidized bed. Such curing devices will hereinafter be called convection curing devices. In such curing devices, it is possible to measure the temperature of the inlet air, i.e. the temperature of the heated air entering the convection curing device and/or the temperature of the exhaust air, i.e. the temperature of the air leaving the convection curing device. It is also possible to determine or at least estimate the temperature of the formulations inside the convection curing device during the curing step, e.g. by using infrared temperature measurement instruments, such as an IR gun, or by measuring the temperature using a temperature probe that was placed inside the curing device near the extended release matrix formulations. Based thereon, when the curing step takes place in a convection curing device, the curing temperature can be defined and the curing time can be measured as the following.

In one embodiment, wherein the curing time is measured according to method 1, the curing temperature is defined to be the target inlet air temperature and the starting point of the curing step is defined to be the point in time when the inlet air temperature reaches the curing temperature. The end point of the curing step is defined to be (1) the point in time when the heating is stopped or at least reduced and the inlet air temperature subsequently drops below the curing temperature by more than about 10° C. and/or below the lower limit of the softening temperature range of high molecular weight polyethylene oxide, for example below about 62° C., in a plateau-like temperature profile or (2) the point in time when the inlet air temperature drops below the curing temperature in a parabolic or triangular temperature profile. Preferably, the curing step starts according to method 1, when the inlet air temperature reaches a curing temperature of at least about 62° C., at least about 68° C. or at least about 70° C., more preferably, of at least about 72° C. or at least about 75° C. In a preferred embodiment, the temperature profile during the curing step shows a plateau-like form, wherein the curing temperature, i.e. the target inlet air temperature, is preferably at least about 72° C., for example about 75° C., and the curing time which is measured according to method 1 is preferably in the range of from about 15 minutes to about 2 hours, for example about 30 minutes or about 1 hour.

In another embodiment, wherein the curing time is measured according to method 2, the curing temperature is defined to be the target exhaust air temperature and the starting point of the curing step is defined to be the point in time when the exhaust air temperature reaches the curing temperature. The end point of the curing step is defined to be (1) the point in time when the heating is stopped or at least reduced and the exhaust air temperature subsequently drops below the curing temperature by more than about 10° C. and/or below the lower limit of the softening temperature range of high molecular weight polyethylene oxide, for example below about 62° C., in a plateau-like temperature profile or (2) the point in time when the exhaust air temperature drops below the curing temperature in a parabolic or triangular temperature profile. Preferably, the curing step starts according to method 2, when the exhaust air temperature reaches a curing temperature of at least about 62° C., at least about 68° C. or at least about 70° C., more preferably, of at least about 72° C. or at least about 75° C. In preferred embodiments, the temperature profile during the curing step shows a plateau-like form, wherein the curing temperature, i.e. the target exhaust air temperature, is preferably at least about 68° C., at least about 70° C. or at least about 72° C., for example the target exhaust air temperature is about 68° C., about 70° C., about 72° C., about 75° C. or about 78° C., and the curing time which is measured according to method 2 is preferably in the range of from about 1 minute to about 2 hours, preferably from about 5 minutes to about 90 minutes, for example the curing time is about 5 minutes, about 10 minutes, about 15 minutes, about 30 minutes, about 60 minutes, about 70 minutes, about 75 minutes or about 90 minutes. In a more preferred embodiment, the curing time which is measured according to method 2 is in the range of from about 15 minutes to about 1 hour.

In a further embodiment, wherein the curing time is measured according to method 3, the curing temperature is defined to be the target temperature of the extended release matrix formulations and the starting point of the curing step is defined to be the point in time when the temperature of the extended release matrix formulations, which can be measured for example by an IR gun, reaches the curing temperature. The end point of the curing step is defined to be (1) the point in time when the heating is stopped or at least reduced and the temperature of the extended release matrix formulations subsequently drops below the curing temperature by more than about 10° C. and/or below the lower limit of the softening temperature range of high molecular weight polyethylene oxide, for example below about 62° C., in a plateau-like temperature profile or (2) the point in time when the temperature of the extended release matrix formulations drops below the curing temperature in a parabolic or triangular temperature profile. Preferably, the curing step starts according to method 3, when the temperature of the extended release matrix formulations reaches a curing temperature of at least about 62° C., at least about 68° C. or at least about 70° C., more preferably, of at least about 72° C. or at least about 75° C.

In still another embodiment, wherein the curing time is measured according to method 4, the curing temperature is defined to be the target temperature measured using a temperature probe, such as a wire thermocouple, that was placed inside the curing device near the extended release matrix formulations and the starting point of the curing step is defined to be the point in time when the temperature measured using a temperature probe that was placed inside the curing device near the extended release matrix formulations reaches the curing temperature. The end point of the curing step is defined to be (1) the point in time when the heating is stopped or at least reduced and the temperature measured using the temperature probe subsequently drops below the curing temperature by more than about 10° C. and/or below the lower limit of the softening temperature range of high molecular weight polyethylene oxide, for example below about 62° C., in a plateau-like temperature profile or (2) the point in time when the temperature measured using the temperature probe drops below the curing temperature in a parabolic or triangular temperature profile. Preferably, the curing step starts according to method 4, when the temperature measured using a temperature probe that was placed inside the curing device near the extended release matrix formulations reaches a curing temperature of at least about 62° C., at least about 68° C. or at least about 70° C., more preferably, of at least about 72° C. or at least about 75° C. In a preferred embodiment, the temperature profile during the curing step shows a plateau-like form, wherein the curing temperature, i.e. the target temperature measured using a temperature probe that was placed inside the curing device near the extended release matrix formulations, is preferably at least about 68° C., for example it is about 70° C., and the curing time which is measured according to method 4 is preferably in the range of from about 15 minutes to about 2 hours, for example the curing time is about 60 minutes or about 90 minutes.

If curing takes place in a convection curing device, the curing time can be measured by any one of methods 1, 2, 3 or 4. In a preferred embodiment, the curing time is measured according to method 2.

In certain embodiments, the curing temperature is defined as a target temperature range, for example the curing temperature is defined as a target inlet air temperature range or a target exhaust air temperature range. In such embodiments, the starting point of the curing step is defined to be the point in time when the lower limit of the target temperature range is reached, and the end point of the curing step is defined to be the point in time when the heating is stopped or at least reduced, and the temperature subsequently drops below the lower limit of the target temperature range by more than about 10° C. and/or below the lower limit of the softening temperature range of high molecular weight polyethylene oxide, for example below about 62° C.

The curing time, i.e. the time period the extended release matrix formulation is subjected to the curing temperature, which can for example be measured according to methods 1, 2, 3 and 4 as described above, is at least about 1 minute or at least about 5 minutes. The curing time may vary from about 1 minute to about 24 hours or from about 5 minutes to about 20 hours or from about 10 minutes to about 15 hours or from about 15 minutes to about 10 hours or from about 30 minutes to about 5 hours depending on the specific composition and on the formulation and the curing temperature. The parameter of the composition, the curing time and the curing temperature are chosen to achieve the tamper resistance as described herein. According to certain embodiments the curing time varies from about 15 minutes to about 30 minutes. According to further embodiments wherein the curing temperature is at least about 60° C. or at least about 62° C., preferably at least about 68° C., at least about 70° C., at least about 72° C. or at least about 75° C. or varies from about 62° C. to about 85° C. or from about 65° C. to about 85° C. the curing time is preferably at least about 15 minutes, at least about 30 minutes, at least about 60 minutes, at least about 75 minutes, at least about 90 minutes or about 120 minutes. In preferred embodiments, wherein the curing temperature is for example at least about 62° C., at least about 68° C. or at least about 70° C., preferably at least about 72° C. or at least about 75° C., or ranges from about 62° C. to about 80° C., from about 65° C. to about 80° C., from about 68° C. to about 80° C., from about 70° C. to about 80° C. or from about 72° C. to about 80° C., the curing time is preferably at least about 1 minute or at least about 5 minutes. More preferably, the curing time is at least about 10 minutes, at least about 15 minutes or at least about 30 minutes. In certain such embodiments, the curing time can be chosen to be as short as possible while still achieving the desired tamper resistance. For example, the curing time preferably does not exceed about 5 hours, more preferably it does not exceed about 3 hours and most preferably it does not exceed about 2 hours. Preferably, the curing time is in the range of from about 1 minute to about 5 hours, from about 5 minutes to about 3 hours, from about 15 minutes to about 2 hours or from about 15 minutes to about 1 hour. Any combination of the curing temperatures and the curing times as disclosed herein lies within the scope of the present invention.

In certain embodiments, the composition is only subjected to the curing temperature until the high molecular weight polyethylene oxide present in the extended release matrix formulation has reached its softening temperature and/or at least partially melts. In certain such embodiments, the curing time may be less than about 5 minutes, for example the curing time may vary from about 0 minutes to about 3 hours or from about 1 minute to about 2 hours or from about 2 minutes to about 1 hour. Instant curing is possible by choosing a curing device which allows for an instant heating of the high molecular weight polyethylene oxide in the extended release matrix formulation to at least its softening temperature, so that the high molecular weight polyethylene oxide at least partially melts. Such curing devices are for example microwave ovens, ultrasound devices, light irradiation apparatus such as UV-irradiation apparatus, ultra-high frequency (UHF) fields or any method known to the person skilled in the art.

The skilled person is aware that the size of the extended release matrix formulation may determine the required curing time and curing temperature to achieve the desired tamper resistance. Without wanting to be bound by any theory, it is believed that in the case of a large extended release matrix formulation, such as a large tablet, a longer curing time is necessary to conduct the heat into the interior of the formulation than in the case of a corresponding formulation with smaller size. Higher temperature increases the thermal conductivity rate and thereby decreases the required curing time.

The curing step c) may take place in an oven. Advantageously, the curing step c) takes place in a bed of free flowing extended release matrix formulations as e.g. in a coating pan. The coating pan allows an efficient batch wise curing step which can subsequently be followed by a coating step without the need to transfer the dosage forms, e.g. the tablets. Such a process may comprise the steps of:

(a) combining at least
  (1) at least one polyethylene oxide having, based on rheological measurements, an approximate molecular weight of at least 1,000,000, and
  (2) at least one active agent,
  to form a composition;
(b) shaping said composition to form the extended release matrix formulation in the form of a tablet by direct compression;
(c) curing said tablet by
  subjecting a bed of free flowing tablets to a temperature from about 62° C. to about 90° C., preferably from about 70° C. to about 90° C. for a time period of at least about 1 minute or at least about 5 minutes, preferably of at least about 30 minutes, in a coating pan and
  subsequently cooling the bed of free flowing tablets to a temperature of below about 50° C.;
  and subsequently
(d) coating the dosage form in said coating pan.

In certain embodiments, an additional curing step can follow after step d) of coating the dosage form. An additional curing step can be performed as described for curing step c). In certain such embodiments, the curing temperature of the additional curing step is preferably at least about 70° C., at least about 72° C. or at least about 75° C., and the curing time is preferably in the range of from about 15 minutes to about 1 hour, for example about 30 minutes.

In certain embodiments an antioxidant, e.g. BHT (butylated hydroxytoluene) is added to the composition.

In certain embodiments, the curing step c) leads to a decrease in the density of the extended release matrix formulation, such that the density of the cured extended release matrix formulation is lower than the density of the extended release matrix formulation prior to the curing step c). Preferably, the density of the cured extended release matrix formulation in comparison to the density of the uncured extended release matrix formulation decreases by at least about 0.5%. More preferably, the density of the cured extended release matrix formulation in comparison to the density of the uncured extended release matrix formulation decreases by at least about 0.7%, at least about 0.8%, at least about 1.0%, at least about 2.0% or at least about 2.5%. Without wanting to be bound by any theory, it is believed that the extended release matrix formulation, due to the absence of elevated pressure during the curing step c), expands, resulting in a density decrease.

According to a further aspect of the invention, the density of the extended release matrix formulation in the solid oral extended release pharmaceutical dosage form, preferably in a dosage form containing oxycodone HCl as active agent, is equal to or less than about 1.20 g/cm³. Preferably, it is equal to or less than about 1.19 g/cm³, equal to or less than about 1.18 g/cm³, or equal to or less than about 1.17 g/cm³. For example, the density of the extended release matrix formulation is in the range of from about 1.10 g/cm³ to about 1.20 g/cm³, from about 1.11 g/cm³ to about 1.20 g/cm³, or from about 1.11 g/cm³ to about 1.19 g/cm³. Preferably it is in the range of from about 1.12 g/cm³ to about 1.19 g/cm³ or from about 1.13 g/cm³ to about 1.19 g/cm³, more preferably from about 1.13 g/cm³ to about 1.18 g/cm³.

The density of the extended release matrix formulation is preferably determined by Archimedes Principle using a liquid of known density ($\rho_0$). The extended release matrix formulation is first weighed in air and then immersed in a liquid and weighed. From these two weights, the density of the extended release matrix formulation $\rho$ can be determined by the equation:

$$\rho = \frac{A}{A-B} \cdot \rho_0$$

wherein $\rho$ is the density of the extended release matrix formulation, A is the weight of the extended release matrix formulation in air, B is the weight of the extended release matrix formulation when immersed in a liquid and $\rho_0$ is the density of the liquid at a given temperature. A suitable liquid of known density $\rho_0$ is for example hexane.

Preferably, the density of an extended release matrix formulation is measured using a Top-loading Mettler Toledo balance Model #AB 135-S/FACT. Serial #1127430072 and a density determination kit 33360. Preferably, hexane is used as liquid of known density $\rho_0$.

The density values throughout this document correspond to the density of the extended release matrix formulation at room temperature.

The density of the extended release matrix formulation preferably refers to the density of the uncoated formulation, for example to the density of a core tablet. In those embodiments, wherein the extended release matrix formulation is coated, for example wherein the extended release matrix formulation is subjected to a coating step d) after the curing step c), the density of the extended release matrix formulation is preferably measured prior to performing the coating step, or by removing the coating from a coated extended release matrix formulation and subsequently measuring the density of the uncoated extended release matrix formulation.

In the above described embodiments high molecular weight polyethylene oxide having, based on rheological measurements, an approximate molecular weight of from 2,000,000 to 15,000,000 or from 2,000,000 to 8,000,000 may be used. In particular polyethylene oxides having, based on rheological measurements, an approximate molecular weight of 2,000,000, 4,000,000, 7,000,000 or 8,000,000 may be used. In particular polyethylene oxides having, based on rheological measurements, an approximate molecular weight of 4,000,000, may be used.

In embodiments wherein the composition further comprises at least one low molecular weight polyethylene oxide is used polyethylene oxides having, based on rheological measurements, an approximate molecular weight of less than 1,000,000, such as polyethylene oxides having, based on rheological measurements, an approximate molecular weight of from 100,000 to 900,000 may be used. The addition of such low molecular weight polyethylene oxides may be used to specifically tailor the release rate such as enhance the release rate of a formulation that otherwise provides a release rate to slow for the specific purpose. In such embodiments at least one polyethylene oxide having, based on rheological measurements, an approximate molecular weight of 100,000 may be used.

In certain such embodiments the composition comprises at least one polyethylene oxide having, based on rheological measurements, an approximate molecular weight of at least 1,000,000 and at least one polyethylene oxide having, based on rheological measurements, an approximate molecular weight of less than 1,000,000, wherein the composition comprises at least about 10% (by wt) or at least about 20% (by wt) of the polyethylene oxide having, based on rheological measurements, an approximate molecular weight of less than 1,000,000. In certain such embodiments the curing temperature is less than about 80° C. or even less than about 77° C.

In certain embodiments the overall content of polyethylene oxide in the composition is at least about 80% (by wt). Without wanting to be bound to any theory it is believed that high contents of polyethylene oxide provide for the tamper resistance as described herein, such as the breaking strength and the resistance to alcohol extraction. According to certain such embodiments the active agent is oxycodone hydrochloride and the composition comprises more than about 5% (by wt) of the oxycodone hydrochloride.

In certain such embodiments the content in the composition of the at least one polyethylene oxide having, based on rheological measurements, an approximate molecular weight of at least 1,000,000 is at least about 80% (by wt). In certain embodiments the content in the composition of the at least one polyethylene oxide having, based on rheological measurements, an approximate molecular weight of at least 1,000,000 is at least about 85% or at least about 90% (by wt). In such embodiments a polyethylene oxide having, based on rheological measurements, an approximate molecular weight of at least 4,000,000 or at least 7,000,000 may be employed. In certain such embodiments the active agent is oxycodone hydrochloride or hydromorphone hydrochloride, although other active agents can also be used according to this aspect of the invention, and the composition comprises more than about 5% (by wt) oxycodone hydrochloride or hydromorphone hydrochloride.

In certain embodiments wherein the amount of drug in the composition is at least about 20% (by wt) the polyethylene oxide content may be as low as about 75% (by wt). In another embodiment, wherein the amount of drug in the composition is in the range of from about 25% (by wt) to about 35% (by wt), the polyethylene oxide content may be in the range of from about 65% (by wt) to about 75% (by wt). For example, in embodiments wherein the amount of drug in the composition is about 32% (by wt) the polyethylene oxide content may be about 67% (by wt).

In certain embodiments of the invention magnesium stearate is added during or after the curing process/curing step in order to avoid that the tablets stick together. In certain such embodiments the magnesium stearate is added at the end of the curing process/curing step before cooling the tablets or during the cooling of the tablets. Other anti-tacking agents that could be used would be talc, silica, fumed silica, colloidal silica dioxide, calcium stearate, carnauba wax, long chain fatty alcohols and waxes, such as stearic acid and stearyl alcohol, mineral oil, paraffin, micro crystalline cellulose, glycerin, propylene glycol, and polyethylene glycol. Additionally or alternatively the coating can be started at the high temperature.

In certain embodiments, wherein curing step c) is carried out in a coating pan, sticking of tablets can be avoided or sticking tablets can be separated by increasing the pan speed during the curing step or after the curing step, in the latter case for example before or during the cooling of the tablets. The pan speed is increased up to a speed where all tablets are separated or no sticking occurs.

In certain embodiments of the invention, an initial film coating or a fraction of a film coating is applied prior to performing curing step c). This film coating provides an "overcoat" for the extended release matrix formulations or tablets to function as an anti-tacking agent, i.e. in order to avoid that the formulations or tablets stick together. In certain such embodiments the film coating which is applied prior to the curing step is an Opadry film coating. After the curing step c), a further film coating step can be performed.

The present invention encompasses also any solid oral extended release pharmaceutical dosage form obtainable by a process according to any process as described above.

Independently, the present invention is also directed to solid oral extended release pharmaceutical dosage forms.

In certain embodiments the invention is directed to solid oral extended release pharmaceutical dosage forms comprising an extended release matrix formulation comprising an active agent in the form of a tablet or multi particulates, wherein the tablet or the individual multi particulates can at least be flattened without breaking, characterized by a thickness of the tablet or of the individual multi particulate after the flattening which corresponds to no more than about 60% of the thickness of the tablet or the individual multi particulate before flattening, and wherein said flattened tablet or the flattened multi particulates provide an in-vitro dissolution rate, when measured in a USP Apparatus 1 (basket) at 100 rpm in 900 ml simulated gastric fluid without enzymes (SGF) at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points at each of said time points from the corresponding in-vitro dissolution rate of a non-flattened reference tablet or reference multi particulates.

In certain such embodiments the tablet or the individual multi particulates can at least be flattened without breaking, characterized by a thickness of the tablet or the individual multi particulate after the flattening which corresponds to no more than about 50%, or no more than about 40%, or no more than about 30%, or no more than about 20%, or no more than about 16% of the thickness of the tablet or the individual multi particulate before flattening, and wherein said flattened tablet or the flattened multi particulates provide an in-vitro dissolution rate, when measured in a USP Apparatus 1 (basket) at 100 rpm in 900 ml simulated gastric fluid without enzymes (SGF) at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points or no more than about 15% points at each of said time points from the corresponding in-vitro dissolution rate of a non-flattened reference tablet or reference multi particulates.

In certain embodiments, the present invention is directed to a solid oral extended release pharmaceutical dosage form comprising an extended release matrix formulation comprising an active agent in the form of a tablet or multi particulates,
  wherein the tablet or the individual multi particulates can at least be flattened without breaking, characterized by a thickness of the tablet or of the individual multi particulate after the flattening which corresponds to no more than about 60% of the thickness of the tablet or the individual multi particulate before flattening, and wherein said flattened tablet or the flattened multi particulates and the non-flattened reference tablet or reference multi particulates provide an in-vitro dissolution rate, which when measured in a USP Apparatus 1 (basket) at 100 rpm in 900 ml simulated gastric fluid without enzymes (SGF) at 37° C., is between about 5 and about 40% (by wt) active agent released after 0.5 hours.

In certain such embodiments, the tablet or the individual multi particulates can at least be flattened without breaking, characterized by a thickness of the tablet or of the individual multi particulate after the flattening which corresponds to no more than about 50%, or no more than about 40%, or no more than about 30%, or no more than about 20%, or no more than about 16% of the thickness of the tablet or the individual multi particulate before flattening, and wherein said flattened tablet or the flattened multi particulates and the non-flattened reference tablet or reference multi particulates provide an in-vitro dissolution rate, which when measured in a USP Apparatus 1 (basket) at 100 rpm in 900 ml simulated gastric fluid without enzymes (SGF) at 37° C., is between about 5 and about 40% (by wt) active agent released after 0.5 hours or is between about 5 and about 30% (by wt) active agent released after 0.5 hours or is between about 5 and about 20% (by wt) active agent released after 0.5 hours or is between about 10 and about 18% (by wt) active agent released after 0.5 hours.

In certain embodiments the invention is directed to a solid oral extended release pharmaceutical dosage form comprising an extended release matrix formulation comprising an active agent in the form of a tablet or multi particulates, wherein the tablet or the individual multi particulates can at least be flattened without breaking, characterized by a thickness of the tablet or the individual multi particulate after the flattening which corresponds to no more than about 60% of the thickness of the tablet or the individual multi particulate before flattening, and wherein the flattened or non flattened tablet or the flattened or non flattened multi particulates provide an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points at each time point from the corresponding in-vitro dissolution rate measured in a USP Apparatus 1 (basket) at 100 rpm in 900 ml simulated gastric fluid without enzymes (SGF) at 37° C. without ethanol, using a flattened and non flattened reference tablet or flattened and non flattened reference multi particulates, respectively.

In certain such embodiments the tablet or the multi particulates can at least be flattened without breaking, characterized by a thickness of the tablet or the individual multi particulate after the flattening which corresponds to no more than about 60%, or no more than about 50%, or no more than about 40%, or no more than about 30%, or no more than about 20%, or no more than about 16% of the thickness of the tablet or the individual multi particulate before flattening, and wherein the flattened or non flattened tablet or the individual multi particulates provide an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points or no more than about 15% points at each of said time points from the corresponding in-vitro dissolution rate measured in a USP Apparatus 1 (basket) at 100 rpm in 900 ml simulated gastric fluid without enzymes (SGF) at 37° C. without ethanol, using a flattened and a non flattened reference tablet or reference multi particulates, respectively.

In certain embodiments, the present invention is directed to a solid oral extended release pharmaceutical dosage form comprising an extended release matrix formulation comprising an active agent in the form of a tablet or multi particulates,
  wherein the tablet or the individual multi particulates can at least be flattened without breaking, characterized by a thickness of the tablet or the individual multi particulate after the flattening which corresponds to no more than about 60% of the thickness of the tablet or the individual multi particulate before flattening, and wherein the flattened or non flattened tablet or the flattened or non flattened multi particulates provide an in-vitro dissolution rate, which when measured in a USP Apparatus 1 (basket) at 100 rpm in 900 ml simulated gastric fluid without enzymes (SGF) comprising 40% or 0% ethanol at 37° C., is between about 5 and about 40% (by wt) active agent released after 0.5 hours.

In certain such embodiments, the tablet or the individual multi particulates can at least be flattened without breaking, characterized by a thickness of the tablet or the individual multi particulate after the flattening which corresponds to no more than about 50%, or no more than about 40%, or no more than about 30%, or no more than about 20%, or no more than about 16% of the thickness of the tablet or the individual multi particulate before flattening, and wherein the flattened or non flattened tablet or the flattened or non flattened multi particulates provide an in-vitro dissolution rate, which when measured in a USP Apparatus 1 (basket) at 100 rpm in 900 ml simulated gastric fluid without enzymes (SGF) comprising 40% or 0% ethanol at 37° C., is between about 5 and about 40% (by wt) active agent released after 0.5 hours or is between about 5 and about 30% (by wt) active agent released after 0.5 hours or is between about 5 and about 20% (by wt) active agent released after 0.5 hours or is between about 10 and about 18% (by wt) active agent released after 0.5 hours.

Such dosage forms may be prepared as described above.

In certain embodiments the invention is directed to a solid oral extended release pharmaceutical dosage form comprising an extended release matrix formulation, the extended release matrix formulation comprising a composition comprising at least:
  (1) at least one polyethylene oxide having, based on rheological measurements, an approximate molecular weight of at least 1,000,000; and
  (2) at least one active agent, preferably selected from opioid analgesics; and
  wherein the composition comprises at least about 80% (by wt) polyethylene oxide. The composition may also comprise at least about 85 or 90% (by wt) polyethylene oxide. According to certain such embodiments wherein the composition comprises at least about 80% (by wt) polyethylene oxide, the active agent is oxycodone hydrochloride or hydromorphone hydrochloride and the composition comprises more than about 5% (by wt) of the oxycodone hydrochloride or hydromorphone hydrochloride.

In certain such embodiments the composition comprises at least about 80% (by wt) polyethylene oxide having, based on rheological measurements, an approximate molecular weight of at least 1,000,000.

In certain embodiments, the present invention is directed to a solid oral extended release pharmaceutical dosage form comprising an extended release matrix formulation, the extended release matrix formulation comprising a composition comprising at least:
  (1) at least one polyethylene oxide having, based on rheological measurements, an approximate molecular weight of at least 1,000,000; and
  (2) 10 mg oxycodone hydrochloride; and
  wherein the composition comprises at least about 85% (by wt) polyethylene oxide.

In certain embodiments, the present invention is directed to a solid oral extended release pharmaceutical dosage form comprising an extended release matrix formulation, the extended release matrix formulation comprising a composition comprising at least:
  (1) at least one polyethylene oxide having, based on rheological measurements, an approximate molecular weight of at least 1,000,000; and
  (2) 15 mg or 20 mg oxycodone hydrochloride; and
  wherein the composition comprises at least about 80% (by wt) polyethylene oxide.

In certain embodiments, the present invention is directed to a solid oral extended release pharmaceutical dosage form comprising an extended release matrix formulation, the extended release matrix formulation comprising a composition comprising at least:
  (1) at least one polyethylene oxide having, based on rheological measurements, an approximate molecular weight of at least 1,000,000; and
  (2) 40 mg oxycodone hydrochloride; and
  wherein the composition comprises at least about 65% (by wt) polyethylene oxide.

In certain embodiments, the present invention is directed to a solid oral extended release pharmaceutical dosage form comprising an extended release matrix formulation, the extended release matrix formulation comprising a composition comprising at least:
  (1) at least one polyethylene oxide having, based on rheological measurements, an approximate molecular weight of at least 1,000.000; and
  (2) 60 mg or 80 mg oxycodone hydrochloride; and
  wherein the composition comprises at least about 60% (by wt) polyethylene oxide.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) 8 mg hydromorphone hydrochloride; and
- wherein the composition comprises at least about 94% (by wt) polyethylene oxide.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) 12 mg hydromorphone hydrochloride; and
- wherein the composition comprises at least about 92% (by wt) polyethylene oxide.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) 32 mg hydromorphone hydrochloride; and
- wherein the composition comprises at least about 90% (by wt) polyethylene oxide.

In certain embodiments the present invention is directed to a solid oral extended release pharmaceutical dosage form comprising an extended release matrix formulation, the extended release matrix formulation comprising a composition comprising at least:
- (1) at least one active agent, preferably selected from opioid analgesics;
- (2) at least one polyethylene oxide having, based on rheological measurements, an approximate molecular weight of at least 1,000,000; and
- (3) at least one polyethylene oxide having, based on rheological measurements, an approximate molecular weight of less than 1,000,000. In certain such embodiments the composition comprises at least about 80% (by wt) of polyethylene oxide. The composition may also comprise at least about 85 or 90% (by wt) polyethylene oxide. According to certain such embodiments wherein the composition comprises at least about 80% (by wt) polyethylene oxide, the active agent is oxycodone hydrochloride or hydromorphone hydrochloride and the composition comprises more than about 5% (by wt) of the oxycodone hydrochloride or the hydromorphone hydrochloride. The composition may also comprise 15 to 30% (by wt) of polyethylene oxide having, based on rheological measurements, a molecular weight of at least 1,000,000; and 65 to 80% (by wt) polyethylene oxide having, based on rheological measurements, a molecular weight of less than 1,000,000, or the composition may comprise at least about 20% (by wt) or at least about 30% (by wt) or at least about 50% (by wt) of polyethylene oxide having, based on rheological measurements, a molecular weight of at least 1,000,000.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, a molecular weight of at least 800,000 or at least 900,000; and
- (2) at least one active agent selected from opioid analgesics; and
- wherein the composition comprises at least about 80% (by wt) polyethylene oxide.

In certain embodiments of the invention the extended release matrix has a density which is equal to or less than about 1.20 g/cm$^3$. In certain such embodiments, the density of the extended release matrix formulation is equal to or less than about 1.19 g/cm$^3$, preferably equal to or less than about 1.18 g/cm$^3$ or equal to or less than about 1.17 g/cm$^3$. For example, the density of the extended release matrix formulation is in the range of from about 1.10 g/cm$^3$ to about 1.20 g/cm$^3$, from about 1.11 g/cm$^3$ to about 1.20 g/cm$^3$, or from about 1.11 g/cm$^3$ to about 1.19 g/cm$^3$. Preferably it is in the range of from about 1.12 g/cm$^3$ to about 1.19 g/cm$^3$ or from about 1.13 g/cm$^3$ to about 1.19 g/cm$^3$, more preferably from about 1.13 g/cm$^3$ to about 1.18 g/cm$^3$. Preferably, the density is determined by Archimedes principle, as described above.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) at least one active agent; and
- wherein the extended release matrix formulation when subjected to an indentation test has a cracking force of at least about 110 N.

In certain embodiments of the invention the extended release matrix formulation has a cracking force of at least about 110 N, preferably of at least about 120 N, at least about 130 N or at least about 140 N, more preferably of at least about 150 N, at least about 160 N or at least about 170 N, most preferably of at least about 180 N, at least about 190 N or at least about 200 N.

In certain embodiments, the present invention is directed to a solid oral extended release pharmaceutical dosage form comprising an extended release matrix formulation, the extended release matrix formulation comprising a composition comprising at least:
- (1) at least one polyethylene oxide having, based on rheological measurements, an approximate molecular weight of at least 1,000,000; and
- (2) at least one active agent; and
- wherein the extended release matrix formulation when subjected to an indentation test has a "penetration depth to crack distance" of at least about 1.0 mm.

In certain embodiments of the invention the extended release matrix formulation has a "penetration depth to crack" distance of at least about 1.0 mm or at least about 1.2 mm, preferably of at least about 1.4 mm, at least about 1.5 mm or at least about 1.6 mm, more preferably of at least about 1.8 mm, at least about 1.9 mm or at least about 2.0 mm, most preferably of at least about 2.2 mm, at least about 2.4 mm or at least about 2.6 mm.

In certain such embodiments of the invention the extended release matrix formulation has a cracking force of at least about 110 N, preferably of at least about 120 N, at least about 130 N or at least about 140 N, more preferably of at least about 150 N, at least about 160 N or at least about 170 N, most preferably of at least about 180 N, at least about 190 N or at least about 200 N, and/or a "penetration depth to crack"

distance of at least about 1.0 mm or at least about 1.2 mm, preferably of at least about 1.4 mm, at least about 1.5 mm or at least about 1.6 mm, more preferably of at least about 1.8 mm, at least about 1.9 mm or at least about 2.0 mm, most preferably of at least about 2.2 mm, at least about 2.4 mm or at least about 2.6 mm. A combination of any of the aforementioned values of cracking force and "penetration depth to crack" distance is included in the scope of the present invention.

In certain such embodiments the extended release matrix formulation when subjected to an indentation test resists a work of at least about 0.06 J or at least about 0.08 J, preferably of at least about 0.09 J, at least about 0.11 J or at least about 0.13 J, more preferably of at least about 0.15 J, at least about 0.17 J or at least about 0.19 J, most preferably of at least about 0.21 J, at least about 0.23 J or at least about 0.25 J, without cracking.

The parameters "cracking force", "penetration depth to crack distance" and "work" are determined in an indentation test as described above, using a Texture Analyzer such as the TA-XT2 Texture Analyzer (Texture Technologies Corp., 18 Fairview Road, Scarsdale, N.Y. 10583). The cracking force and/or "penetration depth to crack" distance can be determined using an uncoated or a coated extended release matrix formulation. Preferably, the cracking force and/or "penetration depth to crack" distance are determined on the uncoated extended release matrix formulation. Without wanting to be bound by any theory, it is believed that a coating, such as the coating applied in step d) of the manufacturing process of the solid oral extended release pharmaceutical dosage form as described above, does not significantly contribute to the observed cracking force and/or "penetration depth to crack" distance. Therefore, the cracking force and/or "penetration depth to crack" distance determined for a specific coated extended release matrix formulation are not expected to vary substantially from the values determined for the corresponding uncoated extended release matrix formulation.

In certain embodiments the extended release matrix formulation is in the form of a tablet or multi particulates, and the tablet or the individual multi particulates can at least be flattened without breaking, characterized by a thickness of the tablet or of the individual multi particulate after the flattening which corresponds to no more than about 60% of the thickness of the tablet or the individual multi particulate before flattening. Preferably, the tablet or the individual multi particulates can at least be flattened without breaking, characterized by a thickness of the tablet or the individual multi particulate after the flattening which corresponds to no more than about 50%, or no more than about 40%, or no more than about 30%, or no more than about 20%, or no more than about 16% of the thickness of the tablet or the individual multi particulate before flattening.

Preferably, the flattening of the tablets or the individual multi particulates is performed with a bench press, such as a carver style bench press, or with a hammer, as described above.

In certain such embodiments the extended release matrix formulation is in the form of a tablet or multi particulates, and the tablet or the individual multi particulates can at least be flattened without breaking, characterized by a thickness of the tablet or of the individual multi particulate after the flattening which corresponds to no more than about 60% of the thickness of the tablet or the individual multi particulate before flattening, and wherein said flattened tablet or the flattened multi particulates provide an in-vitro dissolution rate, when measured in a USP Apparatus 1 (basket) at 100 rpm in 900 ml simulated gastric fluid without enzymes (SGF) at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points at each of said time points from the corresponding in-vitro dissolution rate of a non-flattened reference tablet or reference multi particulates. Preferably, the tablet or the individual multi particulates can at least be flattened without breaking, characterized by a thickness of the tablet or the individual multi particulate after the flattening which corresponds to no more than about 50%, or no more than about 40%, or no more than about 30%, or no more than about 20%, or no more than about 16% of the thickness of the tablet or the individual multi particulate before flattening, and wherein said flattened tablet or the flattened multi particulates provide an in-vitro dissolution rate, when measured in a USP Apparatus 1 (basket) at 100 rpm in 900 ml simulated gastric fluid without enzymes (SGF) at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points or no more than about 15% points at each of said time points from the corresponding in-vitro dissolution rate of a non-flattened reference tablet or reference multi particulates.

In certain embodiments the invention is directed to a solid oral extended release pharmaceutical dosage form comprising an extended release matrix formulation, wherein the extended release matrix formulation is in the form of a tablet or multi particulates, and the tablet or the individual multi particulates can at least be flattened without breaking, characterized by a thickness of the tablet or of the individual multi particulate after the flattening which corresponds to no more than about 60% of the thickness of the tablet or the individual multi particulate before flattening, and wherein the flattened or non flattened tablet or the flattened or non flattened multi particulates provide an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points at each time points from the corresponding in-vitro dissolution rate measured in a USP Apparatus 1 (basket) at 100 rpm in 900 ml simulated gastric fluid without enzymes (SGF) at 37° C. without ethanol, using a flattened and non flattened reference tablet or flattened and non flattened reference multi particulates, respectively. Preferably, the tablet or the multi particulates can at least be flattened without breaking, characterized by a thickness of the tablet or the individual multi particulate after the flattening which corresponds to no more than about 60%, or no more than about 50%, or no more than about 40%, or no more than about 30%, or no more than about 20%, or no more than about 16% of the thickness of the tablet or the individual multi particulate before flattening, and wherein the flattened or non flattened tablet or the individual multi particulates provide an in-vitro dissolution rate, when measured in a USP Apparatus 1 (basket) at 100 rpm in 900 ml simulated gastric fluid without enzymes (SGF) comprising 40% ethanol at 37° C., characterized by the percent amount of active released at 0.5 hours or at 0.5 and 0.75 hours, or at 0.5, 0.75 and 1 hours, or at 0.5, 0.75, 1 and 1.5 hours or at 0.5, 0.75, 1, 1.5 and 2 hours of dissolution that deviates no more than about 20% points or no more than about 15% points at each of said time points from the corresponding in-vitro dissolution rate measured in a USP Apparatus 1 (basket) at 100 rpm in 900 ml simulated gastric fluid without enzymes (SUE) at 37° C. without ethanol, using a flattened and a non flattened reference tablet or reference multi particulates, respectively.

In certain such embodiments the extended release matrix formulation, when subjected to a maximum force of about 196 N or about 439 N in a tablet hardness test, does not break.

Preferably, the tablet hardness test to determine the breaking strength of extended release matrix formulations is performed in a Schleuniger Apparatus as described above. For example, the breaking strength is determined using a Schleuniger 2E/106 Apparatus and applying a force of a maximum of about 196 N, or a Schleuniger Model 6D Apparatus and applying a force of a maximum of about 439 N.

It has also been observed that formulations of the present invention are storage stable, wherein the extended release matrix formulation after having been stored at 25° C. and 60% relative humidity (RH) or 40° C. and 75% relative humidity (RH) for at least 1 month, more preferably for at least 2 months, for at least 3 months or for at least 6 months, provides a dissolution rate, when measured in a USP Apparatus 1 (basket) at 100 rpm in 900 ml simulated gastric fluid without enzymes (SGF) at 37° C., characterized by the percent amount of active released at 1 hours or at 1 and 2 hours, or at 1 and 4 hours, or at 1, 2 and 4 hours, or at 1, 4 and 12 hours, or at 1, 2, 4 and 8 hours or at 1, 2, 4, 8 and 12 hours of dissolution that deviates no more than about 15% points, preferably no more than about 12% points or no more than about 10% points, more preferably no more than about 8% points or no more than about 6% points, most preferably no more than about 5% points at each of said time points from the corresponding in-vitro dissolution rate of a reference formulation prior to storage. Preferably, the extended release matrix formulation is stored in count bottles, such as 100 count bottles. Any combination of the aforementioned storage times, dissolution time points and deviation limits lies within the scope of the present invention.

According to a further storage stability aspect the extended release matrix formulation after having been stored at 25° C. and 60% relative humidity (RH) or at 40° C. and 75% relative humidity (RH) for at least 1 month, more preferably for at least 2 months, for at least 3 months or for at least 6 months, contains an amount of the at least one active agent in % (by wt) relative to the label claim of the active agent for the extended release matrix formulation that deviates no more than about 10% points, preferably no more than about 8% points or no more than about 6% points, more preferably no more than about 5% points or no more than about 4% points or no more than about 3% points from the corresponding amount of active agent in % (by wt) relative to the label claim of the active agent for the extended release matrix formulation of a reference formulation prior to storage. Preferably, the extended release matrix formulation is stored in count bottles, such as 100 count bottles. Any combination of the aforementioned storage times and deviation limits lies within the scope of the present invention.

According to certain such embodiments the active agent is oxycodone hydrochloride.

Preferably, the amount of the at least one active agent in % (by wt) relative to the label claim of the active agent for the extended release matrix formulation is determined by extracting the at least one active agent from the extended release matrix formulation and subsequent analysis using high performance liquid chromatography. In certain embodiments, wherein the at least one active agent is oxycodone hydrochloride, preferably the amount of oxycodone hydrochloride in % (by wt) relative to the label claim of oxycodone hydrochloride for the extended release matrix formulation is determined by extracting the oxycodone hydrochloride from the extended release matrix formulation with a 1:2 mixture of acetonitrile and simulated gastric fluid without enzyme (SGF) under constant magnetic stirring until the extended release matrix formulation is completely dispersed or for overnight and subsequent analysis using high performance liquid chromatography, preferably reversed-phase high performance liquid chromatography. In certain such embodiments, wherein the extended release matrix formulation is in the form of tablets, preferably the amount of oxycodone hydrochloride in % (by wt) relative to the label claim of oxycodone hydrochloride for the tablets is determined by extracting oxycodone hydrochloride from two sets of ten tablets each with 900 mL of a 1:2 mixture of acetonitrile and simulated gastric fluid without enzyme (SGF) under constant magnetic stirring until the tablets are completely dispersed or for overnight and subsequent analysis using high performance liquid chromatography, preferably reversed-phase high performance liquid chromatography. Preferably, the assay results are mean values on two measurements.

In certain embodiments the invention is directed to a solid oral extended release pharmaceutical dosage form wherein the dosage form provides a dissolution rate, which when measured in a USP Apparatus 1 (basket) at 100 rpm in 900 ml simulated gastric fluid without enzymes (SGF) at 37° C., is between 12.5 and 55% (by wt) active agent released after 1 hour, between 25 and 65% (by wt) active agent released after 2 hours, between 45 and 85% (by wt) active agent released after 4 hours and between 55 and 95% (by wt) active agent released after 6 hours, and optionally between 75 and 100% (by wt) active agent released after 8 hours. Preferably, the dosage form provides a dissolution rate, which when measured in a USP Apparatus 1 (basket) at 100 rpm in 900 ml simulated gastric fluid without enzymes (SGF) at 37° C., between 15 and 45% (by wt) active released after 1 hour, is between 30 and 60% (by wt) active agent released after 2 hours, between 50 and 80% (by wt) active agent released after 4 hours and between 60 and 90% (by wt) active agent released after 6 hours and optionally between 80 and 100% (by wt) active agent released after 8 hours. More preferably, the dosage form provides a dissolution rate, which when measured in a USP Apparatus 1 (basket) at 100 rpm in 900 ml simulated gastric fluid without enzymes (SGF) at 37° C., is between 17.5 and 35% (by wt) active agent released after 1 hour, between 35 and 55% (by wt) active agent released after 2 hours, between 55 and 75% (by wt) active agent released after 4 hours and between 65 and 85% (by wt) active agent released after 6 hours and optionally between 85 and 100% (by wt) active agent released after 8 hours.

In certain such embodiments the active agent is oxycodone hydrochloride or hydromorphone hydrochloride.

Such dosage forms may be prepared by the process as described herein.

In embodiments as described above the tablet may be formed by direct compression of the composition and cured by at least subjecting said tablet to a temperature of at least about 60° C., at least about 62° C., at least about 68° C., at least about 70° C., at least about 72° C. or at least about 75° C. for a time period of at least about 1 minute, at least about 5 minutes or at least about 15 minutes.

In certain embodiments of the invention the tablet as described above may be over coated with a polyethylene oxide powder layer by applying to the cured or uncured tablet a powder layer of polyethylene oxide surrounding the core and cure the powder layered tablet as described above. Such an outer polyethylene oxide layer provides a lag time before the release of the active agent starts and/or a slower overall release rate.

In certain embodiments of the invention a stacked bi or multi layered tablet is manufactured, wherein at least one of the layers contains an extended release formulation as described above and at least one of the other layers contains an immediate release formulation of the active agent contained by the extended release formulation or a second different active agent. In certain such embodiments the tablet is a bi layered tablet with on extended release formulation layer as described herein and an immediate release formulation layer. In certain such embodiments, in particular the bi layered tablets, opioid analgesics are contained by the extended release layer and further non opioid analgesics are contained by the immediate release layer. Non opioid analgesics may be non steroidal anti inflammatory agents but also non opioid analgesics such as acetaminophen. Acetaminophen can e.g. be used in combination with hydrocodone as opioid analgesic. Such tablets can be prepared by specific tablet compression techniques which allow the compression of at least two compositions to form tablets with at least two distinct stacked layers each comprising one of the at least two compositions. For example, such tablets can be manufactured in a tablet press by filling the compression tool with the first composition and compressing said first composition and subsequently filling on top of the compressed first composition the second composition and subsequently compressing the two compositions to form the final layered tablet. The immediate release composition may be any composition as known in the art.

The invention also encompasses the use of high molecular weight polyethylene oxide that has, based on rheological measurements, an approximate molecular weight of at least 1,000,000, as matrix forming material in the manufacture of a solid extended release oral dosage form comprising an active selected from opioids for imparting to the solid extended release oral dosage form resistance to alcohol extraction. The use may be accomplished as described herein with respect to the described process or the described formulations or in any other way as conventional in the art.

It has been observed that the formulations of the present invention comprising a high molecular weight polyethylene oxide can be flattened to a thickness of between about 15 and about 18% of the non flattened thickness and that the flat tablet resumes in part or substantially resumes its initial non flattened shape during dissolution, neglecting the swelling that also takes place during dissolution, i.e. the thickness of the tablet increases and the diameter decreases considerably during dissolution. Without wanting to be bound to any theory it is believed that the high molecular weight polyethylene oxide has a form memory and the ability to restore the initial form after deformation, e.g. after flattening, in an environment that allows the restoration, such as an aqueous environment used in dissolution tests. This ability is believed to contribute to the tamper resistance, in particular the alcohol resistance of the dosage forms of the present invention.

The invention also encompasses the method of treatment wherein a dosage form is administered for treatment of a disease or certain condition of a patient that requires treatment in particular pain and the use of a dosage form according to the invention for the manufacture of a medicament for the treatment of a disease or certain condition of a patient that requires treatment in particular pain.

In one aspect of the present invention, a twice-a-day solid oral extended release pharmaceutical dosage form is provided which provides a mean $t_{max}$ at about 2 to about 6 hours or at about 2.5 to about 5.5 hours or at about 2.5 to about 5 hours after administration at steady state or of a single dose to human subjects. The dosage form may comprises oxycodone or a salt thereof or hydromorphone or a salt thereof.

In one aspect of the present invention, a once-a-day solid oral extended release pharmaceutical dosage form is provided which provides a mean $t_{max}$ at about 3 to about 10 hours or at about 4 to about 9 hours or at about 5 to about 8 hours after administration at steady state or of a single dose to human subjects. The dosage form may comprises oxycodone or a salt thereof or hydromorphone or a salt thereof.

In a further aspect of the present invention, a twice-a-day solid oral extended release pharmaceutical dosage form is provided, wherein the dosage form comprises oxycodone or a salt thereof in an amount of from about 10 mg to about 160 mg and wherein the dosage form provides a mean maximum plasma concentration ($C_{max}$) of oxycodone up to about 240 ng/mL or from about 6 ng/mL to about 240 ng/mL after administration at steady state or of a single dose to human subjects.

In a further aspect of the present invention, a solid oral extended release pharmaceutical dosage form is provided, wherein the dosage form comprises oxycodone or a salt thereof in an amount of from about 10 mg to about 40 mg and wherein the dosage form provides a mean maximum plasma concentration ($C_{max}$) of oxycodone from about 6 ng/mL to about 60 ng/mL after administration at steady state or of a single dose to human subjects.

In a further aspect of the invention a solid oral extended release pharmaceutical dosage form is provided that is bioequivalent to the commercial product OxyContin™.

In a further aspect of the invention a solid oral extended release pharmaceutical dosage form is provided that is bioequivalent to the commercial product Palladone™ as sold in the United States in 2005.

In a further aspect of the invention, a solid oral extended release pharmaceutical dosage form is provided, wherein the active agent is oxycodone hydrochloride and wherein a dosage form comprising 10 mg of oxycodone hydrochloride when tested in a comparative clinical study is bioequivalent to a reference tablet containing 10 mg of oxycodone hydrochloride in a matrix formulation containing:
- a) Oxycodone hydrochloride: 10.0 mg/tablet
- b) Lactose (spray-dried): 69.25 mg/tablet
- c) Povidone: 5.0 mg/tablet
- d) Eudragit® RS 30D (solids): 10.0 mg/tablet
- e) Triacetin®: 2.0 mg/tablet
- f) Stearyl alcohol: 25.0 mg/tablet
- g) Talc: 2.5 mg/tablet
- h) Magnesium Stearate: 1.25 mg/tablet;

and wherein the reference tablet is prepared by the following steps:
1. Eudragit® RS 30D and Triacetin® are combined while passing through a 60 mesh screen, and mixed under low shear for approximately 5 minutes or until a uniform dispersion is observed.
2. Oxycodone HCl, lactose, and povidone are placed into a fluid bed granulator/dryer (FBD) bowl, and the suspension sprayed onto the powder in the fluid bed.
3. After spraying, the granulation is passed through a #12 screen if necessary to reduce lumps.
4. The dry granulation is placed in a mixer.
5. In the meantime, the required amount of stearyl alcohol is melted at a temperature of approximately 70° C.
6. The melted stearyl alcohol is incorporated into the granulation while mixing.

7. The waxed granulation is transferred to a fluid bed granulator/dryer or trays and allowed to cool to room temperature or below.
8. The cooled granulation is then passed through a #12 screen.
9. The waxed granulation is placed in a mixer/blender and lubricated with the required amounts of talc and magnesium stearate for approximately 3 minutes.
10. The granulate is compressed into 125 mg tablets on a suitable tabletting machine.

Pharmacokinetic parameters such as $C_{max}$ and $t_{max}$, $AUC_t$, $AUC_{inf}$, etc. describing the blood plasma curve can be obtained in clinical trials, first by single-dose administration of the active agent, e.g. oxycodone to a number of test persons, such as healthy human subjects. The blood plasma values of the individual test persons are then averaged, e.g. a mean AUC, $C_{max}$ and $t_{max}$ value is obtained. In the context of the present invention, pharmacokinetic parameters such as AUC, $C_{max}$ and $t_{max}$ refer to mean values. Further, in the context of the present invention, in vivo parameters such as values for AUC, $C_{max}$, $t_{max}$, or analgesic efficacy refer to parameters or values obtained after administration at steady state or of a single dose to human patients.

The $C_{max}$ value indicates the maximum blood plasma concentration of the active agent. The $t_{max}$ value indicates the time point at which the $C_{max}$ value is reached. In other words, $t_{max}$ is the time point of the maximum observed plasma concentration.

The AUC (Area Under the Curve) value corresponds to the area of the concentration curve. The AUC value is proportional to the amount of active agent absorbed into the blood circulation in total and is hence a measure for the bioavailability.

The $AUC_t$ value corresponds to the area under the plasma concentration-time curve from the time of administration to the last measurable plasma concentration and is calculated by the linear up/log down trapezoidal rule.

$AUC_{inf}$ is the area under the plasma concentration-time curve extrapolated to infinity and is calculated using the formula:

$$AUC_{inf} = AUC_t + \frac{C_t}{\lambda_Z}$$

where $C_t$ is the last measurable plasma concentration and $\lambda_Z$ is the apparent terminal phase rate constant.

$\lambda_Z$ is the apparent terminal phase rate constant, where $\lambda_Z$ is the magnitude of the slope of the linear regression of the log concentration versus time profile during the terminal phase.

$t_{1/2Z}$ is the apparent plasma terminal phase half-life and is commonly determined as $t_{1/2Z} = (\ln 2)/\lambda_Z$.

The lag time $t_{lag}$ is estimated as the timepoint immediately prior to the first measurable plasma concentration value.

The term "healthy" human subject refers to a male or female with average values as regards height, weight and physiological parameters, such as blood pressure, etc. Healthy human subjects for the purposes of the present invention are selected according to inclusion and exclusion criteria which are based on and in accordance with recommendations of the International Conference for Harmonization of Clinical Trials (ICH).

Thus, inclusion criteria comprise males and females aged between 18 to 50 years, inclusive, a body weight ranging from 50 to 100 kg (110 to 220 lbs) and a Body Mass Index (BMI) ≥18 and ≤34 (kg/m$^2$), that subjects are healthy and free of significant abnormal findings as determined by medical history, physical examination, vital signs, and electrocardiogram, that females of child-bearing potential must be using an adequate and reliable method of contraception, such as a barrier with additional spermicide foam or jelly, an intra-uterine device, hormonal contraception (hormonal contraceptives alone are not acceptable), that females who are post-menopausal must have been postmenopausal ≥1 year and have elevated serum follicle stimulating hormone (FSH), and that subjects are willing to eat all the food supplied during the study.

A further inclusion criterium may be that subjects will refrain from strenuous exercise during the entire study and that they will not begin a new exercise program nor participate in any unusually strenuous physical exertion.

Exclusion criteria comprise that females are pregnant (positive beta human chorionic gonadotropin test) or lactating, any history of or current drug or alcohol abuse for five years, a history of or any current conditions that might interfere with drug absorption, distribution, metabolism or excretion, use of an opioid-containing medication in the past thirty (30) days, a history of known sensitivity to oxycodone, naltrexone, or related compounds, any history of frequent nausea or emesis regardless of etiology, any history of seizures or head trauma with current sequelae, participation in a clinical drug study during the thirty (30) days preceding the initial dose in this study, any significant illness during the thirty (30) days preceding the initial dose in this study, use of any medication including thyroid hormone replacement therapy (hormonal contraception is allowed), vitamins, herbal, and/or mineral supplements, during the 7 days preceding the initial dose, refusal to abstain from food for 10 hours preceding and 4 hours following administration or for 4 hours following administration of the study drugs and to abstain from caffeine or xanthine entirely during each confinement, consumption of alcoholic beverages within forty-eight (48) hours of initial study drug administration (Day 1) or anytime following initial study drug administration, history of smoking or use of nicotine products within 45 days of study drug administration or a positive urine cotinine test, blood or blood products donated within 30 days prior to administration of the study drugs or anytime during the study, except as required by the clinical study protocol, positive results for urine drug screen, alcohol screen at check-in of each period, and hepatitis B surface antigen (HBsAg), hepatitis B surface antibody HBsAb (unless immunized), hepatitis C antibody (anti-HCV), a positive Naloxone HCl challenge test, presence of Gilbert's Syndrome or any known hepatobiliary abnormalities and that the Investigator believes the subject to be unsuitable for reason(s) not specifically stated above.

Subjects meeting all the inclusion criteria and none of the exclusion criteria will be randomized into the study.

The enrolled population is the group of subjects who provide informed consent.

The randomized safety population is the group of subjects who are randomized, receive study drug, and have at least one post dose safety assessment.

The full analysis population for PK metrics will be the group of subjects who are randomized, receive study drug, and have at least one valid PK metric. Subjects experiencing emesis within 12 hours after dosing might be included based on visual inspection of the PK profiles prior to database lock. Subjects and profiles/metrics excluded from the analysis set will be documented in the Statistical Analysis Plan.

For the Naloxone HCl challenge test, vital signs and pulse oximetry (SPO$_2$) are obtained prior to the Naloxone HCl challenge test. The Naloxone HCl challenge may be administered intravenously or subcutaneously. For the intravenous route, the needle or cannula should remain in the arm during administration. 0.2 mg of Naloxone HCl (0.5 mL) are administered by intravenous injection. The subject is observed for 30 seconds for evidence of withdrawal signs or symptoms. Then 0.6 mg of Naloxone HCl (1.5 mL) are administered by intravenous injection. The subject is observed for 20 minutes for signs and symptoms of withdrawal. For the subcutaneous route, 0.8 mg of Naloxone HCl (2.0 mL) are administered and the subject is observed for 20 minutes for signs and symptoms of withdrawal. Following the 20-minute observation, post-Naloxone HCl challenge test vital signs and $SPO_2$ are obtained.

Vital signs include systolic blood pressure, diastolic blood pressure, pulse rate, respiratory rate, and oral temperature.

For the "How Do You Feel?" Inquiry, subjects will be asked a non-leading "How Do You Feel?" question such as "Have there been any changes in your health status since screening/since you were last asked?" at each vital sign measurement. Subject's response will be assessed to determine whether an adverse event is to be reported. Subjects will also be encouraged to voluntarily report adverse events occurring at any other time during the study.

Each subject receiving a fed treatment will consume a standard high-fat content meal in accordance with the "Guidance for Industry: Food-Effect Bioavailability and Fed Bioequivalence Studies" (US Department of Health and Human Services, Food and Drug Administration, Center for Drug Evaluation and Research, December 2002). The meal will be provided 30 minutes before dosing and will be eaten at a steady rate over a 25-minute period so that it is completed by 5 minutes before dosing.

Clinical laboratory evaluations performed in the course of clinical studies include biochemistry (fasted at least 10 hours), hematology, serology, urinalysis, screen for drugs of abuse, and further tests.

Biochemistry evaluations (fasted at least 10 hours) include determination of albumin, Alkaline Phosphatase, alanine aminotransferase (alanine transaminase, ALT), aspartate aminotransferase (aspartate transaminase, AST), calcium, chloride, creatinine, glucose, inorganic phosphate, potassium, sodium, total bilirubin, total protein, urea, lactate dehydrogenase (LDH), direct bilirubin and $CO_2$.

Hematology evaluations include determination of hematocrit, hemoglobin, platelet count, red blood cell count, white blood cell count, white blood cell differential (% and absolute): basophils, eosinophils, lymphocytes, monocytes and neutrophils.

Serology evaluations include determination of hepatitis B surface antigen (HBsAg), hepatitis B surface antibody (HBsAb) and hepatitis C antibody (anti-HCV).

Urinalysis evaluations include determination of color, appearance, pH, glucose, ketones, urobilinogen, nitrite, occult blood, protein, leukocyte esterase, microscopic and macroscopic evaluation, specific gravity.

Screen for drugs of abuse includes urin screen with respect to opiates, amphetamines, cannabinoids, benzodiazepines, cocaine, cotinine, barbiturates, phencyclidine, methadone and propoxyphene and alcohol tests, such as blood alcohol and breathalyzer test.

Further tests for females only include serum pregnancy test, urine pregnancy test and serum follicle stimulating hormone (FSH) test (for self reported postmenopausal females only).

DETAILED DESCRIPTION OF THE PREFERRED EMBODIMENTS

The present invention will now be more fully described with reference to the accompanying examples. It should be understood, however, that the following description is illustrative only and should not be taken in any way as a restriction of the invention.

Example 1

In Example 1 a 200 mg tablet including 10 mg of oxycodone HCl was prepared using high molecular weight polyethylene oxide in combination with hydroxypropyl cellulose.

Composition:

| Ingredient | mg/unit | % |
|---|---|---|
| Oxycodone HCl | 10 | 5 |
| Polyethylene Oxide (MW: approximately 4,000,000; Polyox ™ WSR-301) | 160 | 80 |
| Hydroxypropyl Cellulose (Klucel ™ HXF) | 30 | 15 |
| Total | 200 | 100 |

Process of Manufacture:

The processing steps to manufacture tablets were as follows:

1. Oxycodone HCl, Polyethylene Oxide and hydroxypropyl cellulose was dry mixed in a low/high shear Black & Decker Handy Chopper dual blade mixer with a 1.5 cup capacity.
2. Step 1 blend was compressed to target weight on a single station tablet Manesty Type F 3 press
3. Step 2 tablets were spread onto a tray and placed in a Hotpack model 435304 oven at 70° C. for approximately 14.5 hours to cure the tablets.

In vitro testing including testing tamper resistance (hammer and breaking strength test) and resistance to alcohol extraction was performed as follows.

The tablets were tested in vitro using USP Apparatus 2 (paddle) at 50 rpm in 900 ml simulated gastric fluid without enzymes (SGF) at 37° C., using a Perkin Elmer UV/VIS Spectrometer Lambda 20, UV at 230 nM. The results are presented in Table 1.1.

Uncured tablets, cured tablets and tampered, i.e. flattened, cured tablets were tested. The cured tablets were flattened with a hammer using 7 manually conducted hammer strikes to impart physical tampering. The tablet dimensions before and after the flattening and the dissolution profiles were evaluated on separate samples. The results are presented in Table 1.1.

As a further tamper resistance test, the cured tablets were subjected to a breaking strength test applying a force of a maximum of 196 Newton using a Schleuniger 2E/106 Apparatus to evaluate the resistance to breaking. The results are also presented in Table 1.1.

In addition, cured tablets were tested in vitro using ethanol/SGF media at ethanol concentrations of 0%, 20% and 40% to evaluate alcohol extractability. Testing was performed using USP Apparatus 2 (paddle) at 50 rpm in 500 ml of media at 37° C., using a Perkin Elmer UV/VIS Spectrometer Lambda 20, UV at 220 nM. Sample time points include 0.5 and 1 hour. The results are also presented in Table 1.2.

TABLE 1.1

| | | Uncured whole | Cured Whole | Cured Flattened by 7 hammer strikes |
|---|---|---|---|---|
| Tablet Dimensions | Thickness (mm) | 4.52 [1] | 4.39 [1] | 2.23 [2] |
| | Diameter (mm) | — | 7.56 [1] | 10.27 [2] |
| | Breaking strength (N) | — | 196+ [3] | — |
| | Diameter (min) post breaking strength test | — | 7.33 [1] | — |
| Dissolution (% Released) (n = 3 tabs per vessel) | 0.5 hr | 13 | 34 | 33 |
| | 1 hr | 18 | 46 | 45 |
| | 2 hr | 28 | 63 | 62 |
| | 4 hr | 43 | 81 | 83 |
| | 8 hr | 65 | 86 | 87 |
| | 17 hr | 85 | 86 | 87 |

[1] n = median of 3 measurements
[2] n = median of 5 measurements
[3] 196+ means that subjected to the maximum force of 196 Newton the tablets did not break, n = median of 3 measurements

TABLE 1.2

| | Dissolution (% Released) (n = 2 tabs per vessel) | | | | | |
|---|---|---|---|---|---|---|
| | 0% Ethanol Concentration in SGF | | 20% Ethanol Concentration in SGF | | 40% Ethanol Concentration in SGF | |
| Time | uncured | cured | uncured | cured | uncured | cured |
| 0.5 | 13 | 37 | 13 | 32 | 11 | 33 |
| 1 | 22 | 50 | 21 | 46 | 22 | 43 |

Example 2

In Example 2 three different 100 mg tablets including 10 and 20 mg of Oxycodone HCl were prepared using high molecular weight polyethylene oxide and optionally hydroxypropyl cellulose.

Compositions:

| Ingredient | Example 2.1 mg/unit | Example 2.2 mg/unit | Example 2.3 mg/unit |
|---|---|---|---|
| Oxycodone HCl | 10 | 20 | 10 |
| Polyethylene Oxide (MW: approximately 4,000,000; Polyox ™ WSR301) | 90 | 80 | 85 |
| Hydroxypropyl Cellulose (Klucel ™ HXF) | 0 | 0 | 5 |
| Total | 100 | 100 | 100 |

Process of Manufacture:

The processing steps to manufacture tablets were as follows:

1. Oxycodone HCl, Polyethylene Oxide and Hydroxypropyl Cellulose were dry mixed in a low/high shear Black & Decker Handy Chopper dual blade mixer with a 1.5 cup capacity.
2. Step 1 blend was compressed to target weight on a single station tablet Manesty Type F 3 press.
3. Step 2 tablets were spread onto a tray placed in a Hotpack model 435304 oven at 70-75° C. for approximately 6 to 9 hours to cure the tablets.

In vitro testing including testing for tamper resistance (bench press and breaking strength test) was performed as follows.

The cured tablets were tested in vitro using USP Apparatus 2 (paddle) at 50 rpm in 500 ml simulated gastric fluid without enzymes (SGF) at 37° C., using a Perkin Elmer UV/VIS Spectrometer Lambda 20, UV at 220 nM. Cured tablets and cured flattened tablets were tested. The tablets were flattened using 2500 psi with a Carver style bench press to impart physical tampering. The results are presented in Table 2.

As a further tamper resistance test, the cured tablets were subjected to a breaking strength test applying a force of a maximum of 196 Newton using a Schleuniger 2E/106 Apparatus to evaluate the resistance to breaking. The results are presented in Table 2.

TABLE 2

| | | Example 2.1 | | Example 2.2 | | Example 2.3 | |
|---|---|---|---|---|---|---|---|
| | | Whole (n = 6) | Flattened by bench press | Whole (n = 2) | Flattened by bench press | Whole (n = 5) | Flattened by bench press |
| Tablet Dimensions | Thickness (mm) | 3.36 | 0.58 | 3.14 | 0.84 | 3.48 | 0.49 |
| | Diameter (mm) | 6.48 | 12.80 | 6.58 | 13.44 | 6.46 | 12.86 |
| | Thickness (%) | — | 17.3 | — | 26.8 | — | 14.0 |
| | Breaking strength (N) | 196+ [1] | n/a | 196+ [1] | n/a | 196+ [1] | n/a |
| Dissolution (% Released) (n = 1) | 0.5 hr | 34 | 46 | 42 | 50 | 40 | 56 |
| | 1 hr | 50 | 62 | 57 | 71 | 55 | 72 |
| | 2 hr | 72 | 78 | 78 | 91 | 77 | 89 |
| | 4 hr | 81 | 82 | 95 | 93 | 93 | 100 |
| | 8 hr | 82 | 82 | 95 | 93 | 94 | 100 |
| | 12 hr | 83 | 82 | 96 | 94 | 95 | 101 |

[1] 196+ means that subjected to the maximum force of 196 Newton the tablets did not break

Example 3

In Example 3 a 200 mg tablet prepared including 10 mg oxycodone HCl and high molecular weight polyethylene oxide were prepared.
Composition:

| Ingredient | mg/unit | % |
|---|---|---|
| Oxycodone HCl | 10 | 5 |
| Polyethylene Oxide (MW: approximately 4,000,000; Polyox ™ WSR301) | 188 | 94 |
| Magnesium Stearate | 2 | 1 |
| Total | 200 | 100 |

Process of Manufacture:

The processing steps to manufacture tablets were as follows:

1. Oxycodone HCl, Polyethylene Oxide and Magnesium Stearate were dry mixed in a low/high shear Black & Decker Handy Chopper dual blade mixer with a 1.5 cup capacity.
2. Step 1 blend was compressed to target weight on a single station tablet Manesty Type F 3 press.
3. Step 2 tablets were placed onto a tray placed in a Hotpack model 435304 oven at 70° C. for 1 to 14 hours to cure the tablets.

In vitro testing including testing for tamper resistance (breaking strength test) was performed as follows:

The tablets were tested in vitro using USP Apparatus 1 (basket) at 100 rpm in 900 ml simulated gastric fluid without enzymes (SGF) at 37° C., using a Perkin Elmer UV/VIS Spectrometer Lambda 20 USP Apparatus, UV at 220 nM, after having been subjected to curing for 2, 3, 4, 8, and 14 hours. Tablet dimensions of the uncured and cured tablets and dissolution results are presented in Table 3.

As a further tamper resistance test, the cured and uncured tablets were subjected to a breaking strength test applying a force of a maximum of 196 Newton using a Schleuniger 2E/106 Apparatus to evaluate the resistance to breaking. The results are presented in Table 3.

Example 4

In Example 4 six different 100 mg tablets (Examples 4.1 to 4.6) including 10 mg of oxycodone HCl are prepared varying the amount and molecular weight of the used polyethylene oxides.

Compositions:

| Ingredient | 4.1 mg/unit | 4.2 mg/unit | 4.3 mg/unit | 4.4 mg/unit | 4.5 mg/unit | 4.6 mg/unit |
|---|---|---|---|---|---|---|
| Oxycodone HCl | 10 | 10 | 10 | 10 | 10 | 10 |
| Polyethylene Oxide (MW: approximately 4,000,000; Polyox ™ WSR 301) | 89.5 | 79.5 | 69.5 | 89.0 | 0 | 0 |
| Polyethylene Oxide (MW; approximately 100,000; Polyox ™ N10) | 0 | 10 | 20 | 0 | 0 | 0 |
| Polyethylene Oxide (MW: approximately 2,000,000; Polyox ™N-60K) | 0 | 0 | 0 | 0 | 0 | 89.5 |
| Polyethylene Oxide MW; approximately 7,000,000; Polyox ™ WSR 303) | 0 | 0 | 0 | 0 | 89.5 | 0 |
| Butylated Hydroxytoluene (BHT) | 0 | 0 | 0 | 0.5 | 0 | 0 |
| Magnesium Stearate | 0.5 | 0.5 | 0.5 | 0.5 | 0.5 | 0.5 |
| Total | 100 | 100 | 100 | 100 | 100 | 100 |
| Blend size (g) | 125 | 125 | 125 | 125 | 157.5 | 155.5 |
| Total Batch size (g) (amount manufactured) | 250 | 250 | 250 | 250 | 157.5 | 155.5 |

The processing steps to manufacture tablets were as follows:

1. Oxycodone HCl and Polyethylene Oxide (and BHT if required) were dry mixed for 30 seconds in a low/high shear Black & Decker Handy Chopper dual blade mixer
2. Magnesium stearate was added to Step 1 blend and mixed for an additional 30 seconds.

TABLE 3

| | | Un-Cured [2] | Cure Time (hours) | | | | |
|---|---|---|---|---|---|---|---|
| | | | 1 [1] | 2 [1] | 4 [1] | 8 [1] | 14 [2] |
| Tablet Dimensions | Weight (mg) | 208 | 208 | 209 | 209 | 209 | 210 |
| | Thickness (mm) | 4.74 | 5.17 | 5.25 | 5.17 | 5.17 | 4.85 |
| | Diameter (mm) | 7.93 | 7.85 | 7.80 | 7.75 | 7.69 | 7.64 |
| | Breaking strength (N) | 176 | 196+ [3] | 196+ [3] | 196+ [3] | 196+ [3] | 196+ [3] |
| Dissolution (% Released) (n = 2) | 0.5 hr | Not tested | Not tested | 16 | 11 | 15 | 33 |
| | 1 hr | | | 23 | 18 | 23 | 50 |
| | 2 hr | | | 34 | 28 | 36 | 69 |
| | 4 hr | | | 54 | 45 | 58 | 87 |
| | 8 hr | | | 81 | 69 | 83 | 93 |
| | 12 hr | | | 96 | 83 | 92 | 94 |

[1] Tablet dimensions n = 4
[2] Tablet dimensions n = 10
[3] 196+ means that subjected to the maximum force of 196 Newton the tablets did not break.

3. Step 2 blend was compressed to target weight on a single station tablet Manesty Type F 3 press using standard round (0.2656 inch) concave tooling
4. Step 3 tablets were loaded into a 15 inch coating pan (LCDS Vector Laboratory Development Coating System) at 38 rpm equipped with one baffle. A temperature probe (wire thermocouple) was placed inside the coating pan near the bed of tablets to monitor the bed temperature. The tablet bed was heated to a temperature of about 70 about 80° C. (the temperature can be derived from Tables 4.1 to 4.6 for each Example) for a minimum of 30 minutes and a maximum of 2 hours. The tablet bed was then cooled and discharged.

In vitro testing including testing for tamper resistance (breaking strength and hammer test) was performed as follows:

Uncured and tablets cured at 0.5, 1, 1.5 and 2 hours of curing were tested in vitro using USP Apparatus 1 (basket) at 100 rpm in 900 ml simulated gastric fluid without enzymes (SGF) at 37° C., using a Perkin Elmer UV/VIS Spectrometer Lambda 20, UV wavelength at 220 nM. Tablet dimensions and dissolution results corresponding to the respective curing time and temperature are presented in Tables 4.1 to 4.6.

As a further tamper resistance test, the cured and uncured tablets were subjected to a breaking strength test applying a force of a maximum of 196 Newton using a Schleuniger 2E/106 Apparatus to evaluate the resistance to breaking. The results are provided in Tables 4.1 to 4.6.

Additionally, the tablets were flattened with a hammer using 10 manually conducted hammer strikes to impart physical tampering (hammer test).

TABLE 4.1

| | | | Example 4.1 | | | |
|---|---|---|---|---|---|---|
| | | Uncured | Cure Time (hours) (n = 5) | | | |
| | | (n = 10) | 0.5 | 1.0 | 1.5 | 2.0 |
| Tablet Dimensions | Weight (mg) | 108 | 109 | 108 | 107 | 107 |
| | Thickness (mm) | 3.64 | 3.93 | 3.94 | 3.90 | 3.83 |
| | Diameter (mm) | 6.74 | 6.62 | 6.57 | 6.55 | 6.52 |
| | Breaking strength (N) | 94 | 196+ [2] | 196+ [2] | 196+ [2] | 196+ [2] |
| | Diameter (mm) post breaking strength test (measured directly after the test) | mashed [1] | 5.15 | 5.38 | 5.23 | 5.44 |
| Curing Process Tablet Bed Temp ° C. (temperature probe within the pan) | 0 min | 19.7 | — | — | — | — |
| | 10 min | — | 66.2 | — | — | — |
| | 20 min | — | 68.6 | — | — | — |
| | 30 min | — | 73.5 | — | — | — |
| | 40 min | — | — | 76.9 | — | — |
| | 60 min | — | — | 78.9 | — | — |
| | 90 min | — | — | — | 79.8 | — |
| | 120 min | — | — | — | — | 80.2 |
| | n = | 3 | 3 | 2 | 2 | 2 |
| Dissolution (% Released) | 0.5 hr | 19 | 21 | 18 | 18 | 19 |
| | 1 hr | 30 | 32 | 30 | 29 | 31 |
| | 2 hr | 47 | 49 | 46 | 46 | 50 |
| | 4 hr | 71 | 76 | 70 | 69 | 75 |
| | 8 hr | 93 | 96 | 91 | 89 | 93 |
| | 12 hr | 99 | 99 | 96 | 93 | 96 |
| | n = | | 1 | 1 | 1 | 1 |
| Post Hammer Test [3] (10 strikes applied manually) Thickness (mm) | | n/a | 1.70 2.31 2.39 | 2.18 2.06 2.66 | 2.37 2.26 2.28 | 2.09 |

[1] Tablets mashed and crumbled during the breaking strength test
[2] 196+ means that subjected to the maximum force of 196 Newton the tablets did not break
[3] Applied 10 hammer strikes, the tablets flattened but did not break apart, hammering imparted some edge splits.

TABLE 4.2

| | | | Example 4.2 | | | |
|---|---|---|---|---|---|---|
| | | Uncured | Cure Time (hours) (n = 5) | | | |
| | | (n = 10) | 0.5 | 1.0 | 1.5 | 2.0 |
| Tablet Dimensions | Weight (mg) | 108 | 109 | 109 | 109 | 107 |
| | Thickness (mm) | 3.65 | 3.90 | 3.92 | 3.87 | 3.74 |
| | Diameter (mm) | 6.74 | 6.61 | 6.54 | 6.52 | 6.46 |
| | Breaking strength (N) | 93 | 196+ [3] | 196+ [3] | 196+ [3] | 196+ [3] |
| | Diameter (mm) post breaking strength test (measured directly after the test) | mashed [2] | 5.40 | 5.37 | 5.36 | 5.61 |
| | Relaxed diameter (mm) post breaking strength | — | 5.60 | 5.52 | 5.48 | 5.73 |

TABLE 4.2-continued

|  |  | Uncured | Example 4.2 | | | |
|---|---|---|---|---|---|---|
|  |  |  | Cure Time (hours) (n = 5) | | | |
|  |  | (n = 10) | 0.5 | 1.0 | 1.5 | 2.0 |
|  | test (NLT 15 min relax period) |  |  |  |  |  |
| Curing | 0 min |  | 20.2 | — | — | — |
| Process | 10 min | — | 71.6 | — | — | — |
| Tablet Bed | 20 min | — | 74.9 | — | — | — |
| Temp ° C. | 30 min | — | 76.1 | — | — | — |
| (temperature | 40 min | — | — | 79.8 | — | — |
| probe within | 60 min | — | — | 80.2 | — | — |
| the pan) | 90 min | — | — | — | 76.4 | — |
|  | 120 min | — | — | — | — | 77.5 |
| Dissolution | 0.5 hr | — | 20 | 20 | — | 29 |
| (% Released) | 1 hr | — | 30 | 31 | — | 44 |
| (n = 3) | 2 hr | — | 47 | 47 | — | 66 |
|  | 4 hr | — | 70 | 70 | — | 90 |
|  | 8 hr | — | 89 | 91 | — | 95 |
|  | 12 hr | — | 92 | 94 | — | 94 |
|  | n = |  | 1 | 1 | 1 | 1 |
| Post Hammer Test (10 strikes | | n/a | 1.98 | 2.00 | 1.80 | 1.62 |
| applied manually) | |  | 1.96 | 1.76 | 2.06 | 1.95 |
| Thickness (mm) | |  | 1.99 | 1.79 | 1.98 | 1.53 |

[2] Tablets mashed and crumbled during the breaking strength test
[3] 196+ means that subjected to the maximum force of 196 Newton the tablets did not break.

TABLE 4.3

|  |  | Uncured | Example 4.3 | | | |
|---|---|---|---|---|---|---|
|  |  |  | Cure Time (hours) (n = 5) | | | |
|  |  | (n = 10) | 0.5 | 1.0 | 1.5 | 2.0 |
| Tablet | Weight (mg) | 108 | 107 | 108 | 108 | 107 |
| Dimensions | Thickness (mm) | 3.63 | 3.85 | 3.82 | 3.78 | 3.72 |
|  | Diameter (mm) | 6.74 | 6.61 | 6.55 | 6.48 | 6.46 |
|  | Breaking strength (N) | 91 | 196+ [3] | 196+ [3] | 196+ [3] | 196+ [3] |
|  | Diameter (mm) post breaking strength test (measured directly after the test) | mashed [2] | 5.58 | 5.60 | 5.56 | 5.72 |
|  | Relaxed diameter (mm) post breaking strength test (NLT 15 min relax period) | — | 5.77 | 5.75 | 5.68 | 5.82 |
| Curing | 0 min |  | 20.3 | — | — | — |
| Process | 10 min | — | 71.0 | — | — | — |
| Tablet Bed | 20 min | — | 74.1 | — | — | — |
| Temp ° C. | 30 min | — | 75.9 | — | — | — |
| (temperature | 40 min | — | — | 76.5 | — | — |
| probe within | 60 min | — | — | 77.8 | — | — |
| the pan | 90 min | — | — | — | 76.0 | — |
| within the | 120 min | — | — | — | — | 80.2 |
| pan) |  |  |  |  |  |  |
|  | n = |  | 3 | 3 |  | 2 |
| Dissolution | 0.5 hr | — | 22 | 23 | — | 33 |
| (% Released) | 1 hr | — | 32 | 35 | — | 52 |
|  | 2 hr | — | 49 | 54 | — | 76 |
|  | 4 hr | — | 70 | 80 | — | 93 |
|  | 8 hr | — | 94 | 95 | — | 96 |
|  | 12 hr | — | 96 | 96 | — | 96 |
|  | n = |  | 1 | 1 | 1 | 1 |
| Post Hammer Test (10 strikes | | n/a | 2.16 | 1.95 | 1.43 | 1.53 |
| applied manually) | |  | 1.96 | 1.85 | 1.67 | 1.66 |
| Thickness (mm) | |  | 1.91 | 2.03 | 1.65 | 2.08 |

[2] Tablets mashed and crumbled during the breaking strength test
[3] 196+ means that subjected to the maximum force of 196 Newton the tablets did not break.

TABLE 4.4

| | | Uncured (n = 10) | Example 4.4 Cure Time (hours) (n = 5) | | | |
|---|---|---|---|---|---|---|
| | | | 0.5 | 1.0 | 1.5 | 2.0 |
| Tablet Dimensions | Weight (mg) | 101 | 101 | 101 | 101 | 101 |
| | Thickness (mm) | 3.49 | 3.75 | 3.71 | 3.69 | 3.70 |
| | Diameter (mm) | 6.75 | 6.59 | 6.55 | 6.55 | 6.52 |
| | Breaking strength (N) | 81 | 196+ [3] | 196+ [3] | 196+ [3] | 196+ [3] |
| | Diameter (mm) post breaking strength test (measured directly after the test | mashed [2] | 5.39 | 5.39 | 5.39 | 5.47 |
| | Relaxed diameter (mm) post breaking strength test (NLT 15 min relax period) | — | 5.58 | 5.59 | 5.58 | 5.63 |
| Curing Process Tablet Bed Temp ° C. (temperature probe within the pan) | 0 min | | 37.3 | | | |
| | 5 min | — | 67.0 | — | — | — |
| | 10 min | — | 71.8 | — | — | — |
| | 20 min | — | 74.6 | — | — | — |
| | 30 min | — | 76.2 | — | — | — |
| | 40 min | — | — | 77.0 | — | — |
| | 60 min | — | — | 78.7 | — | — |
| | 90 min | — | — | — | 80.3 | — |
| | 120 min | — | — | — | — | 79.3 |
| Dissolution (% Released) (n = 3) | 0.5 hr | — | 17 | 16 | — | — |
| | 1 hr | — | 26 | 25 | — | — |
| | 2 hr | — | 41 | 40 | — | — |
| | 4 hr | — | 63 | 59 | — | — |
| | 8 hr | — | 79 | 75 | — | — |
| | 12 hr | — | 82 | 80 | — | — |
| | n = | | 1 | 1 | 1 | 1 |
| Post Hammer Test (10 strikes applied manually) Thickness (mm) | | — | 2.11 | 2.42 | 2.14 | 2.18 |
| | | | 2.29 | 2.25 | 2.28 | 2.09 |
| | | | 2.32 | 2.13 | 2.07 | 2.36 |

[2] Tablets mashed and crumbled during the breaking strength test.
[3] 196+ means that subjected to the maximum force of 196 Newton the tablets did not break.

TABLE 4.5

| | | Uncured (n = 10) | Example 4.5 Cure Time (hours) (n = 5) | | | |
|---|---|---|---|---|---|---|
| | | | 0.5 | 1.0 | 1.5 | 2.0 |
| Tablet Dimensions | Weight (mg) | 108 | 108 | 107 | 107 | 107 |
| | Thickness (mm) | 3.61 | 3.87 | 3.84 | 3.84 | 3.84 |
| | Diameter (mm) | 6.74 | 6.69 | 6.63 | 6.61 | 6.59 |
| | Breaking strength (N) | 116 | 196+ [3] | 196+ [3] | 196+ [3] | 196+ [3] |
| | Diameter (mm) post breaking strength test (measured directly after the test | mashed [2] | 5.49 | 5.59 | 5.51 | 5.54 |
| | Diameter (mm) post breaking strength test (NLT 15 min relax period) | — | 5.67 | 5.76 | 5.67 | 5.68 |
| Curing Process Tablet Bed Temp ° C. (temperature probe within the pan) | 0 min | | 19.8 | | | |
| | 5 min | — | 56.8 | — | — | — |
| | 10 min | — | 70.0 | — | — | — |
| | 20 min | — | 74.6 | — | — | — |
| | 30 min | — | 76.2 | — | — | — |
| | 40 min | — | — | 77.0 | — | — |
| | 60 min | — | — | 78.2 | — | — |
| | 90 min | — | — | — | 80.2 | — |
| | 120 min | — | — | — | — | 80.3 |
| Dissolution (% Released) n = 3) | 0.5 hr | — | 21 | 20 | — | — |
| | 1 hr | — | 33 | 32 | — | — |
| | 2 hr | — | 51 | 51 | — | — |
| | 4 hr | — | 75 | 76 | — | — |
| | 8 hr | — | 96 | 96 | — | — |
| | 12 hr | — | 100 | 100 | — | — |
| | n = | | 1 | 1 | 1 | 1 |

TABLE 4.5-continued

|  | Example 4.5 | | | |
|---|---|---|---|---|
|  | Uncured | Cure Time (hours) (n = 5) | | |
|  | (n = 10) | 0.5 | 1.0 | 1.5 | 2.0 |
| Post Hammer Test (10 strikes applied manually) Thickness (mm) | — | 2.19 2.15 2.10 | 2.31 2.48 2.28 | 2.36 2.42 2.19 | 2.45 2.08 2.28 |

[2] Tablets mashed and crumbled during the breaking strength test
[3] 196+ means that subjected to the maximum force of 196 Newton the tablets did not break.

TABLE 4.6

| | | Example 4.6 | | | | | | |
|---|---|---|---|---|---|---|---|---|
| | | UnCured | Cure Time (n = 5) | | | | | |
| | | (n = 6) | 10 min | 20 min | 0.5 hr | 1.0 hr | 1.5 hr | 2.0 hr |
| Tablet Dimensions | Weight (mg) | 110 | 108 | 108 | 109 | 108 | 109 | 109 |
| | Thickness (mm) | 3.65 | 3.93 | 3.89 | 3.89 | 3.87 | 3.85 | 3.85 |
| | Diameter (mm) | 6.73 | 6.71 | 6.63 | 6.61 | 6.57 | 6.55 | 6.53 |
| | Breaking strength (N) | 128 | | | 196+ [2] | | | |
| | Diameter (mm) post breaking strength test (measured directly after the test | mashed [1] | 5.27 | 5.47 | 5.51 | 5.51 | 5.56 | 5.63 |
| | Diameter (mm) post breaking strength test (NLT 15 min relax period) | — | 5.48 | 5.60 | 5.67 | 5.66 | 5.69 | 5.76 |
| Curing Process Tablet Bed Temp ° C. (temperature probe within the pan) | 0 min | | 30.8 | | | | | |
| | 5 min | | 70.5 | — | — | — | — | — |
| | 10 min | | 79.5 | | | | | |
| | 20 min | | — | 79.9 | — | — | — | — |
| | 30 min | | — | — | 79.6 | — | — | — |
| | 40 min | | — | — | — | 80.0 | — | — |
| | 60 min | | — | — | — | 79.8 | — | — |
| | 90 min | | — | — | — | — | 80.2 | — |
| | 120 min | | — | — | — | — | — | 80.4 |
| Dissolution (% Released) (n = 3) | 0.5 hr | | — | — | 19 | 20 | — | — |
| | 1 hr | | — | — | 30 | 30 | — | — |
| | 2 hr | | — | — | 48 | 51 | — | — |
| | 4 hr | | — | — | 73 | 78 | — | — |
| | 8 hr | | — | — | 99 | 99 | — | — |
| | 12 hr | | — | — | 99 | 102 | — | — |
| | n = | | 1 | 1 | 1 | 1 | 1 | 1 |
| Post Hammer Test [3] (10 strikes applied manually) Thickness (mm) | | — | 1.46 1.19 1.24 | 2.18 2.20 2.18 | 2.45 2.34 2.03 | 2.23 2.39 2.52 | 2.38 2.26 2.50 | 2.42 2.40 2.16 |

[1] Tablets mashed and crumbled during the breaking strength test
[2] 196+ means that subjected to the maximum force of 196 Newton the tablets did not break.
[3] The tablets flattened but did not break apart, hammering imparted some edge splits.

Example 5

In Example 5 three further tablets including 10% (by wt) of oxycodone HCl were prepared.

Compositions:

| Tablet | Example 5.1 mg/unit (%) | Example 5.2 mg/unit (%) | Example 5.3 mg/unit (%) |
|---|---|---|---|
| Oxycodone HCl | 12 (10) | 20 (10) | 12 (10) |
| Polyethylene Oxide (MW: approximately 4,000,000; Polyox ™ WSR 301) | 106.8 (89) | 178 (89) | 82.8 (69) |
| Polyethylene Oxide (1MW; approximately 100,000; Polyox ™ N10) | 0 | 0 | 24 (20) |
| Magnesium Stearate | 1.2 (1) | 2.0 (1) | 1.2 (1) |
| Total | 120 | 200 | 120 |
| Total Batch size (kg) (amount manufactured) | 100 | 100 | 100 |
| Coating | mg/unit | mg/unit | mg/unit |
| Opadry white film coating concentrate formula Y-5-18024-A | 3.6 (3) | 6.0 (3) | 3. (3) |

The processing steps to manufacture tablets were as follows:

1. The polyethylene oxide was passed through a Sweco Sifter equipped with a 20 mesh screen, into separate suitable containers.
2. A Gemco "V" blender (with 1 bar)—10 cu. ft. was charged in the following order:
   Approximately ½ of the polyethylene oxide WSR 301
   Oxycodone hydrochloride\
   Polyethylene oxide N10 (only Example 5.3)
   Remaining polyethylene oxide WSR 301
3. Step 2 materials were blended for 10 minutes (Example 5.1) or 20 minutes (Example 5.2) and 15 minutes (Example 5.3) with the T bar on.
4. Magnesium stearate was charged into the Gemco "V" blender.
5. Step 4 materials were blended for 3 minutes with the I bar off.
6. Step 5 blend was charged into clean, tared, stainless steel containers.
7. Step 5 blend was compressed to target weight on a 40 station tablet press at 135,000 tph speed using 9/32 standard round, concave (plain) tooling.
8. Step 7 tablets were loaded into a 48 inch Accela-Coat coating pan at 7 rpm at a pan load of 98.6 kg (Example 5.1), 92.2 kg (Example 5.2) and 96.9 kg (Example 5.3) and the tablet bed was heated using an exhaust air temperature to achieve approximately 80° C. (Example 5.2 and 5.3) and 75° C. (Example 5.1) inlet temperature and cured for 1 hour at the target inlet temperature.
9. The pan speed was continued at 7 to 10 rpm and the tablet bed was cooled using an exhaust air temperature to achieve a 25° C. inlet temperature until the bed temperature achieves 30-34° C.
10. The tablet bed was warmed using an exhaust air temperature to achieve a 55° C. inlet temperature. The film coating was started once the outlet temperature approached 39° C. and continued until the target weight gain of 3% was achieved.
11. After coating was completed, the pan speed was set to 1.5 rpm and the exhaust temperature was set to 27° C., the airflow was maintained at the current setting and the system cooled to an exhaust temperature of 27-30° C.
12. The tablets were discharged.

In vitro testing including testing for tamper resistance (breaking strength and hammer test) and resistance to alcohol extraction were performed as follows:

Tablets cured at 0.5 hours and tablets cured at 1.0 hour and coated were tested in vitro using USP Apparatus 1 (basket) at 100 rpm in 900 ml simulated gastric fluid without enzymes (SGF) at 37° C., using an Agilent UV/VIS Spectrometer Model HP8453, UV wavelength at 220 nM. Tablet dimensions and dissolution results corresponding to the respective curing time and temperature are presented in Tables 5.1 to 5.3.

Tablets cured at 1.0 hour and coated were tested in vitro using ethanol/SGF media at a concentration of 40% ethanol to evaluate alcohol extractability. Testing was performed using USP Apparatus 1 (basket) at 100 rpm in 900 ml simulated gastric fluid without enzymes (SGF) at 37° C., using an Agilent UV/VIS Spectrometer Model HP8453, UV wavelength at 230 nM. Tablet dissolution results are presented in Table 5.3.

As a further tamper resistance test, the uncured tablets and cured tablets were subjected to a breaking strength test applying a force of a maximum of 439 Newton using a Schleuniger Model 6D apparatus to evaluate the resistance to breaking. The results are provided in Tables 5.1 to 5.3.

Additionally, the tablets were flattened with a hammer using 10 manually conducted hammer strikes to impart physical tampering (hammer test).

TABLE 5.1

| | | Example 5.1 | | |
|---|---|---|---|---|
| | | Uncured | 30 min cure (n = 10) | 1 hr cure/ coated (n = 10) |
| Tablet Dimensions | Weight (mg) | 119.7 [1] | 120 | 122 |
| | Thickness (mm) | 3.63[2] | 3.91 | 3.88 |
| | Diameter (mm) | — | 7.03 | 7.02 |
| | Breaking strength (N) | 54 [3] | 439 [4] | 438 [4] |
| | diameter (mm) post breaking strength | — | 4.18 | 4.26 |
| Curing Process Inlet Temp ° C. | 10 min | — | 75.8 | 75.8 |
| | 20 min | — | 75.1 | 75.1 |
| | 30 min | — | 76.0 | 76.0 |
| | 40 min | — | — | 74.5 |
| | 50 min | — | — | 73.5 |
| | 60 min | — | — | 75.6 |
| Dissolution (% Released) (n = 3) | 0.5 hr | — | 19 | 19 |
| | 1 hr | — | 31 | 33 |
| | 2 hr | — | 47 | 50 |
| | 4 hr | — | 71 | 76 |
| | 8 hr | — | 93 | 97 |
| | 12 hr | — | 99 | 102 |

| | pre | post | pre | post |
|---|---|---|---|---|
| Hammer Test (10 strikes applied manually) Tablet thickness measured (mm) pre and post test (n = 3) | — | 3.90 | 1.77 | 3.87 | 2.09 |

[1] Fourteen in-process samples taken (40 tablets per each sample) and each sample averaged. The reported value is the average of the averages.
[2] n = 39
[3] n = 130
[4] n = 10; The tablets did not break when subjected to a maximum force of 438 N/439 N.

TABLE 5.2

| | | Example 5.2 | | |
|---|---|---|---|---|
| | | Uncured | 30 min cure (n = 10) | 1 hr cure/ coated (n = 10) |
| Tablet Dimensions | Weight (mg) | 200.4 [1] | 201 | 206 |
| | Thickness (mm) | 5.50[2] | 5.92 | 5.86 |
| | Diameter (mm) | — | 7.03 | 7.01 |
| | Breaking strength (N) | 85 [3] | 439 [4] | 439 [4] |
| | diameter (mm) post breaking strength | — | 5.52 | 5.72 |
| Curing Process Inlet Temp ° C. | 10 min | — | 79.7 | 79.7 |
| | 20 min | — | 80.3 | 80.3 |
| | 30 min | — | 79.3 | 79.3 |
| | 40 min | — | — | 79.5 |
| | 50 min | — | — | 80.9 |
| | 60 min | — | — | 81.0 |
| Dissolution (% Released) | 0.5 hr | — | 14 | 15 |
| | 1 hr | — | 23 | 24 |
| | 2 hr | — | 36 | 38 |
| | 4 hr | — | 57 | 60 |

TABLE 5.2-continued

| (n = 3) | 8 hr | — | 83 | 85 |
| | 12 hr | — | 94 | 95 |

| | | pre | post | pre | post |
|---|---|---|---|---|---|
| Hammer Test (10 strikes applied manually) Tablet thickness measured (mm) pre and post test (n =3) | — | 5.92 | 2.97 | 5.91 | 2.84 |

[1] Nine in-process samples taken (40 tablets per each sample) and each sample averaged. The reported value is the average of the averages.
[2] n = 27
[3] n = 90
[4] n = 10; The tablets did not break when subjected to a maximum force of 438 N/439 N.

TABLE 5.3

| | | | Example 5.3 | |
|---|---|---|---|---|
| | | Uncured | 30 min cure (n = 10) | 1 hr cure/coated (n = 10) |
| Tablet Dimensions | Weight (mg) | 120.5 [1] | 122 | 125 |
| | Thickness (mm) | 3.64[2] | 3.85 | 3.77 |
| | Diameter (mm) | — | 7.03 | 7.01 |
| | Breaking strength (N) | 56 [3] | 43 8[4] | 439 [4] |
| | diameter (mm) post breaking strength | — | 3.96 | 4.28 |
| Curing Process Inlet Temp ° C. | 10 min | — | 80.0 | 80.0 |
| | 20 min | — | 82.3 | 82.3 |
| | 30 min | — | 78.9 | 78.9 |
| | 40 min | — | — | 79.5 |
| | 50 min | — | — | 79.5 |
| | 60 min | — | — | 80.7 |

| | | SGF | SGF | 40% EtOH |
|---|---|---|---|---|
| Dissolution (% Released) (n = 3) | 0.5 hr | — | 20 | 23 | 21 |
| | 1 hr | — | 31 | 37 | 31 |
| | 2 hr | — | 50 | 58 | 50 |
| | 4 hr | — | 76 | 86 | 76 |
| | 8 hr | — | 95 | 100 | 99 |
| | 12 hr | — | 98 | 100 | 104 |

| | | pre | post | pre | post |
|---|---|---|---|---|---|
| Hammer Test (10 strikes applied manually) Tablet thickness measured (mm) pre and post test (n = 3) | — | 3.81 | 1.63 | 3.79 | 1.62 |

[1] Twelve in-process samples taken (40 tablets per each sample) and each sample averaged. The reported value is the average of the averages.
[2] n = 33
[3] n = 130
[4] n = 10; The tablets did not break when subjected to a maximum force of 438 N/439 N.

Example 6

In Example 6 tablets comprising Naltrexone HCl were prepared.

Compositions:

| Tablet | mg/unit |
|---|---|
| Naltrexone HCl | 10 |
| Polyethylene Oxide (MW: approximately 4,000,000; Polyox ™ WSR 301) | 89.0 |
| Magnesium Stearate | 1.0 |
| Total | 100 |
| Total Batch size (kg) (amount manufactured) | 20 |

| Coating | mg/unit |
|---|---|
| Base coat Opadry Red film coating concentration formula Y-5-1-15139 | 3.0 |
| Special effects overcoat Opadry FX - Silver formula 62W28547 | 3.0 |

The tablets were prepared as outlined in Example 5, wherein a Gemco "V" blender (with I bar)—2 cu.ft, a 8 station rotary tablet press set at 24,000 tph speed with a 9/32 standard round concave (embossed upper/plain lower) tooling and a 24 inch Compu-Lab coater were used. The blending time in step 2 was 8 minutes, the pan load was 9.2 kg and the curing time 2 hours.

Example 7

Three further examples comprising each 10 mg of oxycodone hydrochloride were manufactured and tested.

Compositions:

| Tablet | Example 7.1 mg/unit (%) | Example 7.2 mg/unit (%) | Example 7.3 mg/unit (%) |
|---|---|---|---|
| Oxycodone HCl | 10 (5) | 10 (6.67) | 10 (10) |
| Polyethylene Oxide (MW: approximately 4,000,000; Polyox ™ WSR 301) | 188 (94) | 138.5 (92.3) | 69 (69) |
| Polyethylene Oxide (MW; approximately 100,000; Polyox ™ N10) | 0 | 0 | 20 (20) |
| Magnesium Stearate | 2 (1) | 1.5 (1) | 1 (1) |
| Total | 200 | 150 | 100 |
| Total Batch size (kg) (amount manufactured) | 100 | 100 | 100 |

| Film Coating | mg/unit | mg/unit | mg/unit |
|---|---|---|---|
| Opadry white film coating concentrate formula Y-5-18024-A | 6 | 4.5 | 3 |

The processing steps to manufacture tablets were as follows:
1. The magnesium stearate was passed through a Sweco Sifter equipped with a 20 mesh screen, into separate suitable containers.
2. A Gemco "V" blender (with I bar)—10 cu. ft. was charged in the following order:

Approximately ½ of the polyethylene oxide WSR 301
Oxycodone hydrochloride
Polyethylene oxide N10 (only Example 7.3)
Remaining polyethylene oxide WSR 301
3. Step 2 materials were blended for 10 minutes with the I bar on.
4. Magnesium stearate was charged into the Gemco "V" blender.
5. Step 4 materials were blended for 3 minutes with the I bar off.
6. Step 5 blend was charged into clean, tared, stainless steel containers.
7. Step 5 blend was compressed to target weight on a 40 station tablet press at 135,000 tph speed using 9/32 inch standard round, concave (plain) tooling (Example 7.1 and 7.2) and using ¼ inch standard round, concave (plain) tooling (Example 7.3).
8. Step 7 tablets were loaded into a 48 inch Accela-Coat coating pan at a load of 97.388 kg (Example 7.1), 91.051 kg (Example 7.2) and 89.527 kg (Example 7.3).
9. The pan speed was set to 7 rpm and the tablet bed was heated by setting the exhaust air temperature to achieve an inlet temperature of approximately 75° C. The tablets were cured at the target inlet temperature for 1 hour (Example 7.1 and 7.2) and for 30 minutes (Example 7.3).
10. The pan speed was continued at 6 to 8 rpm and the tablet bed was cooled using an exhaust air temperature to achieve a 25° C. inlet temperature until the exhaust temperature achieves 30-34° C.
11. The tablet bed was warmed using an exhaust air temperature to target a 55° C. inlet temperature. The film coating was started once the outlet temperature approached 39° C. and continued until the target weight gain of 3% was achieved.
12. After coating was completed, the pan speed was set to 1.5 rpm and the exhaust temperature was set to 27° C., the airflow was maintained at the current setting and the system cooled to an exhaust temperature of 27-30° C.
13. The tablets were discharged.

In vitro testing including testing for tamper resistance (breaking strength, hammer test and flattened tablets) and resistance to alcohol extraction, as well as stability tests were performed as follows:

Cured, coated tablets (whole and flattened) were tested in vitro using USP Apparatus 1 (basket) at 100 rpm in 900 ml simulated gastric fluid without enzymes (SGF) at 37° C. Samples were analyzed by reversed-phase high performance liquid chromatography (HPLC) on Waters Atlantis dC18 3.0×150 mm, 3 µm column, using a mobile phase consisting of a mixture of acetonitrile and non basic potassium phosphate buffer (pH 3.0) at 230 nm UV detection. Sample time points include 0.5, 0.75, 1.0, 1.5 and 2.0 hours. Additionally sample time points include 1.0, 4.0 and 12 hours.

Cured, coated tablets (whole and flattened) were tested in vitro using ethanol/SGF media at concentrations of 0% and 40% to evaluate alcohol extractability. Testing was performed using USP Apparatus 1 (basket) at 100 rpm in 900 ml simulated gastric fluid without enzymes (SGF) at 37° C. Samples were analyzed by reversed-phase high performance liquid chromatography (HPLC) on Waters Atlantis dC18 3.0×150 mm, column, using a mobile phase consisting of a mixture of acetonitrile and non basic potassium phosphate buffer (pH 3.0) at 230 nm UV detection. Sample time points include 0.5, 0.75, 1.0, 1.5 and 2.0 hours.

Cured tablets were subjected to a breaking strength test by applying a force of a maximum of 439 Newton using a Schleuniger Model 6D apparatus to evaluate tablet resistance to breaking.

Cured tablets were subject to a high amount of pressure using a Carver manual bench press (hydraulic unit model #3912) to impart physical tampering by flattening the tablets.

Cured tablets were subjected to a further breaking strength test by the manual application of 10 hammer strikes to impart physical tampering.

Cured, coated tablets were subjected to a stability test by storing them in 100 count bottles at different storage conditions (25° C./60% relative humidity or 40° C./75% relative humidity) for a certain period of time and subsequently testing the tablets in vitro as described above. Sample time points regarding storage include initial sample (i.e. prior to storage), one month, two months, three months and six months of storage, sample time points regarding dissolution test include 1.0, 4.0 and 12.0 hours.

Cured, coated tablets were subjected to a further stability test by storing them in 100 count bottles at different storage conditions (25° C./60% relative humidity or 40° C./75% relative humidity) for a certain period of time and subsequently subjecting the tablets to the assay test to determine the content of oxycodone HCl in the tablet samples, in percent relative to the label claim. Sample time points regarding storage include initial sample (i.e. prior to storage), one month, two months, three months and six months of storage. In the assay test, oxycodone hydrochloride was extracted from two sets of ten tablets each with 900 mL of a 1:2 mixture of acetonitrile and simulated gastric fluid without enzyme (SGF) under constant magnetic stirring in a 1000-mL volumetric flask until all tablets were completely dispersed or for overnight. The sample solutions were diluted and analyzed by reversed-phase high performance liquid chromatography (HPLC) on Waters Atlantis $dC_{18}$ 3.0×250 mm, 5 µm column maintained at 60° C. using a mobile phase consisting of acetonitrile and potassium phosphate monobasic buffer at pH 3.0 with UV detection at 280 nm.

Cured, coated tablets were subjected to a further stability test by storing them in 100 count bottles at different storage conditions (25° C./60% relative humidity or 40° C./75% relative humidity) for a certain period of time and subsequently subjecting the tablets to the oxycodone-N-oxide (ONO) test to determine the content of the degradation product oxycodone-N-oxide in percent relative to the oxycodone HCl label claim. Sample time points regarding storage include initial sample (i.e. prior to storage), one month, two months, three months and six months of storage. In the ONO test, oxycodone hydrochloride and its degradation products were extracted from a set of ten tablets with 900 mL of a 1:2 mixture of acetonitrile and simulated gastric fluid without enzyme (SGF) under constant magnetic stirring in a 1000-mL volumetric flask until all tablets were completely dispersed or for overnight. The sample solutions were diluted and analyzed by reversed-phase high performance liquid chromatography (HPLC) on Waters Atlantis $dC_{18}$ 3.0×250 mm, 5 µm column maintained at 60° C. using a mobile phase consisting of acetonitrile and potassium phosphate monobasic buffer at pH 3.0 with UV detection at 206 nm.

The results are presented in Tables 7.1 to 7.3

TABLE 7.1.1

| | | Example 7.1 | | |
|---|---|---|---|---|
| | | Whole (n = 10) | Flattened (n = 3) (15,000 lbs applied) | |
| Tablet Dimensions | Weight (mg) | 205 | 207 | 204 |
| | Thickness (mm) | 5.95 | 1.01[1] | 0.96[1] |
| | % Thickness | | 17.0 | 16.1 |
| | Diameter (mm) | 7.02 | 17.13[2] | 17.35[2] |
| | Breaking strength (N) | ≥438[3] | | |
| | Diameter (mm) post Breaking strength | 5.84 | | |

| | | pre | post |
|---|---|---|---|
| Hammer Test pre and post tablet thickness measured (mm) | | 6.04 | 2.96 |
| | | 5.95 | 3.10 |
| | | 6.03 | 3.32 |

| | | Whole SGF | Whole 40% EtOH | Flattened SGF | Flattened 40% EtOH |
|---|---|---|---|---|---|
| Dissolution (% Released) (n = 3) | 0.5 hr | 11 | 9 | 17 | 13 |
| | 0.75 hr | 15 | 12 | 23 | 18 |
| | 1.0 hr | 20 | 16 | 28 | 21 |
| | 1.5 hr | 27 | 21 | 36 | 29 |
| | 2.0 hr | 34 | 27 | 44 | 35 |

| | | Whole |
|---|---|---|
| Dissolution (% Released) (n = 6) | 0.5 hr | — |
| | 1 hr | 22 |
| | 2 hr | — |
| | 4 hr | 57 |
| | 8 hr | — |
| | 12 hr | 97 |

[1] 3 measurements per tablet
[2] 2 measurements per tablet
[3] tablets did not break when subjected to the maximum force of 438 Newton

TABLE 7.1.2

| | | Stability tests Example 7.1 Storage conditions (° C./% RH) and storage time[1] | | | | |
|---|---|---|---|---|---|---|
| | | Initial | 1 Mo 40/75 | 2 Mo 40/75 | 3 Mo 25/60 | 3 Mo 40/75 |
| Dissolution (% Released) (n = 6) SGF | 1 hr | 22 | 21 | 21 | 20 | 21 |
| | 4 hr | 57 | 57 | 58 | 56 | 58 |
| | 12 hr | 97 | 98 | 98 | 97 | 97 |
| Assay test (% oxycodone HCl)[2] | Assay 1 | 96.6 | 96.2 | 97.3 | 97.1 | 95.0 |
| | Assay 2 | 95.3 | 97.2 | 95.7 | 98.7 | 96.0 |
| | Average | 96.0 | 96.7 | 96.5 | 97.9 | 95.5 |
| ONO test (% oxycodone N-oxide)[2] | | 0.02 | 0.06 | 0.06 | 0.04 | 0.05 |

[1] [Mo = month(s)];
[2] relative to the label claim of oxycodone HCl.

TABLE 7.2.1

| | | Example 7.2 | | |
|---|---|---|---|---|
| | | Whole (n = 10) | Flattened (n = 3) (20,000 lbs applied) | |
| Tablet Dimensions | Weight (mg) | 154 | 154 | 153 |
| | Thickness (mm) | 4.68 | 0.75[1] | 0.77[1] |
| | % Thickness | | 16.0 | 16.5 |
| | Diameter (mm) | 7.02 | 17.14[2] | 16.90[2] |
| | Breaking strength (N) | 438[3] | | |
| | Diameter (mm) post Breaking strength | 4.93 | | |

| | | pre | post |
|---|---|---|---|
| Hammer Test pre and post tablet thickness measured (mm) | | 4.73 | 2.65 |
| | | 4.64 | 2.95 |
| | | 4.67 | 2.60 |

| | | Whole SGF | Whole 40% EtOH | Flattened SGF | Flattened 40% EtOH |
|---|---|---|---|---|---|
| Dissolution (% Released) (n = 3) | 0.5 hr | 14 | 10 | 21 | 15 |
| | 0.75 hr | 19 | 14 | 27 | 20 |
| | 1.0 hr | 24 | 17 | 33 | 26 |
| | 1.5 hr | 33 | 23 | 44 | 36 |
| | 2.0 hr | 40 | 29 | 53 | 43 |

| | | Whole |
|---|---|---|
| Dissolution (% Released) (n = 6) | 0.5 hr | — |
| | 1 hr | 26 |
| | 2 hr | — |
| | 4 hr | 67 |
| | 8 hr | — |
| | 12 hr | 98 |

[1] 3 measurements per tablet
[2] 2 measurements per tablet

TABLE 7.2.2

Stability tests Example 7.2

| | | Storage conditions (° C./% RH) and storage time[1] | | | | | | |
|---|---|---|---|---|---|---|---|---|
| | | Initial | 1 Mo 40/75 | 2 Mo 40/75 | 3 Mo 25/60 | 3 Mo 40/75 | 6 Mo 25/60 | 6 Mo 40/75 |
| Dissolution (% Released) (n = 6) SGF | 1 hr | 26 | 24 | 22 | 23 | 24 | 25 | 25 |
| | 4 hr | 67 | 66 | 61 | 65 | 64 | 64 | 69 |
| | 12 hr | 98 | 101 | 97 | 98 | 99 | 99 | 97 |
| Assay test (% oxycodone HCl)[2] | Assay 1 | 97.1 | 97.7 | 96.4 | 98.4 | 97.3 | 96.3 | 94.1 |
| | Assay 2 | 96.6 | 96.6 | 96.2 | 98.0 | 96.9 | 96.3 | 94.2 |
| | Average | 96.9 | 97.1 | 96.3 | 98.2 | 97.1 | 96.3 | 94.2 |
| ONO test (% oxycodone N-oxide)[2] | | 0.02 | 0.08 | 0.04 | 0.03 | 0.04 | 0.06 | 0.26 |

[1][Mo = month(s)];
[2]relative to the label claim of oxycodone HCl.

TABLE 7.3.1

Example 7.3

| | | Whole (n = 10) | Flattened (n = 3) (15,000 lbs applied) | |
|---|---|---|---|---|
| Tablet Dimensions | Weight (mg) | 103 | 102 | 104 |
| | Thickness (mm) | 3.92 | 0.61[1] (15.6) | 0.66[1] (16.8) |
| | Diameter (mm) | 6.25 | 15.36 [2] | 15.24 [2] |
| | Breaking strength (N) | 439[3] | | |
| | Diameter (mm) post Breaking strength | 3.80 | | |

| | | Pre | post |
|---|---|---|---|
| Hammer Test pre and post tablet thickness measured (mm) | | 3.90 | 1.66 |
| | | 3.89 | 1.97 |
| | | 3.91 | 1.56 |

| | | Whole SGF | Whole 40% EtOH | Flattened SGF | Flattened 40% EtOH |
|---|---|---|---|---|---|
| Dissolution (% Released) (n = 3) | 0.5 hr | 19 | 15 | 26 | 19 |
| | 0.75 hr | 25 | 20 | 34 | 25 |
| | 1.0 hr | 30 | 25 | 40 | 31 |
| | 1.5 hr | 41 | 33 | 51 | 41 |
| | 2.0 hr | 50 | 41 | 60 | 50 |

| | | Whole | | | |
|---|---|---|---|---|---|
| Dissolution (% Released) (n = 6) | 0.5 hr | — | | | |
| | 1 hr | 32 | | | |
| | 2 hr | — | | | |
| | 4 hr | 83 | | | |
| | 8 hr | — | | | |
| | 12 hr | 101 | | | |

[1]3 measurements per tablet
[2] 2 measurements per tablet
[3]The tablets did not break when subjected to the maximum force of 439 Newton.

TABLE 7.3.2

Stability tests Example 7.3

| | | Storage conditions (° C./% RH) and storage time[1] | | | |
|---|---|---|---|---|---|
| | | Initial | 1 Mo 40/75 | 2 Mo 40/75 | 3 Mo 25/60 |
| Dissolution (% Released) (n = 6) SGF | 1 hr | 32 | 29 | 30 | 31 |
| | 4 hr | 83 | 76 | 77 | 78 |
| | 12 hr | 101 | 103 | 102 | 103 |
| Assay test (% oxycodone HCl)[2] | Assay 1 | 99.4 | 99.4 | 97.3 | 101.0 |
| | Assay 2 | 98.8 | 98.9 | 100.0 | 101.0 |
| | Average | 99.1 | 99.1 | 98.6 | 101.0 |
| ONO test (% oxycodone N-oxide)[2] | | 0.05 | 0.01 | 0.01 | 0.02 |

[1][Mo = month(s)];
[2]relative to the label claim of oxycodone HCl

Example 8

Two further 160 mg oxycodone hydrochloride tablets (Examples 8.1 and 8.2) were manufactured.

Compositions:

| | Example 8.1 | | Example 8.2 | |
|---|---|---|---|---|
| Ingredient | mg/unit | % | mg/unit | % |
| Oxycodone Hydrochloride | 160 | 25 | 160 | 25 |
| Polyethylene Oxide (high MW, grade 301) | 476.8 | 74.5 | 284.8 | 44.5 |
| Polyethylene Oxide (low MW, grade N10) | 0 | 0 | 192 | 30 |
| Magnesium Stearate | 3.2 | 0.5 | 3.2 | 0.5 |
| Total | 640 | 100 | 640 | 100 |

The processing steps to manufacture tablets were as follows:

1. Oxycodone HCl and Polyethylene Oxide were dry mixed in a low/high shear Black & Decker Handy Chopper dual blade mixer with a 1.5 cup capacity for 30 seconds.
2. Magnesium Stearate was added and mixed with the step 1 blend for additional 30 seconds 3. Step 2 blend was compressed to target weight on a single station tablet Manesty Type F 3 press using a capsule shaped tooling (7.937×14.290 mm).
4. Step 2 tablets were placed onto a tray placed in a Hotpack model 435304 oven at 73° C. for 3 hours to cure the tablets.

In vitro testing including testing for tamper resistance (breaking strength test) was performed as follows:

The tablets were tested in vitro using USP Apparatus 1 (basket) at 100 rpm in 900 ml simulated gastric fluid without enzymes (SGF) at 37° C., using an Agilent UV/VIS Spectrometer Model HP8453, UV wavelength at 280 nM, after having been subjected to curing for 3 hours. Tablet dimensions of the uncured and cured tablets and dissolution results are presented in Table 8.

As a further tamper resistance test, the cured and uncured tablets were subjected to a breaking strength test applying a force of a maximum of 196 Newton using a Schleuniger 2E/106 Apparatus to evaluate the resistance to breaking. The results are presented in Table 8.

Additionally, the tablets were flattened with a hammer using 10 manually conducted hammer strikes to impart physical tampering (hammer test). Results are presented in Table 8.

TABLE 8

|  |  | Example 8.1 | | Example 8.2 | |
|---|---|---|---|---|---|
|  |  | Uncured (n = 12) | 3 hr cure (n = 5) | Uncured (n = 12) | 3 hr cure (n = 10) |
| Tablet Dimensions | Weight (mg) | 648 | 648 | 643 | 643 |
|  | Thickness (mm) | 7.07 | 7.42 | 7.01 | 7.20 |
|  | Width (mm) | 7.96 | 7.97 | 7.96 | 7.91 |
|  | Breaking strength (N) | 196+ [1] (n = 2) | 196+ [1] (n = 1) | 196+ [1] (n = 2) | 196+ [1] (n = 2) |
| Dissolution (% Released) | 0.5 hr | Not tested | 9 | Not tested | 13 |
|  | 1 hr |  | 15 |  | 21 |
|  | 2 hr |  | 23 |  | 35 |
|  | 4 hr |  | 38 |  | 59 |
|  | 8 hr |  | 60 |  | 89 |
|  | 12 hr |  | 76 |  | 92 |
| Post Hammer Test (10 strikes applied manually) Thickness (mm) |  | Readily broke apart | — | Readily broke apart | 3.80 |

[1] The hardness tester would max at 20+ Kp equivalent to 196+ Newtons (1 Kp = 9.807 Newtons), the tablets did not break when subjected to the maximum force of 196 N.

Example 9

Three examples comprising each 12 mg of hydromorphone hydrochloride were manufactured and tested.

Compositions:

|  | Example 9.1 | Example 9.2 | Example 9.3 |
|---|---|---|---|
| Tablet | mg/unit | mg/unit | mg/unit |
| Hydromorphone HCl | 12 | 12 | 12 |
| Polyethylene Oxide (MW: approximately 7,000,000; Polyox ™ WSR 303) | 483 | 681 | 829.5 |
| Magnesium Stearate | 5 | 7 | 8.5 |
| Total | 500 | 700 | 850 |
| Total Batch size (kg) (amount manufactured) | 100 | 100 | 100 |

| Film Coating | mg/unit | mg/unit | mg/unit |
|---|---|---|---|
| Magnesium Stearate | 0.100 | 0.142 | 0.170 |
| Opadry white film coating concentrate formula Y-5-18024-A | 15 | 21 | 25.5 |
| Coating Batch Size (kg) | 80 | 79 | 80 |

The processing steps to manufacture tablets were as follows:
1. The Hydromorphone HCl and magnesium stearate were passed through a Sweco Sifter equipped with a 20 mesh screen, into separate suitable containers.
2. A Gemco "V" blender (with 1 bar)—10 cu. ft. was charged in the following order:
   Approximately 25 kg of the polyethylene oxide WSR 303
   Hydromorphone hydrochloride
   Approximately 25 kg of the polyethylene oxide WSR 303
3. Step 2 materials were blended for 10 minutes with the I bar on.
4. The remaining polyethylene oxide WSR 303 was charged into the Gemco "V" blender.
5. Step 4 materials were blended for 10 minutes with the I bar on.
6. Magnesium stearate was charged into the Gemco "V" blender.
7. Step 6 materials were blended for 3 minutes with the I bar off.
8. Step 7 blend was charged into clean, tared, stainless steel containers.
9. Step 8 blend was compressed to target weight on a 40 station tablet press at 133,000 tph speed using ½ inch standard round, concave (plain) tooling.
10. Step 9 tablets were loaded into a 48 inch Accela-Coat coating pan at a load of 80 kg (Example 9.1 and 9.3) and 79 kg (Example 9.2).
11. The pan speed was set to 2 rpm and the tablet bed was heated by setting the exhaust air temperature to achieve a target inlet temperature of approximately 75° C. The tablets were cured for 1 hour and 15 minutes at the following inlet temperature range, 75-87° C. (Example 9.1), 75-89° C. (Example 9.2) and 75-86° C. (Example 9.3).
12. At the onset of cooling the pan speed was increased to 7 rpm and the tablet bed was cooled using an exhaust air temperature to achieve a 25° C. inlet temperature until the exhaust temperature achieves 30-34° C. During the cooling process, magnesium stearate was added to the tablet bed to reduce tablet sticking.
13. The tablet bed was warmed using an exhaust air temperature to target a 55° C. inlet temperature. The film coating was started once the outlet temperature approached 39° C. and continued until the target weight gain of 3% was achieved.
14. After coating was completed, the pan speed was set to 1.5 rpm and the exhaust temperature was set to 27° C., the airflow was maintained at the current setting and the system cooled to an exhaust temperature of 27-30° C.
15. The tablets were discharged.

Example 10

A further tablet comprising 12 mg of hydromorphone hydrochloride was prepared.

Composition:

| Tablet | Example 10 mg/unit |
|---|---|
| Hydromorphone HCl | 12 |
| Polyethylene Oxide (MW: approximately 7,000.000; Polyox ™ WSR 303) | 483 |
| Magnesium Stearate | 5 |
| Total | 500 |
| Total Batch size (kg) (amount manufactured) | 119.98 |

The processing steps to manufacture tablets were as follows:
1. The hydromorphone HCl and magnesium stearate were passed through a Sweco Sifter equipped with a 20 mesh screen, into separate suitable containers.
2. A Gemco "V" blender (with 1 bar)—10 cu. ft. was charged in the following order:
   Approximately 60 kg of the polyethylene oxide WSR 303
   Hydromorphone hydrochloride
3. Step 2 materials were blended for 10 minutes with the I bar on.
4. The remaining polyethylene oxide WSR 303 was charged into the Gemco "V" blender.
5. Step 4 materials were blended for 10 minutes with the I bar on.
6. Magnesium stearate was charged into the Gemco "V" blender.
7. Step 6 materials were blended for 3 minutes with the I bar off.
8. Step 7 blend was charged into clean, tared, stainless steel containers.
9. Step 8 blend was compressed to target weight on a 40 station tablet press at 150,000 tph speed using ½ inch standard round, concave (plain) tooling.
10. Step 9 tablets were loaded into a 48 inch Accela-Coat coating pan at a load of 92.887 kg.
11. The pan speed was set to 1.9 rpm and the tablet bed was heated by setting the exhaust air temperature to achieve a target inlet temperature of approximately 80° C. The tablets were cured for 2 hours at the following inlet temperature range 80-85° C.
12. At the end of curing and onset of cooling, the tablet bed began to agglomerate (tablets sticking together). The pan speed was increased up to 2.8 rpm, but the tablet bed fully agglomerated and was non-recoverable for coating.

It is assumed that the agglomeration of tablets can be avoided, for example by lowering the curing temperature, by increasing the pan speed, by the use of Magnesium Stearate as anti-tacking agent, or by applying a sub-coating prior to curing.

However some tablets were sampled prior to cooling for In vitro testing which was performed as follows:

Cured tablets were tested in vitro using USP Apparatus 2 (paddle) at 75 rpm in 900 ml simulated gastric fluid without enzymes (SGF) at 37° C. using an on Waters Alliance System equipped with a Waters Novapak $C_{18}$ 3.9 mm×150 mm column, using a mobile phase consisting of a mixture of acetonitrile, SDS, and mono basic sodium phosphate buffer (pH 2.9). Detection was done with a PDA detector. Sample time points include 1, 2, 4, 8, 12, 18, and 22 hours.

TABLE 10

| | | USP Apparatus 2 |
|---|---|---|
| Dissolution (% Released) (n = 6) | 1 hr | 19 |
| | 2 hr | 30 |
| | 4 hr | 48 |
| | 8 hr | 77 |
| | 12 hr | 95 |
| | 18 hr | 103 |
| | 22 hr | 104 |

Example 11

A further tablet comprising 12 mg of hydromorphone hydrochloride was prepared.
Composition:

| Tablet | mg/unit |
|---|---|
| Hydromorphone HCl | 12 |
| Polyethylene Oxide (MW: approximately 7,000,000; Polyox ™ WSR 303) | 681 |
| Magnesium Stearate | 7 |
| Total | 700 |
| Total Batch size (kg) (amount manufactured) | 122.53 |
| Film Coating | |
| Opadry white film coating concentrate formula Y-5-18024-A | 21 |
| Coating Batch Size (kg) | 80 |

The processing steps to manufacture tablets were as follows:
1. The hydromorphone HCl and magnesium stearate were passed through a Sweco Sifter equipped with a 20 mesh screen, into separate suitable containers.
2. A Gemco "V" blender (with I bar)—10 cu. ft. was charged in the following order:
   Approximately 60 kg of the polyethylene oxide WSR 303
   Hydromorphone hydrochloride
3. The remaining polyethylene oxide WSR 303 was charged into the Gemco "V" blender.
4. Step 4 materials were blended for 10 minutes with the I bar on.
5. Magnesium stearate was charged into the Gemco "V" blender.
6. Step 5 materials were blended for 3 minutes with the I bar off.
7. Step 6 blend was charged into clean, tared, stainless steel containers.
8. Step 7 blend was compressed to target weight on a 40 station tablet press at 150,000 tph speed using ½ inch standard round, concave (plain) tooling.
9. Step 8 tablets were loaded into a 48 inch Accela-Coat coating pan at a load of 80.000 kg.
10. The pan speed was set to 1.8 rpm and the tablet bed was heated by setting the exhaust air temperature to achieve a target inlet temperature of approximately 80° C. The tablets were cured for 1.25 hours at the following inlet temperature range 75-85° C.
11. At the end of curing and onset of cooling, the tablet bed began to agglomerate (tablets sticking together). The pan speed was increased up to 10 rpm, and the tablets separated.
12. The pan speed was continued at approximately 10 rpm and the tablet bed was cooled using an exhaust air temperature to achieve a 25° C. inlet temperature until the exhaust temperature achieves 30-34° C.
13. The tablet bed was warmed using an exhaust air temperature to target a 55° C. inlet temperature. The film coating was started once the outlet temperature approached 39° C. and continued until the target weight gain of 3% was achieved.
14. After coating was completed, the pan speed was set to 1.5 rpm and the exhaust temperature was set to 27° C., the airflow was maintained at the current setting and the system cooled to an exhaust temperature of 27-30° C.
15. The tablets were discharged.

In vitro testing was performed as follows:

Coated tablets were tested in vitro using USP Apparatus 2 (paddle) at 75 rpm in 900 ml simulated gastric fluid without enzymes (SGF) at 37° C. using an a Waters Alliance System equipped with a Waters Novapak $C_{18}$ 3.9 mm×150 mm column, using a mobile phase consisting of a mixture of acetonitrile, SDS, and mono basic sodium phosphate buffer (pH 2.9). Detection was done with a PDA detector. Sample time points include 1, 2, 4, 8, 12, 18, 22, and 24 hours. The results are presented in Table 11.

TABLE 11

|  |  | USP Apparatus 2 |
|---|---|---|
| Dissolution | 1 hr | 12 |
| (% Released) | 2 hr | 19 |
| (Mean n = 6) | 4 hr | 29 |
|  | 8 hr | 46 |
|  | 12 hr | 60 |
|  | 18 hr | 76 |
|  | 22 hr | 84 |
|  | 24 hr | 88 |

Example 12

Two further examples comprising 10 mg of oxycodone hydrochloride which include core tablets as presented in Example 2.3 were manufactured which were coated by a polyethylene oxide coating to provide a delay of the release.

Composition: Core Tablet

| Ingredient | mg/unit |
|---|---|
| Oxycodone HCl | 10 |
| Polyethylene Oxide (MW: approximately 4,000,000; Polyox ™ WSR301) | 85 |
| Hydroxypropyl Cellulose (Klucel ™ HXF) | 5 |
| Total Tablet Core | 100 |

Composition: Compression Coat Over Core Tablet

| Ingredient | Example 12.1 mg/unit | Example 12.2 mg/unit |
|---|---|---|
| Polyethylene Oxide (MW: approximately 4,000,000; Polyox ™ WSR301) | 200 | 100 |
| Core tablet | 100 | 100 |
| Total Tablet Weight | 300 | 200 |

Process of Manufacture:

The processing steps to manufacture tablets were as follows:
1. A tablet from Example 2.3 was used as the tablet core.
2. A single station Manesty Type F 3 tablet press was equipped with 0.3125 inch, round, standard concave plain tooling.
3. For Example 12.1, approximately 100 mg of Polyethylene Oxide was placed in the die, the tablet core was manually centered in the die (on top of the powder bed), an additional 100 mg of Polyethylene Oxide was placed on top of the tablet in the die.
4. The materials were manually compressed by turning the compression wheel.
5. For Example 12.2, approximately 50 mg of Polyethylene Oxide was placed in the die, the tablet core was manually centered in the die (on top of the powder bed), an additional 50 mg of Polyethylene Oxide was placed on top of the tablet in the die.
6. The materials were manually compressed by turning the compression wheel.
7. Step 4 and step 6 tablets were placed onto a tray placed in a Hotpack model 435304 oven targeting 75° C. for 3 hours to cure the compression coated tablets.

In vitro testing was performed as follows:

The tablets were tested in vitro using USP Apparatus 1 (basket) at 100 rpm in 900 ml simulated gastric fluid without enzymes (SGF) at 37° C., using a Perkin Elmer UV/VIS Spectrometer Lambda 20 USP Apparatus, UV at 220 nM. The cured compression coated tablet dimensions and dissolution results are presented in Table 12.

TABLE 12

|  |  | Example 12.1 | | Example 12.2 | |
|---|---|---|---|---|---|
| Tablet Dimensions | Weight (mg) | 304 | 312 | 209 | 210 |
|  | Thickness (mm) | 5.62 | 5.73 | 5.24 | 5.29 |
|  | Diameter (mm) | 9.10 | 9.10 | 7.61 | 7.54 |
| Dissolution | 0.5 hr |  | 0 |  | 1 |
| (% Released) | 1 hr |  | 0 |  | 15 |
| (n = 2) | 2 hr |  | 1 |  | 47 |
|  | 4 hr |  | 9 |  | 95 |
|  | 8 hr |  | 82 |  | 96 |
|  | 12 hr |  | 97 |  | 96 |

Example 13

In Example 13, five different 156 mg tablets (Examples 13.1 to 13.5) including 10, 15, 20, 30 and 40 mg of Oxycodone HCl were prepared using high molecular weight polyethylene oxide.

Compositions:

|  | Example 13.1 mg/unit | Example 13.2 mg/unit | Example 13.3 mg/unit | Example 13.4 mg/unit | Example 13.5 mg/unit |
|---|---|---|---|---|---|
| Ingredient |  |  |  |  |  |
| Oxycodone HCl | 10 | 15 | 20 | 30 | 40 |
| Polyethylene oxide (MW: approximately 4,000,000; Polyox ™ WSR-301) | 138.5 | 133.5 | 128.5 | 118.5 | 108.5 |

-continued

| | Example 13.1 mg/unit | Example 13.2 mg/unit | Example 13.3 mg/unit | Example 13.4 mg/unit | Example 13.5 mg/unit |
|---|---|---|---|---|---|
| Magnesium Stearate | 1.5 | 1.5 | 1.5 | 1.5 | 1.5 |
| Total Core Tablet Weight (mg) | 150 | 150 | 150 | 150 | 150 |
| Total Batch size Coating | 10 kg | 10 kg | 10 kg | 10 kg | 10 kg |
| Opadry film coating | 6 | 6 | 6 | 6 | 6 |
| Total Tablet Weight (mg) | 156 | 156 | 156 | 156 | 156 |
| Coating Batch Size (kg) | 8.754 | 9.447 | 9.403 | 8.717 | 8.902 |

The processing steps to manufacture tablets were as follows:
1. A Patterson Kelly "V" blender (with I bar)—16 quart was charged in the following order:
   Approximately ½ of the polyethylene oxide WSR 301
   Oxycodone hydrochloride
   Remaining polyethylene oxide WSR 301
2. Step 1 materials were blended for 5 minutes with the I bar on.
3. Magnesium stearate was charged into the "V" blender.
4. Step 3 materials were blended for 1 minute with the I bar off.
5. Step 4 blend was charged into a plastic bag.
6. Step 5 blend was compressed to target weight on an 8 station tablet press at 35,000 tph speed using 9/32 inch standard round, concave (embossed) tooling.
7. Step 6 tablets were loaded into a 24 inch Compu-Lab coating pan at a pan load of 8.754 kg (Example 13.1), 9.447 kg (Example 13.2), 9.403 kg (Example 13.3), 8.717 kg (Example 13.4), 8.902 kg (Example 13.5).
8. A temperature probe (wire thermocouple) was placed into the pan directly above the tablet bed so that the probe tip was near the moving bed of tablets.
9. The pan speed was set to 7 rpm and the tablet bed was heated by setting the inlet temperature to achieve a probe target temperature of 75° C. The curing starting point (as described by method 4) was initiated once the temperature probe indicated approximately 70° C. (Example 13.1 at 68.3° C., Example 13.2 at 69.9° C., Example 13.3 and 13.4 at 70.0° C., and Example 13.5 at 71.0° C.). Once the target probe temperature was achieved, the inlet temperature was adjusted as necessary to maintain this target probe temperature. The tablets were cured for 90 minutes. The pan speed was increased to 12 rpm at approximately 60 minutes of curing (except for Example 13.5, the pan speed was maintained at 7 rpm throughout curing). Samples were taken after 30 minutes, 60 minutes and 90 minutes of curing. The temperature profile of the curing processes for Examples 13.1 to 13.5 is presented in Tables 13.1.1 to 13.5.1 and in FIGS. 10 to 14.
10. At the end of curing, magnesium stearate was added to the moving be of tablets as an anti-tacking agent. The amount of magnesium stearate added was 8.75 g (Example 13.1), 1.8887 g (Example 13.2), 1.8808 g (Example 13.3), 1.7400 g (Example 13.4), and 1.784 g (Example 13.5). The magnesium stearate was weighed in a weigh boat and was applied by manually dispensing (dusting) the powder across the moving tablet bed. The pan speed was continued at 12 rpm (Example 13.5 at 7 rpm) and the tablet bed was cooled by setting the inlet temperature to 21° C. The tablet bed was cooled to an exhaust temperature of <41° C.
11. The tablet bed was warmed using an inlet setting of 55° C. The film coating was started once the exhaust temperature achieved approximately 43° C. and continued until the target weight gain of 4% was achieved.
12. After film coating was completed, the pan speed was reduced (3 to 6 rpm) and the inlet temperature was set to 21° to 25° C. to cool the system, the airflow was maintained at the current setting.
13. The tablets were discharged.

In vitro testing including breaking strength tests and density measurement was performed as follows:

Tablets cured for 30 minutes and 60 minutes, and tablets cured for 90 minutes and coated were tested in vitro using USP Apparatus 1 (basket) at 100 rpm in 900 ml simulated gastric fluid without enzymes (SGF) at 37° C. Samples were analyzed by reversed-phase high performance liquid chromatography (HPLC) on Waters Atlantis dC18 3.0×150 mm, 3 μm column, using a mobile phase consisting of a mixture of acetonitrile and non basic potassium phosphate buffer (pH 3.0) at 230 nm UV detection. Sample time points include 1.0, 2.0, 4.0, 8.0 and 12.0 hours. Tablet dimensions and dissolution results corresponding to the respective curing time and temperature are presented in Tables 13.1.2 to 13.5.2.

Uncured tablets, cured tablets and cured, coated tablets were subjected to a breaking strength test by applying a force of a maximum of 439 Newton using a Schleuniger Model 6D apparatus to evaluate tablet resistance to breaking or to a breaking strength test applying a force of a maximum of 196 Newton using a Schleuniger 2E/106 Apparatus to evaluate the resistance to breaking.

The density of uncured tablets and tablets cured for different periods of time (30, 60 and 90 minutes samples) was determined by Archimedes principle, using a Top-loading Mettler Toledo balance Model #AB 135-S/FACT, Serial #1127430072 and a density determination kit 33360, according to the following procedure:
1. Set-up the Mettler Toledo balance with the Density Determination Kit.
2. Fill an appropriately sized beaker (200 ml) with hexane.
3. Weigh the tablet in air and record the weight as Weight A.
4. Transfer the same tablet onto the lower coil within the beaker filled with hexane.
5. Determine the weight of the tablet in hexane and record the weight as Weight B.
6. Perform the density calculation according to the equation $$\rho = \frac{A}{A-B} \cdot \rho_0,$$

wherein
ρ; Density of the tablet
A: Weight of the tablet in air
B: Weight of the tablet when immersed in the liquid
$\rho_0$: Density of the liquid at a given temperature (density of hexane at 20° C.=0.660 g/ml (Merck Index)
7. Record the density.

The reported density values are mean values of 3 tablets and all refer to uncoated tablets.

The results are presented in the following Tables.

TABLE 13.1.1

Temperature profile of the curing process for Ex. 13.1

| Total Time (min.) | Curing time (min.)[1] | Set inlet temperature (° C.) | Actual inlet temperature (° C.)[2] | Probe temperature (° C.)[3] | Exhaust temperature (° C.)[4] | Comments |
|---|---|---|---|---|---|---|
| 0 | — | 27 | 26.9 | 26.8 | 25.7 | |
| 10 | — | 75 | 74.9 | 59.5 | 56.8 | |
| 15 | 0 | 85 | 84.8 | 68.3 | 65.5 | Curing starts |
| 20 | 5 | 85 | 84.7 | 71 | 68.4 | |
| 26 | 11 | 85 | 84.8 | 72.8 | 70.1 | |
| 30 | 15 | 85 | 84.8 | 74 | 70.9 | |
| 45 | 30 | 83 | 83 | 74.8 | 74.7 | 30 min sample |
| 55 | 40 | 81 | 81.2 | 74.8 | 76 | |
| 61 | 46 | 81 | 81.2 | 74.7 | 75.9 | |
| 65 | 50 | 81 | 81 | 74.8 | 75.8 | |
| 70 | 55 | 81 | 81 | 74.7 | 75.8 | |
| 75 | 60 | 81 | 81.1 | 75 | 75.9 | 60 min sample |
| 85 | 70 | 81 | 81.1 | 74.6 | 75.8 | |
| 95 | 80 | 81 | 81.1 | 74.8 | 75.9 | |
| 105 | 90 | 81 | 80.9 | 74.9 | 76 | End of curing, 90 min sample |
| 112 | — | 21 | 35.3 | 49 | 55.6 | |
| 128 | — | 21 | 33.4 | 32 | — | |

[1]determined according to method 4,
[2]temperature measured at the inlet;
[3]temperature measured using the temperature probe (wire thermocouple)
[4]temperature measured at the exhaust.

TABLE 13.1.2

| | | Example 13.1 | | | |
|---|---|---|---|---|---|
| | | Uncured (n = 5) | 30 min cure (n = 5) | 60 min cure (n = 5) | 90 min cure, coated (n = 5) |
| Tablet Dimensions | Weight (mg) | 153 | 153 | 152 | 158 |
| | Thickness (mm) | 4.63 | 4.98 | 4.89 | 4.89 |
| | Diameter (mm) | 7.14 | 7.00 | 6.98 | 6.98 |
| | Breaking strength (N) | 80 | 196 [1] | 196 [1] | 438 [2] |
| | | | n = 3 | n = 3 | n = 6 |
| Dissolution (% Released) SGF | 1 hr | — | 25 (9.5) | 24 (8.4) | 27 (7.3) |
| | 2 hr | — | 39 (7.7) | 39 (8.7) | 43 (6.6) |
| | 4 hr | — | 62 (7.0) | 62 (5.8) | 67 (6.8) |
| | 8 hr | — | 89 (4.7) | 91 (5.0) | 92 (2.9) |
| | 12 hr | — | 100 (3.3) | 100 (3.6) | 101 (2.4) |

[1] maximum force of the hardness tester, the tablets did not break when subjected to the maximum force of 196 N.
[2] maximum force of the hardness tester, the tablets did not break when subjected to the maximum force of 438 N.

TABLE 13.2.1

Temperature profile of the curing process for Ex. 13.2

| Total Time (min.) | Curing time (min.)[1] | Set inlet temperature (° C.) | Actual inlet temperature (° C.)[2] | Probe temperature (° C.)[3] | Exhaust temperature (° C.)[4] | Comments |
|---|---|---|---|---|---|---|
| 0 | — | 23 | 22.7 | 26.1 | 23.8 | |
| 5 | — | 85 | 81 | 55.7 | 51.1 | |
| 10 | — | 85 | 85.1 | 63.7 | 62.3 | |
| 21 | 0 | 85 | 84.8 | 69.9 | 69.1 | Curing starts |
| 31 | 10 | 85 | 85.1 | 72.4 | 70.9 | |
| 41 | 20 | 85 | 85.1 | 73.7 | 72.5 | |
| 51 | 30 | 82 | 82 | 74.8 | 75.8 | 30 min sample |
| 61 | 40 | 82 | 81.9 | 75 | 76.2 | |
| 71 | 50 | 81 | 81 | 74.8 | 75.9 | |
| 81 | 60 | 81 | 80.8 | 75 | 75.9 | 60 min sample |
| 91 | 70 | 81 | 81 | 74.9 | 76 | |
| 101 | 80 | 80.5 | 80.5 | 74.8 | 75.8 | |
| 111 | 90 | 80.5 | 80.5 | 74.8 | 75.7 | End of curing, 90 min sample |
| 118 | — | 21 | 23.1 | 50 | 55.1 | |
| 131 | — | 21 | 22.4 | 34.1 | 37.7 | |

[1]determined according to method 4,
[2]temperature measured at the inlet;
[3]temperature measured using the temperature probe (wire thermocouple),
[4]temperature measured at the exhaust.

TABLE 13.2.2

| | | Example 13.2 | | | |
|---|---|---|---|---|---|
| | | Uncured (n = 5) | 30 min cure (n = 5) | 60 min cure (n = 5) | 90 min cure, coated (n = 5) |
| Tablet Dimensions | Weight (mg) | 152 | 153 | 152 | 157 |
| | Thickness (mm) | 4.69 | 4.99 | 4.90 | 4.84 |
| | Diameter (mm) | 7.14 | 6.98 | 6.95 | 6.95 |
| | Breaking strength (N) | 62 | 196 [1] | 196 [1] | 196 [1] |
| | | | n = 6 | n = 6 | n = 6 |
| Dissolution (% Released) SGF | 1 hr | — | 23 (10.6) | 22 (8.5) | 25 (5.2) |
| | 2 hr | — | 38 (10.1) | 37 (7.7) | 41 (4.6) |
| | 4 hr | — | 64 (9.5) | 61 (8.1) | 65 (3.6) |
| | 8 hr | — | 92 (6.8) | 90 (4.6) | 91 (2.4) |
| | 12 hr | — | 100 (3.4) | 100 (3.2) | 99 (2.9) |

[1] maximum force of the hardness tester, the tablets did not break when subjected to the maximum force of 196 N.

TABLE 13.3.2

| | | Example 13.3 | | | |
|---|---|---|---|---|---|
| | | Uncured (n = 5) | 30 min cure (n = 5) | 60 min cure (n = 5) | 90 min cure, coated (n = 5) |
| Tablet Dimensions | Weight (mg) | 154 | 154 | 152 | 160 |
| | Thickness (mm) | 4.56 | 4.85 | 4.79 | 4.77 |
| | Diameter (mm) | 7.13 | 7.01 | 6.96 | 6.98 |
| | Breaking strength (N) | 83 | 196 [1] | 196 [1] | 196 [1] |
| | | | n = 6 | n = 6 | n = 6 |
| Dissolution (% Released) SGF | 1 hr | — | 22 (5.8) | 26 (9.2) | 23 (5.7) |
| | 2 hr | — | 37 (6.4) | 42 (8.6) | 39 (4.7) |
| | 4 hr | — | 61 (6.3) | 67 (6.3) | 64 (3.7) |
| | 8 hr | — | 90 (4.5) | 93 (3.3) | 92 (2.7) |
| | 12 hr | — | 99 (3.1) | 101 (2.2) | 101 (1.8) |

[1] maximum force of the hardness tester, the tablets did not break when subjected to the maximum force of 196 N.

TABLE 13.3.1

Temperature profile of the curing process for Ex. 13.3:

| Total Time (min.) | Curing time (min.)[1] | Set inlet temperature (° C.) | Actual inlet temperature (° C.)[2] | Probe temperature (° C.)[3] | Exhaust temperature (° C.)[4] | Comments |
|---|---|---|---|---|---|---|
| 0 | — | 25 | 24.9 | 27.8 | 26.2 | |
| 5 | — | 90 | 85 | 58.2 | 53.9 | |
| 10 | — | 90 | 89.8 | 67 | 65.1 | |
| 13 | 0 | 90 | 90.1 | 70 | 68.3 | Curing starts |
| 23 | 10 | 90 | 90 | 74.6 | 72.2 | |
| 33 | 20 | 86 | 85.9 | 74.7 | 73.4 | |
| 43 | 30 | 83 | 83.1 | 75.4 | 76.5 | 30 min sample |
| 53 | 40 | 82 | 82.1 | 74.9 | 76.3 | |
| 63 | 50 | 81.5 | 81.8 | 75 | 76.4 | |
| 73 | 60 | 81.5 | 81.5 | 74.7 | 76.1 | 60 min sample |
| 83 | 70 | 81.5 | 81.5 | 75 | 76.1 | |
| 93 | 80 | 81.5 | 81.6 | 75 | 76.1 | |
| 103 | 90 | 81.5 | 81.3 | 75 | 76.1 | End of curing, 90 min sample |
| 109 | — | 21 | 35.5 | 50 | 57.5 | |
| 121 | — | 21 | 22.6 | 33.8 | 39.3 | |

[1] determined according to method 4,
[2] temperature measured at the inlet;
[3] temperature measured using the temperature probe (wire thermocouple),
[4] temperature measured at the exhaust.

TABLE 13.4.1

Temperature profile of the curing process for Ex. 13.4:

| Total Time (min.) | Curing time (min.)[1] | Set inlet temperature (° C.) | Actual inlet temperature (° C.)[2] | Probe temperature (° C.)[3] | Exhaust temperature (° C.)[4] | Comments |
|---|---|---|---|---|---|---|
| 0 | — | 25 | 25 | 24.6 | 23.4 | |
| 5 | — | 90 | 85 | 46.8 | 51 | |
| 10 | — | 90 | 89.9 | 56.6 | 63.8 | |
| 15 | — | 90 | 89.8 | 68.5 | 68.7 | |
| 16 | 0 | 90 | 90.1 | 70 | 69.5 | Curing starts |
| 26 | 10 | 90 | 90 | 73.6 | 72.9 | |
| 36 | 20 | 86 | 86 | 75.4 | 76.8 | |
| 46 | 30 | 84 | 84 | 75.4 | 77.2 | 30 min sample |

TABLE 13.4.1-continued

Temperature profile of the curing process for Ex. 13.4:

| Total Time (min.) | Curing time (min.)[1] | Set inlet temperature (° C.) | Actual inlet temperature (° C.)[2] | Probe temperature (° C.)[3] | Exhaust temperature (° C.)[4] | Comments |
|---|---|---|---|---|---|---|
| 56 | 40 | 83 | 82.9 | 75.1 | 76.8 | |
| 66 | 50 | 82 | 81.4 | 74.8 | 76.6 | |
| 76 | 60 | 82 | 81.7 | 74.7 | 76.3 | 60 min sample |
| 86 | 70 | 82 | 82.1 | 75 | 76.3 | |
| 96 | 80 | 82 | 82.1 | 75.1 | 76.3 | |
| 106 | 90 | 82 | 82.1 | 75.1 | 76.4 | End of curing, 90 min sample |
| 112 | — | 21 | 33.8 | 55.9 | 50 | |
| 126 | — | 21 | 22.1 | 31.6 | 34.6 | |

[1] determined according to method 4,
[2] temperature measured at the inlet;
[3] temperature measured using the temperature probe (wire thermocouple),
[4] temperature measured at the exhaust.

TABLE 13.4.2

| | | Example 13.4 | | | |
|---|---|---|---|---|---|
| | | Uncured (n = 5) | 30 min cure (n = 5) | 60 min cure (n = 5) | 90 min cure, coated (n = 5) |
| Tablet Dimensions | Weight (mg) | 150 | 151 | 150 | 159 |
| | Thickness (mm) | 4.43 | 4.73 | 4.67 | 4.68 |
| | Diameter (mm) | 7.13 | 7.00 | 6.97 | 7.00 |
| | Breaking strength (N) | 65 | 196[1] | 196[1] | 196[1] |

TABLE 13.4.2-continued

| | | | n = 6 | n = 6 |
|---|---|---|---|---|
| Dissolution (% Released) SGF | 1 hr | — | 29 (3.2) | 25 (7.9) | 24 (5.5) |
| | 2 hr | — | 47 (3.1) | 42 (6.7) | 41 (5.2) |
| | 4 hr | — | 71 (2.4) | 67 (5.2) | 67 (6.2) |
| | 8 hr | — | 92 (2.5) | 92 (4.3) | 94 (3.2) |
| | 12 hr | — | 99 (2.1) | 100 (2.8) | 101 (2.2) |

[1] maximum force of the hardness tester, the tablets did not break when subjected to the maximum force of 196 N.

TABLE 13.5.1

Temperature profile of the curing process for Ex. 13.5:

| Total Time (min.) | Curing time (min.)[1] | Set inlet temperature (° C.) | Actual inlet temperature (° C.)[2] | Probe temperature (° C.)[3] | Exhaust temperature (° C.)[4] | Comments |
|---|---|---|---|---|---|---|
| 0 | — | 80 | 69.2 | 39.8 | 35.6 | |
| 10 | — | 90 | 80.2 | 64.9 | 65.6 | |
| 20 | 0 | 90 | 90.2 | 70.9 | 71 | Curing starts |
| 25 | 5 | 90 | 89.9 | 71.7 | 72.4 | |
| 30 | 10 | 90 | 90.1 | 72.8 | 73.4 | |
| 35 | 15 | 85 | 87.1 | 74.1 | 76.1 | |
| 50 | 30 | 85 | 85 | 75.2 | 77.5 | 30 min sample |
| 60 | 40 | 83 | 83.2 | 74.7 | 76.8 | |
| 80 | 60 | 83 | 83.1 | 75.1 | 76.5 | 60 min sample |
| 90 | 70 | 83 | 83 | 75.3 | 76.6 | |
| 100 | 80 | 80 | 79.1 | 74.4 | 76 | |
| 110 | 90 | 80 | 80.1 | 73.6 | 74.7 | End of curing, 90 min sample |
| 115 | — | 21 | 39.6 | 55.6 | 59.4 | |
| 120 | — | 21 | 24.5 | 41.5 | 45.2 | |
| 125 | — | 21 | 23 | 37.7 | 40.7 | |

[1] determined according to method 4,
[2] temperature measured at the inlet;
[3] temperature measured using the temperature probe (wire thermocouple),
[4] temperature measured at the exhaust.

TABLE 13.5.2

|   |   | Uncured (n = 5) | 30 min cure (n = 5) | 60 min cure (n = 5) | 90 min cure (n = 5) | 90 min cure, coated (n = 5) |
|---|---|---|---|---|---|---|
|   |   |   |   | Example 13.5 | | |
| Tablet Dimensions | Weight (mg) | 156 | 157 | 154 | 153 | 158 |
|   | Thickness (mm) | 4.45 | 4.66 | 4.57 | 4.52 | 4.51 |
|   | Diameter (mm) | 7.12 | 7.06 | 7.04 | 7.03 | 7.08 |
|   | Breaking strength (N) | 90 | 438 [1] | 438 [1] | 438 [1] | 438 [1] |
|   | Relaxed diameter (mm) post breaking strength test (NLT 15 min relax period) | — | 4.57 | 4.68 | 4.69 | 4.67 |
|   |   |   |   | n = 6 |   | n = 6 |
| Dissolution (% Released) SGF | 1 hr | — | 28 (5.0) | 29 (5.9) | — | 26 (1.4) |
|   | 2 hr | — | 45 (5.2) | 45 (5.6) | — | 42 (1.4) |
|   | 4 hr | — | 69 (4.8) | 70 (4.4) | — | 68 (2.0) |
|   | 8 hr | — | 93 (4.2) | 94 (4.0) | — | 94 (4.0) |
|   | 12 hr | — | 98 (3.9) | 102 (5.2) | — | 99 (5.1) |

[1] maximum force of the hardness tester, the tablets did not break when subjected to the maximum force of 438 N.

TABLE 13.6

|   | Density (g/cm$^3$)[1] | | | | Density change after curing (%)[2] |
|---|---|---|---|---|---|
|   | Uncured | 30 min cure | 60 min cure | 90 min cure | |
| Example 13.1 | 1.172 | 1.131 | 1.134 | 1.137 | −2.986 |
| Example 13.2 | 1.174 | 1.137 | 1.137 | 1.140 | −2.896 |
| Example 13.3 | 1.179 | 1.151 | 1.152 | 1.152 | −2.290 |
| Example 13.4 | 1.182 | 1.167 | 1.168 | 1.172 | −0.846 |
| Example 13.5 | 1.222 | 1.183 | 1.183 | 1.187 | −2.864 |

[1] The density value is a mean value of 3 tablets measured;

[2] The density change after curing corresponds to the observed density change in % of the tablets cured for 90 min in comparison to the uncured tablets.

Example 14

In Example 14, five different 156 mg tablets (Examples 14.1 to 14.5) including 10, 15, 20, 30 and 40 mg of oxycodone HCl were prepared using high molecular weight polyethylene oxide, in a larger batch size compared to Example 13.

Compositions:

|   | Example 14.1 mg/unit | Example 14.2 mg/unit | Example 14.3 mg/unit | Example 14.4 mg/unit | Example 14.5 mg/unit |
|---|---|---|---|---|---|
| Ingredient | | | | | |
| Oxycodone HCl | 10 | 15 | 20 | 30 | 40 |
| Polyethylene oxide (MW: approximately 4,000,000; Polyox ™ WS-301) | 138.5 | 133.5 | 128.5 | 118.5 | 108.5 |
| Magnesium Stearate | 1.5 | 1.5 | 1.5 | 1.5 | 1.5 |
| Total Core Tablet Weight (mg) | 150 | 150 | 150 | 150 | 150 |
| Total | 100 kg | 100 kg | 100 kg | 100 kg | 100 kg |

-continued

|   | Example 14.1 mg/unit | Example 14.2 mg/unit | Example 14.3 mg/unit | Example 14.4 mg/unit | Example 14.5 mg/unit |
|---|---|---|---|---|---|
| Batch size Coating | | | | | |
| Opadry film coating | 6 | 6 | 6 | 6 | 6 |
| Total Tablet Weight (mg) | 156 | 156 | 156 | 156 | 156 |
| Coating Batch Size (kg) | 97.480 | 98.808 | 97.864 | 99.511 | 98.788 |

The processing steps to manufacture tablets were as follows:
1. The magnesium stearate was passed through a Sweco Sifter equipped with a 20 mesh screen, into a separate suitable container.
2. A Gemco "V" blender (with I bar) 10 cu. ft. was charged in the following order:
   Approximately ½ of the polyethylene oxide WSR 301
   Oxycodone hydrochloride
   Remaining polyethylene oxide WSR 301
3. Step 2 materials were blended for 10 minutes with the I bar on.
4. Magnesium stearate was charged into the Gemco "V" blender.
5. Step 4 materials were blended for 3 minutes with the I bar off.
6. Step 5 blend was charged into clean, tared, stainless steel containers.
7. Step 6 blend was compressed to target weight on a 40 station tablet press at 135,000 tph using 9/32 inch standard round, concave (embossed) tooling.
8. Step 7 tablets were loaded into a 48 inch Accela-Coat coating pan at a load of 97.480 kg (Example 14.1), 98.808 kg (Example 14.2), 97.864 kg (Example 14.3), 99.511 kg (Example 14.4) and 98.788 kg (Example 14.5).
9. The pan speed was set to 7 rpm and the tablet bed was heated by setting the exhaust air temperature to achieve an inlet air temperature of 75° C. The tablets were cured at the target inlet temperature for 1 hour (Examples 14.1 to 14.5). The starting point used for the determination of the curing time according to method 1 was the point when the inlet temperature achieved the target temperature of 75° C. The temperature profile of the curing processes of Examples 14.1 to 14.5 is presented in Tables 14.1.1 to 14.5.1 and in FIGS. 15 to 19.

10. The pan speed was continued at 7 rpm for Examples 14.2, 14.4 and 14.5. The pan speed was increased up to 10 rpm for Example 14.1 and up to 8 rpm for Example 14.3. For Examples 14.2 to 14.5, 20 g of magnesium stearate was added as an anti-tacking agent. The tablet bed was cooled by slowly lowering the exhaust temperature setting (Example 14.1) or by immediately setting the exhaust temperature setting to 25° C. (Example 14.2) or 30° C. (Examples 14.3 to 14.5). until a specific exhaust temperature of 30 to 34° C. was reached.
11. The tablet bed was warmed using an exhaust air temperature to target a 55° C. inlet temperature. The film coating was started once the exhaust temperature approached 39° C. and continued until the target weight gain of 4% was achieved.
12. After coating was completed, the pan speed was set to 1.5 rpm and the exhaust temperature was set to 27° C., the airflow was maintained at the current setting and the system cooled to an exhaust temperature of 27-30° C.
13. The tablets were discharged.

In vitro testing including breaking strength tests and stability tests was performed as follows:

Tablets cured for 1 hour and coated were tested in vitro using USP Apparatus 1 (basket) at 100 rpm in 900 ml simulated gastric fluid without enzymes (SGF) at 37° C. Samples were analyzed by reversed-phase high performance liquid chromatography (HPLC) on Waters Atlantis dC18 3.0×150 mm, 3 μm column, using a mobile phase consisting of a mixture of acetonitrile and non basic potassium phosphate buffer (pH 3.0) at 230 nm UV detection. Sample time points include 1.0, 2.0, 4.0, 6.0, 8.0 and 12.0 hours. Tablet dimensions and dissolution results corresponding to the respective curing time and temperature are presented in Tables 14.1.2 to 14.5.2.

Uncured tablets were subjected to a breaking strength test by applying a force of a maximum of 196 Newton using a Schleuniger 2E/106 Apparatus to evaluate tablet resistance to breaking.

Cured, coated tablets were subjected to a stability test by storing them in 100 count bottles at different storage conditions (25° C./60% relative humidity or 40° C./75% relative humidity) for a certain period of time and subsequently testing the tablets in vitro as described above. Sample time points regarding storage include initial sample (i.e. prior to storage), one month, two months, three months and six months of storage, sample time points regarding dissolution test include 1.0, 2.0, 4.0, 8.0 and 12.0 hours.

Cured, coated tablets were subjected to a further stability test by storing them in 100 count bottles at different storage conditions (25° C./60% relative humidity or 40° C./75% relative humidity) for a certain period of time and subsequently subjecting the tablets to the assay test to determine the content of oxycodone HCl in the tablet samples. Sample time points regarding storage include initial sample (i.e. prior to storage), one month, two months, three months and six months of storage. In the assay test, oxycodone hydrochloride was extracted from two sets of ten tablets each with 900 mL of a 1:2 mixture of acetonitrile and simulated gastric fluid without enzyme (SGF) under constant magnetic stirring in a 1000-mL volumetric flask until all tablets were completely dispersed or for overnight. The sample solutions were diluted and analyzed by reversed-phase high performance liquid chromatography (HPLC) on Waters Atlantis dC$_{18}$ 3.0×250 mm, 5 μm column maintained at 60° C. using a mobile phase consisting of acetonitrile and potassium phosphate monobasic buffer at pH 3.0 with UV detection at 280 nm.

Cured, coated tablets were subjected to a further stability test by storing them in 100 count bottles at different storage conditions (25° C./60% relative humidity or 40° C./75% relative humidity) for a certain period of time and subsequently subjecting the tablets to the oxycodone-N-oxide (ONO) test to determine the content of the degradation product oxycodone-N-oxide and unknown degradation products in percent by weight, relative to the oxycodone HCl label claim. Sample time points regarding storage include initial sample (i.e. prior to storage), one month, two months, three months and six months of storage. In the ONO test, oxycodone hydrochloride and its degradation products were extracted from a set of ten tablets with 900 mL of a 1:2 mixture of acetonitrile and simulated gastric fluid without enzyme (SGF) under constant magnetic stirring in a 1000-mL volumetric flask until all tablets were completely dispersed or for overnight. The sample solutions were diluted and analyzed by reversed-phase high performance liquid chromatography (HPLC) on Waters Atlantis dC$_{18}$ 3.0×250 mm, 5 μm column maintained at 60° C. using a mobile phase consisting of acetonitrile and potassium phosphate monobasic buffer at pH 3.0 with UV detection at 206 nm.

The density of uncured tablets, cured tablets and cured/coated tablets was determined as described for Example 13.

The results are presented in the following Tables.

TABLE 14.1.1

Temperature profile of the curing process for Ex. 14.1

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 0 | — | — | — | — | 7 | Load pan, start warming |
| 20 | — | 65 | 57 | 56 | 7 | |
| 21 | — | 65.0 | | | 7 | |
| 28 | — | 70.0 | | | 7 | |
| 30 | — | 72.0 | 64 | 63 | 7 | |
| 36 | 0 | 75.0 | 65 | 65 | 7 | Curing starts 0 min sample |
| 43 | 7 | 73.2 | | | 7 | |
| 46 | 10 | 73 | 67 | 67 | | |
| 51 | 15 | 72.2 | | | 7 | 15 min sample |
| 56 | 20 | 71.8 | 67 | 67 | 8 | |
| 66 | 30 | 75.0 | 68 | 68 | 8 | 30 min sample |
| 76 | 40 | 73.0 | 68 | 68 | 8 | |

TABLE 14.1.1-continued

Temperature profile of the curing process for Ex. 14.1

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 81 | 45 | 74.8 | | | 8 | 45 min sample |
| 86 | 50 | 74.3 | 69 | 69 | 8 | |
| 92 | 56 | 72.3 | | | 8 | |
| 96 | 60 | 71.0 | 69 | 69 | 8 | End of curing, 60 min sample, Mg stearate not used, start cool down, tablet flow was sticky |
| 101 | — | 62.0 | | | 8 | Tablet flow starting to get chunky |
| 104 | — | 59.2 | | | 9 | Flow very chunky (tablet bed "sheeting") |
| 106 | — | 57 | 62 | 62 | 10 | |
| 109 | — | 54.9 | | | 9 | Tablet flow still slightly chunky, but better |
| 110 | — | 53.2 | | | 8 | Back to normal tablet flow |
| 116 | — | 48.0 | 58 | 58 | 8 | |
| 126 | — | 29.0 | 30 | 46 | 7 | |
| 132 | — | 24.0 | 30 | 33 | 7 | |

[1] determined according to method 1,
[2] temperature measured at the inlet,
[3] temperature measured at the exhaust.

TABLE 14.1.2

| | | Example 14.1 | | |
|---|---|---|---|---|
| | | Uncured | 60 min cure (n = 5) | 60 min cure, coated (n = 5) |
| Tablet Dimensions | Weight (mg) | 150 (n = 120) | 150 | 158 |
| | Thickness (mm) | 4.42 (n = 5) | 4.71 | 4.75 |
| | Diameter (mm) | 7.14 (n = 5) | 7.05 | 7.07 |
| | Breaking strength (N) | 68 (n = 100) | 196 [1] | 196 [1] |
| Dissolution (% Released) SGF | 1 hr | — | — | 25 |
| | 2 hr | — | — | 42 |
| | 4 hr | — | — | 67 |
| | 8 hr | — | — | 94 |
| | 12 hr | — | — | 101 | n = 6

[1] maximum force of the hardness tester, the tablets did not break when subjected to the maximum force of 196 N.

TABLE 14.1.3

Stability tests Example 14.1, storage at 25° C./60% RH

| | | Storage time | | | | |
|---|---|---|---|---|---|---|
| | | Initial | 1 month | 2 months | 3 months | 6 months |
| Dissolution (% Released) (n = 6) SGF | 1 hr | 25 | 24 | 24 | 23 | 23 |
| | 2 hr | 42 | 40 | 38 | 38 | 39 |
| | 4 hr | 67 | 64 | 61 | 61 | 64 |
| | 8 hr | 94 | 90 | 87 | 89 | 90 |
| | 12 hr | 101 | 99 | 94 | 100 | 97 |
| Assay test (mg oxycodone HCl) | Assay 1 | 9.8 | 9.8 | 9.8 | 9.8 | 9.7 |
| | Assay 2 | 9.8 | 9.9 | 9.8 | 9.9 | 9.8 |
| | Average | 9.8 | 9.8 | 9.8 | 9.9 | 9.8 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.1.4

Stability tests Example 14.1, storage at 40° C./75% RH

|  |  | Storage time | | | | |
| --- | --- | --- | --- | --- | --- | --- |
|  |  | Initial | 1 month | 2 months | 3 months | 6 months |
| Dissolution | 1 hr | 25 | 25 | 25 | 24 | 23 |
| (% Released) | 2 hr | 42 | — | 41 | 38 | 39 |
| (n = 6) | 4 hr | 67 | 66 | 63 | 62 | 64 |
| SGF | 8 hr | 94 | — | 89 | 88 | 90 |
|  | 12 hr | 101 | 100 | 96 | 98 | 96 |
| Assay test | Assay 1 | 9.8 | 9.8 | 9.7 | 9.6 | 9.8 |
| (mg oxycodone | Assay 2 | 9.8 | 10.0 | 9.7 | 9.8 | 9.8 |
| HCl) | Average | 9.8 | 9.9 | 9.7 | 9.7 | 9.8 |
| Degradation products test | oxycodone N-oxide (%)[1] | ≤0.1 | ≤0.1 | ≤0.1 | ≤0.1 | ≤0.1 |
|  | Each individual unknown (%)[1] | ≤0.1 | ≤0.1 | ≤0.1 | ≤0.1 | ≤0.1 |
|  | Total degradation products (%)[1] | ≤0.1 | ≤0.1 | ≤0.1 | ≤0.1 | ≤0.1 |

[1]relative to the label claim of oxycodone HCl.

TABLE 14.2.1

Temperature profile of the curing process for Ex. 14.2

| Total time (min.) | Curing time (min.)[1] | Inlet temp. (° C.)[2] | Set exhaust temp. (° C.) | Actual exhaust temp. (° C.)[3] | Pan speed (rpm) | Comments |
| --- | --- | --- | --- | --- | --- | --- |
| 0 | — | 18 | 50 | 20 | 7 | Load pan, start warming |
| 1 | — | 41.0 |  |  | 7 |  |
| 5 | — |  | 50.0 | 62.0 |  |  |
| 8 | — | 67.7 | 51.0 | 50.5 | 7 | Slowly adjusting exhaust set |
| 10 | — | 71 | 56 | 55 |  |  |
| 14 | 0 | 75.0 | 61.7 | 61.9 | 7 | curing starts, 0 min sample |
| 19 | 5 | 77.2 | 61.7 | 64.8 | 7 |  |
| 21 | 7 | 77.8 |  |  | 7 | High inlet, then dropped to 71° C. |
| 24 | 10 | 68.9 | 65.3 | 65.3 | 7 |  |
| 29 | 15 | 70.6 | 66.1 | 65.5 | 7 | 15 min sample |
| 33 | 19 | 72.6 |  |  | 7 |  |
| 34 | 20 | 73.6 | 67.0 | 66.3 | 7 |  |
| 36 | 22 | 75.0 |  |  | 7 |  |
| 39 | 25 | 75.9 | 67.0 | 67.3 | 7 |  |
| 44 | 30 | 73.3 | 67.0 | 67.4 | 7 | 30 min sample |
| 49 | 35 | 70.1 | 67.2 | 67.0 | 7 |  |
| 54 | 40 | 71.7 | 67.5 | 67.3 | 7 | Couple of tablets sticking at pan support arms, no permanent stick |
| 59 | 45 | 74.3 | 68.0 | 67.9 | 7 | 45 min sample |
| 64 | 50 | 75 | 68 | 68 | 7 |  |
| 66 | 52 | 73.6 | 68.0 | 68.2 | 7 |  |
| 69 | 55 | 72.4 | 68.0 | 68.1 | 7 |  |
| 74 | 60 | 73.0 | 68 | 68 | 7 | End of curing, 60 min sample, add 20 g Mg stearate, tablet flow was slightly sticky (based on visual cascade flow), flow instantly improved after adding Mg stearate |
| 75 | — | 73 | 25 | 68 | 7 | Normal tablet flow observed during cool down |
| 78 | — | 44.7 | 25 | 62.3 | 7 |  |
| 81 | — | 36.8 | 25 | 57.4 | 7 |  |
| 84 | — | 31.8 | 25 | 54.6 | 7 |  |
| 85 | — | 30 | 25 | 53 | 7 |  |
| 94 | — | 23 | 25 | 33 | 7 |  |

[1]determined according to method 1,
[2]temperature measured at the inlet,
[3]temperature measured at the exhaust.

TABLE 14.2.2

| | | Example 14.2 | | |
|---|---|---|---|---|
| | | Uncured | 60 min cure (n =5) | 60 min cure, coated (n =5) |
| Tablet Dimensions | Weight (mg) | 150 (n = 120) | 149 | 156 |
| | Thickness (mm) | 4.38 (n =5) | 4.68 | 4.70 |
| | Diameter (mm) | 7.13 (n =5) | 7.07 | 7.09 |
| | Breaking strength (N) | 70 (n =100) | 196[1] | 196[1] |

TABLE 14.2.2-continued

| | | | | n = 6 |
|---|---|---|---|---|
| Dissolution | 1 hr | — | — | 23 |
| (% Released) | 2 hr | — | — | 39 |
| SGF | 4 hr | — | — | 64 |
| | 8 hr | — | — | 93 |
| | 12 hr | — | — | 100 |

[1] maximumforce of the hardness tester, the tablets did not break when subjected to the maximum force of 196 N.

TABLE 14.2.3

Stability tests Example 14.2, storage at 25° C./60% RH

| | | Storage time | | | | |
|---|---|---|---|---|---|---|
| | | Initial | 1 month | 2 months | 3 months | 6 months |
| Dissolution | 1 hr | 23 | 24 | 26 | 22 | 24 |
| (% Released) | 2 hr | 39 | 40 | 41 | 37 | 40 |
| (n = 6) | 4 hr | 64 | 65 | 65 | 61 | 65 |
| SGF | 8 hr | 93 | 91 | 90 | 90 | 91 |
| | 12 hr | 100 | 100 | 97 | 99 | 99 |
| Assay test | Assay 1 | 14.6 | 14.9 | 14.6 | 14.7 | 14.8 |
| (mg oxycodone | Assay 2 | 14.8 | 14.9 | 14.7 | 14.8 | 14.9 |
| HCl) | Average | 14.7 | 14.9 | 14.7 | 14.7 | 14.8 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.2.4

Stability tests Example 14.2, storage at 40° C./75% RH

| | | Storage time | | | | |
|---|---|---|---|---|---|---|
| | | Initial | 1 month | 2 months | 3 months | 6 months |
| Dissolution | 1 hr | 23 | 25 | 26 | 22 | 24 |
| (% Released) | 2 hr | 39 | 41 | 42 | 36 | 40 |
| (n = 6) | 4 hr | 64 | 66 | 66 | 58 | 65 |
| SGF | 8 hr | 93 | 94 | 92 | 87 | 91 |
| | 12 hr | 100 | 102 | 97 | 97 | 98 |
| Assay test | Assay 1 | 14.6 | 14.8 | 14.7 | 14.6 | 14.9 |
| (mg oxycodone | Assay 2 | 14.8 | 14.8 | 14.7 | 14.5 | 14.7 |
| HCl) | Average | 14.7 | 14.8 | 14.7 | 14.5 | 14.8 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.3.1

Temperature profile of the curing process for Ex. 14.3

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 0 | — | 17.1 | 50 | 18 | 7 | Load pan, start warming |
| 5 | — | 61.0 | 50 | 42.5 | 7 | |
| 10 | — | 70.2 | 56 | 55.8 | 7 | |

TABLE 14.3.1-continued

Temperature profile of the curing process for Ex. 14.3

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 15 | 0 | 75.0 | 61.6 | 61.9 | 7 | Curing starts, 0 min sample |
| 20 | 5 | 78.5 | 62.8 | 65.4 | 7 | |
| 22 | 7 | 79.0 | 62.8 | 66.3 | 7 | Inlet high |
| 25 | 10 | 69.7 | 65.6 | 65.6 | 7 | |
| 30 | 15 | 68.4 | 66.0 | 65.3 | 7 | 15 min sample |
| 35 | 20 | 72.4 | 66.7 | 66.1 | 7 | |
| 40 | 25 | 75.6 | 67.5 | 67.3 | 7 | |
| 45 | 30 | 76.9 | 68.0 | 67.9 | 7 | 30 min sample |
| 55 | 40 | 73.0 | 68.4 | 68.2 | 7 | |
| 60 | 45 | 73.9 | 68.6 | 68.4 | 7 | 45 min sample |
| 65 | 50 | 75 | 68.9 | 68.8 | 7 | |
| 68 | 53 | — | — | — | 7 | Couple of tablets (1-4) sticking at pan support arms, good tablet flow |
| 70 | 55 | 76.2 | 69.6 | 69.6 | 8 | |
| 75 | 60 | 77.0 | 70.5 | 70.8 | 8 | End of curing, 60 min sample, add 20 g Mg stearate, tablet flow instantly improved |
| 76 | — | 76 | 30 | 71 | 8 | Normal tablet flow observed during cool down |
| 79 | — | 43.9 | 30 | 60.6 | 8 | |
| 85 | — | 31.1 | 30 | 54.1 | 8 | No sticking |
| 86 | — | 30 | 30 | 53 | 8 | |
| 96 | — | 23 | 30 | 33 | 8 | |

[1] determined according to method 1,
[2] temperature measured at the inlet,
[3] temperature measured at the exhaust.

TABLE 14.3.2

| | | Example 14.3 | | |
|---|---|---|---|---|
| | | Uncured | 60 min cure (n = 5) | 60 min cure, coated (n = 5) |
| Tablet Dimensions | Weight (mg) | 150 (n = 120) | 150 | 156 |
| | Thickness (mm) | 4.38 (n = 5) | 4.69 | 4.67 |
| | Diameter (mm) | 7.14 (n = 5) | 7.08 | 7.10 |
| | Breaking strength (N) | 64 (n = 110) | 196[1] | 196[1] |

| | | | | n = 6 |
|---|---|---|---|---|
| Dissolution (% Released) SGF | 1 hr | — | — | 24 |
| | 2 hr | — | — | 41 |
| | 4 hr | — | — | 66 |
| | 8 hr | — | — | 92 |
| | 12 hr | — | — | 98 |

[1] maximum force of the hardness tester, the tablets did not break when subjected to the maximum force of 196 N.

TABLE 14.3.3

Stability tests Example 14.3, storage at 25° C./60% RH

| | | Storage time | | | | |
|---|---|---|---|---|---|---|
| | | Initial | 1 month | 2 months | 3 months | 6 months |
| Dissolution (% Released) (n = 6) SGF | 1 hr | 24 | 25 | 22 | 24 | 21 |
| | 2 hr | 41 | 42 | 38 | 40 | 38 |
| | 4 hr | 66 | 69 | 61 | 66 | 63 |
| | 8 hr | 92 | 96 | 89 | 91 | 88 |
| | 12 hr | 98 | 102 | 97 | 99 | 96 |
| Assay test (mg oxycodone HCl) | Assay 1 | 19.6 | 19.4 | 19.5 | 19.4 | 19.8 |
| | Assay 2 | 19.4 | 19.3 | 19.4 | 19.4 | 19.4 |
| | Average | 19.5 | 19.4 | 19.4 | 19.4 | 19.6 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.3.4

Stability tests Example 14.3, storage at 40° C./75% RH

| | | Storage time | | | | |
|---|---|---|---|---|---|---|
| | | Initial | 1 month | 2 months | 3 months | 6 months |
| Dissolution | 1 hr | 24 | 27 | 24 | 23 | 22 |
| (% Released) | 2 hr | 41 | 44 | 40 | 39 | 40 |
| (n = 6) | 4 hr | 66 | 70 | 63 | 63 | 65 |
| SGF | 8 hr | 92 | 94 | 90 | 89 | 90 |
| | 12 hr | 98 | 102 | 98 | 98 | 98 |
| Assay test | Assay 1 | 19.6 | 19.3 | 19.6 | 19.3 | 19.7 |
| (mg oxycodone | Assay 2 | 19.4 | 19.3 | 19.7 | 19.4 | 19.4 |
| HCl) | Average | 19.5 | 19.3 | 19.6 | 19.4 | 19.6 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.4.1

Temperature profile of the curing process for Ex. 14.4

| Total time (min.) | Curing time (min.)[1] | Inlet temp. (° C.)[2] | Bed temp. (° C.)[3] | Set exhaust temp. (° C.) | Actual exhaust temp. (° C.)[4] | Comments[5] |
|---|---|---|---|---|---|---|
| 0 | | | | | | Load pan, start warming |
| 3 | | 63.0 | 46.5 | 50.0 | 41.2 | |
| 5 | | 66.7 | 49.9 | 50.0 | 48.0 | |
| 10 | 0 | 75.0 | 60.5 | 60.0 | 59.0 | curing starts, 0 min sample |
| 14 | 4 | 78.4 | 65.2 | 61.5 | 63.6 | |
| 15 | 5 | 79.1 | 66.0 | 61.5 | 64.5 | |
| 20 | 10 | 67.6 | 66.2 | 63.0 | 64.7 | |
| 24 | 15 | 69.2 | 66.7 | 65.7 | 64.9 | 15 min sample |
| 28 | 19 | 73.0 | 67.8 | 66.4 | 65.8 | |
| 29 | 20 | 73.5 | 68.0 | 67.0 | 66.0 | |
| 32 | 23 | 75.6 | 69.0 | 67.0 | 66.7 | |
| 34 | 25 | 75.9 | 69.4 | 67.0 | 67.0 | |
| 39 | 30 | 76.5 | 70.2 | 67.7 | 67.7 | 30 min sample |
| 44 | 35 | 76.8 | 70.8 | 68.2 | 68.2 | |
| 47 | 38 | 76.7 | 71.0 | 68.8 | 68.4 | Couple of tablets sticking at pan support arms, no permanent sticking |
| 49 | 40 | 77.4 | 71.0 | 69.3 | 68.7 | |
| 52 | 43 | 78.7 | 71.5 | 69.5 | 69.2 | |
| 54 | 45 | 79.1 | 72.1 | 70.0 | 69.5 | 45 min sample |
| 58 | 49 | — | 73.3 | — | — | |
| 59 | 50 | 81.0 | 73.8 | 70.1 | 70.8 | |
| 65 | 56 | 73.0 | 74.1 | 71.7 | 71.5 | |
| 69 | 60 | 74.0 | 74.5 | 71.7 | 71.3 | End of curing, 60 min sample, add 20 g Mg stearate, start cool down, tablet flow slightly sticky (based on visual cascade flow), still couple of tablets sticking at support arms, flow/cascade instantly improved after adding Mg stearate |
| 72 | — | 48.9 | 65.3 | 30.0 | 65.3 | Normal tablet flow observed during cool down |
| 75 | — | 39.7 | 58.6 | 30.0 | 56.8 | |
| 79 | — | 33.2 | 56.4 | 30.0 | 54.6 | |
| 84 | — | 27.7 | 50.0 | 30.0 | 48.4 | |

[1] determined according to method 1,
[2] temperature measured at the inlet,
[3] tablet bed temperature, i.e. temperature of extended release matrix formulations, measured with an IR gun,
[4] temperature measured at the exhaust,
[5] The pan speed was 7 rpm throughout the curing process.

TABLE 14.4.2

| | | Example 14.4 | | |
|---|---|---|---|---|
| | | Uncured | 60 min cure (n = 5) | 60 min cure, coated (n = 5) |
| Tablet Dimensions | Weight (mg) | 150 (n = 120) | 149 | 157 |
| | Thickness (mm) | 4.34 (n = 5) | 4.60 | 4.63 |
| | Diameter (mm) | 7.14 (n = 5) | 7.09 | 7.14 |
| | Breaking strength (N) | 61 (n = 100) | 196 [1] | 196 [1] |

TABLE 14.4.2-continued

| | | | | n = 6 |
|---|---|---|---|---|
| Dissolution | 1 hr | — | — | 22 |
| (% Released) | 2 hr | — | — | 39 |
| SGF | 4 hr | — | — | 66 |
| | 8 hr | — | — | 94 |
| | 12 hr | — | — | 100 |

[1] maximum force of the hardness tester, the tablets did not break when subjected to the maximum force of 196 N.

TABLE 14.4.3

Stability tests Example 14.4, storage at 25° C./60% RH

| | | Storage time | | | | |
|---|---|---|---|---|---|---|
| | | Initial | 1 month | 2 months | 3 months | 6 months |
| Dissolution | 1 hr | 22 | 23 | 24 | 24 | 23 |
| (% Released) | 2 hr | 39 | 39 | 39 | 41 | 40 |
| (n = 6) | 4 hr | 66 | 64 | 63 | 68 | 65 |
| SGF | 8 hr | 94 | 91 | 88 | 93 | 91 |
| | 12 hr | 100 | 98 | 96 | 99 | 98 |
| Assay test | Assay 1 | 28.8 | 28.8 | 28.4 | 28.8 | 29.2 |
| (mg oxycodone | Assay 2 | 29.1 | 29.0 | 28.8 | 28.8 | 29.2 |
| HCl) | Average | 29.0 | 28.9 | 28.6 | 28.8 | 29.2 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.4.4

Stability tests Example 14.4, storage at 40° C./75% RH

| | | Storage time | | | | |
|---|---|---|---|---|---|---|
| | | Initial | 1 month | 2 months | 3 months | 6 months |
| Dissolution | 1 hr | 22 | 26 | 24 | 24 | 24 |
| (% Released) | 2 hr | 39 | 44 | 41 | 41 | 41 |
| (n = 6) | 4 hr | 66 | 70 | 64 | 67 | 67 |
| SGF | 8 hr | 94 | 93 | 88 | 92 | 93 |
| | 12 hr | 100 | 99 | 96 | 98 | 98 |
| Assay test | Assay 1 | 28.8 | 29.3 | 28.2 | 29.0 | 28.4 |
| (mg oxycodone | Assay 2 | 29.1 | 29.3 | 28.1 | 28.9 | 28.6 |
| HCl) | Average | 29.0 | 29.3 | 28.1 | 28.9 | 28.5 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.5.1

Temperature profile of the curing process for Ex. 14.5

| Total time (min.) | Curing time (min.)[1] | Inlet temp. (° C.)[2] | Bed temp. (° C.)[3] | Set exhaust temp. (° C.) | Actual exhaust temp. (° C.)[4] | Comments[5] |
|---|---|---|---|---|---|---|
| 0 | — | 16.6 | 30 | 60.0 | 19.7 | Load pan, start warming |
| 1 | — | — | 32 | 60.0 | — | |
| 4 | — | 56.8 | 39.8 | 60.0 | 36.7 | |

TABLE 14.5.1-continued

Temperature profile of the curing process for Ex. 14.5

| Total time (min.) | Curing time (min.)[1] | Inlet temp. (° C.)[2] | Bed temp. (° C.)[3] | Set exhaust temp. (° C.) | Actual exhaust temp. (° C.)[4] | Comments[5] |
|---|---|---|---|---|---|---|
| 5 | — | 60.1 | 43.9 | 60.0 | 40.4 | |
| 8 | — | 66.8 | 52.5 | 60.0 | 49.4 | |
| 10 | — | 69.1 | 56.9 | 60.0 | 53.8 | |
| 13 | — | 71.7 | 61.3 | 60.0 | 58.8 | |
| 15 | — | 73.3 | 63.5 | 61.0 | 60.8 | |
| 17 | 0 | 75.0 | 65.3 | 63.0 | 62.5 | Curing starts, 0 min sample |
| 21 | 4 | 77.7 | 67.3 | 66.0 | 65.0 | |
| 23 | 6 | 78.8 | 68.1 | 67.0 | 65.9 | |
| 25 | 8 | 79.9 | 69.3 | 67.0 | 66.7 | |
| 27 | 10 | 80.9 | 69.5 | 67.0 | 67.3 | |
| 30 | 13 | 82.4 | 70.1 | 67.0 | 68.2 | |
| 32 | 15 | 83.1 | 70.8 | 70.0 | 68.7 | 15 min sample |
| 37 | 20 | 80.9 | 72.4 | 70.4 | 69.4 | |
| 38 | 21 | 80.9 | 71.8 | 71.0 | 69.5 | |
| 42 | 25 | 82.5 | 73.1 | 72.0 | 70.4 | Good tablet flow and cascade |
| 45 | 28 | 84.2 | 76.6 | 71.0 | 72.2 | |
| 47 | 30 | 82.7 | 77.6 | 72.2 | 74.1 | 30 min sample |
| 49 | 32 | 72.9 | 74.7 | 72.2 | 73.2 | |
| 52 | 35 | 71.2 | 73.8 | 72.2 | 71.4 | Tablet flow slightly sticky, 1-2 tablets sticking at support arms |
| 56 | 39 | 75.4 | 74.7 | 72.2 | 71.5 | |
| 57 | 40 | 75.9 | 74.7 | 72.2 | 71.9 | |
| 60 | 43 | 76.9 | 75.5 | 72.2 | 72.8 | |
| 62 | 45 | 75.4 | 75.3 | 72.2 | 72.9 | 45 min sample |
| 66 | 49 | 73.4 | 74.5 | 72.2 | 71.8 | Tablet flow slightly sticky, 1-2 tablets sticking at support arms (not permanent sticking) |
| 69 | 52 | 75.0 | 75.1 | 72.2 | 71.9 | |
| 72 | 55 | 75.8 | 75.4 | 72.2 | 72.4 | |
| 74 | 57 | 74.8 | 74.8 | 72.2 | 72.5 | |
| 77 | 60 | 73.9 | 74.9 | 72.2 | 72.2 | End of curing, 60 min sample, add 20 g Mg stearate, instantly improved flow/cascade start cool down, no sticking at pan support arms, |
| 80 | — | 46.8 | 64.9 | 30.0 | 64.7 | Cooling |
| — | — | — | — | 30.0 | — | 2 tablets sticking at support arms (not permanent sticking) |
| 82 | — | 40.3 | 58.6 | 30.0 | 57.4 | Tablets still appear bouncy, no sticking observed |
| 84 | — | 35.8 | 57.4 | 30.0 | 55.6 | Normal tablet flow observed |
| 86 | — | 32.5 | 55.9 | 30.0 | 54.2 | during cool down period. |
| 87 | — | 30.3 | 54.1 | 30.0 | 52.8 | Continue cooling to exhaust |
| 89 | — | 28.8 | 51.8 | 30.0 | 51.3 | temperature of 30-34° C. for |
| 91 | — | 26.9 | 47.2 | 30.0 | 47.9 | coating start-up |
| 97 | — | — | ~29 | 30.0 | — | Top of bed 30.3° C., bottom of bed 28.5° C. |

[1] determined according to method 1,
[2] temperature measured at the inlet,
[3] tablet bed temperature, i.e. temperature of extended release matrix formulations, measured with an IR gun,
[4] temperature measured at the exhaust,
[5] The pan speed was 7 rpm throughout the curing process.

TABLE 14.5.2

| | | | Example 14.5 | | |
|---|---|---|---|---|---|
| | | Uncured | 60 min cure (n = 5) | 60 min cure, coated (n = 5) | |
| Tablet Dimensions | Weight (mg) | 150 (n = 120) | 149 | 155 | |
| | Thickness (mm) | 4.30 (n = 5) | 4.49 | 4.52 | |
| | Diameter (mm) | 7.15 (n = 5) | 7.10 | 7.15 | |
| | Breaking strength (N) | 55 (n = 110) | 196[1] | 196[1] | |
| Dissolution (% Released) SGF | 1 hr | — | — | 24 | n = 6 |
| | 2 hr | — | — | 41 | |
| | 4 hr | — | — | 68 | |
| | 8 hr | — | — | 93 | |
| | 12 hr | — | — | 98 | |

[1] maximum force of the hardness tester, the tablets did not break when subjected to the maximum force of 196 N.

TABLE 14.5.3

Stability tests Example 14.5, storage at 25° C./60% RH

| | | Storage time | | | | |
|---|---|---|---|---|---|---|
| | | Initial | 1 month | 2 months | 3 months | 6 months |
| Dissolution | 1 hr | 24 | 25 | 27 | 23 | 25 |
| (% Released) | 2 hr | 41 | 43 | 44 | 40 | 43 |
| (n = 6) | 4 hr | 68 | 69 | 69 | 66 | 69 |
| SGF | 8 hr | 93 | 94 | 93 | 89 | 92 |
| | 12 hr | 98 | 98 | 97 | 96 | 96 |
| Assay test | Assay 1 | 37.8 | 38.4 | 36.9 | 37.6 | 39.2 |
| (mg oxycodone | Assay 2 | 37.9 | 37.6 | 36.5 | 38.1 | 39.2 |
| HCl) | Average | 37.8 | 38.0 | 36.7 | 37.9 | 39.2 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.5.4

Stability tests Example 14.5, storage at 40° C./75% RH

| | | Storage time | | | | |
|---|---|---|---|---|---|---|
| | | Initial | 1 month | 2 months | 3 months | 6 months |
| Dissolution | 1 hr | 24 | 26 | 27 | 25 | 25 |
| (% Released) | 2 hr | 41 | — | 45 | 42 | 43 |
| (n = 6) | 4 hr | 68 | 71 | 72 | 68 | 69 |
| SGF | 8 hr | 93 | — | 95 | 93 | 92 |
| | 12 hr | 98 | 97 | 98 | 99 | 95 |
| Assay test | Assay 1 | 37.8 | 38.3 | 37.3 | 37.6 | 37.9 |
| (mg oxycodone | Assay 2 | 37.9 | 38.6 | 36.9 | 37.6 | 38.1 |
| HCl) | Average | 37.8 | 38.5 | 37.1 | 37.6 | 38.0 |
| Degradation products test | oxycodone N-oxide (%)[1] | ≤0.1 | ≤0.1 | ≤0.1 | ≤0.1 | ≤0.1 |
| | Each individual unknown (%)[1] | ≤0.1 | ≤0.1 | ≤0.1 | ≤0.1 | ≤0.1 |
| | Total degradation products (%)[1] | ≤0.1 | ≤0.1 | ≤0.1 | ≤0.1 | ≤0.1 |

[1] relative to the label claim of oxycodone HCl.

TABLE 14.6

| | Density (g/cm³) | | | Density change after curing (%) | Density change after curing and coating (%) |
|---|---|---|---|---|---|
| | Uncured | Cured | Cured and Coated | | |
| Example 14.1 | 1.186 | 1.145 | 1.138 | −3.457 | −4.047 |
| Example 14.2 | 1.184 | 1.152 | 1.129 | −2.703 | −4.645 |
| Example 14.3 | 1.183 | 1.151 | 1.144 | −2.705 | −3.297 |
| Example 14.4 | 1.206 | 1.162 | 1.130 | −3.648 | −6.302 |
| Example 14.5 | 1.208 | 1.174 | 1.172 | −2.815 | −2.980 |

Example 15

In Example 15, two different Oxycodone HCl tablet formulations were prepared using high molecular weight polyethylene oxide. One formulation at 234 mg tablet weight (Example 15.1) with 60 mg of Oxycodone HCl and one formulation at 260 mg tablet weight (Example 15.2) with 80 mg of Oxycodone HCl.

Compositions:

| Ingredient | Example 15.1 mg/unit | Example 15.2 mg/unit |
|---|---|---|
| Oxycodone HCl | 60 | 80 |
| Polyethylene oxide (MW: approximately 4,000,000; Polyox ™ WSR- 301) | 162.75 | 167.5 |
| Magnesium Stearate | 2.25 | 2.50 |
| Total Core Tablet Weight (mg) | 225 | 250 |
| Total Batch size | 10 kg | 10 kg |
| Coating | | |
| Opadry film coating | 9 | 10 |
| Total Tablet Weight (mg) | 234 | 260 |
| Coating Batch Size (kg) | 8.367 | 8.205 |

The processing steps to manufacture tablets were as follows:
1. A Patterson Kelly "V" blender (with I bar)—16 quart was charged in the following order:
   Approximately ½ of the polyethylene oxide WSR 301
   Oxycodone hydrochloride (screened through a 20-mesh screen)
   Remaining polyethylene oxide WSR 301

2. Step 1 materials were blended for 5 minutes with the I bar on.
3. Magnesium stearate was charged into the "V" blender (screened through a 20-mesh screen).
4. Step 3 materials were blended for 1 minute with the T bar off.
5. Step 4 blend was charged into a plastic bag (note: two 5 kg blends were prepared to provide 10 kgs of tablet blend for compression).
6. Step 5 blend was compressed to target weight on an 8 station tablet press at 35,000 tph speed using ⅜ inch standard round, concave (embossed) tooling. A sample of tablet cores was taken.
7 Step 6 tablets were loaded into a 24 inch Compu-Lab coating pan at a pan load of 8.367 kg (Example 15.1) and 8.205 kg (Example 15.2).
8. A temperature probe (wire thermocouple) was placed into the pan directly above the tablet bed so that the probe tip was near the cascading bed of tablets.
9. The pan speed was set to 10 rpm and the tablet bed was heated by setting the inlet temperature to achieve an exhaust target temperature of 72° C. The curing starting point (as described by method 2) was initiated once the exhaust temperature achieved 72° C. The inlet temperature was adjusted as necessary to maintain the target exhaust temperature. The tablets were cured for 15 minutes. The pan speed was maintained at 10 rpm. The temperature profile of the curing processes for Examples 15.1 and 15.2 is presented in Tables 15.1.1 and 15.2.1.
10. The pan speed was continued at 10 rpm. The inlet temperature was set to 22° C. and the tablet bed was cooled until an exhaust temperature of 30.0° C. was achieved. A sample of cured tablets was taken at the end of cooling.
11. The tablet bed was warmed using an inlet setting of 53° C. The filmcoating was started once the exhaust temperature achieved approximately 41° C. and continued until the target weight gain of 4% was achieved. The pan speed was increased up to 20 rpm during filmcoating.
12. After filmcoating was completed, the pan speed was reduced and the inlet temperature was set to 22° C., the airflow was maintained at the current setting and the system cooled to an exhaust temperature of <30° C. A sample of cured/coated tablets was taken.
13. The tablets were discharged.

In vitro testing including breaking strength tests was performed as follows:

Core tablets (uncured), 15 minute cured tablets and cured/coated tablets were tested in vitro using USP Apparatus 1 (basket with a retaining spring placed at the top of the basket to reduce the propensity of the tablet to slick to the base of the shaft) at 100 rpm in 900 ml simulated gastric fluid without enzymes (SGF) at 37.0° C. Samples were analyzed by reversed-phase high performance liquid chromatography (HPLC) on Waters Atlantis dC18 3.0×250 mm, 5 μm column, using a mobile phase consisting of a mixture of acetonitrile and potassium phosphate monobasic buffer (pH 3.0) at 230 nm UV detection. Sample time points include 1.0, 2.0, 4.0, 6.0, 8.0, 12.0 and 16.0 hours.

Core tablets (uncured), 15 minute cured tablets and cured/coated tablets were subjected to a breaking strength test by applying a force of a maximum of 196 Newton using a Schleuniger 2E/106 apparatus to evaluate tablet resistance to breaking.

Tablet dimensions and dissolution results are presented in Tables 15.1.2 to 15.2.2.

TABLE 15.1.1

Temperature profile of the curing process for Ex. 15.1

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| 0 | — | 22 to 85 | 47.4 | — | 26.4 | Start heating |
| 10 | — | 85 | 81.3 | 66.3 | 62.0 | |
| 20 | — | 85 | 84.8 | 73.7 | 70.4 | Good tablet flow, no sticking |
| 25.5 | 0 | 85 to 74 | 85.0 | 75.1 | 72.0 | Start of curing; 74° C inlet set too low, exhaust dropped to 70.9° C, reset inlet to 80° C |
| 30.5 | 5 | 80 | 80.0 | 73.6 | 71.9 | Good tablet flow, no sticking |
| 35.5 | 10 | 75 | 75.8 | 72.2 | 73.3 | Good tablet flow, no sticking |
| 40.5 | 15 | 73 to 22 | 72.8 | 70.6 | 71.9 | End of curing, good tablet flow, no sticking, start cooling |
| 60 | — | 22 | 21.5 | 27.9 | 31.4 | |
| 61 | — | 22 | 22.0 | 27.2 | 29.7 | End cooling, no sticking observed during cool down, good tablet flow, take cured tablet sample |

[1]determined according to method 2,
[2]temperature measured at the inlet,
[3]temperature measured using the temperature probe (wire thermocouple)
[4]temperature measured at the exhaust.

TABLE 15.1.2

| | | Example 15.1 | | |
|---|---|---|---|---|
| | | Uncured n = 3 | 15 min cure n = 3 | Coated n = 6 |
| Dissolution (% Released) SGF | 1 hr | 28 | 28 | 24 |
| | 2 hr | 44 | 44 | 41 |
| | 4 hr | 69 | 69 | 67 |
| | 6 hr | 85 | 85 | 84 |
| | 8 hr | 95 | 95 | 93 |
| | 12 hr | 102 | 102 | 99 |
| | 16 hr | 104 | 103 | 102 |

TABLE 15.2.1

Temperature profile of the curing process for Ex. 15.2

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| 0 | — | 22 to 80 | 23.3 | 27.7 | 25.5 | Start heating |
| 10 | — | 80 | 77.0 | 62.2 | 60.4 | |
| 20 | — | 80 | 80.0 | 70.1 | 68.4 | Good tablet flow, no sticking |
| 30 | — | 80 | 80.1 | 72.5 | 70.6 | Good tablet flow, no sticking |
| 35 | 0 | 80 | 79.9 | 73.6 | 72.0 | Start of curing; good tablet flow, no sticking |
| 38 | 3 | — | — | — | 72.7 | Maximum exhaust temp |
| 40 | 5 | 74 | 73.5 | 71.8 | 72.3 | |
| 45 | 10 | 74 | 73.9 | 71.9 | 72.3 | Good tablet flow, no sticking |
| 50 | 15 | 74 to 22 | 74.2 | 72.0 | 72.4 | End of curing, start cooling |
| 71 | — | 22 | 21.7 | 28.4 | 30.0 | End cooling, no sticking observed during cool down, good tablet flow, take cured tablet sample |

[1] determined according to method 2,
[2] temperature measured at the inlet,
[3] temperature measured using the temperature probe (wire thermocouple)
[4] temperature measured at the exhaust.

TABLE 15.2.2

| | | Example 15.2 | | |
|---|---|---|---|---|
| | | Uncured (n = 25) | 15 min cure (n = 5) | Coated (n = 5) |
| Tablet Dimensions | Weight (mg) | 254 | 250 | 257 |
| | Thickness (mm) | 4.20 | 4.28 | 4.29 |
| | Breaking strength (N) | 92 | 196[1] | 194[2] |
| | | n = 3 | n = 3 | n = 6 |
| Dissolution (% Released) SOF | 1 hr | 26 | 28 | 25 |
| | 2 hr | 43 | 42 | 39 |
| | 4 hr | 65 | 67 | 64 |
| | 6 hr | 83 | 83 | 82 |
| | 8 hr | 92 | 94 | 92 |
| | 12 hr | 101 | 102 | 100 |
| | 16 hr | 104 | 103 | 102 |

[1] maximum force of the hardness tester, the tablets did not break when subjected to the maximum force of 196 N.
[2] Four of the tablets did not break when subjected to the maximum force of 196 N, one tablet provided a breaking strength of 185 N (average of sample, n = 5, 194 N).

Example 16

In Example 16, two different Oxycodone HCl tablet formulations were prepared using high molecular weight polyethylene oxide. One formulation at 234 mg tablet weight (Example 16.1) with 60 mg of Oxycodone HCl and one formulation at 260 mg tablet weight (Example 16.2) with 80 mg of Oxycodone HCl. The formulations manufactured at a larger batch size compared to Example 15.

Compositions:

| Ingredient | Example 16.1 mg/unit | Example 16.2 mg/unit |
|---|---|---|
| Oxycodone HCl | 60 | 80 |
| Polyethylene oxide (MW: approximately 4,000,000; Polyox ™ WSR- 301, LEO) | 162.75 | 167.5 |
| Magnesium Stearate | 2.25 | 2.50 |
| Total Core Tablet Weight (mg) | 225 | 250 |
| Total Batch size | 100 kg | 100 kg |
| Coating | | |
| Opadry film coating | 9 | 10 |
| Total Tablet Weight (mg) | 234 | 260 |
| Coating Batch Size (kg) | 94.122 | 93.530 |

The processing steps to manufacture tablets were as follows:
1. The Oxycodone HCl and magnesium stearate were passed through a Sweco Sifter equipped with a 20 mesh screen, into separate suitable containers.
2. A Gemco "V" blender (with 1 bar)—10 cu. ft. was charged in the following order:
   Approximately ½ of the polyethylene oxide WSR 301
   Oxycodone hydrochloride
   Remaining polyethylene oxide WSR 301
3. Step 2 materials were blended for 10 minutes with the I bar on.
4. Magnesium stearate was charged into the Gemco "V" blender.
5. Step 4 materials were blended for 2 minutes with the I bar off.
6. Step 5 blend was charged into clean, tared, stainless steel containers.
7. Step 6 blend was compressed to target weight on a 40 station tablet press at 135,000 tph speed using ⅜ inch standard round, concave embossed tooling, and a compression force of 16.5 kN for Example 16.1 and a compression force of 16.0 kN for Example 16.2. A sample of core tablets was taken.
8. Step 7 tablets were loaded into a 48 inch Accela-Coat coating pan at a load of 94.122 kg (Example 16.1) and 93.530 kg (Example 16.2).
9. The pan speed was set to 7 rpm and the tablet bed was heated by setting the exhaust air temperature to achieve an exhaust temperature of 72° C. The curing starting point (as described by method 2) was initiated once the exhaust temperature achieved 72° C. The tablets were cured at the target exhaust temperature for 15 minutes. The temperature profile of the curing processes of Examples 16.1 and 16.2 is presented in Tables 16.1.1 and 16.2.1.
10. The pan speed was continued at 7 rpm. The exhaust temperature was set to 25° C. and the tablet bed was cooled until an exhaust temperature of 30° C. was achieved.
11. The tablet bed was warmed using an exhaust setting of 30° to 38° C. The filmcoating was started once the exhaust temperature achieved 40° C. and continued until the target weight gain of 4% was achieved. The pan speed was maintained at 7 rpm during filmcoating.
12. After filmcoating was completed, the pan speed was reduced to 1.5 rpm and the exhaust temperature was set to 27° C., the airflow was maintained at the current setting and the tablet bed cooled to an exhaust temperature of <30° C.
13. The tablets were discharged.

In vitro testing including breaking strength tests was performed as follows:

Coated tablets were tested in vitro using USP Apparatus 1 (basket with a retaining spring placed at the top of the basket to reduce the propensity of the tablet to stick to the base of the shaft) at 100 rpm in 900 ml simulated gastric fluid without enzymes (SGF) at 37.0° C. Samples were analyzed by reversed-phase high performance liquid chromatography (HPLC) on Waters Atlantis dC18 3.0×250 mm, 5 μm column, using a mobile phase consisting of a mixture of acetonitrile and potassium phosphate monobasic buffer (pH 3.0) at 230 nm UV detection. Sample time points include 1.0, 2.0, 4.0, 8.0, and 12.0 hours.

Uncured tablets were subjected to weight, thickness and hardness tests on-line by Key Checkweigher.

Tablet dimensions and dissolution results are presented in Tables 16.1.2 to 16.2.2.

TABLE 16.1.1

Temperature profile of the curing process for Ex. 16.1

| Total Time (min.) | Curing time (min.)[1] | Inlet (° C.)[2] | IR gun (° C.)[3] | Exhaust set (° C.) | Exhaust (° C.)[4] | Comments |
|---|---|---|---|---|---|---|
| 0 | — | 34 | 32 | 65 | 24 | Start heating |
| 5 | — | 82 | 54 | 65 | 49 | |
| 10 | — | 89 | 68 | 65 | 63 | |
| 11 | — | — | — | 72 | — | |
| 15 | — | 91 | 71 | 72 | 67 | |
| 20 | — | 91 | 75 | 72 | 70 | |
| 21 | 0 | 92 | 79 | 72 | 72 | Start curing |
| 26 | 5 | 90 | 85 | 70 | 79 | |
| 30 | 9 | 63 | — | — | — | |
| 31 | 10 | 69 | 74 | 72 | 69 | |
| 36 | 15 | 80 | 78 | 72 | 72 | |
| 37 | 16 | 80 | 77 | 72 to 25 | 73 | End of curing, good tablet flow, no sticking, start cooling |
| 42 | — | 31 | 57 | 25 | 54 | |
| 47 | — | 25 | 50 | 25 | 49 | |
| 52 | — | 22 | 36 | 25 | 36 | |
| 57 | — | 22 | 26 | 25 | 29 | End cooling, no sticking observed during cool down, good tablet flow |

[1]determined according to method 2,
[2]temperature measured at the inlet,
[3]temperature measured using an IR gun
[4]temperature measured at the exhaust.

TABLE 16.1.2

| | | Example 16.1 | |
|---|---|---|---|
| | | Uncured (n = 70) | Coated |
| Tablet Dimensions | Weight (mg) | 224.6 | — |
| | Thickness (mm) | 3.77 | — |
| | Breaking strength (Kp) | 5.7 | — |
| | | | n = 6 |
| Dissolution (% Released) SGF | 1 hr | — | 24 |
| | 2 hr | — | 41 |
| | 4 hr | — | 67 |
| | 8 hr | — | 93 |
| | 12 hr | — | 99 |

TABLE 16.2.1

Temperature profile of the curing process for Ex. 16.2

| Total Time (min.) | Curing time (min.)[1] | Inlet (° C.)[2] | IR gun (° C.)[3] | Exhaust set (° C.) | Exhaust (° C.)[4] | Comments |
|---|---|---|---|---|---|---|
| 0 | — | 26 | 22 | 20 | 23 | |
| 2 | — | — | — | 20 to 65 | — | Start heating |
| 7 | — | 84 | 61 | 65 | 56 | |
| 12 | — | 89 | 69 | 65 | 65 | |
| 13.5 | — | 90 | — | 66 | 66 | |
| 14.5 | — | 89 | — | 67 | 67 | |
| 16.5 | — | — | — | 68 | 67 | |
| 17 | — | 90 | 72 | 68 | 68 | |
| 19 | — | 91 | 73 | 68 | 69 | |
| 20 | — | 91 | — | 68 | 70 | |
| 21 | — | — | — | 68 | 71 | |
| 22 | 0 | 91 | 77 | 68 | 72 | Start curing |
| 24 | 2 | 90 | 81 | 70 | 75 | |
| 24.5 | 2.5 | — | — | 70 | 76 | |
| 25 | 3 | 90 | — | 72 | 77 | |
| 26 | 4 | 90 | — | 72 | 78 | |
| 27.5 | 5.5 | — | — | 72 | 79 | |
| 28 | 6 | 82 | 83 | 72 | 78 | Good tablet flow, no sticking |
| 32 | 10 | 65 | 73 | 72 | 69 | |
| 33 | 11 | — | — | — | 68 | |
| 35 | 13 | 79 | 74 | 72 | 70 | |
| 37 | 15 | 81 | 76 | 72 to 25 | 72 | End of curing, good tablet flow, no sticking, start cooling |
| 42 | — | 32 | 56 | 25 | 54 | |
| 47 | — | 25 | 50 | 25 | 48 | good tablet flow, no sticking |
| 52 | — | 22 | 36 | 25 | 36 | |
| 56 | — | 21 | 29 | 25 | 30 | End cooling, no sticking observed during cool down, good tablet flow |

[1] determined according to method 2,
[2] temperature measured at the inlet,
[3] temperature measured using an IR gun
[4] temperature measured at the exhaust.

TABLE 16.2.2

| | | Example 16.2 | |
|---|---|---|---|
| | | Uncured (n = 60) | Coated |
| Tablet Dimensions | Weight (mg) | 250.8 | — |
| | Thickness (mm) | 4.05 | — |
| | Breaking strength (Kp) | 6.8 | — |
| | | | n = 6 |
| Dissolution (% Released) SGF | 1 hr | — | 22 |
| | 2 hr | — | 37 |
| | 4 hr | — | 62 |
| | 8 hr | — | 89 |
| | 12 hr | — | 97 |

Example 17

In Example 17, two Oxycodone HCl tablet formulations containing 60 mg of Oxycodone HCl were prepared using high molecular weight polyethylene oxide. Example 17.1 is the same formulation as presented in Example 15.1. The second formulation (Example 17.2) contains 0.1% of butylated hydroxytoluene. Each tablet formulation was cured at the target exhaust temperature of 72° C. and 75° C. for 15 minutes, followed by filmcoating, and then an additional curing step at the target exhaust temperature for 30 minutes.

Compositions:

| Ingredient | Example 17.1 mg/unit | Example 17.2 mg/unit |
|---|---|---|
| Oxycodone HCl | 60 | 60 |
| Polyethylene oxide (MW: approximately 4,000,000; Polyox ™ WSR- 301) | 162.75 | 162.525 |
| Butylated Hydroxytoluene (BHT) | 0 | 0.225 |
| Magnesium Stearate | 2.25 | 2.25 |
| Total Core Tablet Weight (mg) | 225 | 225 |
| Total Batch size | 5 kg | 10 kg |
| Coating | | |
| Opadry film coating | 9 | 9 |
| Total Tablet Weight (mg) | 234 | 234 |
| Coating Batch Size (kg) | 2 kg at 72° C. 2 kg at 75° C. | 6 kg at 72° C. 2 kg at 75° C. |

The processing steps to manufacture tablets were as follows:
1. A Patterson Kelly "V" blender (with I bar)—16 quart was charged in the following order:
   Approximately ½ of the polyethylene oxide WSR 301
   Oxycodone hydrochloride (screened through a 20-mesh screen)
   Remaining polyethylene oxide WSR 301
2. Step 1 materials were blended for 5 minutes with the I bar on.
3. Magnesium stearate was charged into the "V" blender.
4. Step 3 materials were blended for 1 minute with the I bar off.

5. Step 4 blend was charged into a plastic bag (note: two 5 kg blends were prepared for Example 17.2 to provide 10 kgs of tablet blend for compression).
6. Step 5 blend was compressed to target weight on an 8 station tablet press at 30,000 tph speed using ⅜ inch standard round, concave (embossed) tooling. Example 17.1 was compressed at a compression force at 12 kN and Example 17.2 at 6 kN, 12 kN and 18 kN.
7. Step 6 tablets were loaded into a 15 inch (for 2 kg batch size) or a 24 inch (for 6 kg batch size) Accela-Coat coating pan.
8. A temperature probe (wire thermocouple) was placed into the pan directly above the tablet bed so that the probe tip was near the cascading bed of tablets.
9. The pan speed was set at 7 or 10 rpm and the tablet bed was heated by setting the inlet temperature to achieve an exhaust target temperature of 72° C. or 75° C. The curing starting point (as described by method 2) was initiated once the exhaust temperature achieved target. The inlet temperature was adjusted as necessary to maintain the target exhaust temperature. The tablets were cured for 15 minutes. The pan speed was maintained at the current rpm. The temperature profile of the curing processes for Examples 17.1 and 17.2 is presented in Tables 17.1.1 and 17.2.1.
10. The pan speed was continued at the current rpm. The inlet temperature was set to 20° or 22° C. and the tablet bed was cooled until an exhaust temperature of approximately 30° C. was achieved. NOTE: Magnesium Stearate was not used.
11. The tablet bed was warmed using an inlet setting of 52°-54° C. The filmcoating was started once the exhaust temperature achieved approximately 39°-42° C. and continued until the target weight gain of 4% was achieved. The pan speed was increased to 15 or 20 rpm during filmcoating.
12. After filmcoating was completed, the pan speed was reduced to the level used during curing. The tablet bed was heated by setting the inlet temperature to achieve the exhaust target temperature of 72° C. or 75° C. The curing starting point (as described by method 2) was initiated once the exhaust temperature achieved target. The inlet temperature was adjusted as necessary to maintain the target exhaust temperature. The coated tablets were cured for an additional 30 minutes. The pan speed was maintained at the current rpm. The temperature profile of the additional curing process for Examples 17.1 and 17.2 is presented in Tables 17.1.1 and 17.2.1.
13. The tablets were discharged.

In vitro testing including breaking strength tests was performed as follows:

Core tablets (uncured), cured tablets and cured/coated tablets were tested in vitro using USP Apparatus 1 (basket with a retaining spring placed at the top of the basket to reduce the propensity of the tablet to stick to the base of the shaft) at 100 rpm in 900 ml simulated gastric fluid without enzymes (SGF) at 37.0° C. Samples were analyzed by reversed-phase high performance liquid chromatography (HPLC) on Waters Atlantis dC18 3.0×250 mm, 5 μm column, using a mobile phase consisting of a mixture of acetonitrile and potassium phosphate monobasic buffer (pH 3.0) at 230 nm UV detection. Sample time points include 1.0, 2.0, 4.0, 6.0, 8.0, 12.0 and 16.0 hours.

Uncured tablets were subjected to a breaking strength test by applying a force of a maximum of 196 Newton using a Schleuniger 2E/106 apparatus to evaluate tablet resistance to breaking.

Tablet dimensions and dissolution results are presented in Tables 17.1.2 to 17.2.2.

TABLE 17.1.1

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| Curing process at 72° C. for Example 17.1 ||||||||
| 0 | — | 22 to 80 | 25.5 | 28.4 | 28.5 | Start heating |
| 10 | — | 80 | 80.2 | 69.6 | 68.1 | |
| 19 | 0 | 80 to 78 | 80.0 | 73.2 | 72.0 | Start of curing |
| 24 | 5 | 78 | 77.9 | 73.2 | 73.0 | |
| 29 | 10 | 75 | 75.0 | 71.8 | 72.3 | |
| 34 | 15 | 75 | 75.0 | 72.3 | 72.0 | End of curing, start cooling |
| 50 | — | 22 | 22.8 | 28.2 | 29.2 | End cooling, ready to coat |
| Apply 4% filmcoat to the tablets, once achieved start heating |||||||
| 0 | — | 48 to 80 | 47.8 | 45.1 | 43.1 | Start heating for additional curing |
| 5 | — | 80 | 80.0 | 68.7 | 64.9 | |
| 13 | 0 | 80 to 76 | 80.1 | 73.2 | 72.0 | Start additional curing |
| 28 | 15 | 75 | 74.9 | 72.0 | 72.4 | 15 minute additional curing |
| 43 | 30 | 74 to 22 | 74.0 | 71.5 | 72.1 | 30 minute additional curing, start cooling |
| 55 | — | 22 | 24.6 | 32.2 | 34 | End cooling, discharge |
| Curing process at 75° C. for Example 17.1 ||||||||
| 0 | — | 42 to 80 | 42.1 | 38.6 | 38.5 | Start heating |
| 18 | — | 80 to 83 | 80.1 | 73.0 | 72.4 | |
| 21 | 0 | 82 | 81.5 | 75.1 | 75.0 | Start of curing |
| 26 | 5 | 77 | 76.6 | 73.5 | 74.7 | |
| 31 | 10 | 77.5 | 77.4 | 73.8 | 75.0 | |
| 36 | 15 | 77.5 to 22 | 77.6 | 74.1 | 75.2 | End of curing, start cooling |
| 53 | — | 22 | 23.1 | 29.5 | 29.6 | End cooling, ready to coat |
| Apply 4% filmcoat to the tablets, once achieved start heating |||||||
| 0 | — | 48 to 83 | 48.1 | 44.4 | 41.5 | Start heating for additional curing |
| 12 | 0 | 83 | 83.1 | 75.1 | 75.0 | Start additional curing |

TABLE 17.1.1-continued

| Total Time (min.) | Curing time (min.)[1] | Set inlet (°C.) | Temperature Actual inlet (°C.)[2] | Probe (°C.)[3] | Exhaust (°C.)[4] | Comments |
|---|---|---|---|---|---|---|
| 27 | 15 | 78 | 78.11 | 74.4 | 75.4 | 15 minute additional curing |
| 42 | 30 | 76.5 to 22 | 76.5 | 73.9 | 74.9 | 30 minute additional curing, start cooling |
| 56 | — | 22 | 23.9 | 30.3 | 30.0 | End cooling, discharge |

[1] determined according to method 2,
[2] temperature measured at the inlet,
[3] temperature measured using the temperature probe (wire thermocouple)
[4] temperature measured at the exhaust.

TABLE 17.1.2

| | | Example 17.1 | | | | |
|---|---|---|---|---|---|---|
| | | Uncured (n = 25) | | | | |
| Tablet Dimensions | Weight (mg) | 225 | — | — | | |
| | Thickness (mm) | 3.86 | — | — | | |
| | Breaking strength (N) | 75 | — | — | | |

| | | | Example 17.1 cured at 72° C. | | Example 17.1 cured at 75° C. | |
|---|---|---|---|---|---|---|
| | | n = 3 | 15 min cure n = 3 | Coated n = 6 | 15 min cure n = 3 | Coated n = 3 |
| Dissolution (% Released) SGF | 1 hr | 27 | 27 | 26 | 28 | 26 |
| | 2 hr | 44 | 42 | 41 | 44 | 42 |
| | 4 hr | 68 | 67 | 66 | 69 | 67 |
| | 6 hr | 83 | 83 | 84 | 85 | 83 |
| | 8 hr | 93 | 92 | 93 | 95 | 93 |
| | 12 hr | 99 | 100 | 100 | 100 | 98 |
| | 16 hr | 100 | 102 | 102 | 102 | 99 |

TABLE 17.2.1

| Total Time (min.) | Curing time (min.)[1] | Set inlet (°C.) | Temperature Actual inlet (°C.)[2] | Probe (°C.)[3] | Exhaust (°C.)[4] | Comments |
|---|---|---|---|---|---|---|
| Curing process at 72° C. for Example 17.2 | | | | | | |
| 0 | — | 80 | 34.8 | 33.8 | 32.1 | Pan load 6 kg; start heating |
| 10 | — | 80 | 76.5 | 64.5 | 63.3 | |
| 20 | — | 80 | 80.1 | 71.1 | 69.9 | |
| 27.5 | 0 | 80 | 80.3 | 73.0 | 72.0 | Start of curing |
| 32.5 | 5 | 73.0 | 73.3 | 71.0 | 73.3 | |
| 37.5 | 10 | 72.5 | 72.7 | 70.2 | 71.8 | |
| 42.5 | 15 | 73.6 to 22 | 73.5 | 70.6 | 72.1 | End of curing, start cooling |
| 61 | — | 22 | 22.7 | 30.1 | 30 | End cooling, ready to coat |
| Apply 4% filmcoat to the tablets, once achieved start heating | | | | | | |
| 0 | — | 80 to 53 | 53 | — | 39.5 | Start heating for additional curing |
| 15 | — | 80 | 79.9 | 72.3 | 69.7 | |
| 18 | 0 | 80 | 79.9 | 74.1 | 72.0 | Start additional curing |
| 33 | 15 | 73.5 | 73.4 | 70.9 | 72.3 | 15 minute additional curing |
| 48 | 30 | 73.5 | 73.5 | 71.4 | 72.5 | 30 minute additional curing, start cooling |
| 64 | — | 23.0 | 23.9 | — | 30.0 | End cooling, discharge |
| Curing process at 75° C. for Example 17.2 | | | | | | |
| 0 | — | 82 | 52.9 | 53 | 48.4 | Pan load 2 kg, start heating |
| 12 | — | 82 | 82.2 | 75.4 | 72.8 | |
| 16 | — | 82 to 85 | 72.6 | 70.0 | 69.7 | |
| 23.5 | 0 | 85 to 82 | 81.8 | 76.4 | 75.0 | Start of curing |
| 26.5 | 3 | 82 to 80 | 81.8 | 77.2 | 77.0 | |
| 32 | 8.5 | 78 | 80.1 | 76.8 | 77.1 | |
| 38.5 | 15 | 78 | 78 | 75.6 | 76.1 | End of curing, start cooling |
| 53 | — | 20 | 32.4 | 30.0 | 32.1 | End cooling, ready to coat |

TABLE 17.2.1-continued

| Total Time (min.) | Curing time (min.)[1] | Set inlet (°C.) | Actual inlet (°C.)[2] | Probe (°C.)[3] | Exhaust (°C.)[4] | Comments |
|---|---|---|---|---|---|---|
| Apply 4% filmcoat to the tablets, once achieved start heating | | | | | | |
| 0 | — | 53.5 to 83 | 53.7 | — | 46.5 | Start heating for additional curing |
| — | 0 | 83 | 83 | 73.7 | 75 | Start additional curing |
| — | 15 | 78 | 77.9 | 74.3 | 75.9 | 15 minute additional curing |
| — | 23 | 78 | 78 | 75.1 | 76.3 | |
| — | 30 | 78 to 22 | 78 | 75.1 | 76.4 | 30 minute additional curing, start cooling |
| — | — | 22 | 23.6 | 31.0 | 32.1 | End cooling (15 minutes of cooling), discharge |

[1] determined according to method 2,
[2] temperature measured at the inlet,
[3] temperature measured using the temperature probe (wire thermocouple)
[4] temperature measured at the exhaust.

TABLE 17.2.2

| | | Example 17.2 Uncured core tablets (n = 5) | | | |
|---|---|---|---|---|---|
| | Compression force (kN) | 6 | 12 | 18 | 12 |
| Tablet Dimensions | Weight (mg) | 226 | 227 | 227 | 226 |
| | Thickness (mm) | 3.93 | 3.87 | 3.86 | 3.91 |
| | Breaking strength (N) | 43 | 71 | 83 | 72 |

| | | Example 17.2 cured at 72° C. (6 kg batch) 15 min cure, coated | | | Example 17.2 cured at 75° C. (2 kg batch) | | |
|---|---|---|---|---|---|---|---|
| | | | | | Uncured (core) | 15 min cure | Coated |
| | | Compression force (kN) | | | | | |
| | | 6 | 12 | 18 | 12 | | |
| | | n = 3 | n = 3 | n = 3 | n = 3 | n = 3 | n = 3 |
| Dissolution (% Released) SGF No spring | 1 hr | 25 | 23 | 23 | 26 | 27 | 24 |
| | 2 hr | 41 | 39 | 37 | 41 | 43 | 40 |
| | 4 hr | 65 | 64 | 59 | 64 | 66 | 64 |
| | 6 hr | 80 | 81 | 75 | 79 | 81 | 80 |
| | 8 hr | 90 | 91 | 86 | 88 | 91 | 90 |
| | 12 hr | 98 | 100 | 97 | 99 | 101 | 100 |
| Dissolution (% Released) SGF Basket with spring | 1 hr | | 26 | 24 | | | |
| | 2 hr | | 42 | 40 | | | |
| | 4 hr | | 66 | 66 | | | |
| | 6 hr | | 83 | 83 | | | |
| | 8 hr | | 93 | 92 | | | |
| | 12 hr | | 100 | 98 | | | |
| | 16 hr | | 102 | 101 | | | |

Example 18

In Example 18, four different Oxycodone HCl tablet formulations containing 80 mg of Oxycodone HCl were prepared using high molecular weight polyethylene oxide at a tablet weight of 250 mg. Two of the formulations (Examples 18.2 and 18.3) contained 0.1% of butylated hydroxytoluene. One of the formulations (Example 18.4) contained 0.5% of butylated hydroxytoluene. Three of the formulations (Examples 18.1, 18.2, and 18.4) contained 1% of magnesium stearate. One of the formulations (Example 18.3) contained 0.5% of magnesium stearate.

Compositions:

| Ingredient | Example 18.1 mg/unit | Example 18.2 mg/unit | Example 18.3 mg/unit | Example 18.4 mg/unit |
|---|---|---|---|---|
| Oxycodone HCl | 80 (32%) | 80 (32%) | 80 (32%) | 80 (32%) |
| Polyethylene oxide (MW: approximately 4,000,000; Polyox ™ WSR- 301) | 167.5 (67%) | 167.25 (66.9%) | 166.25 (67.4%) | 166.25 (66.5%) |

-continued

|  | Example 18.1 mg/unit | Example 18.2 mg/unit | Example 18.3 mg/unit | Example 18.4 mg/unit |
|---|---|---|---|---|
| Butylated Hydroxytoluene (BHT) | 0 | 0.25 (0.1%) | 0.25 (0.1%) | 1.25 (0.5%) |
| Magnesium Stearate | 2.5 (1%) | 2.5 (1%) | 1.25 (0.5%) | 2.5 (1%) |
| Total Core Tablet Weight (mg) | 250 | 250 | 250 | 250 |
| Total Batch size (kg) | 5 and 6.3 | 5 | 5 | 5 |
| Coating |  |  |  |  |
| Opadry film coating | n/a | 7.5 | 10 | n/a |
| Total Tablet Weight (mg) | n/a | 257.5 | 260 | n/a |
| Coating Batch size (kg) | n/a | 1.975 | 2.0 | n/a |

The processing steps to manufacture tablets were as follows:
1. A Patterson Kelly "V" blender (with I bar)—16 quart was charged in the following order:
   Approximately ½ of the polyethylene oxide WSR 301
   Oxycodone hydrochloride
   BHT (if required)
   Remaining polyethylene oxide WSR 301
2. Step 1 materials were blended for 10 minutes (Example 18.1, 6.3 kg batch size), 6 minutes (Example 18.2), or 5 minutes (Example 18.1, 5 kg batch size, Example 18.3 and 18.4) with the I bar on.
3. Magnesium stearate was charged into the "V" blender.
4. Step 3 materials were blended for 1 minute with the I bar off.
5. Step 4 blend was charged into a plastic bag.
6. Step 5 blend was compressed to target weight on an 8 station tablet press. The compression parameters are presented in Tables 18.1 to 18.4.
7. Step 6 tablets were loaded into an 18 inch Compu-Lab coating pan at a pan load of 1.5 kg (Example 18.1 cured at 72° C.), 2.0 kg (Example 18.1 cured at 75° and 78° C.), 1.975 kg (Example 18.2 cured at 72° C. and 75° C.), 2.0 kg (Example 18.3), 2.0 kg (Example 18.4 cured at 72° C. and 75° C.).
8. A temperature probe (wire thermocouple) was placed into the pan directly above the tablet bed so that the probe tip was near the moving bed of tablets.
9. For Examples 18.1 to 18.4, the tablet bed was heated by setting the inlet temperature to achieve an target exhaust temperature of 72° C., 75° C. or 78° C. The curing starting point (as described by method 2) was initiated once the exhaust temperature reached the target exhaust temperature. Once the target exhaust temperature was achieved, the inlet temperature was adjusted as necessary to maintain the target exhaust temperature. The tablets were cured for durations of 15 minutes up to 90 minutes. After curing, the tablet bed was cooled. The temperature profiles for the curing processes for Examples 18.1 to 18.4 are presented in Tables 18.1.1 to 18.4.1.
10. After cooling, the tablet bed was warmed using an inlet setting of 53° C. (Examples 18.2 and 18.3, for Examples 18.1 and 18.4 film coating was not performed). The film coating was started once the exhaust temperature achieved approximately 40° C. and continued until the target weight gain of 3% (Example 18.2) and 4% (Example 18.3) was achieved.
11. After film coating was completed (Example 18.2), the tablet bed was heated by setting the inlet temperature to achieve the exhaust target temperature (72° C. for one batch and 75° C. for one batch). The curing starting point (as described by method 2) was initiated once the exhaust temperature reached the target exhaust temperature. Once the target exhaust temperature was achieved, the inlet temperature was adjusted as necessary to maintain the target exhaust temperature. The film coated tablets were cured for an additional 30 minutes. After the additional curing, the tablet bed was cooled. The temperature profile for the curing process for Example 18.2 is presented in Table 18.2.1.
12. The pan speed was reduced and the inlet temperature was set to 22° C. The system cooled to an exhaust temperature of 30° C.
13. The tablets were discharged.

In vitro testing including breaking strength tests and stability tests was performed as follows:

Core tablets (uncured), cured tablets, and cured/coated tablets were tested in vitro using USP Apparatus 1 (some testing included basket with a retaining spring placed at the top of the basket to reduce the propensity of the tablet to stick to the base of the shaft) at 100 rpm in 900 ml simulated gastric fluid without enzymes (SGF) at 37.0° C. Samples were analyzed by reversed-phase high performance liquid chromatography (HPLC) on Waters Atlantis dC18 3.0×250 mm, 5 μm column, using a mobile phase consisting of a mixture of acetonitrile and potassium phosphate monobasic buffer (pH 3.0) at 230 nm UV detection. Sample time points included 1.0, 2.0, 4.0, 6.0, 8.0, and 12.0 hours.

Uncured tablets were subjected to a breaking strength test by applying a force of a maximum of 196 Newton using a Schleuniger 2E/106 apparatus to evaluate tablet resistance to breaking.

Example 18.4 tablets (cured at 72° C. and 75° C. respectively) were subjected to a stability test by storing them in 6 count bottles at different storage conditions (25° C./60% relative humidity or 40° C./75% relative humidity or 50° C.) for a certain period of time and subsequently testing the tablets in vitro as described above. Sample time points regarding storage include initial sample (i.e. prior to storage), two weeks and one month, sample time points regarding dissolution test include 1.0, 2.0, 4.0, 6.0, 8.0 and 12.0 hours.

Tablet dimensions and dissolution results are presented in Tables 18.2.2 to 18.4.2.

TABLE 18.1.1

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| Curing process at 72° C. for Example 18.1 | | | | | | |
| 0 | — | 23 to 80 | 24.8 | 28.4 | 28.9 | Pan load 1.5 kg; start heating |
| 10 | — | 80 | 76.4 | 65.5 | 65.2 | |
| 15 | — | 80 | 79.9 | 70.8 | 70.b;normal3 | |

TABLE 18.1.1-continued

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| 20 | 0 | 80 to 78 | 80.0 | 72.3 | 72.0 | Start of curing |
| 25 | 5 | 78 to 75 | 76.6 | 71.9 | 72.9 | |
| 35 | 15 | 75 | 75 | 71.4 | 72.0 | Sample |
| 40 | 20 | 75 | 75.1 | 71.7 | 72.5 | |
| 50 | 30 | 75 | 74.9 | 72.0 | 72.7 | Sample |
| 60 | 40 | 74 | 73.9 | 71.4 | 72.2 | |
| 65 | 45 | 74 | 74 | 71.5 | 72.1 | Sample |
| 80 | 60 | 74 | 74 | 71.2 | 71.8 | Sample |
| 95 | 75 | 74 | 73.9 | 71.7 | 72.3 | Sample |
| 110 | 90 | 74 to 22 | 74 | 71.7 | 72.3 | End of curing, take sample, add 0.3 g of magnesium stearate, start cooling |
| 129 | — | 22 | 23.1 | 27.4 | 26.9 | End cooling, no sticking during cool down, discharge |
| Curing process at 75° C. for Example 18.1 | | | | | | |
| 0 | — | 23 to 85 | 24.1 | 25.0 | 24.9 | Pan load 2.0 kg, start heating |
| 10 | — | 85 | 79.6 | 67.4 | 66.5 | |
| 15 | — | 85 | 85 | 73.8 | 72.3 | |
| 19 | 0 | 85 to 82 | 85.1 | 76.2 | 75 | Start of curing |
| 22 | 3 | 82 to 80 | 80.5 | 75.3 | 76.2 | |
| 29 | 10 | 78 | 78 | 74.2 | 75.1 | |
| 34 | 15 | 78 | 78.2 | 73.6 | 75.1 | Sample |
| 49 | 30 | 78 | 77.8 | 74.5 | 75.5 | Sample |
| 59 | 40 | 77.5 | 77.6 | 74.66 | 75.4 | |
| 64 | 45 | 77.5 | 77.6 | 74.8 | 75.4 | Sample |
| 79 | 60 | 77.5 | 77.6 | 74.6 | 75.1 | Sample |
| 94 | 75 | 77.5 | 77.5 | 74.5 | 75.1 | Sample, minor sticking |
| 109 | 90 | 77.5 | 77.6 | 75.0 | 75.6 | End of curing, take sample, start cooling |
| 116 | — | 22 | 30.6 | 42.6 | 46.7 | Minor sticking at support arms |
| 122 | — | 22 | 25 | — | 33.5 | End cooling |
| Curing process at 78° C. for Example 18.1 | | | | | | |
| 0 | — | 82 | 35 | 37.6 | 35.9 | Pan load 2 kg, start heating |
| 7 | — | 85 | 84.9 | 71.3 | 69.8 | |
| 14 | — | 85 | 84.9 | 75.9 | 75.0 | |
| 17.5 | 0 | 85 to 83 | 85.1 | 77.4 | 78.0 | Start of curing |
| 22.5 | 5 | 83 | 83.2 | 77.5 | 78.6 | |
| 32.5 | 15 | 82 | 81.9 | 76.9 | 78.4 | Sample |
| 47.5 | 30 | 81 | 80.9 | 77.4 | 78.3 | Sample |
| 57.5 | 40 | 80.5 | 80.6 | 77.5 | 78.1 | |
| 62.5 | 45 | 80.5 | 80.7 | 77.4 | 78.2 | Sample |
| 69.5 | 52 | 80.5 | 80.4 | 77.5 | 78.2 | Minor sticking |
| 77.5 | 60 | 80.5 | 80.6 | 77.6 | 78.3 | Sample, sticking |
| 87.5 | 70 | — | — | — | — | Add 0.3 g of magnesium stearate |
| 92.5 | 75 | 80.0 | 79.8 | 77.1 | 78.1 | Sample, sticking continued, brief improvement of tablet flow with magnesium stearate addition |
| 107.5 | 90 | 80.0 | 79.9 | 77.5 | 78.0 | Sample, start cooling |

[1]determined according to method 2,
[2]temperature measured at the inlet,
[3]temperature measured using the temperature probe (wire thermocouple)
[4]temperature measured at the exhaust.

TABLE 18.1.2

| | | Example 18.1 (6.3 kg batch) Uncured core tablets n = 12 |
|---|---|---|
| Tablet Dimensions | Compression force (kN) | 15 |
| | Weight (mg) | 250 |
| | Thickness (mm) | 4.08 |
| | Breaking strength (N) | 87 |

TABLE 18.1.2-continued

| | | Example 18.1 cured at 72° C. | | |
|---|---|---|---|---|
| | | uncured n = 3 | 15 min cure n = 3 | 60 min cure n = 2 |
| Dissolution (% Released) SGF No spring | 1 hr | 25 | 26 | 25 |
| | 2 hr | 40 | 40 | 40 |
| | 4 hr | 66 | 64 | 62 |
| | 8 hr | 95 | 89 | 91 |
| | 12 hr | 102 | 97 | 92 |

TABLE 18.1.2-continued

| | | Example 18.1 (5.0 kg batch) Uncured core tablets n = 25 |
|---|---|---|
| | Compression force (kN) | 15 |
| Tablet Dimensions | Weight (mg) | 253 |
| | Thickness (mm) | 4.13 |
| | Breaking strength (N) | 92 |

TABLE 18.1.2-continued

| | | uncured n = 3 | Example 18.1 cured at 75° C. 15 min cure n = 3 | Example 18.1 cured at 75° C. 60 min cure n = 3 | Example 18.1 cured at 78° C. 30 min cure n = 3 |
|---|---|---|---|---|---|
| Dissolution (% Released) SGF No spring | 1 hr | 26 | 26 | 26 | 26 |
| | 2 hr | 40 | 41 | 42 | 41 |
| | 4 hr | 63 | 67 | 68 | 66 |
| | 8 hr | 90 | 94 | 94 | 93 |
| | 12 hr | 101 | 101 | 100 | 101 |

TABLE 18.2.1

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| Curing process at 72° C. for Example 18.2 | | | | | | |
| 0 | — | 42 to 80 | 41.9 | 37.4 | 37.8 | Pan load 1.975 kg, start heating |
| 10 | — | 80 | 80.0 | 68.0 | 68.6 | |
| 18 | 0 | 80 | 80.1 | 71.6 | 72.0 | Start of curing |
| 28 | 10 | 75 | 74.5 | 70.7 | 72.4 | |
| 33 | 15 | 75 to 22 | 75.0 | 71.1 | 72.3 | End of curing, start cooling |
| 47.5 | — | 22 | 22.5 | 30.4 | 30.0 | End cooling, sample, ready to coat |
| Apply 3% filmcoat to the tablets, once achieved start heating | | | | | | |
| 0 | — | 50 to 80 | 50 | 48.0 | 43.0 | Start heating for additional curing |
| 12 | 0 | 80 to 77 | 80.0 | 72.1 | 72.0 | Start additional curing |
| 27 | 15 | 75 | 74.9 | 71.0 | 72.4 | Sample 15 minute additional curing |
| 42 | 30 | 74 to 22 | 73.9 | 70.7 | 72.1 | Sample, 30 minute additional curing, start cooling |
| 61 | — | 22 | — | — | 30 | End cooling, discharge, sample |
| Curing process at 75° C. for Example 18.2 | | | | | | |
| 0 | — | 42 to 82 | 41.8 | 39.7 | 40.1 | Pan load 1.975 kg, start heating |
| 13 | — | 82 | 82 | 73.0 | 72.2 | |
| 18 | 0 | 82 to 80 | 81.9 | 75.2 | 75.0 | Start of curing |
| 33 | 15 | 78 to 22 | 77.8 | 74.2 | 75.4 | End of curing, start cooling, no sticking |
| 49 | — | 22 | 22.5 | 28.8 | 29.5 | End cooling, sample, ready to coat |
| Apply 3% filmcoat to the tablets, once achieved start heating | | | | | | |
| 0 | — | 48 to 83 | 48.0 | 44.5 | 41.5 | Start heating for additional curing |
| 13 | 0 | 83 | 83.3 | 75.6 | 75.4 | Start additional curing |
| 28 | 15 | 78 | 78.0 | 74.6 | 75.4 | Sample 15 minute additional curing |
| 44.5 | 31.5 | 77.5 to 22 | 77.4 | 74.4 | 75.4 | Sample 30 minute additional curing, start cooling |
| 58.5 | — | 22 | 24.2 | — | 30 | End cooling, discharge, sample |

[1] determined according to method 2,
[2] temperature measured at the inlet,
[3] temperature measured using the temperature probe (wire thermocouple)
[4] temperature measured at the exhaust.

TABLE 18.2.2

| | | Example 18.2 Uncured core tablets | | |
|---|---|---|---|---|
| | | n = 10 | n = 10 | n = 10 |
| | Tooling size, round (in) | 3/8 | 3/8 | 13/32 |
| | Compression force (kN) | 8 | 15 | 15 |
| Tablet Dimensions | Weight (mg) | 253 | 253 | 252 |
| | Thickness (mm) | 4.24 | 4.21 | 3.77 |
| | Breaking strength (N) | 50 | 68 | 55 |

TABLE 18.2.2-continued

| | | Example 18.2 cured at 72° C. Compression force (kN) | | | | | |
|---|---|---|---|---|---|---|---|
| | | 8 15 min cure, coated | | 15 15 min cure, coated | | 15 15 min cure, coated | |
| | Dissolution Basket* | n = 3 No spring | n = 6 With spring | n = 3 No spring | n = 6 With spring | n = 3 No spring | With spring |
| Dissolution[1] (% Released) SGF | 1 hr | 22 (4.9) | 23 (6.5) | 22 (4.8) | 24 (5.6) | 23 (2.2) | |
| | 2 hr | 36 (6.1) | 38 (5.4) | 36 (6.7) | 39 (4.4) | 37 (3.9) | |
| | 4 hr | 58 (5.8) | 63 (2.3) | 58 (7.0) | 63 (2.3) | 59 (5.2) | |
| | 6 hr | 75 (4.9) | 80 (1.2) | 75 (4.9) | 80 (1.6) | 76 (4.2) | |
| | 8 hr | 87 (4.1) | 90 (1.2) | 88 (3.1) | 90 (1.8) | 88 (3.2) | |
| | 12 hr | 96 (1.9) | 99 (0.8) | 97 (1.2) | 98 (1.6) | 97 (1.1) | |
| | 16 hr | — | 100 (1.4) | — | 101 (2.8) | — | |

*Some testing included the use of a retaining spring placed at the top of the basket to reduce the propensity of the tablet to stick to the base of the shaft;
[1]the values in parantheses indicate relative standard deviation.

TABLE 18.3.1

Curing process at 72° C. for Example 18.3

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| 0 | — | 22 to 80 | 25.1 | 29.4 | 30.1 | Pan load 2.0 kg, start heating |
| 10 | — | 80 | 80.2 | 68.3 | 68.0 | |
| 19 | 0 | 80 | 80.0 | 71.8 | 72.0 | Start of curing |
| 24 | 5 | 76 | 75.7 | 71.2 | 72.5 | |
| 29 | 10 | 76 to 75 | 76.0 | 71.3 | 72.7 | |
| 34 | 15 | 75 to 22 | 74.9 | 70.7 | 72.2 | End of curing, start cooling |
| 49 | — | 22 | 22.9 | 29.1 | 29.7 | End cooling |

[1]determined according to method 2,
[2]temperature measured at the inlet,
[3]temperature measured using the temperature probe (wire thermocouple)
[4]temperature measured at the exhaust.

TABLE 18.3.2

| | | Example 18.3 Uncured core tablets | |
|---|---|---|---|
| | Tooling | Round ⅜ inch | Oval 0.600 × 0.270 inch |
| | Compression force (kN) | 15 | 10-11 |
| | | n = 5 | n = 5 |
| Tablet Dimensions | Weight (mg) | 250 | 250 |
| | Thickness (mm) | 4.20 | 3.80-184 |
| | Breaking strength (N) | 83-110 | 71-76 |
| | | Example 18.3 cured at 72° C. | |
| | | 15 min cure, coated Round ⅜ inch | 15 min cure, coated Oval 0.600 × 0.270 inch |
| | | n = 6  n = 6 | n = 6 |
| | Dissolution Basket * | No spring   With spring | No spring |
| Dissolution[1] (% Released) SGF | 1 hr | 23 (7.0)   23 (4.9) | 24 (7.2) |
| | 2 hr | 37 (6.2)   38 (3.4) | 40 (6.0) |
| | 4 hr | 59 (4.6)   61 (1.9) | 64 (5.0) |
| | 6 hr | 75 (3.5)   79 (1.5) | 81 (2.8) |
| | 8 hr | 87 (2.7)   89 (2.1) | 91 (2.0) |
| | 12 hr | 98 (2.6)   98 (2.6) | 98 (1.6) |

* Some testing included the use of a retainig spring placed at the top of the basket to reduce the propensity of the tablet to stick to the base of the shaft.
[1]the values in parentheses indicate relative standard deviation.

TABLE 18.4.1

| Total Time (min.) | Curing time (min.)[1] | Set inlet (° C.) | Actual inlet (° C.)[2] | Probe (° C.)[3] | Exhaust (° C.)[4] | Comments |
|---|---|---|---|---|---|---|
| \multicolumn{7}{c}{Curing process at 72° C. for Example 18.4} ||||||| 
| 0 | — | 82 | 35.6 | 37.3 | 36.3 | Pan load 2.0 kg; start heating |
| 8 | — | 82 | 82 | 69.8 | 68.8 | |
| 13.5 | 0 | 82 | 82 | 72.6 | 72.0 | Start of curing |
| 18.5 | 5 | 80 to 79 | 79.6 | 72.0 | 73.5 | |
| 23.5 | 10 | 76 | 75.9 | 71.4 | 73.0 | |
| 28.5 | 15 | 75 | 75 | 70.9 | 72.4 | Sample |
| 38.5 | 25 | 75 | 74.9 | 70.9 | 72.5 | |
| 43.5 | 30 | 75 | 75 | 71.1 | 72.6 | Sample |
| 51.5 | 38 | 75 | 75.1 | 71.4 | 72.7 | |
| 58.5 | 45 | 75 | 75 | 71.4 | 72.8 | Sample |
| 68.5 | 55 | 75 | 75.2 | 71.6 | 73.0 | |
| 73.5 | 60 | 75 | 75 | 71.5 | 73 | End of curing, sample, start cooling |
| 78.5 | — | 23 | 37.4 | 48 | 52.2 | Continue cooling |
| \multicolumn{7}{c}{Curing process at 75° C. for Example 18.4} |||||||
| 0 | — | 85 | 26.1 | 31.0 | 29.1 | Pan load 2.0 kg, start heating |
| 5 | — | 82 | 73.8 | 61.9 | 61.1 | |
| 11 | — | 82 | 79.9 | 69.3 | 68.3 | |
| 17.5 | 0 | 85 | 85 | 76.2 | 75 | Start of curing |
| 27.5 | 10 | 78 | 77.8 | 74.4 | 76.1 | |
| 32.5 | 15 | 78 | 77.9 | 74.5 | 75.9 | Sample |
| 39.5 | 22 | 77.55 | 77.4 | 74.1 | 75.6 | |
| 47.5 | 30 | 77.5 | 77.4 | 74.2 | 75.6 | Sample |
| 55.5 | 38 | 77 | 76.9 | 74.0 | 75.4 | |
| 62.5 | 45 | 77 | 77 | 73.9 | 75.3 | Sample |
| 69.5 | 52 | 77 | 77.2 | 73.8 | 75.3 | |
| 77.5 | 60 | 77 | 77.0 | 73.7 | 75.3 | End of curing, sample, start cooling |

[1] determined according to method 2,
[2] temperature measured at the inlet,
[3] temperature measured using the temperature probe (wire thermocouple)
[4] temperature measured at the exhaust.

TABLE 18.4.2

| | | Example 18.4 |
|---|---|---|
| | | Uncured core tablets n = 25 |
| | Compression force (kN) | 15 |
| Tablet Dimensions | Weight (mg) | 254 |
| | Thickness (mm) | 4.15 |
| | Breaking strength (N) | 85 |

| | | | Example 18.4 cured at 72° C. | | Example 18.4 cured at 75° C. | |
|---|---|---|---|---|---|---|
| | | uncured n = 3 | 15 min cure n = 3 | 60 min cure n = 3 | 15 min cure n = 3 | 60 min cure n = 3 |
| Dissolution (% Released) SGF No spring | 1 hr | 26 | 26 | 26 | 26 | 25 |
| | 2 hr | 41 | 41 | 41 | 42 | 40 |
| | 4 hr | 63 | 64 | 65 | 65 | 64 |
| | 8 hr | 89 | 89 | 94 | 91 | 89 |
| | 12 hr | 98 | 99 | 100 | 100 | 99 |

| | | Example 18.4, 2 week stability 15 min cure at 72° C. | | | |
|---|---|---|---|---|---|
| | | initial n = 3 | 25/60[1] n = 4 | 40/75[1] n = 4 | 50° C. n = 4 |
| Dissolution (% Released) SGF | 1 hr | 26 | 26 | 26 | 27 |
| | 2 hr | 41 | 40 | 41 | 42 |
| | 4 hr | 64 | 62 | 63 | 65 |

TABLE 18.4.2-continued

| | | | | | |
|---|---|---|---|---|---|
| No spring | 6 hr | — | — | — | — |
| | 8 hr | 89 | 88 | 90 | 92 |
| | 12 hr | 99 | 99 | 99 | 102 |

| | | Example 18.4, 2 week stability 15 min cure at 75° C. | | | |
|---|---|---|---|---|---|
| | | initial n = 3 | 25/60[1] n = 4 | 40/75[1] n = 4 | 50° C. n = 4 |
| Dissolution | 1 hr | 26 | 25 | 26 | 25 |
| (% Released) | 2 hr | 42 | 39 | 41 | 40 |
| SGF | 4 hr | 65 | 60 | 64 | 63 |
| No spring | 6 hr | — | — | — | — |
| | 8 hr | 91 | 84 | 90 | 91 |
| | 12 hr | 100 | 95 | 99 | 99 |

| | | Example 18.4 1 month stability 15 min cure at 72° C. | | | |
|---|---|---|---|---|---|
| | | initial n = 3 | 25/60[1] n = 4 | 40/75[1] n = 4 | 50° C. n = 3 |
| Dissolution | 1 hr | 26 | 26 | 26 | 26 |
| (% Released) | 2 hr | 41 | 41 | 40 | 41 |
| SGF | 4 hr | 64 | 63 | 63 | 66 |
| No spring | 6 hr | — | 79 | 79 | 83 |
| | 8 hr | 89 | 89 | 91 | 93 |
| | 12 hr | 99 | 98 | 99 | 101 |

[1]storage conditions, i.e. 25° C./60% RH or 40° C./75% RH

Example 19

In Example 19, two different Oxycodone HCl tablet formulations containing 80 mg of Oxycodone HCl were prepared using high molecular weight polyethylene oxide at a tablet weight of 250 mg. One of the formulations (Example 19.1) contained Polyethylene oxide N60K and one formulation (Example 19.2) contained Polyethylene oxide N12K. Compositions:

| Ingredient | Example 19.1 mg/unit | Example 19.2 mg/unit |
|---|---|---|
| Oxycodone HCl | 80 (32%) | 80 (32%) |
| Polyethylene oxide (MW: approximately 2,000,000; Polyox ™ WSR- N60K) | 168.75 (67.5%) | 0 |
| Polyethylene oxide (MW: approximately 1,000,000; Polyox ™ WSR- N12K) | 0 | 168.75 (67.5%) |
| Magnesium Stearate | 1.25 (0.5%) | 1.25 (0.5%) |
| Total Core Tablet Weight (mg) | 250 | 250 |
| Total Batch size (kg) | 2.0 | 2.0 |
| Coating | | |
| Opadry film coating | 10 | 10 |
| Total Tablet Weight (mg) | 260 | 260 |
| Coating Batch size (kg) | 1.4 | 1.4 |

The processing steps to manufacture tablets were as follows:
1. A Patterson Kelly "V" blender (with 1 bar)—8 quart was charged in the following order:
   Approximately ½ of the polyethylene oxide
   Oxycodone hydrochloride
   Remaining polyethylene oxide
   Note: the polyethylene oxide was screened through a 20-mesh screen, retain material was not used.
2. Step 1 materials were blended for 5 minutes with the T bar on.
3. Magnesium stearate was charged into the "V" blender.
4. Step 3 materials were blended for 1 minute with the I bar off.
5. Step 4 blend was charged into a plastic bag.
6. Step 5 blend was compressed to target weight on an 8 station tablet press at 30,000 tph speed using ⅜ inch standard round, concave (embossed) tooling. The compression parameters are presented in Tables 19.1 and 19.2.
7. Step 6 tablets were loaded into an 18 inch Compu-Lab coating pan.
8. A temperature probe (wire thermocouple) was placed into the pan directly above the tablet bed so that the probe tip was near the moving bed of tablets.
9. The tablet bed was heated by setting the inlet temperature to achieve an exhaust target temperature of 72° C. The curing starting point (as described by method 2) was initiated once the exhaust temperature reached the target temperature. Once the target exhaust temperature was achieved, the inlet temperature was adjusted as necessary to maintain the target exhaust temperature. The tablets were cured for 15 minutes. After curing, the inlet temperature was set to 22° C. and the tablet bed was cooled. The temperature profiles for the curing processes for Examples 19.1 and 19.2 are presented in Tables 19.1.1 and 19.2.1.
10. After cooling, the tablet bed was warmed using an inlet setting of 53° C. The film coating was started once the exhaust temperature achieved approximately 41° C. and continued until the target weight gain of 4% was achieved.
11. After film coating was completed, the tablet bed was cooled by setting the inlet temperature to 22° C. The tablet bed was cooled to an exhaust temperature of 30° C. or less was achieved.
12. The tablets were discharged.

In vitro testing including breaking strength tests was performed as follows:

Core tablets (uncured), cured tablets, and cured/coated tablets were tested in vitro using USP Apparatus 1 (basket with a retaining spring placed at the top of the basket to reduce the propensity of the tablet to stick to the base of the shaft) at 100 rpm in 900 ml simulated gastric fluid without enzymes (SGF) at 37.0° C. Samples were analyzed by reversed-phase high performance liquid chromatography (HPLC) on Waters Atlantis dC18 3.0×250 mm, 5 μm column, using a mobile phase consisting of a mixture of acetonitrile and potassium phosphate monobasic buffer (pH 3.0) at 230 nm UV detection. Sample time points included 1.0, 2.0, 4.0, 6.0, 8.0, 12.0 and 16.0 hours.

Uncured tablets were subjected to a breaking strength test by applying a force of a maximum of 196 Newton using a Schleuniger 2E/106 apparatus to evaluate tablet resistance to breaking.

Tablet dimensions and dissolution results are presented in Tables 19.1.2 and 19.2.2.

TABLE 19.1.2-continued

| Dimensions | Thickness (mm) | 4.12 |
| | Breaking strength (N) | 112 |

|  |  | Example 19.1 cured at 72° C. | | |
| --- | --- | --- | --- | --- |
|  |  | uncured n = 3 | 15 min cure n = 3 | Cured/coated n = 6 |
| Dissolution | 1 hr | 25 (2.3) | 25 (2.1) | 25 (3.7) |
| (% Released) | 2 hr | 40 (1.8) | 40 (1.3) | 40 (3.8) |
| SGF | 4 hr | 67 (0.7) | 66 (1.5) | 65 (1.4) |
| Basket with | 6 hr | 85 (1.0) | 86 (3.9) | 84 (1.0) |
| spring | 8 hr | 97 (0.8) | 98 (1.8) | 95 (0.7) |
|  | 12 hr | 101 (1.2) | 103 (1.2) | 102 (0.8) |
|  | 16 hr | 102 (0.7) | 103 (2.0) | 103 (1.1) |

TABLE 19.1.1

Example 19.1 (PEO N60K)

| Total Time (min.) | Curing time (min.)[1] | Set inlet (° C.) | Actual inlet (° C.)[2] | Probe (° C.)[3] | Exhaust (° C.)[4] | Comments |
| --- | --- | --- | --- | --- | --- | --- |
| 0 | — | 22 to 80 | 25.3 | 26.4 | 26.9 | Pan load 1.4 kg; start heating |
| 21 | 0 | 80 | 79.9 | 70.0 * | 72.0 | Start of curing |
| 31 | 10 | 75.5 | 75.5 | 69.1 * | 72.2 | Good tablet flow, no sticking |
| 36 | 15 | 75.5 to 22 | 75.4 | 69.5 * | 72.4 | End of curing, start cooling |
| 50 | — | 22 | 22.6 | 27.5 | 30.0 | End of cooling, sample |

[1]determined according to method 2,
[2]temperature measured at the inlet,
[3]temperature measured using the temperature probe (wire thermocouple)
[4]temperature measured at the exhaust;
* Low temperature values compared to the exhaust temperature. Changed the battery prior to processing Example 19.2.

TABLE 19.1.2

Example 19.1 (PEO N60K)
Uncured core tablets
n = 15

| Tablet | Compression force (kN) | 15 |
| --- | --- | --- |
|  | Weight (mg) | 252 |

TABLE 19.2.1

Example 19.2 (PEO N12K)

| Total Time (min.) | Curing time (min.)[1] | Set inlet (° C.) | Actual inlet (° C.)[2] | Probe (° C.)[3] | Exhaust (° C.)[4] | Comments |
| --- | --- | --- | --- | --- | --- | --- |
| 0 | — | 22 to 80 | 27.0 | 31.4 | 30.9 | Pan load 1.4 kg; start heating |
| 19.5 | 0 | 80 | 80.1 | 71.5 | 72.0 | Start of curing |
| 24.5 | 5 | 77 | 76.7 | 71.0 | 72.8 |  |
| 29.5 | 10 | 75 | 75.0 | 70.3 | 72.0 | Good tablet flow, no sticking |
| 34.5 | 15 | 75 to 22 | 75.1 | 70.4 | 72.0 | End of curing, start cooling |
| 49 | — | 22 | 22.4 | 30.0 | 30.0 | End of cooling, sample |

[1]determined according to method 2,
[2]temperature measured at the inlet,
[3]temperature measured using the temperature probe (wire thermocouple)
[4]temperature measured at the exhaust.

TABLE 19.2.2

| | | Example 19.1 (PEO N12K) Uncured core tablets n = 15 |
|---|---|---|
| Tablet Dimensions | Compression force (kN) | 15 |
| | Weight (mg) | 257 |
| | Thickness (mm) | 4.17 |
| | Breaking strength (N) | 107 |

| | | Example 19.2 cured at 72° C. | | |
|---|---|---|---|---|
| | | uncured n = 3 | 15 min cure n = 3 | Cured/coated n = 6 |
| Dissolution (% Released) SGF Basket with spring | 1 hr | 277 (7.6) | 25 (1.0) | 26 (4.0) |
| | 2 hr | 44 (4.9) | 42 (0.6) | 43 (3.7) |
| | 4 hr | 72 (2.5) | 70 (0.6) | 71 (1.8) |
| | 6 hr | 92 (1.1) | 92 (0.6) | 91 (1.2) |
| | 8 hr | 102 (0.9) | 101 (1.1) | 100 (1.4) |
| | 12 hr | 102 (1.1) | 101 (0.9) | 101 (1.3) |
| | 16 hr | 103 (0.3) | 103 (1.3) | 102 (1.1) |

Example 20

Indentation Test

In Example 20, tablets corresponding to Examples 13.1 to 13.5, 14.1 to 14.5, 16.1, 16.2, 17.1 and 18.2 were subjected to an indentation test with a Texture Analyzer to quantify the tablet strength.

The indentation tests were performed with a TA-XT2 Texture Analyzer (Texture Technologies Corp., 18 Fairview Road, Scarsdale, N.Y. 10583) equipped with a TA-8A ⅛ inch diameter stainless steel ball probe. The probe height was calibrated to 6 mm above a stainless stand with slightly concaved surface. The tablets were placed on top of the stainless stand and aligned directly under the probe. Each type of tablets was tested at least once. Single measurement values are reported. Testing performed on the same type of tablet produced similar results unless the tablet and the probe were misaligned. In such an event, the data would be rejected upon confirmation by visual examination of the tested tablet.

The indentation tests were run with the following parameters:

| | |
|---|---|
| pre-test speed | 0.5 mm/s, |
| test speed | 0.5 mm/s, |
| automatic trigger force | 10 grams, |
| post-test speed | 1.0 mm/s, |
| test distance | 3.0 mm. |

The results are presented in Tables 20.1 to 20.3 and in FIGS. 20 to 33.

TABLE 20.1

Cracking force, "penetration depth to crack" distance and work values

| | Indentation Test Results | | | |
|---|---|---|---|---|
| | Cracking Force (N) | Maximum Force (N) [6] | Distance (mm) [7] | Work (J) [8] |
| Example 13.1[1] | — | 189 | 3.00 | 0.284 |
| Example 13.2[1] | — | 188 | 3.00 | 0.282 |
| Example 13.3[1] | 191 | — | 2.91 | 0.278 |
| Example 13.4[1] | 132 | — | 1.81 | 0.119 |
| Example 13.5[1] | 167 | — | 1.82 | 0.152 |
| Example 17.1[2] | >250[5] | — | >2.0 | >0.250 |
| Example 18.2[2] | 194 | — | 1.80 | 0.175 |
| Example 14.1[3] | 213 | — | 2.52 | 0.268 |
| Example 14.2[3] | 196 | — | 2.27 | 0.222 |
| Example 14.3[3] | 161 | — | 1.90 | 0.153 |
| Example 14.4[3] | 137 | — | 1.51 | 0.103 |
| Example 14.5[3] | 134 | — | 1.39 | 0.093 |
| Example 16.1[4] | 227 | — | 2.23 | 0.253 |
| Example 16.2[4] | 224 | — | 2.17 | 0.243 |

[1] indentation test performed with tablets cured for 30 min and uncoated (curing time determined according to method 4, curing started when the probe temperature reached 70° C., see Example 13).
[2] indentation test performed with tablets cured at 72° C. for 15 minutes and coated (curing time determined according to method 2, curing started when the exhaust air temperature reached 72° C., see Examples 17 and 18),
[3] indentation test performed with tablets cured for 1 hour and coated (curing time determined according to method 1, curing started when the inlet air temperature reached 75° C., see Example 14),
[4] indentation test performed with tablets cured for 15 minutes and coated (curing time determined according to method 2, curing started when the exhaust air temperature reached 72° C., see Example 16),
[5] The peak force exceeded the detection limit,
[6] In the indentation tests where the tablets did not crack under the test conditions given above, the maximum force at penetration depth of 3.0 mm is given instead of a cracking force;
[7] "penetration depth to crack" distance
[8] approximated value, calculated using the equation: Work ≈ ½ · Force [N] × Distance [m].

TABLE 20.2

Selective force values at incremental distance change of 0.1 mm

| Distance (mm) | Force (N) | | | | | | |
|---|---|---|---|---|---|---|---|
| | Ex. 13.1 | Ex. 13.2 | Ex. 13.3 | Ex. 13.4 | Ex. 13.5 | Ex. 17.1 | Ex. 18.2 |
| 0.0 | 0.18 | 0.18 | 0.15 | 0.17 | 0.24 | 0.14 | 0.35 |
| 0.1 | 3.54 | 4.86 | 3.67 | 4.38 | 5.35 | 6.12 | 6.88 |
| 0.2 | 8.76 | 10.56 | 9.95 | 10.29 | 12.37 | 15.13 | 15.51 |
| 0.3 | 15.49 | 16.97 | 16.85 | 17.62 | 22.22 | 25.57 | 25.33 |
| 0.4 | 22.85 | 24.19 | 23.81 | 25.44 | 32.98 | 35.86 | 35.21 |
| 0.5 | 30.43 | 31.59 | 30.81 | 33.42 | 43.85 | 46.10 | 45.25 |
| 0.6 | 37.80 | 38.82 | 38.42 | 41.49 | 55.41 | 56.87 | 55.60 |
| 0.7 | 45.61 | 46.10 | 46.61 | 49.73 | 67.02 | 67.69 | 66.85 |
| 0.8 | 53.30 | 53.08 | 54.53 | 58.37 | 78.43 | 78.71 | 78.24 |
| 0.9 | 60.67 | 60.25 | 62.38 | 67.00 | 89.60 | 90.74 | 89.60 |
| 1.0 | 68.02 | 67.55 | 70.89 | 75.45 | 100.38 | 103.18 | 101.69 |
| 1.1 | 75.29 | 74.67 | 80.12 | 83.75 | 110.46 | 116.10 | 114.50 |
| 1.2 | 82.81 | 81.40 | 89.03 | 91.14 | 119.87 | 129.90 | 127.13 |
| 1.3 | 90.04 | 88.23 | 97.49 | 98.35 | 129.16 | 144.28 | 139.46 |
| 1.4 | 96.85 | 95.21 | 105.89 | 105.88 | 138.29 | 158.94 | 151.41 |
| 1.5 | 103.92 | 101.84 | 114.37 | 112.94 | 146.76 | 173.41 | 162.88 |
| 1.6 | 111.30 | 108.30 | 122.31 | 119.59 | 154.61 | 188.13 | 173.95 |
| 1.7 | 118.27 | 115.16 | 129.99 | 125.85 | 161.87 | 202.39 | 184.52 |
| 1.8 | 125.02 | 121.81 | 136.94 | 131.63 | 167.65 | 216.08 | 193.31 |
| 1.9 | 131.71 | 128.37 | 143.45 | 137.30 | 165.05 | 229.06 | 190.80 |
| 2.0 | 138.09 | 134.64 | 149.56 | 142.86 | 163.03 | 241.23 | 191.16 |
| 2.1 | 144.38 | 140.46 | 155.52 | 148.05 | 165.82 | 250.17[1] | 192.11 |
| 2.2 | 150.54 | 146.46 | 160.93 | 153.34 | 168.86 | — | 191.84 |
| 2.3 | 156.18 | 152.31 | 166.39 | 158.55 | 171.13 | — | 189.31 |
| 2.4 | 161.57 | 157.73 | 171.41 | 163.52 | 172.21 | — | 185.17 |
| 2.5 | 166.80 | 163.24 | 176.29 | 168.34 | 171.66 | — | 179.55 |
| 2.6 | 171.67 | 168.53 | 180.67 | 172.34 | 169.90 | — | 173.09 |
| 2.7 | 176.24 | 173.45 | 184.52 | 175.57 | 167.51 | — | 166.68 |
| 2.8 | 180.39 | 178.37 | 187.79 | 177.84 | 164.67 | — | 158.70 |
| 2.9 | 184.61 | 183.24 | 190.54 | 180.35 | 161.12 | — | 148.39 |
| 3.0 | 188.65 | 187.97 | 192.92 | 182.88 | 156.21 | — | 137.65 |

[1] Force value at a distance of 2.0825 mm

TABLE 20.3

Selective force values at incremental distance change of 0.1 mm

| Distance (mm) | Ex. 14.1 | Ex. 14.2 | Ex. 14.3 | Ex. 14.4 | Ex. 14.5 | Ex. 16.1 | Ex. 16.2 |
|---|---|---|---|---|---|---|---|
| 0.0 | 0.33 | 0.27 | 0.33 | 0.31 | 0.41 | 0.27 | 0.26 |
| 0.1 | 6.06 | 6.03 | 6.55 | 6.61 | 5.78 | 6.22 | 7.25 |
| 0.2 | 13.81 | 13.05 | 13.65 | 15.53 | 13.51 | 13.88 | 15.52 |
| 0.3 | 22.48 | 21.42 | 21.55 | 24.82 | 21.87 | 23.31 | 25.11 |
| 0.4 | 31.41 | 29.68 | 29.51 | 34.09 | 31.12 | 33.72 | 35.29 |
| 0.5 | 40.00 | 37.79 | 37.99 | 43.44 | 41.26 | 43.82 | 45.31 |
| 0.6 | 48.85 | 46.69 | 47.69 | 52.78 | 52.22 | 54.19 | 55.47 |
| 0.7 | 57.85 | 55.26 | 57.19 | 62.09 | 63.53 | 64.60 | 66.58 |
| 0.8 | 66.76 | 64.45 | 66.87 | 71.64 | 74.72 | 75.69 | 78.37 |
| 0.9 | 75.69 | 73.68 | 76.43 | 81.47 | 85.73 | 87.70 | 90.38 |
| 1.0 | 84.63 | 83.33 | 86.31 | 91.14 | 96.72 | 99.88 | 103.07 |
| 1.1 | 94.04 | 92.81 | 95.86 | 100.28 | 107.27 | 112.14 | 116.67 |
| 1.2 | 103.45 | 101.93 | 105.14 | 109.77 | 118.11 | 124.54 | 130.10 |
| 1.3 | 112.69 | 111.76 | 115.04 | 119.97 | 128.22 | 137.12 | 143.13 |
| 1.4 | 122.63 | 122.04 | 125.05 | 129.55 | 133.77 | 149.34 | 155.78 |
| 1.5 | 132.50 | 132.04 | 134.14 | 137.20 | 134.95 | 161.51 | 168.25 |
| 1.6 | 141.98 | 141.82 | 142.58 | 135.04 | 139.81 | 173.01 | 180.44 |
| 1.7 | 151.21 | 150.82 | 139.12 | 139.12 | 144.84 | 184.28 | 192.28 |
| 1.8 | 160.27 | 159.44 | 157.82 | 143.60 | 148.83 | 194.58 | 203.45 |
| 1.9 | 169.02 | 168.09 | 161.72 | 146.81 | 151.39 | 204.27 | 212.71 |
| 2.0 | 177.84 | 176.40 | 162.87 | 148.59 | 152.52 | 213.25 | 218.71 |
| 2.1 | 186.18 | 184.67 | 165.88 | 149.32 | 152.56 | 221.06 | 223.17 |
| 2.2 | 194.39 | 192.38 | 169.78 | 149.19 | 151.29 | 226.97 | 224.84 |
| 2.3 | 202.16 | 196.66 | 173.59 | 148.16 | 147.83 | 219.64 | 226.60 |
| 2.4 | 208.46 | 199.43 | 176.38 | 146.05 | 141.54 | 210.57 | 228.33 |
| 2.5 | 212.94 | 202.98 | 178.44 | 142.81 | 134.06 | 203.85 | 228.97 |
| 2.6 | 213.83 | 206.77 | 179.87 | 137.70 | 124.24 | 197.33 | 228.49 |
| 2.7 | 216.58 | 209.46 | 181.13 | 131.34 | 109.53 | 189.49 | 227.40 |
| 2.8 | 219.71 | 211.32 | 182.02 | 123.72 | 88.60 | 181.26 | 225.10 |
| 2.9 | 222.51 | 211.01 | 181.70 | 114.09 | 20.86 | 174.45 | 222.87 |
| 3.0 | 224.59 | 208.85 | 179.91 | 102.93 | 0.16 | 168.70 | 220.36 |

Example 21

Indentation Test

In Example 21, tablets corresponding to Examples 16.1 (60 mg Oxycodone HCl) and 16.2 (80 mg oxycodone HCL) and commercial Oxycontin™ 60 mg and Oxycontin™ 80 mg tablets were subjected to an indentation test with a Texture Analyzer to quantify the tablet strength.

The indentation tests were performed as described in Example 20.

Figure 34:
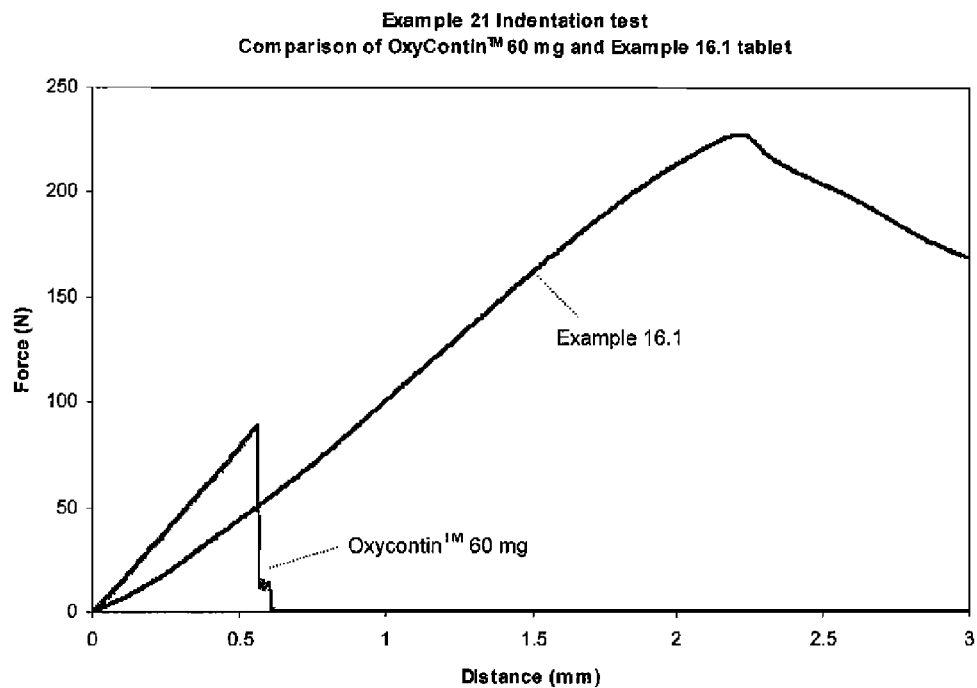
FIG. 34 is a diagram of Example 21 indentation tests performed with an Example 16.1 tablet (cured for 15 minutes, coated) and with a commercial Oxycontin™ 60 mg tablet.
Figure 35:
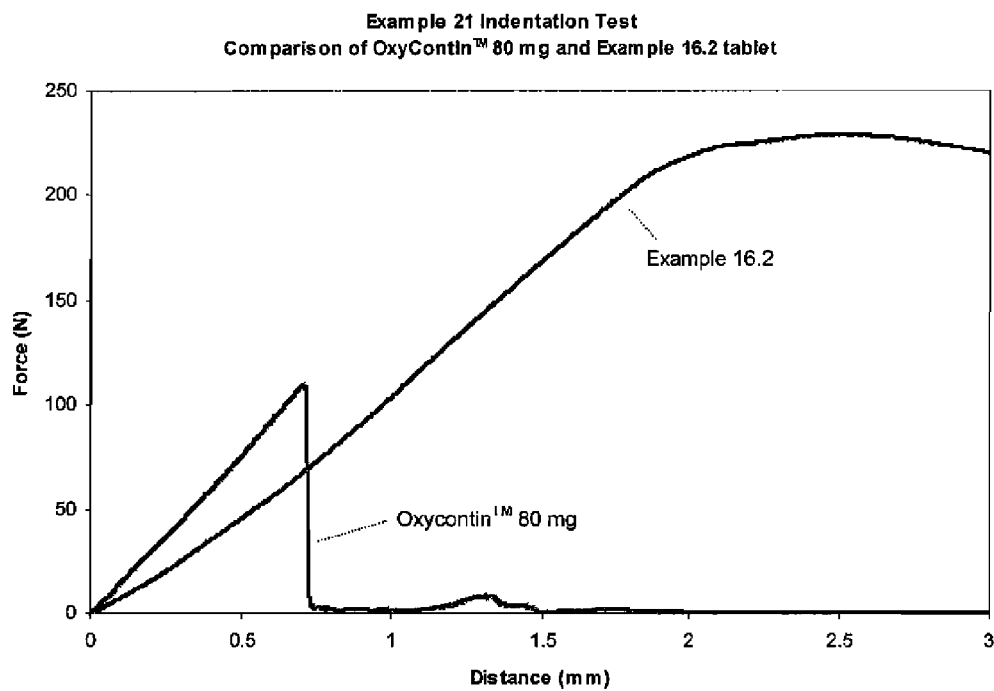
FIG. 35 is a diagram of Example 21 indentation tests performed with an Example 16.2 tablet (cured for 15 minutes, coated) and with a commercial Oxycontin™ 80 mg tablet.
Figure 36:
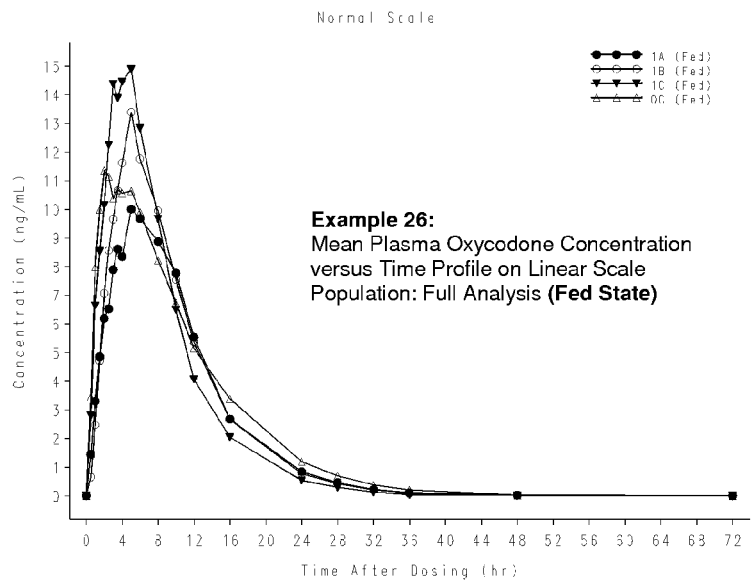
FIG. 36 shows the mean plasma oxycodone concentration versus time profile on linear scale [Population: Full Analysis (Fed State)] according to Example 26.
Figure 37:
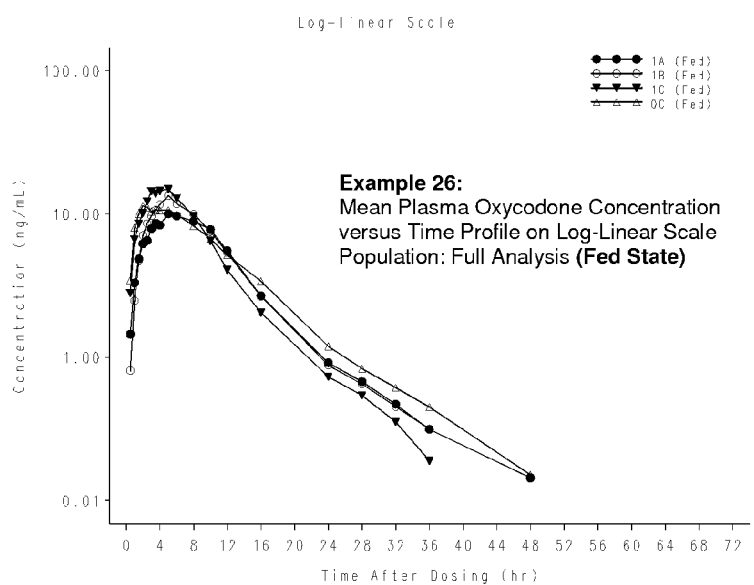
FIG. 37 shows the mean plasma oxycodone concentration versus time profile on log-linear scale [Population: Full Analysis (Fed State)] according to Example 26.
Figure 38:
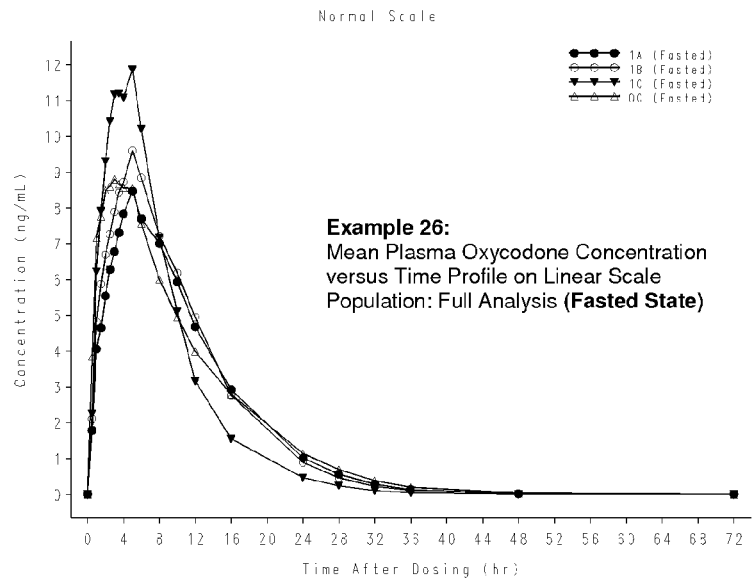
FIG. 38 shows the mean plasma oxycodone concentration versus time profile on linear scale [Population: Full Analysis (Fasted State)] according to Example 26.
Figure 39:
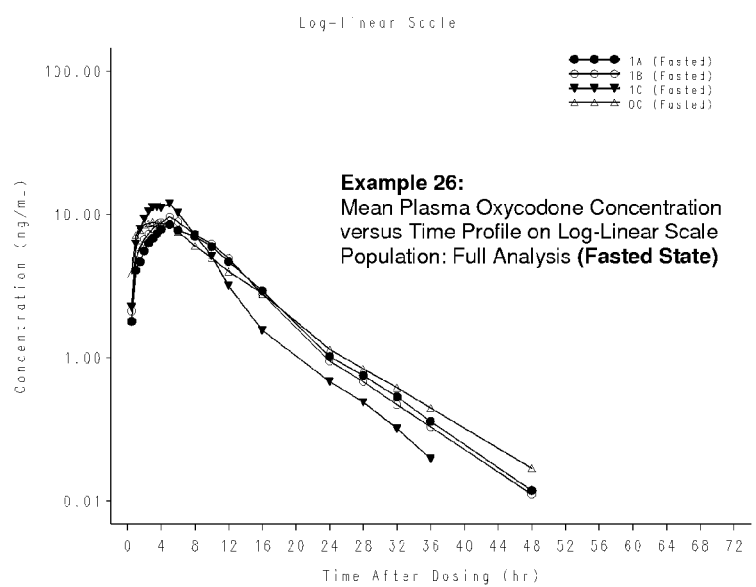
FIG. 39 shows the mean plasma oxycodone concentration versus time profile on log-linear scale [Population: Full Analysis (Fasted State)] according to Example 26.

The results are presented in Table 21 and in FIGS. 34 and 35.

TABLE 21

Selective force values at incremental distance change of 0.1 mm

| Distance (mm) | Ex. 16.1 | Oxycontin™ 60 mg | Ex. 16.2 | Oxycontin™ 80 mg |
|---|---|---|---|---|
| 0.0 | 0.27 | 0.42 | 0.26 | 0.42 |
| 0.1 | 6.22 | 14.14 | 7.25 | 14.21 |
| 0.2 | 13.88 | 30.39 | 15.52 | 29.75 |
| 0.3 | 23.31 | 46.53 | 25.11 | 44.30 |
| 0.4 | 33.72 | 61.94 | 35.29 | 59.46 |
| 0.5 | 43.82 | 78.14 | 45.31 | 75.33 |
| 0.6 | 54.19 | 13.58 | 55.47 | 91.91 |
| 0.7 | 64.60 | 0.30 | 66.58 | 108.71 |
| 0.8 | 75.69 | 0.09 | 78.37 | 1.48 |
| 0.9 | 87.70 | 0.00 | 90.38 | 1.52 |
| 1.0 | 99.88 | 0.01 | 103.07 | 1.17 |
| 1.1 | 112.14 | 0.01 | 116.67 | 1.31 |
| 1.2 | 124.54 | 0.00 | 130.10 | 3.61 |
| 1.3 | 137.12 | 0.01 | 143.13 | 7.85 |
| 1.4 | 149.34 | 0.00 | 155.78 | 3.49 |
| 1.5 | 161.51 | 0.00 | 168.25 | 0.15 |
| 1.6 | 173.01 | 0.00 | 180.44 | 0.85 |
| 1.7 | 184.28 | 0.00 | 192.28 | 1.46 |
| 1.8 | 194.58 | 0.00 | 203.45 | 1.12 |
| 1.9 | 204.27 | 0.00 | 212.71 | 0.81 |
| 2.0 | 213.25 | 0.02 | 218.71 | 0.52 |
| 2.1 | 221.06 | −0.01 | 223.17 | 0.14 |
| 2.2 | 226.97 | −0.01 | 224.84 | 0.13 |
| 2.3 | 219.64 | −0.01 | 226.60 | 0.10 |
| 2.4 | 210.57 | 0.01 | 228.33 | 0.09 |
| 2.5 | 203.85 | 0.00 | 228.97 | 0.08 |
| 2.6 | 197.33 | 0.00 | 228.49 | 0.08 |
| 2.7 | 189.49 | −0.01 | 227.40 | 0.07 |
| 2.8 | 181.26 | 0.00 | 225.10 | 0.08 |
| 2.9 | 174.45 | 0.00 | 222.87 | 0.07 |
| 3.0 | 168.70 | 0.00 | 220.36 | 0.08 |

Comparative Example 22

In Comparative Example 22, five different 150 mg tablets (Examples 22.1 to 22.5) including 10, 15, 20, 30 and 40 mg of oxycodone HCl were prepared using the compositions as described in Example 13, and amending the manufacturing process of Example 13 insofar that the tablets were subjected to a molding step instead of a curing step.

Compositions:

| Ingredient | Example 22.1 mg/unit | Example 22.2 mg/unit | Example 22.3 mg/unit | Example 22.4 mg/unit | Example 22.5 mg/unit |
|---|---|---|---|---|---|
| Oxycodone HCl | 10 | 15 | 20 | 30 | 40 |
| Polyethylene oxide (MW: approximately 4,000,000; Polyox™ WSR-301) | 138.5 | 133.5 | 128.5 | 118.5 | 108.5 |
| Magnesium Stearate | 1.5 | 1.5 | 1.5 | 1.5 | 1.5 |
| Total Core Tablet Weight (mg) | 150 | 150 | 150 | 150 | 150 |
| Total Batch size | 10 kg | 10 kg | 10 kg | 10 kg | 10 kg |

The processing steps to manufacture tablets were as follows:
1. A Patterson Kelly "V" blender (with I bar)—16 quart was charged in the following order:
   Approximately ½ of the polyethylene oxide WSR 301
   Oxycodone hydrochloride
   Remaining polyethylene oxide WSR 301
2. Step 1 materials were blended for 5 minutes with the I bar on.
3. Magnesium stearate was charged into the "V" blender.
4. Step 3 materials were blended for 1 minute with the I bar off.
5. Step 4 blend was charged into a plastic bag.
6. Step 5 blend was compressed to target weight on an 8 station tablet press at 35,000 tph speed using 9/32 inch standard round, concave (embossed) tooling.
7. Step 6 tablets were molded with a temperature controlled Specac press. The compressed tablets from step 6 were placed between two heated plates which were preheated to 120° C. and then compressed at a pressured setting of 1000 kg and held for 3 minutes. The molten tablets were cooled to room temperature prior to density measurement.

The density measurement was performed as follows:

The density of tablets before and after the molding step was determined by Archimedes principle, using a Top-loading Mettler Toledo balance Model #AB 135-S/FACT, Serial #1127430072 and a density determination kit 33360, according to the following procedure:
1. Set-up the Mettler Toledo balance with the Density Determination Kit.
2. Fill an appropriately sized beaker (200 ml) with hexane.
3. Weigh the tablet in air and record the weight as Weight A.
4. Transfer the same tablet onto the lower coil within the beaker filled with hexane.
5. Determine the weight of the tablet in hexane and record the weight as Weight B.
6. Perform the density calculation according to the equation $$\rho = \frac{A}{A-B} \cdot \rho_0,$$

wherein
ρ: Density of the tablet
A: Weight of the tablet in air
B: Weight of the tablet when immersed in the liquid
$\rho_0$: Density of the liquid at a given temperature (density of hexane at 20° C.=0.660 g/ml (Merck Index)
7. Record the density.

The reported density values are mean values of 3 tablets and all refer to uncoated tablets.

The results are presented in Table 22.1.

TABLE 22.1

| | Density (g/cm³)[1] | | Density change after |
|---|---|---|---|
| | Unmolded tablet[2] | Molded tablet | molding (%)[3] |
| Example 22.1 | 1.172 | 1.213 | +3.498 |
| Example 22.2 | 1.174 | 1.213 | +3.322 |
| Example 22.3 | 1.179 | 1.222 | +3.647 |
| Example 22.4 | 1.182 | 1.231 | +4.146 |
| Example 22.5 | 1.222 | 1.237 | +1.227 |

[1]The density value is a mean value of 3 tablets measured;
[2]The density of the "unmolded tablet" corresponds to the density of the "uncured tablet" of Examples 13.1 to 13.5;
[3]The density change after molding corresponds to the observed density change in % of the molded tablets in comparison to the unmolded tablets.

Example 23

In Example 23, 154.5 mg tablets including 30 mg Hydromorphone HCl were prepared using high molecular weight polyethylene oxide.

Composition:

| Ingredient | mg/unit | g/batch |
|---|---|---|
| Hydromorphone HCl | 30 | 1000 |
| Polyethylene oxide (MW: approximately 4,000,000: Polyox ™ WSR-301) | 119.25 | 3975 |
| Magnesium Stearate | 0.75 | 25 |
| Total Core Tablet Weight (mg) | 150 | |
| Total Batch size | 10 kg (2 × 5 kg) | |

| Coating | mg/unit |
|---|---|
| Opadry film coating | 4.5 |
| Total Tablet Weight (mg) | 154.5 |
| Coating Batch Size (kg) | 8.835 kg |

The processing steps to manufacture tablets were as follows:
1. A PK V-blender (with I-bar)—16 quart was charged in the following order:
   Approximately half of the Polyethylene Oxide 301
   Hydromorphone HCl
   Remaining Polyethylene Oxide 301
2. Step 1 materials were blended for 5 minutes with the intensifier bar ON.
3. Magnesium stearate was charged in the PK V-blender.
4. Step 3 materials were blended for 1 minute with the intensifier bar OFF.
5. Step 4 blend was charged into a plastic bag (Note: two 5 kg blends were produced to provide 10 kgs available for compression).
6. Step 5 blend was compressed to target weight on an 8 station rotary tablet press using 9/32 inch standard round, concave (embossed) tooling at 35,000 to 40,800 tph speed using 5-8 kN compression force.
7. Step 6 tablets were loaded into a 24 inch Compu-Lab coating pan at a pan load of 9.068 kg.
8. The pan speed was set to 10 rpm and the tablet bed was heated by setting the inlet air temperature to achieve an exhaust temperature of approximately 72° C. The curing starting point (as described by method 2) was initiated once the exhaust temperature achieved 72° C. The tablets were cured at the target exhaust temperature for 1 hour. Tablet samples were taken after 30 minutes of curing.
9. After 1 hour of curing at the target exhaust temperature of 72° C., the inlet temperature was set to 90° C. to increase the exhaust temperature (the bed temperature).
10. After 10 minutes of increased heating, the exhaust temperature reached 82° C. The tablet continued to maintain good flow/bed movement. No sticking was observed.
11. The inlet temperature was set to 22° C. to initiate cooling. During the cool down period (to an exhaust temperature of 42° C.), no sticking or agglomerating of tablets was observed.
12. Step 11 tablets were loaded into a 24 inch Compu-Lab coating pan at a pan load of 8.835 kg.
13. The tablet bed was warmed by setting the inlet air temperature at 55° C. The film coating was started once the exhaust temperature approached 42° C. and continued until the target weight gain of 3% was achieved.
14. Film coating was conducted at a spray rate of 40-45 g/min, airflow target at 350 cfm, and pan speed initiated at 10 rpm and increased to 15 rpm. After coating was completed the pan speed was set to 3.5 rpm and the tablets were allowed to cool.
15. The tablets were discharged.

In vitro testing including dissolution, assay and content uniformity test was performed as follows:

Tablets cured for 30 minutes (uncoated) were tested in vitro using USP Apparatus 1 (basket) at 100 rpm in 900 ml simulated gastric fluid without enzymes (SGF) at 37.0° C. Samples were analyzed by reversed-phase high performance liquid chromatography (HPLC) on Waters Atlantis dC18 3.0× 250 mm, 5 μm column, using a mobile phase consisting of a mixture of acetonitrile and potassium phosphate monobasic buffer (pH 3.0) at 220 nm UV detection. Sample time points include 1.0, 2.0, 4.0, 8.0 and 12.0 hours.

Tablets cured for 30 minutes (uncoated) were subjected to the assay test. Oxycodone hydrochloride was extracted from two sets of ten tablets each with 900 mL of a 1:2 mixture of acetonitrile and simulated gastric fluid without enzyme (SGF) under constant magnetic stirring in a 1000-mL volumetric flask until all tablets were completely dispersed or for overnight. The sample solutions were diluted and analyzed by reversed-phase high performance liquid chromatography (HPLC) on Waters Atlantis $dC_{18}$ 3.0×250 mm, 5 µm column maintained at 60° C. using a mobile phase consisting of acetonitrile and potassium phosphate monobasic buffer at pH 3.0 with UV detection at 280 nm.

Tablets cured for 30 minutes (uncoated) were subjected to the content uniformity test. Oxycodone hydrochloride was extracted from ten separate tablets each with 90 mL of a 1:2 mixture of acetonitrile and simulated gastric fluid without enzyme (SGF) under constant magnetic stirring in a 100-mL volumetric flask until the tablets were completely dispersed or for overnight. The sample solutions were diluted and analyzed by reversed-phase high performance liquid chromatography (HPLC) on Waters Atlantis $dC_{18}$ 3.0×250 mm, 5 µm column maintained at 60° C. using a mobile phase consisting of acetonitrile and potassium phosphate monobasic buffer at pH 3.0 with UV detection at 280 nm.

The results are presented in Table 23.

TABLE 23

|  |  | Example 23 30 min cure |
|---|---|---|
| Assay (% oxycodone HCl)[1] |  | 98.9 |
| Content uniformity (% oxycodone HCl)[1] |  | 97.9 |
| Dissolution (% Released) (n = 6) | 1 hr | 26 |
|  | 2 hr | 42 |
|  | 4 hr | 66 |
|  | 8 hr | 92 |
|  | 12 hr | 101 |

[1]relative to the label claim of Oxycodone HCl

Example 24

In Example 24, 150 mg tablets including 2 mg Hydromorphone HCl were prepared using high molecular weight polyethylene oxide.

Composition:

| Ingredient | mg/unit | g/batch |
|---|---|---|
| Hydromorphone HCl | 2 | 66.5 |
| Polyethylene oxide (MW: approximately 4,000,000; Polyox ™ WSR-301) | 147.25 | 4908.5 |
| Magnesium Stearate | 0.75 | 25 |
| Total Core Tablet Weight (mg) | 150 |  |
| Total Batch size | 10 kg (2 × 5 kg) |  |

The processing steps to manufacture tablets were as follows:
1. A PK V-blender (with I-bar)—4 quart was charged in the following order:
   Approximately 600 g of the Polyethylene Oxide 301
   Hydromorphone HCl
   Approximately 600 g of the Polyethylene Oxide 301
2. Step 1 materials were blended for 2 minutes with the I-bar ON and then discharged.
3. A PK V-blender (with I-bar)—16 quart was charged in the following order:
   Approximately half of the remaining Polyethylene Oxide 301
   Pre-blend material (from step 2)
   Remaining Polyethylene Oxide 301
4. Step 3 materials were blended for 5 minutes with the intensifier bar ON.
5. Magnesium stearate was charged in the PK V-blender.
6. Step 5 materials were blended for 1 minute with the intensifier bar OFF.
7. Step 6 blend was charged into a plastic bag (Note: two 5 kg blends were produced to provide 10 kgs available for compression).
8. Step 7 blend was compressed to target weight on an 8 station rotary tablet press using 9/32 inch standard round, concave (embossed) tooling at 40,800 tph speed using 2 kN compression force.
9. Step 8 tablets were loaded into a 24 inch Compu-Lab coating pan at a pan load of 9.146 kg.
10. The pan speed was set to 10 rpm and the tablet bed was heated by setting the inlet air temperature to achieve an exhaust temperature of approximately 72° C. The curing starting point (as described by method 2) was initiated once the exhaust temperature achieved 72° C. The tablets were cured at the target exhaust temperature for 1 hour. Tablet samples were taken after 30 minutes of curing.
11. The pan speed was increased to 15 rpm once the exhaust temperature reached 72° C.
12. After 1 hour of curing at the target exhaust temperature, the inlet temperature was set to 22° C. to initiate cooling. After 3 minutes of cooling the tablet bed massed forming large agglomerates of tablets. Coating was not feasible.
13. The tablets were discharged.

It is assumed that the agglomeration of tablets can be avoided, for example by increasing the pan speed, by the use of Magnesium Stearate as anti-tacking agent, or by applying a sub-coating prior to curing.

In vitro testing including dissolution, assay and content uniformity test was performed as follows:

Tablets cured for 30 minutes (uncoated) were tested in vitro using USP Apparatus 1 (basket) at 100 rpm in 900 ml simulated gastric fluid without enzymes (SGF) at 37.0° C. Samples were analyzed by reversed-phase high performance liquid chromatography (HPLC) on Waters Atlantis dC18 3.0× 250 mm, 5 µm column, using a mobile phase consisting of a mixture of acetonitrile and potassium phosphate monobasic buffer (pH 3.0) at 220 nm UV detection. Sample time points include 1.0, 2.0, 4.0, 8.0 and 12.0 hours.

Tablets cured for 30 minutes (uncoated) were subjected to the assay test. Oxycodone hydrochloride was extracted from two sets of ten tablets each with 900 mL of a 1:2 mixture of acetonitrile and simulated gastric fluid without enzyme (SGF) under constant magnetic stirring in a 1000-mL volumetric flask until all tablets were completely dispersed or for overnight. The sample solutions were diluted and analyzed by reversed-phase high performance liquid chromatography (HPLC) on Waters Atlantis $dC_{18}$ 3.0×250 mm, 5 µm column maintained at 60° C. using a mobile phase consisting of acetonitrile and potassium phosphate monobasic buffer at pH 3.0 with UV detection at 280 nm.

Tablets cured for 30 minutes (uncoated) were subjected to the content uniformity test. Oxycodone hydrochloride was extracted from ten separate tablets each with 90 mL of a 1:2 mixture of acetonitrile and simulated gastric fluid without enzyme (SGF) under constant magnetic stirring in a 100-mL volumetric flask until the tablets were completely dispersed or for overnight. The sample solutions were diluted and analyzed by reversed-phase high performance liquid chromatography (HPLC) on Waters Atlantis $dC_{18}$ 3.0×250 mm, 5 µm column maintained at 60° C. using a mobile phase consisting of acetonitrile and potassium phosphate monobasic buffer at pH 3.0 with UV detection at 280 nm.

The results are presented in Table 24.

TABLE 24

|  |  | Example 24 30 min cure |
|---|---|---|
| Assay (% oxycodone HCl)[1] |  | 95.7 |
| Content uniformity (% oxycodone HCl)[1] |  | 94.9 |
| Dissolution (% Released) (n = 6) | 1 hr | 26 |
|  | 2 hr | 39 |
|  | 4 hr | 62 |
|  | 8 hr | 89 |
|  | 12 hr | 98 |

[1]relative to the label claim of Oxycodone HCl

Example 25

In Example 25, two different 400 mg tablets including 60 mg (Example 25.1 and 25.2) and 80 mg (Example 25.3 and 25.4) of oxycodone HCl were prepared using high molecular weight polyethylene oxide and low molecular weight polyethylene oxide. Two 100 kg batches were prepared for each formulation.

|  | Example 25 | |
|---|---|---|
| Ingredient | mg/unit | mg/unit |
| Oxycodone HCl | 60 | 80 |
| Polyethylene oxide (MW: approximately 4,000,000; Polyox ™ WSR-301) | 229.7 | 216 |
| Polyethylene oxide (MW: approximately 100,000; Polyox ™ WSR-N10) | 106.3 | 100 |
| Magnesium Stearate | 4 | 4 |
| Total Core Tablet Weight (mg) | 400 | 400 |

| Example | 25.1 | 25.2 | 25.3 | 25.4 |
|---|---|---|---|---|
| Total Batch size | 100 kg | 100 kg | 100 kg | 100 kg |

| Coating | mg/unit | | mg/unit | |
|---|---|---|---|---|
| Opadry film coating | 16 | | 16 | |
| Total Tablet Weight (mg) | 416 | | 416 | |

| Example | 25.1 | 25.2 | 25.3 | 25.4 |
|---|---|---|---|---|
| Coating Batch Size (kg) | 91.440 | 96.307 | 95.568 | 98.924 |

The processing steps to manufacture tablets were as follows:
1. The magnesium stearate was passed through a Sweco Sifter equipped with a 20 mesh screen, into a separate suitable container.
2. A Gemco "V" blender (with I bar)—10 cu. ft. was charged in the following order:
   Approximately ½ of the polyethylene oxide WSR 301
   Oxycodone hydrochloride
   Polyethylene oxide WSR N10
   Remaining polyethylene oxide WSR 301
3. Step 2 materials were blended for 10 minutes with the I bar on.
4. Magnesium stearate was charged into the Gemco "V" blender.
5. Step 4 materials were blended for 2 minutes with the I bar off.
6. Step 5 blend was charged into a clean, tared, stainless steel container.
7. Step 6 blend was compressed to target weight on a 40 station tablet press at 124,000 tph using 13/32 inch standard round, concave (embossed) tooling.
8. Step 7 tablets were loaded into a 48 inch Accela-Coat coating pan at a load of 91.440 kg (Example 25.1), 96.307 kg (Example 25.2), 95.568 kg (Example 25.3) and 98.924 kg (Example 25.4).
9. The pan speed was set at 6 to 10 rpm and the tablet bed was warmed using an exhaust air temperature to target a 55° C. inlet temperature. Film coating was started once the exhaust temperature approached 40° C. and continued for 10, 15 or 16 minutes. This initial film coat was performed to provide an "overcoat" for the tablets to function as an anti-tacking agent during the curing process.
10. After completion of the "overcoat", the tablet bed was heated by setting the exhaust air temperature to achieve a target inlet air temperature of 75° C. (Example 25.1 and 25.3) or to achieve a target exhaust temperature of 78° C. (Example 25.2 and 25.4). The tablets were cured at the target temperature for 65 minutes (Example 25.1), 52 minutes (Example 25.2), 80 minutes (Example 25.3) and 55 minutes (Example 25.4). For Example 25.1 and 25.3, the curing starting point (as described by method 1) was initiated once the inlet temperature reached the target inlet temperature. For Example 25.2 and 25.4, the curing starting point (as described by method 2) was initiated once the exhaust temperature reached the target exhaust temperature. The temperature profile of the curing processes of Examples 25.1 to 25.4 is presented in Tables 25.1.1 to 25.4.1.
11. During the curing process, the pan speed was increased from 7 to 9 rpm (Example 25.1 and 25.3) and from 10 to 12 rpm (Example 25.2 and 25.4). For examples 25.1 to 25.4, 20 g of magnesium stearate was added as an anti-tacking agent. The tablet bed was cooled by setting the exhaust temperature setting to 30° C.
12. After cooling, the tablet bed was warmed using an inlet setting of 53° C. The film coating was started once the exhaust temperature achieved approximately 39° C. and continued until the target weight gain of 4% was achieved.
13. After film coating was completed, the tablet bed was cooled by setting the exhaust temperature to 27° C. The tablet bed was cooled to an exhaust temperature of 30° C. or less was achieved.
14. The tablets were discharged.

In vitro testing including breaking strength tests was performed as follows.

Cured and coated tablets were tested in vitro using USP Apparatus 1 (basket) at 100 rpm in 900 ml simulated gastric fluid without enzymes (SGF) at 37° C. Samples were analyzed by reversed-phase high performance liquid chromatography (HPLC) on Waters Atlantis dC18 3.0×150 mm, 3 µm column, using a mobile phase consisting of a mixture of acetonitrile and non basic potassium phosphate buffer (pH 3.0) at 230 nm UV detection. Sample time points include 1.0, 2.0, 4.0, 6.0, 8.0 and 12.0 hours.

Uncured tablets were subjected to a breaking strength test by applying a force of a maximum of 196 Newton using a Schleuniger 2E/106 apparatus to evaluate tablet resistance to breaking.

The results are presented in Tables 25.1.2 to 25.4.2

TABLE 25.1.1

Temperature profile of the curing process for Ex. 25.1

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 0 | — | 52 | 60 | 41 | 7 | |
| 5 | 0 | 75 | 60 | 59 | 7 | Start curing |
| 15 | 10 | 81 | 65 | 66 | 7 | |
| 25 | 20 | 85 | 68 | 70 | 7 | |
| 35 | 30 | 73 | 71 | 70 | 9 | |
| 45 | 40 | 75 | 72 | 72 | 9 | |
| 55 | 50 | 75 | 72 | 72 | 9 | |
| 65 | 60 | 74 | 72 | 72 | 9 | |
| 70 | 65 | 75 | 72 | 72 | 9 | End curing, add 20 g Mg St |
| 71 | — | 74 | 30 | 72 | 9 | Start cooling |
| 81 | — | 32 | 30 | 52 | 9 | |
| 91 | — | 24 | 30 | 36 | 9 | |
| 94 | — | 23 | 30 | 30 | 9 | End cooling |

[1]determined according to method 1,
[2]temperature measured at the inlet,
[3]temperature measured at the exhaust.

TABLE 25.1.2

| | | Example 25.1 | |
|---|---|---|---|
| | | Uncured | cured, coated |
| Tablet Dimensions | Weight (mg) | 401 (n = 120) | — |
| | Breaking strength (N) | 112 (n = 50) | — |

TABLE 25.2.1

Temperature profile of the curing process for Ex. 25.2

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 0 | — | 69 | 65 | 46 | 10 | |
| 3 | — | 75 | 65 | 53 | 10 | |
| 13 | — | 85 | 70 | 65 | 10 | |
| 23 | — | 90 | 75 | 69 | 10 | |
| 33 | 0 | 90 | 77 | 77 | 10 | Start curing |
| 43 | 10 | 78 | 77 | 75 | 10 | |
| 53 | 20 | 79 | 77 | 77 | 10 | |
| 63 | 30 | 81 | 77 | 77 | 10 | |
| 73 | 40 | 80 | 77 | 77 | 12 | |
| 83 | 50 | 79 | 77 | 77 | 12 | |
| 85 | 52 | 80 | 77 | 77 | 12 | End curing, add 20 g Mg St |
| 86 | — | 80 | 30 | 77 | 12 | Start cooling |
| 96 | — | 37 | 30 | 54 | 12 | |
| 106 | — | 29 | 25 | 47 | 12 | |
| 116 | — | 24 | 25 | 30 | 12 | End cooling |

[1]determined according to method 2,
[2]temperature measured at the inlet,
[3]temperature measured at the exhaust.

TABLE 25.2.2

| | | Example 25.2 | | |
|---|---|---|---|---|
| | | Uncured | cured, coated Initial data | cured, coated 2nd test data |
| Tablet Dimensions | Weight (mg) | 400 (n = 120) | — | — |
| | Breaking strength (N) | 103 (n = 40) | — | — |

TABLE 25.2.2-continued

| | | Example 25.2 | | |
|---|---|---|---|---|
| | | Uncured | cured, coated Initial data | cured, coated 2nd test data |
| | | | n = 6 | n = 6 |
| Dissolution (% Released) SGF | 1 hr | — | 23 | 24 |
| | 2 hr | — | 39 | 43 |
| | 4 hr | — | 62 | 70 |
| | 6 hr | — | 79 | 88 |
| | 8 hr | — | 90 | 99 |
| | 12 hr | — | 97 | 103 |

TABLE 25.3.1

Temperature profile of the curing process for Ex. 25.3

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 0 | — | 55 | 65 | 39 | 7 | |
| 5 | 0 | 75 | 65 | 58 | 7 | Start curing |
| 15 | 10 | 82 | 66 | 66 | 7 | |
| 25 | 20 | 86 | 68 | 70 | 7 | |
| 35 | 30 | 76 | 72 | 72 | 7 | |
| 45 | 40 | 75 | 72 | 72 | 7 | |
| 55 | 50 | 75 | 72 | 72 | 7 | |
| 65 | 60 | 75 | 72 | 72 | 9 | |
| 75 | 70 | 74 | 72 | 72 | 9 | |
| 85 | 80 | 74 | 72 | 72 | 9 | End curing, add 20 g Mg St |
| 86 | — | 75 | 30 | 72 | 9 | Start cooling |
| 96 | — | 33 | 30 | 53 | 9 | |
| 106 | — | 26 | 30 | 39 | 9 | |
| 112 | — | 23 | 30 | 30 | 9 | End cooling |

[1]determined according to method 1,
[2]temperature measured at the inlet,
[3]temperature measured at the exhaust.

TABLE 25.3.2

| | | Example 25.3 | | |
|---|---|---|---|---|
| | | Uncured | cured, coated Initial data | cured, coated 2$^{nd}$ test data |
| Tablet Dimensions | Weight (mg) | 400 (n = 120) | — | — |
| | Thickness (mm) | — | — | — |
| | Diameter (mm) | — | — | — |
| | Breaking strength (N) | 111 (n = 40) | — | — |

TABLE 25.4.2

| | | Example 25.4 | | |
|---|---|---|---|---|
| | | Uncured | cured, coated Initial data | cured, coated 2$^{nd}$ test data |
| Tablet Dimensions | Weight (mg) | 400 (n = 120) | — | — |
| | Thickness (mm) | — | — | — |
| | Diameter (mm) | — | — | — |
| | Breaking strength (N) | 101 (n = 40) | — | — |

TABLE 25.4.1

Temperature profile of the curing process for Ex. 25.4

| Total time (min.) | Curing time (min.)[1] | Inlet temp. (° C.)[2] | Set exhaust temp. (° C.) | Actual exhaust temp. (° C.)[3] | Pan speed (rpm) | Comments |
|---|---|---|---|---|---|---|
| 0 | — | 60 | 70 | 43 | 10 | |
| 10 | — | 80 | 75 | 64 | 10 | |
| 20 | — | 85 | 75 | 69 | 10 | |
| 30 | — | 88 | 76 | 74 | 10 | |
| 33 | 0 | 88 | 78 | 78 | 10 | Start curing |
| 43 | 10 | 75 | 78 | 76 | 12 | |
| 53 | 20 | 84 | 78 | 79 | 12 | |
| 63 | 30 | 82 | 78 | 78 | 12 | |
| 73 | 40 | 79 | 78 | 78 | 12 | |
| 83 | 50 | 82 | 78 | 78 | 12 | |
| 88 | 55 | 80 | 78 | 78 | 12 | End curing, add 20 g Mg St |
| 89 | — | 79 | 30 | 78 | 12 | Start cooling |
| 99 | — | 38 | 25 | 54 | 12 | |
| 109 | — | 26 | 25 | 45 | 12 | |
| 113 | — | 23 | 25 | 34 | 12 | End cooling |

[1]determined according to method 2,
[2]temperature measured at the inlet,
[3]temperature measured at the exhaust.

TABLE 25.4.2-continued

| | | Example 25.4 | | |
|---|---|---|---|---|
| | | Uncured | cured, coated Initial data | cured, coated 2$^{nd}$ test data |
| | | | n = 6 | n = 6 |
| Dissolution (% Released) SGF | 1 hr | — | 25 | 29 |
| | 2 hr | — | 42 | 47 |
| | 4 hr | — | 66 | 73 |
| | 6 hr | — | 84 | 91 |
| | 8 hr | — | 96 | 99 |
| | 12 hr | — | 100 | 101 |

TABLE 25.5

| | Density (g/cm$^3$)[1] | | | |
|---|---|---|---|---|
| | Uncured | 30 min cure | 60 min cure | Density change after curing (%)[2] |
| Example 25.1 | 1.205 | 1.153 | 1.138 | −5.560 |
| Example 25.3 | 1.207 | 1.158 | 1.156 | −4.225 |

[1] The density was measured as described for Example 13. The density value is a mean value of 3 tablets measured;
[2] The density change after curing corresponds to the observed density change in % of the tablets cured for 60 min in comparison to the uncured tablets.

Example 26

In Example 26, a randomized, open-label, single-dose, four-treatment, four-period, four-way crossover study in healthy human subjects was conducted to assess the pharmacokinetic characteristics and relative bioavailability of three oxycodone tamper resistant formulations (10 mg oxycodone HCl tablets of Examples 7.1 to 7.3 relative to the commercial OxyContin® formulation (10 mg), in the fasted and fed state.

The study treatments were as follows:
Test Treatments:
  Treatment 1A: 1× Oxycodone HCl 10 mg Tablet of Example 7.3 (Formulation 1A) administered in the fasted or fed state.
  Treatment 1B: 1× Oxycodone HCl 10 mg Tablet of Example 7.2 (Formulation 1B) administered in the fasted or fed state.
  Treatment 1C: 1× Oxycodone HCl 10 mg Tablet of Example 7.1 (Formulation 1C) administered in the fasted or fed state.
Reference Treatment:
  Treatment OC: 1× OxyContin® 10 mg tablet administered in the fasted or fed state.

The treatments were each administered orally with 8 oz. (240 mL) water as a single dose in the fasted or fed state.

As this study was conducted in healthy human subjects, the opioid antagonist naltrexone hydrochloride was administered to minimize opioid-related adverse events.
Subject Selection
Screening Procedures
The following screening procedures were performed for all potential subjects at a screening visit conducted within 28 days prior to first dose administration:
  Informed consent.
  Weight, height, body mass index (BMI), and demographic data.
  Evaluation of inclusion/exclusion criteria.
  Medical and medication history, including concomitant medication.
  Vital signs—blood pressure, respiratory rate, oral temperature, and pulse rate (after being seated for approximately 5 minutes) and blood pressure and pulse rate after standing for approximately 2 minutes—and pulse oximetry (SPO$_2$), including "How do you feel?" Inquiry.
  Routine physical examination (may alternately be performed at Check-in of Period 1).
  Clinical laboratory evaluations (including biochemistry, hematology, and urinalysis [UA]).
  12-lead electrocardiogram (ECG).
  Screens for hepatitis (including hepatitis B surface antigen [HBsAg], hepatitis B surface antibody [HBsAb], hepatitis C antibody [anti-HCV]), and selected drugs of abuse.
  Serum pregnancy test (female subjects only).
  Serum follicle stimulating hormone (FSH) test (postmenopausal females only)
Inclusion Criteria
Subjects who met the following criteria were included in the study.
  Males and females aged 18 to 50, inclusive.
  Body weight ranging from 50 to 100 kg (110 to 220 lbs) and a BMI ≥18 and ≤34 (kg/m$^2$).
  Healthy and free of significant abnormal findings as determined by medical history, physical examination, vital signs, and ECG.
  Females of child-bearing potential must be using an adequate and reliable method of contraception (e.g., barrier with additional spermicide foam or jelly, intra-uterine device, hormonal contraception (hormonal contraceptives alone are not acceptable). Females who are postmenopausal must have been postmenopausal ≥1 year and have elevated serum FSH.
  Willing to eat all the food supplied during the study.
Exclusion Criteria
The following criteria excluded potential subjects from the study.
  Females who are pregnant (positive beta human chorionic gonadotropin test) or lactating.
  Any history of or current drug or alcohol abuse for 5 years.
  History of or any current conditions that might interfere with drug absorption, distribution, metabolism or excretion.
  Use of an opioid-containing medication in the past 30 days.
  History of known sensitivity to oxycodone, naltrexone, or related compounds.
  Any history of frequent nausea or emesis regardless of etiology.
  Any history of seizures or head trauma with current sequelae.
  Participation in a clinical drug study during the 30 days preceding the initial dose in this study.
  Any significant illness during the 30 days preceding the initial dose in this study.
  Use of any medication including thyroid hormone replacement therapy (hormonal contraception is allowed), vitamins, herbal, and/or mineral supplements, during the 7 days preceding the initial dose.
  Refusal to abstain from food for 10 hours preceding and 4 hours following administration of the study drugs and to abstain from caffeine or xanthine entirely during each confinement.

Consumption of alcoholic beverages within forty-eight (48) hours of initial study drug administration (Day 1) or anytime following initial study drug administration.

History of smoking or use of nicotine products within 45 days of study drug administration or a positive urine cotinine test.

Blood or blood products donated within 30 days prior to administration of the study drugs or anytime during the study, except as required by this protocol.

Positive results for urine drug screen, alcohol screen at Check-in of each period, and HBsAg, HBsAb (unless immunized), anti-HCV.

Positive Naloxone HCl challenge test.

Presence of Gilbert's Syndrome or any known hepatobiliary abnormalities.

The Investigator believes the subject to be unsuitable for reason(s) not specifically stated in the exclusion criteria.

Subjects meeting all the inclusion criteria and none of the exclusion criteria were randomized into the study. It was anticipated that approximately 34 subjects would be randomized, with 30 subjects targeted to complete the study. Any subject who discontinued could be replaced.

Subjects were assigned by the random allocation schedule (RAS) in a 2:1 ratio to fasted or fed state, with twenty subjects to be randomized to a fasted state and 10 subjects to be randomized to a fed state.

Check-In Procedures

On Day −1 of Period 1, subjects were admitted to the study unit and received a Naloxone HCl challenge test. The results of the test had to be negative for subjects to continue in the study. Vital signs and $SPO_2$ were measured prior to and following the Naloxone HCl.

The following procedures were also performed for all subjects at Check-in for each period:

Verification of inclusion/exclusion criteria, including verification of willingness to comply with caffeine or xanthine restriction criteria.

Routine physical examination at Check-in of Period 1 only (if not performed at Screening).

Vital signs-blood pressure, respiratory rate, and pulse rate (after being seated for approximately 5 minutes)—and $SPO_2$, including How Do You Feel? Inquiry.

Screen for alcohol (via breathalyzer test), cotinine, and selected drugs of abuse.

Urine pregnancy test (for all female subjects).

Verification of medication and medical history.

Concomitant medication monitoring and recording.

Adverse Event monitoring and recording.

For subjects to continue their participation in the study, the results of the drug screen (including alcohol and cotinine) had to be available and negative prior to dosing. In addition, continued compliance with concomitant medication and other restrictions were verified at Check-in and throughout the study in the appropriate source documentation.

Prior to the first dose in Period 1, subjects were randomized to a treatment sequence in which test and reference treatments are received in a specified order. The treatment sequence according to the random allocation schedule (RAS) was prepared by a bio statistician who was not involved in the evaluation of the results of the study. Randomization was used in this study to enhance the validity of statistical comparisons across treatments.

The treatment sequences for this study are presented in Table 26.1:

TABLE 26.1

| Sequence | Period 1 | Period 2 | Period 3 | Period 4 |
|---|---|---|---|---|
| | | Treatment | | |
| 1 | OC | 1C | 1A | 1B |
| 2 | 1A | OC | 1B | 1C |
| 3 | 1B | 1A | 1C | OC |
| 4 | 1C | 1B | OC | 1A |

Study Procedures

The study included four study periods, each with a single dose administration. There was a washout period of seven days between dose administrations in each study period. During each period, subjects were confined to the study site from the day prior to administration of the study drugs through 48 hours following administration of the study drugs, and returned to the study site for 72-hour procedures.

At each study period, the subjects were administered one of the test oxycodone formulations (10 mg) or OxyContin® 10 mg tablets (OC) with 240 mL of water, following a 10 hour overnight fast (for fasted treatments). Subjects receiving fasted treatments continued fasting from food for 4 hours following dosing. Subjects receiving fed treatments started the standard meal (FDA high-fat breakfast) 30 minutes prior to administration of the drug. Subjects were dosed 30 minutes after start of the meal and no food was allowed for at least 4 hours post-dose.

Subjects received naltrexone HCl 50 mg tablets at −12, 0, 12, 24, and 36 hours relative to each test formulation or OxyContin® dosing.

Subjects were standing or in an upright sitting position while receiving their dose of study medication. Subjects remained in an upright position for a minimum of 4 hours.

Clinical laboratory sampling was preceded by a fast (i.e. at least 10 hours) from food (not including water). Fasting was not required for non-dosing study days.

During the study, adverse events and concomitant medications were recorded, and vital signs (including blood pressure, body temperature, pulse rate, and respiration rate) and $SPO_2$ were monitored.

Blood samples for determining oxycodone plasma concentrations were obtained for each subject at predose and at 0.5, 1, 1.5, 2, 2.5, 3, 3.5, 4, 5, 6, 8, 10, 12, 16, 24, 28, 32, 36, 48, and 72 hours postdose for each period.

For each sample, 6 mL of venous blood were drawn via an indwelling catheter and/or direct venipuncture into tubes containing $K_2EDTA$ anticoagulant (6 mL-draw $K_2EDTA$ Vacutainer® evacuated collection tubes). Plasma concentrations of oxycodone were quantified by a validated liquid chromatography tandem mass spectrometric method.

Study Completion Procedures

The following procedures were performed in the clinic for all subjects at End of Study (Study Completion) or upon discontinuation from the study:

Concomitant medication evaluation.

Vital signs and $SPO_2$, including How Do You Feel? inquiry.

Physical examination.

12-Lead ECG.

Clinical laboratory evaluations (including biochemistry [fasted at least 10 hours], hematology, and urinalysis).

Adverse event evaluations.

Serum pregnancy test (for female subjects only).

The results of this study are shown in Tables 26.2 to 26.5.

TABLE 26.2

Mean plasma pharmacokinetic metrics data
Treatments 1A, 1B, 1C and OC (fed state)

| | $C_{max}$ (ng/mL) | $t_{max}$ (hr) | $AUC_t$ (ng·hr/mL) | $AUC_{inf}$ (ng·hr/mL) | $t_{1/2z}$ (hr) | $\lambda_z$ (1/hr) | $t_{lag}$ (hr) |
|---|---|---|---|---|---|---|---|
| Treatment 1A-fed | | | | | | | |
| N | 12 | 12 | 12 | 11 | 12 | 12 | 12 |
| MEAN | 11.3 | 5.08 | 122 | 134 | 4.22 | 0.170 | 0.0833 |
| SD | 5.54 | 2.46 | 55.3 | 42.5 | 0.884 | 0.0292 | 0.195 |
| MIN | 0.372 | 1.00 | 1.13 | 86.2 | 3.34 | 0.114 | 0 |
| MEDIAN | 10.7 | 5.00 | 120 | 121 | 3.94 | 0.177 | 0 |
| MAX | 20.5 | 10.0 | 221 | 223 | 6.10 | 0.207 | 0.500 |
| GEOMEAN | 8.63 | NA | 85.8 | 128 | NA | NA | NA |
| Treatment 1B-fed | | | | | | | |
| N | 12 | 12 | 12 | 12 | 12 | 12 | 12 |
| MEAN | 14.2 | 5.25 | 133 | 134 | 4.37 | 0.164 | 0.0833 |
| SD | 3.36 | 1.48 | 40.2 | 40.3 | 0.947 | 0.0283 | 0.195 |
| MIN | 8.11 | 3.00 | 63.7 | 64.5 | 3.28 | 0.0990 | 0 |
| MEDIAN | 14.2 | 5.00 | 126 | 127 | 4.22 | 0.165 | 0 |
| MAX | 18.5 | 8.00 | 205 | 207 | 7.00 | 0.211 | 0.500 |
| GEOMEAN | 13.8 | NA | 127 | 128 | NA | NA | NA |
| Treatment 1C-fed | | | | | | | |
| N | 12 | 12 | 12 | 12 | 12 | 12 | 12 |
| MEAN | 17.1 | 4.21 | 138 | 139 | 4.41 | 0.162 | 0.0417 |
| SD | 4.66 | 1.21 | 42.9 | 42.9 | 0.843 | 0.0263 | 0.144 |
| MIN | 11.6 | 1.50 | 91.4 | 92.5 | 3.43 | 0.107 | 0 |
| MEDIAN | 16.5 | 4.50 | 122 | 123 | 4.03 | 0.173 | 0 |
| MAX | 27.9 | 6.00 | 218 | 219 | 6.49 | 0.202 | 0.500 |
| GEOMEAN | 16.5 | NA | 133 | 134 | NA | NA | NA |
| Treatment OC-fed | | | | | | | |
| N | 12 | 12 | 12 | 12 | 12 | 12 | 12 |
| MEAN | 13.2 | 3.17 | 142 | 143 | 4.83 | 0.146 | 0 |
| SD | 3.20 | 1.85 | 39.3 | 39.5 | 0.702 | 0.0189 | 0 |
| MIN | 8.85 | 1.00 | 95.2 | 95.9 | 3.93 | 0.105 | 0 |
| MEDIAN | 12.3 | 2.25 | 124 | 125 | 4.76 | 0.146 | 0 |
| MAX | 18.1 | 6.00 | 218 | 219 | 6.59 | 0.176 | 0 |
| GEOMEAN | 12.8 | NA | 137 | 138 | NA | NA | NA |

NA = not applicable.

TABLE 26.3

Mean plasma pharmacokinetic metrics data Treatments
1A, 1B, 1C and OC (fasted state)

| | $C_{max}$ (ng/mL) | $t_{max}$ (hr) | $AUC_t$ (ng·hr/mL) | $AUC_{inf}$ (ng·hr/mL) | $t_{1/2z}$ (hr) | $\lambda_z$ (1/hr) | $t_{lag}$ (hr) |
|---|---|---|---|---|---|---|---|
| Treatment 1A-fasted | | | | | | | |
| N | 20 | 20 | 20 | 20 | 20 | 20 | 20 |
| MEAN | 8.84 | 4.60 | 109 | 111 | 4.66 | 0.156 | 0.0250 |
| SD | 2.25 | 1.90 | 20.1 | 20.3 | 1.26 | 0.0279 | 0.112 |
| MIN | 4.85 | 2.00 | 69.0 | 69.8 | 3.56 | 0.0752 | 0 |
| MEDIAN | 8.53 | 5.00 | 114 | 114 | 4.29 | 0.162 | 0 |
| MAX | 13.2 | 10.0 | 138 | 139 | 9.22 | 0.195 | 0.500 |
| GEOMEAN | 8.56 | NA | 108 | 109 | NA | NA | NA |
| Treatment 1B-fasted | | | | | | | |
| N | 19 | 19 | 19 | 19 | 19 | 19 | 19 |
| MEAN | 9.97 | 4.58 | 115 | 116 | 4.67 | 0.156 | 0 |
| SD | 1.82 | 1.18 | 23.8 | 23.8 | 1.24 | 0.0309 | 0 |
| MIN | 6.90 | 2.00 | 75.2 | 76.3 | 3.53 | 0.0878 | 0 |
| MEDIAN | 10.0 | 5.00 | 121 | 122 | 4.35 | 0.159 | 0 |
| MAX | 14.1 | 6.00 | 152 | 153 | 7.90 | 0.197 | 0 |
| GEOMEAN | 9.81 | NA | 113 | 114 | NA | NA | NA |
| Treatment 1C-fasted | | | | | | | |
| N | 22 | 22 | 22 | 22 | 22 | 22 | 22 |
| MEAN | 13.6 | 3.75 | 110 | 111 | 4.18 | 0.169 | 0.0227 |
| SD | 3.79 | 1.38 | 18.5 | 18.5 | 0.594 | 0.0256 | 0.107 |
| MIN | 8.64 | 1.00 | 70.6 | 71.1 | 2.92 | 0.135 | 0 |
| MEDIAN | 12.9 | 3.75 | 112 | 113 | 4.13 | 0.169 | 0 |

TABLE 26.3-continued

Mean plasma pharmacokinetic metrics data Treatments
1A, 1B, 1C and OC (fasted state)

| | $C_{max}$ (ng/mL) | $t_{max}$ (hr) | $AUC_t$ (ng·hr/mL) | $AUC_{inf}$ (ng·hr/mL) | $t_{1/2z}$ (hr) | $\lambda_z$ (1/hr) | $t_{lag}$ (hr) |
|---|---|---|---|---|---|---|---|
| MAX | 23.7 | 6.00 | 142 | 143 | 5.14 | 0.237 | 0.500 |
| GEOMEAN | 13.2 | NA | 108 | 109 | NA | NA | NA |
| | | | Treatment OC-fasted | | | | |
| N | 19 | 19 | 19 | 19 | 19 | 19 | 19 |
| MEAN | 9.73 | 2.82 | 114 | 115 | 4.82 | 0.154 | 0 |
| SD | 1.67 | 0.960 | 26.0 | 26.2 | 1.41 | 0.0379 | 0 |
| MIN | 7.38 | 1.00 | 76.3 | 77.8 | 3.11 | 0.0839 | 0 |
| MEDIAN | 9.57 | 3.00 | 112 | 112 | 4.37 | 0.159 | 0 |
| MAX | 13.2 | 5.00 | 181 | 183 | 8.27 | 0.223 | 0 |
| GEOMEAN | 9.60 | NA | 112 | 113 | NA | NA | NA |

NA = not applicable.

TABLE 26.4

Statistical Results of Oxycodone Pharmacokinetic Metrics:
Bioavailability Example 7.1 to 7.3 Tablets Relative to OxyContin ®
10 mg in the Fed State (Population: Full Analysis)

| | Cmax | | AUCt | |
|---|---|---|---|---|
| Comparison (Test vs. Ref) | LS Mean Ratio (test/reference)[a] | 90% Confidence Interval[b] | LS Mean Ratio (test/reference)[a] | 90% Confidence Interval[b] |
| 1A vs. OC | 67.5 | [47.84, 95.16] | 62.6 | [39.30, 99.83] |
| 1B vs. OC | 108.0 | [76.59, 152.33] | 92.9 | [58.31, 148.14] |
| 1C vs. OC | 129.0 | [91.54, 182.07] | 97.0 | [60.83, 154.52] |

[a]Least squares mean from ANOVA. Natural log (ln) metric means calculated by transforming the ln means back to the linear scale, i.e., geometric means; Ratio of metric means for ln-transformed metric (expressed as a percent). Ln-transformed ratio transformed back to linear scale (test = Treatment 1A, 1B, 1C; reference = Treatment OC);
[b]90% confidence interval for ratio of metric means (expressed as a percent). Ln-transformed confidence limits transformed back to linear scale.

TABLE 26.5

Statistical Results of Oxycodone Pharmacokinetic Metrics:
Bioavailability Example 7.1 to 7.3 Tablets Relative to OxyContin ®
10 mg in the Fasted State (Population: Full Analysis)

| | Cmax | | AUCt | |
|---|---|---|---|---|
| Comparison (Test vs. Ret) | LS Mean Ratio (test/reference)[a] | 90% Confidence Interval[b] | LS Mean Ratio (test/reference)[a] | 90% Confidence Interval[b] |
| 1A vs. OC | 89.5 | [82.76, 96.89] | 97.0 | [92.26, 102.79] |
| 1B vs. OC | 99.0 | [91.33, 107.30] | 101.0 | [95.42, 106.57] |
| 1C vs. OC | 133.0 | [123.23, 143.86] | 96.4 | [91.43, 101.68] |

[a]Least squares mean from ANOVA. Natural log (ln) metric means calculated by transforming the ln means back to the linear scale, i.e., geometric means; Ratio of metric means for ln-transformed metric (expressed as a percent). Ln-transformed ratio transformed back to linear scale (test = Treatment 1A, 1B, 1C; reference = Treatment OC);
[b]90% confidence interval for ratio of metric means (expressed as a percent). Ln-transformed confidence limits transformed back to linear scale.

Example 27

In Example 27, oxycodone HCl tablets of Example 7.2, and Example 14.2 to 14.5 containing 10, 15, 20, 30, and 40 mg oxycodone HCl respectively were subjected to a variety of tamper resistance testing, using mechanical force and chemical extraction to evaluate their resistance to physical and chemical manipulation.

Test results are compared to control data, defined as percent Active Pharmaceutical Ingredient (API) released for intact tablets after in vitro dissolution in Simulated Gastric Fluid without enzyme (SGF) for 45 minutes. This comparator was chosen as a reference point to approximate the amount of API present in the body (after 45 min) when the product is taken as directed. Available results for the current marketed formulation, OxyContin™, are presented for comparison as well.

Five different strength tablets (10, 15, 20, 30 and 40 mg oxycodone HCl, corresponding to Example 7.2, and Examples 14.2 to 14.5) were manufactured. All tablet strengths are about the same size and weight, therefore all testing was performed on the bracketing tablet strengths with the lowest API to excipient ratio (10 mg, Example 7.2) and the highest API to excipient ratio (40 mg, Example 14.5). In addition, level 1 testing was performed on the intermediate tablet strengths (15, 20 and 30 mg, Examples 14.2, 14.3 and 14.4) to assess the resistance to physical manipulation, and subsequent chemical extraction, when using a mortar and pestle. Further testing was not performed on these tablets as higher levels of testing employ a coffee mill which resulted in similar particle size distributions and similar amount of extracted API for the milled bracketing tablets (Example 7.2 and 14.5).

The experimental techniques used for this testing were designed to provide procedures for simulating and evaluating common methods of abuse. Four levels of tamper resistance were broadly defined to provide an approximation of the relative level of tamper resistance. Several approaches to tampering were considered; these include mechanical force (applied to damage the drug product), availability and toxicity of extraction solvents, length of extraction, and thermal treatment. Each higher level of tamper resistance represents an increase in the degree of difficulty necessary to successfully tamper with a drug product. The definitions of levels of tamper resistance, including examples of equipment and reagents, are presented in Table 27.1.

TABLE 27.1

Definitions and Examples of Testing

| Level | Definition | Degree Of Difficulty | Equipment Examples | Reagent Examples |
|---|---|---|---|---|
| 0 | Able to be directly abused without preparation | Negligible | N/A | None |
| 1 | Readily abused through a variety of means without reagent or with an easily obtainable reagent Reagents are directly ingestible and extraction time is shorter | Minimal | Crushing tool (hammer, shoe, pill crusher, etc) | water, distilled spirits (vodka, gin, etc), vinegar, baking soda, cooking oil |
| 2 | Readily abused with additional preparation requiring some planning Reagents are directly ingestible, although more harmful, extraction time is shorter, and thermal treatment is applied | Moderate | Tools for IV preparation, milling tool (coffee mill, blender), microwave oven | 100% ethanol (grain alcohol, Everclear) strong acidic and basic solutions |
| 3 | Preparation for abuse requires knowledge of drug chemistry, includes less readily available reagents, may require industrial tools, involves complex processes (e.g., two-phase extraction) Some reagents are harmful and not directly ingestible, extraction time and temperature are increased | Substantial | Impact mill (e.g., Fitzmill) | In addition to previously listed solvents: methanol, ether, isopropanol, acetone, ethyl acetate |

Testing Results

Control Data ("Taken as Directed") and Specification Limits

Dissolution testing on intact Example 7.2, and Example 14.2 to 14.5 tablets was performed in vitro using USP Apparatus 1 (basket) at 100 rpm in 900 ml simulated gastric fluid without enzymes (SGF) at 37° C. Samples were taken at 45 minutes of dissolution and analyzed by reversed-phase high performance liquid chromatography (HPLC). The average results of a triplicate analysis are reported in Table 27.2 and compared to equivalent data for OxyContin™ 10 mg tablets.

TABLE 27.2

Control Results - % API Released at 45 minutes

% oxycodone HCl[1] released at 45 minutes

| Sample Preparation | OxyContin ™ 10 mg | Ex. 7.2 (10 mg) | Ex. 14.2 (15 mg) | Ex. 14.3 (20 mg) | Ex. 14.4 (30 mg) | Ex. 14.5 (40 mg) |
|---|---|---|---|---|---|---|
| None (intact tablets) | 34 | 19 | 20 | 20 | 18 | 19 |

[1]relative to label claim

In addition, Table 27.3 contains the one hour dissolution specification limits for each of the tablets studied. This illustrates the range of acceptable drug release at one hour for all formulations tested in this study. It should be noted that the upper acceptable limit for one hour in vitro release of oxycodone HCl from OxyContin 10 mg tablets is 49%.

TABLE 27.3

Dissolution (% Released) Specification Limits

| Product | 1 Hr Specification Limit |
|---|---|
| Example 7.2 | 15-35 |
| Example 14.2 | 15-35 |
| Example 14.3 | 15-35 |
| Example 14.4 | 15-35 |
| Example 14.5 | 15-35 |
| OxyContin ™ 10 mg | 29-49 |

Level 1 Testing

Level one testing included crushing with a mortar and pestle and simple extraction.

Level 1 Results—Crushing

Figure 40:
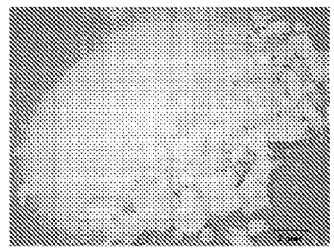
FIG. 40 shows representative images of crushed OxyContin™ 10 mg and crushed Example 7.2 tablets, according to Example 27.
Figure 40:
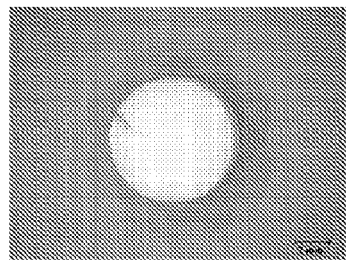

After crushing in a mortar and pestle, in vitro dissolution testing was performed in triplicate for each product using USP Apparatus 1 (basket) at 100 rpm in 900 ml simulated gastric fluid without enzymes (SGF) at 37° C., as described above for control data. Example 7.2 tablets were not able to be crushed using a mortar and pestle and therefore release of the API was not significantly increased as compared to the control results. Although difficult, tablets of Examples 14.2 to 14.5 (15, 20, 30 and 40 mg tablets) could be broken into large pieces using a mortar and pestle producing little to no powder. This reduction in particle size resulted in higher release of the API; however, the swelling of the tablet matrix, when dissolved in SGF, provides protection against dose dumping as less than half of the API was released after 45 minutes. The OxyContin™ tablets were easily reduced to a powder using a mortar and pestle resulting in release of most of the API. FIG. 40 contains representative images of crushed tablets. Table 27.4 contains the average results for percent API released after crushing.

TABLE 27.4

Crushing Results - % API Released at 45 Minutes

| Sample Preparation | % oxycodone HCl[1] released at 45 min. | | | | | |
|---|---|---|---|---|---|---|
| | Oxy-Contin™ 10 mg | Ex. 7.2 (10 mg) | Ex. 14.2 (15 mg) | Ex. 14.3 (20 mg) | Ex. 14.4 (30 mg) | Ex. 14.5 (40 mg) |
| Crushed tablets | 92 | 20 | 41 | 44 | 42 | 43 |
| Control - intact tablets (45 min release) | 34 | 19 | 20 | 20 | 18 | 19 |

[1]relative to label claim

Additionally, Example 14.5 tablets could not be crushed between two spoons demonstrating that additional tools would need to be employed to crush the tablets. Conversely, the OxyContin™ tablets were easily crushed between two spoons.

Level 1 Results—Simple Extraction

Example 7.2, and Example 14.2 to 14.5 tablets were crushed in a mortar and pestle and vigorously shaken on a wrist-action shaker, over a 10° angle, for 15 minutes in various solvents at room temperature. As previously stated, Example 7.2 tablets were unaffected by crushing in a mortar and pestle and therefore extraction amounts were not increased. Example 14.2 to 14.5 tablets were crushed using a mortar and pestle before extraction. Due to the swelling of the tablet matrix in the solvents tested, the crushed tablets remained resistant to comprehensive dose dumping, whereas the OxyContin™ tablets released nearly all of the API. Table 27.5 contains the average amount of APT released in each solvent.

TABLE 27.5

Simple Extraction Results - % API Released at 15 Minutes

| Crushed Tablets in Extraction Solvent | % oxycodone HCl[1] released | | | | | |
|---|---|---|---|---|---|---|
| | Oxy-Contin™ (10 mg) | Ex. 7.2 (10 mg) | Ex. 14.2 (15 mg) | Ex. 14.3 (20 mg) | Ex. 14.4 (30 mg) | Ex. 14.5 (40 mg) |
| Water | 92 | 8 | 32 | 30 | 28 | 51 |
| 40% EtOH (v/v) | 101 | 5 | 24 | 18 | 22 | 40 |
| Vinegar | 102 | 11 | 28 | 35 | 41 | 54 |
| Cooking Oil | 79 | 0 | 2 | 1 | 2 | 6 |
| 0.026M Baking Soda Solution | 95 | 6 | 26 | 25 | 29 | 50 |
| Control - intact tablets (45 min release) | 34 | 19 | 20 | 20 | 18 | 19 |

[1]relative to label claim

Level 2 Testing

Level two testing included milling, simulated intravenous (IV) preparation, thermal treatment and extraction.

Level 2 Results—Milling

Figure 41:
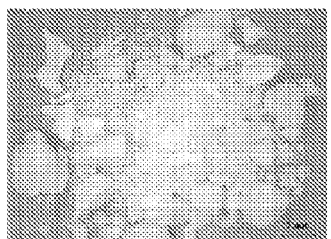
FIG. 41 shows representative images of milled Example 7.2 and OxyContin™ 10 mg tablets before and after 45 minutes of dissolution, according to Example 27.
Figure 41:
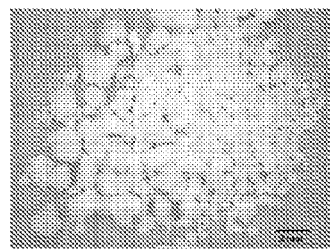
Figure 41:
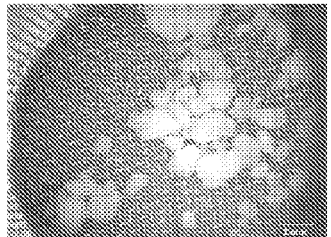
Figure 41:
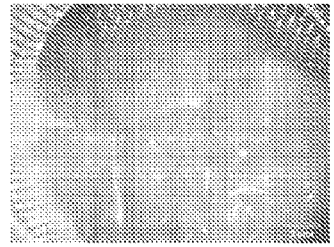

Example 7.2 and Example 14.5 tablets were ground in a Cuisanart® coffee mill with stainless steel blades (model DCG-12BC) for 1 minute. The energy output of the coffee mill (1 minute) was determined to be 10.5 kJ. In triplicate, material equivalent to one dosage unit was removed and analyzed by dissolution testing using USP Apparatus 1 (basket) at 100 rpm in 900 ml simulated gastric fluid without enzymes (SGF) at 37° C., as described above for the control data. After one minute, Example 7.2 and Example 14.5 tablets were milled to similar particle size distributions resulting in both tablet strengths releasing approximately half of the API. The OxyContin™ tablets were milled into a mixture of larger pieces and some powder resulting in nearly complete release of the API. Table 27.6 contains the average amount of API released from the milled tablets. As previously mentioned, the ground Example 7.2 and 14.5 tablets swell and become gelatinous. This phenomenon provides protection against dose dumping. FIG. 41 contains representative images of milled tablets before and after dissolution.

TABLE 27.6

Milling Results-% API Released at 45 Minutes

| Sample Preparation | % oxycodone HCl[1] released | | |
|---|---|---|---|
| | OxyContin (10 mg) | Ex. 7.2 (10 mg) | Ex. 14.5 (40 mg) |
| Milled tablets | 93 | 47 | 52 |
| Control-intact tablets (45 min release) | 34 | 19 | 19 |

[1]relative to label claim

Relative In Vitro Dissolution Rate

Figure 42:
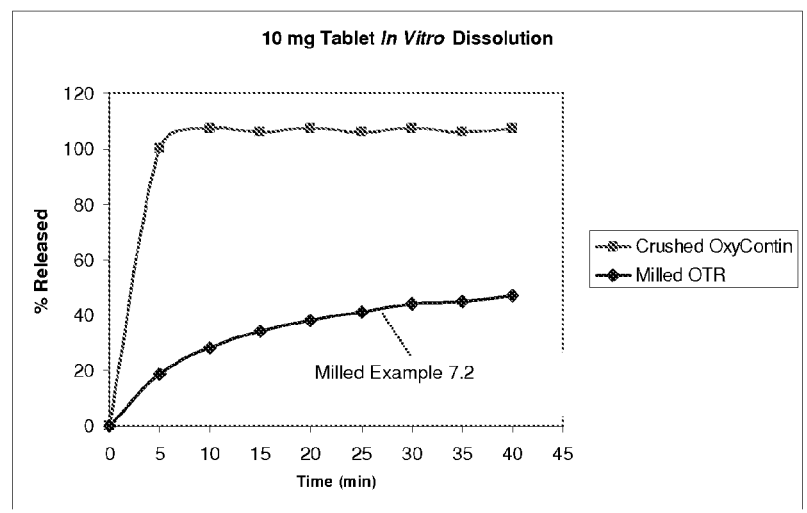
FIG. 42 shows dissolution profiles of milled Example 7.2 tablets and crushed OxyContin™ 10 mg tablets, according to Example 27.
Figure 43:
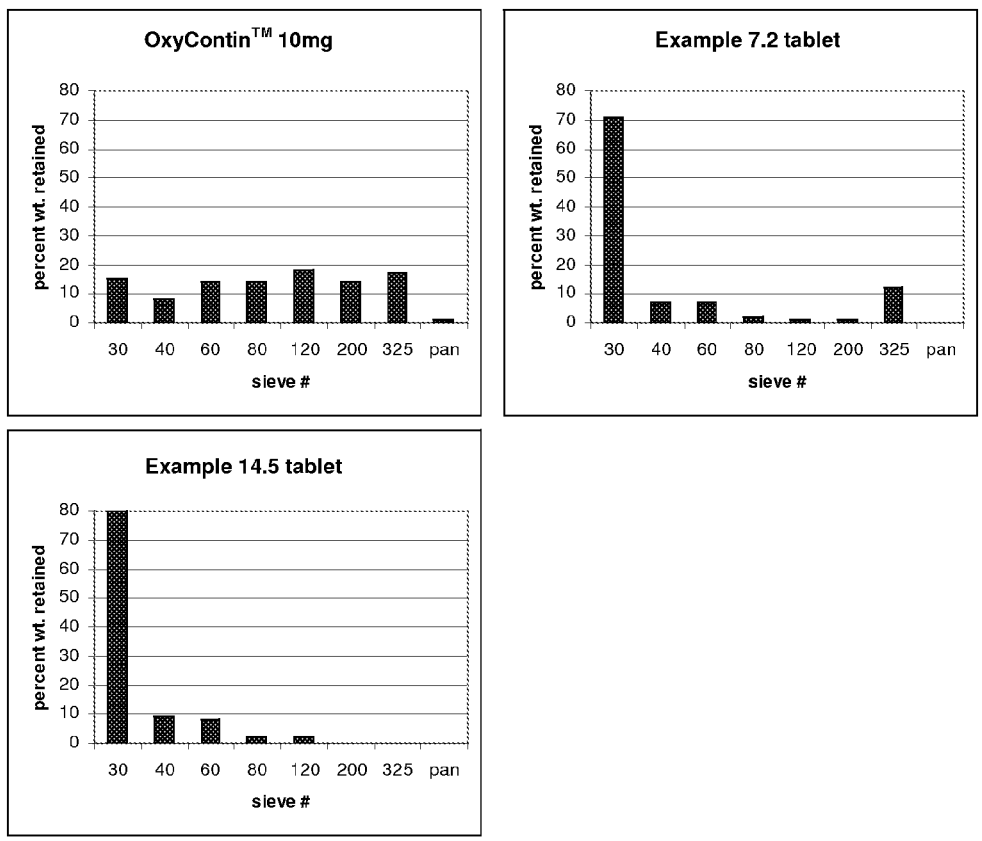
FIG. 43 shows particle size distribution graphs of milled tablets (OxyContin™ 10 mg, Example 7.2 and Example 14.5 tablets), according to Example 27.

To assess the relative rate of release of the API, dissolution samples were collected every five minutes from t=0 to t=40 minutes for milled Ex 7.2 tablets (coffee mill) and crushed OxyContin™ 10 mg tablets (mortar and pestle). The OxyContin™ tablet is more easily and effectively crushed using a mortar and pestle. Although approximately half of the API is released from milled Example 7.2 tablets over 45 minutes, it is released at a gradual rate that is characteristic of a controlled released product. Dose dumping is not observed. Conversely, dissolution of milled OxyContin™ tablets results in complete dose dumping within 10 minutes. This is illustrated in FIG. 42.

Particle Size Distribution of Milled Tablets

Milled Example 7.2 and 14.5 tablets (coffee mill) and crushed OxyContin™ 10 mg tablets (mortar and pestle) were analyzed by sieving to evaluate the particle size distribution of the milled material. The tablets were sieved for 12 minutes using vibration. The sieves used and the corresponding mesh sizes are presented in Table 27.7. As shown in the particle size distribution graphs in FIG. 43, 70-80% of the milled Example 7.2 and 14.5 tablets are larger than 600 μm. The large particle size of the milled material is likely disagreeable to snorting. OxyContin™ 10 mg resulted in a much smaller particle size distribution.

TABLE 27.7

Sieve Sizes and Corresponding Mesh Size

| Sieve Number | Mesh Size (μm) |
|---|---|
| 30 | 600 |
| 40 | 425 |
| 60 | 250 |
| 80 | 180 |
| 120 | 125 |
| 200 | 75 |
| 325 | 45 |

Level 2 Results—Simulated Intravenous Preparation

Example 7.2 and 14.5 tablets were milled in the coffee mill (as described above) and placed onto a spoon. The OxyContin™ 10 mg tablets were crushed between two spoons. Two milliliters of water were added to each spoon to extract or dissolve the drug product. The milled Example 7.2 and 14.5 tablets became viscous after the water was added which resulted in a small amount (<0.3 ml) of the liquid being able to be drawn into an insulin syringe and analyzed for API content. Very little API was recovered. Approximately one milliliter containing half of the API was recovered for the crushed OxyContin 10 mg tablets. Table 27.8 contains the simulated intravenous preparation results.

TABLE 27.8

Simulated IV Results-% API Released

| Sample Preparation | % oxycodone HCl[1] released | | |
|---|---|---|---|
| | OxyContin ™ (10 mg) | Ex. 7.2 (10 mg) | Ex. 14.5 (40 mg) |
| Simulated IV prep | 49 | 1 | 4 |
| Control-intact tablets (45 min release) | 34 | 19 | 19 |

[1]relative to label claim

Level 2 Results—Thermal Treatment

Thermal treatment was attempted in the microwave; however, testing was unsuccessful in small volumes of water. The milled Example 7.2 and 14.5 tablet material could not be contained in 10-20 ml of boiling water therefore the amount of water was increased to 100 ml. After 3 minutes at high power in an 800 Watt microwave oven (GE Model JE835), the remaining liquid was analyzed for API content. Additionally, extraction in a small amount of boiling water was assessed by adding 10 ml of boiling water to a vial containing a milled tablet. The vial was vigorously shaken for 15 minutes. As shown in Table 27.9, after applying thermal treatment the milled tablet retained controlled release properties that prevented complete dose dumping. The microwave experiment was not performed on crushed OxyContin tablets; however, comparison data from the boiling water experiment is presented.

TABLE 27.9

Thermal Treatment Results-% API Released

| Sample Preparation | % oxycodone HCl[1] released | | |
|---|---|---|---|
| | OxyContin (10 mg) | Ex. 7.2 (10 mg) | Ex. 14.5 (40 mg) |
| Milled tablets in 100 ml hot water (microwave 3 min) | N/A | 44 | 52 |
| Milled tablets with 10 ml hot water (15 minutes shaken) | 89 | 58 | 61 |
| Control-intact tablets (45 min release) | 34 | 19 | 19 |

[1]relative to label claim

Level 2 Results—Extraction

Example 7.2 and 14.5 tablets were milled in a coffee mill (as per the method described above) and subsequently shaken for 15 minutes in various solvents at room temperature. The OxyContin™ tablets were crushed using a mortar and pestle. Table 27.10 contains the average amount of API released in each solvent. The milled tablets remained resistant to comprehensive dose dumping in a variety of solvents.

TABLE 27.10

Extraction Results-% API Released at 15 Minutes

| Milled Tablets with Extraction Solvent | % oxycodone HCl[1] released | | |
|---|---|---|---|
| | OxyContin (10 mg) | Ex. 7.2 (10 mg) | Ex. 14.5 (40 mg) |
| 100% EtOH | 96 | 53 | 48 |
| 0.1N HCl | 97 | 45 | 51 |
| 0.2N NaOH | 16 | 27 | 17 |
| Control-intact tablets (45 min release) | 34 | 19 | 19 |

[1]relative to label claim

Level 3 Testing

Level 3 testing included extraction for 60 minutes at Room Temperature (RT) and 50° C.

Level 3 Results—Advanced Extraction (RT, 50° C.)

Example 7.2 and 14.5 tablets were milled in a coffee mill (as per the method described above) and subsequently vigorously shaken for 60 minutes in various solvents at room temperature. Additionally, the milled tablets were extracted in various solvents held at 50° C. for 60 minutes using a heated water bath. Stir bars were placed in each vial to agitate the liquid. After one hour of extraction the ground tablets retained some controlled release properties that provided protection against complete dose dumping. Extraction at elevated temperatures is not significantly more effective due to the increased solubility of the tablet matrix at higher temperatures in most of the solvents tested. In Table 27.11, amounts released for Example 7.2 and 14.5 tablets are compared to 15 minute extraction for crushed OxyContin™ 10 mg tablets.

TABLE 27.11

Advanced Extraction Results - % API Released at 60 Minutes

| Milled Tablets with Extraction Solvent | % Oxycodone[1] Released (RT) | | | % Oxycodone[1] Released (50° C.) | | |
|---|---|---|---|---|---|---|
| | *Oxy-Contin (10 mg) | Ex. 7.2 (10 mg) | Ex. 14.5 (40 mg) | *Oxy-Contin 10 mg | Ex. 7.2 (10 mg) | Ex. 14.5 (40 mg) |
| 40% Ethanol (v/v) | 101 | 55 | 56 | N/A | 61 | 65 |
| 100% Ethanol | 96 | 66 | 61 | | 78 | 67 |
| Cooking Oil | 79 | 2 | 4 | | 7 | 4 |
| 0.1N HCl | 97 | 58 | 62 | | 62 | 69 |
| 0.2N NaOH | 16 | 38 | 35 | | 41 | 17 |
| 70% iso-propanol (v/v) | 97 | 48 | 35 | | 49 | 69 |
| Acetone | 60 | 37 | 38 | | N/A | N/A |
| Methanol | 92 | 71 | 82 | | 72 | 61 |
| Ethyl Acetate | 83 | 25 | 5 | | 39 | 30 |
| Ether | 78 | 10 | 2 | | N/A | N/A |
| Control - intact tablets (45 min release) | 34 | 19 | 19 | 34 | 19 | 19 |

[1]relative to label claim;
*Crushed OxyContin data at 15 min for comparison.

Example 28

In Example 28, a randomized, open-label, single-center, single-dose, two-treatment, two-period, two-way crossover study in healthy human subjects was conducted to assess the bioequivalence of Example 14.1 oxycodone HCl (10 mg) formulation relative to the commercial OxyContin® formulation (10 mg) in the fed state.

The study treatments were as follows:
Test treatment: 1× Example 14.1 tablet (10 mg oxycodone HCl)
Reference treatment: 1× OxyContin® 10 mg tablet The treatments were each administered orally with 8 oz. (240 mL) water as a single dose in the fed state.

As this study was conducted in healthy human subjects, the opioid antagonist naltrexone hydrochloride was administered to minimize opioid-related adverse events.

Subject Selection

Screening procedures were performed as described for Example 26.

Subjects who met the inclusion criteria as described for Example 26 were included in the study. Potential subjects were excluded from the study according to the exclusion criteria as described for Example 26, except that item 11 of the exclusion criteria for this study refers to "refusal to abstain from food for 4 hours following administration of the study drugs and to abstain from caffeine or xanthine entirely during each confinement."

Subjects meeting all the inclusion criteria and none of the exclusion criteria were randomized into the study. It was anticipated that approximately 84 subjects would be randomized, with approximately 76 subjects targeted to complete the study.

Check-In Procedures

The check-in procedures performed on day −1 of period 1 and at check-in for each period were performed as described in Example 26. Pre-dose (Day −1, Period 1 only) laboratory samples (hematology, biochemistry, and urinalysis) were collected after vital signs and $SPO_2$ had been measured following overnight fasting (10 hours).

Prior to the first dose in Period 1, subjects were randomized to a treatment sequence according to the random allocation schedule (RAS) as described for Example 26. The treatment sequences for this study are presented in Table 28.1.

TABLE 28.1

| Sequence | Period 1 Treatment | Period 2 Treatment |
|---|---|---|
| 1 | 1× OxyContin ® 10 mg | 1× Example 14.1 |
| 2 | 1× Example 14.1 | 1× OxyContin ® 10 mg |

Study Procedures

The study included two study periods, each with a single dose administration. There was a washout period of at least six days between dose administrations in each study period. During each period, subjects were confined to the study site from the day prior to administration of the study drugs through 48 hours following administration of the study drugs, and subjects returned to the study site for 72-hour procedures.

At each study period, following a 10 hour overnight fast, the subjects were fed a standard meal (FDA high-fat breakfast) 30 minutes prior to administration of either Example 14.1 formulation or OxyContin® 10 mg tablets with 240 mL of water. No food was allowed for at least 4 hours post-dose.

Subjects received naltrexone HCl 25 mg tablets at −12, 0, and 12 hours relative to Example 14.1 formulation or OxyContin® dosing.

Subjects were standing or in an upright sitting position while receiving their dose of Example 14.1 formulation or OxyContin®. Subjects remained in an upright position for a minimum of 4 hours.

Fasting was not required for non-dosing study days.

During the study, adverse events and concomitant medications were recorded, and vital signs (including blood pressure, body temperature, pulse rate, and respiration rate) and $SPO_2$ were monitored.

Blood samples for determining oxycodone plasma concentrations were obtained for each subject at predose and at 0.5, 1, 1.5, 2, 2.5, 3, 3.5, 4, 4.5, 5, 6, 8, 10, 12, 16, 24, 28, 32, 36, 48, and 72 hours postdose for each period.

For each sample, 6 mL of venous blood were drawn via an indwelling catheter and/or direct venipuncture into tubes containing $K_2EDTA$ anticoagulant. Plasma concentrations of oxycodone were quantified by a validated liquid chromatography tandem mass spectrometric method.

The study completion procedures were performed as described for Example 26.

The results of this study are shown in Table 28.2.

TABLE 28.2

Statistical Results of Oxycodone Pharmacokinetic Metrics: Bioavailability Example 14.1 Formulation Relative to OxyContin ® 10 mg in the Fed State (Population: Full Analysis)

| Metric | N | LS Mean[a] (Test)[b] | N | LS Mean[a] (Reference)[b] | Test/ Reference[c] | 90% Confidence Interval[d] |
|---|---|---|---|---|---|---|
| $C_{max}$ (ng/mL) | 79 | 13.9 | 81 | 13.3 | 105 | (101.06; 108.51) |
| $AUC_t$ (ng*hr/mL) | 79 | 138 | 81 | 145 | 95.7 | (93.85; 97.68) |
| $AUC_{inf}$ (ng*hr/mL) | 79 | 139 | 81 | 146 | 95.6 | (93.73; 97.53) |

[a]Least squares mean from ANOVA. Natural log (ln) metric means calculated by transforming the ln means back to the linear scale, i.e., geometric means.
[b]Test = Example 14.1 tablet; Reference = OxyContin ® 10 mg tablet.
[c]Ratio of metric means for ln-transformed metric (expressed as a percent). Ln-transformed ratio transformed back to linear scale.
[d]90% confidence interval for ratio of metric means (expressed as a percent). Ln-transformed confidence limits transformed back to linear scale.

The results show that Example 14.1 tablets are bioequivalent to OxyContin® 10 mg tablets in the fed state.

Example 29

In Example 29, a randomized, open-label, single-center, single-dose, two-treatment, two-period, two-way crossover study in healthy human subjects was conducted to assess the bioequivalence of Example 14.1 oxycodone HCl (10 mg) formulation relative to the commercial OxyContin® formulation (10 mg) in the fasted state.

The study treatments were as follows:
Test treatment: 1× Example 14.1 tablet (10 mg oxycodone HCl)
Reference treatment: 1× OxyContin® 10 mg tablet The treatments were each administered orally with 8 oz. (240 mL) water as a single dose in the fasted state.

As this study was conducted in healthy human subjects, the opioid antagonist naltrexone hydrochloride was administered to minimize opioid-related adverse events.

Subject Selection

Screening procedures were performed as described for Example 26.

Subjects who met the inclusion criteria as described for Example 26 were included in the study. Potential subjects were excluded from the study according to the exclusion criteria as described for Example 26.

Subjects meeting all the inclusion criteria and none of the exclusion criteria were randomized into the study. It was anticipated that approximately 84 subjects would be randomized, with approximately 76 subjects targeted to complete the study.

Check-In Procedures

The check-in procedures performed on day −1 of period 1 and at check-in for each period were performed as described in Example 26. Pre-dose (Day −1, Period 1 only) laboratory samples (hematology, biochemistry, and urinalysis) were collected after vital signs and $SPO_2$ had been measured following overnight fasting (10 hours).

Prior to the first dose in Period 1, subjects were randomized to a treatment sequence according to the random allocation schedule (RAS) as described for Example 26. The treatment sequences for this study are presented in Table 29.1.

TABLE 29.1

| Sequence | Period 1 Treatment | Period 2 |
|---|---|---|
| 1 | 1x OxyContin ® 10 mg | 1x Example 14.1 |
| 2 | 1x Example 14.1 | 1x OxyContin ® 10 mg |

Study Procedures

The study included two study periods, each with a single dose administration. There was a washout period of at least six days between dose administrations in each study period. During each period, subjects were confined to the study site from the day prior to administration of the study drugs through 48 hours following administration of the study drugs, and subjects returned to the study site for 72-hour procedures.

At each study period, the subjects were administered the Example 14.1 formulation or OxyContin® 10 mg tablets with 240 mL of water, following a 10 hour overnight fast. Subjects continued fasting from food for at least 4 hours post-dose.

Subjects received naltrexone HCl 25 mg tablets at −12, 0, and 12 hours relative to Example 14.1 formulation or OxyContin® dosing.

Subjects were standing or in an upright sitting position while receiving their dose of Example 14.1 formulation or OxyConthin®. Subjects remained in an upright position for a minimum of 4 hours.

Clinical laboratory sampling (Day −1) was preceded by a fast (i.e. at least 10 hours) from food (not including water). Fasting was not required for non-dosing study days.

During the study, adverse events and concomitant medications were recorded, and vital signs (including blood pressure, body temperature, pulse rate, and respiration rate) and $SPO_2$ were monitored.

Blood samples for determining oxycodone plasma concentrations were obtained for each subject at predose and at 0.5, 1, 1.5, 2, 2.5, 3, 3.5, 4, 4.5, 5, 6, 8, 10, 12, 16, 24, 28, 32, 36, 48, and 72 hours postdose for each period.

For each sample, 6 mL of venous blood were drawn via an indwelling catheter and/or direct venipuncture into tubes containing $K_2EDTA$ anticoagulant. Plasma concentrations of oxycodone were quantified by a validated liquid chromatography tandem mass spectrometric method.

The study completion procedures were performed as described for Example 26.

The results of this study are shown in Table 29.2.

TABLE 29.2

Statistical Results of Oxycodone Pharmacokinetic Metrics: Bioavailability Example 14.1 Formulation Relative to OxyContin ® 10 mg in the Fasted State (Population: Full Analysis)

| Metric | N | LS Mean[a] (Test)[b] | N | (Reference)[b] | Test/ Reference[c] | 90% Confidence Interval[d] |
|---|---|---|---|---|---|---|
| $C_{max}$ (ng/mL) | 81 | 9.36 | 81 | 9.15 | 102 | (99.35, 105.42) |
| $AUC_t$ (ng*hr/mL) | 81 | 107 | 81 | 109 | 98.3 | (95.20, 101.48) |
| $AUC_{inf}$ (ng*hr/mL) | 81 | 108 | 81 | 110 | 98.0 | (94.94, 101.19) |

[a]Least squares mean from ANOVA. Natural log (ln) metric means calculated by transforming the ln means back to the linear scale, i.e., geometric means.
[b]Test = Example 14.1 tablet; Reference = OxyContin ® 10 mg tablet.
[c]Ratio of metric means for ln-transformed metric (expressed as a percent). Ln-transformed ratio transformed back to linear scale.
[d]90% confidence interval for ratio of metric means (expressed as a percent). Ln-transformed confidence limits transformed back to linear scale.

The results show that Example 14.1 tablets are bioequivalent to OxyContin® 10 mg tablets in the fasted state.

Example 30

In Example 30, a randomized, open-label, single-center, single-dose, two-treatment, two-period, two-way crossover study in healthy human subjects was conducted to assess the bioequivalence of Example 14.5 oxycodone HCl (40 mg) formulation relative to the commercial OxyContin® formulation (40 mg) in the fed state.

The study treatments were as follows:
Test treatment: 1x Example 14.5 tablet (40 mg oxycodone HCl)
Reference treatment: 1x OxyContin® 40 mg tablet The treatments were each administered orally with 8 oz. (240 mL) water as a single dose in the fed state.

As this study was conducted in healthy human subjects, the opioid antagonist naltrexone hydrochloride was administered to minimize opioid-related adverse events.

Subject Selection

Screening procedures were performed as described for Example 26.

Subjects who met the inclusion criteria as described for Example 26 were included in the study. Potential subjects were excluded from the study according to the exclusion criteria as described for Example 26, except that item 11 of the exclusion criteria for this study refers to "refusal to abstain from food for 4 hours following administration of the study drugs and to abstain from caffeine or xanthine entirely during each confinement."

Subjects meeting all the inclusion criteria and none of the exclusion criteria were randomized into the study. It was anticipated that approximately 84 subjects would be randomized, with approximately 76 subjects targeted to complete the study.

Check-In Procedures

The check-in procedures performed on day −1 of period 1 and at check-in for each period were performed as described in Example 26. Pre-dose (Day −1, Period 1 only) laboratory samples (hematology, biochemistry, and urinalysis) were collected after vital signs and $SPO_2$ had been measured following fasting for a minimum of 4 hours.

Prior to the first dose in Period 1, subjects were randomized to a treatment sequence according to the random allocation schedule (RAS) as described for Example 26. The treatment sequences for this study are presented in Table 30.1.

TABLE 30.1

| Sequence | Period 1 Treatment | Period 2 |
|---|---|---|
| 1 | 1x OxyContin® 40 mg | 1x Example 14.5 |
| 2 | 1x Example 14.5 | 1x OxyContin® 40 mg |

Study Procedures

The study included two study periods, each with a single dose administration. There was a washout period of at least six days between dose administrations in each study period. During each period, subjects were confined to the study site from the day prior to administration of the study drugs through 48 hours following administration of the study drugs, and subjects returned to the study site for 72-hour procedures.

At each study period, following a 10 hour overnight fast, the subjects were fed a standard meal (FDA high-fat breakfast) 30 minutes prior to administration of either Example 14.5 formulation or OxyContin® 40 mg tablets with 240 mL of water. No food was allowed for at least 4 hours post-dose.

Subjects received naltrexone HCl 50 mg tablets at −12, 0, 12, 24, and 36 hours relative to Example 14.5 formulation or OxyContin® dosing.

Subjects were standing or in an upright sitting position while receiving their dose of Example 14.5 formulation or OxyContin®. Subjects remained in an upright position for a minimum of 4 hours.

Fasting was not required for non-dosing study days.

During the study, adverse events and concomitant medications were recorded, and vital signs (including blood pressure, body temperature, pulse rate, and respiration rate) and $SPO_2$ were monitored.

Blood samples for determining oxycodone plasma concentrations were obtained for each subject at predose and at 0.5, 1, 1.5, 2, 2.5, 3, 3.5, 4, 4.5, 5, 6, 8, 10, 12, 16, 24, 28, 32, 36, 48, and 72 hours postdose for each period.

For each sample, 6 mL of venous blood were drawn via an indwelling catheter and/or direct venipuncture into tubes containing $K_2EDTA$ anticoagulant. Plasma concentrations of oxycodone were quantified by a validated liquid chromatography tandem mass spectrometric method.

The study completion procedures were performed as described for Example 26.

The results of this study are shown in Table 30.2.

TABLE 30.2

Statistical Results of Oxycodone Pharmacokinetic Metrics: Bioavailability Example 14.5 Formulation Relative to OxyContin® 40 mg in the Fed State (Population: Full Analysis)

| Metric | N | LS Mean[a] (Test)[b] | N | (Reference)[b] | Test/ Reference[c] | 90% Confidence Interval[d] |
|---|---|---|---|---|---|---|
| $C_{max}$ (ng/mL) | 76 | 59.8 | 80 | 59.9 | 99.9 | (95.40, 104.52) |
| $AUC_t$ (ng*hr/mL) | 76 | 514 | 80 | 556 | 92.5 | (90.01, 94.99) |
| $AUC_{inf}$ (ng*hr/mL) | 76 | 516 | 80 | 558 | 92.4 | (90.00, 94.96) |

[a]Least squares mean from ANOVA. Natural log (ln) metric means calculated by transforming the ln means back to the linear scale, i.e., geometric means.
[b]Test = Example 14.5 tablet; Reference = OxyContin® 40 mg tablet.
[c]Ratio of metric means for ln-transformed metric (expressed as a percent). Ln-transformed ratio transformed back to linear scale.
[d]90% confidence interval for ratio of metric means (expressed as a percent). Ln-transformed confidence limits transformed back to linear scale.

The results show that Example 14.5 tablets are bioequivalent to OxyContin® 40 mg tablets in the fed state.

Example 31

In Example 31, a randomized, open-label, single-center, single-dose, two-treatment, two-period, two-way crossover study in healthy human subjects was conducted to assess the bioequivalence of Example 14.5 oxycodone HCl (40 mg) formulation relative to the commercial OxyContin® formulation (40 mg) in the fasted state.

The study treatments were as follows:
Test treatment: 1× Example 14.5 tablet (40 mg oxycodone HCl)
Reference treatment: 1× OxyContin® 40 mg tablet The treatments were each administered orally with 8 oz. (240 mL) water as a single dose in the fasted state.

As this study was conducted in healthy human subjects, the opioid antagonist naltrexone hydrochloride was administered to minimize opioid-related adverse events.

Subject Selection

Screening procedures were performed as described for Example 26.

Subjects who met the inclusion criteria as described for Example 26 were included in the study. Potential subjects were excluded from the study according to the exclusion criteria as described for Example 26.

Subjects meeting all the inclusion criteria and none of the exclusion criteria were randomized into the study. It was anticipated that approximately 84 subjects would be randomized, with approximately 76 subjects targeted to complete the study.

Check-In Procedures

The check-in procedures performed on day −1 of period 1 and at check-in for each period were performed as described in Example 26. Pre-dose (Day −1, Period 1 only) laboratory samples (hematology, biochemistry, and urinalysis) were collected after vital signs and $SPO_2$ had been measured following fasting for a minimum of 4 hours.

Prior to the first dose in Period 1, subjects were randomized to a treatment sequence according to the random allocation schedule (RAS) as described for Example 26. The treatment sequences for this study are presented in Table 31.1.

TABLE 31.1

| Sequence | Period 1 Treatment | Period 2 |
|---|---|---|
| 1 | 1x OxyContin® 40 mg | 1x Example 14.5 |
| 2 | 1x Example 14.5 | 1x OxyContin® 40 mg |

Study Procedures

The study included two study periods, each with a single dose administration. There was a washout period of at least six days between dose administrations in each study period. During each period, subjects were confined to the study site from the day prior to administration of the study drugs through 48 hours following administration of the study drugs, and subjects returned to the study site for 72-hour procedures.

At each study period, the subjects were administered the Example 14.5 formulation or OxyContin® 40 mg tablets with 240 mL of water, following a 10 hour overnight fast. Subjects continued fasting from food for at least 4 hours post-dose.

Subjects received naltrexone HCl 50 mg tablets at −12, 0, 12, 24, and 36 hours relative to Example 14.5 formulation or OxyContin® dosing.

Subjects were standing or in an upright sitting position while receiving their dose of Example 14.5 formulation or OxyContin®. Subjects remained in an upright position for a minimum of 4 hours.

Fasting was not required for non-dosing study days.

During the study, adverse events and concomitant medications were recorded, and vital signs (including blood pressure, body temperature, pulse rate, and respiration rate) and $SPO_2$ were monitored.

Blood samples for determining oxycodone plasma concentrations were obtained for each subject at predose and at 0.5, 1, 1.5, 2, 2.5, 3, 3.5, 4, 4.5, 5, 6, 8, 10, 12, 16, 24, 28, 32, 36, 48, and 72 hours postdose for each period.

For each sample, 6 mL of venous blood were drawn via an indwelling catheter and/or direct venipuncture into tubes containing $K_2EDTA$ anticoagulant. Plasma concentrations of oxycodone were quantified by a validated liquid chromatography tandem mass spectrometric method.

The study completion procedures were performed as described for Example 26.

The results of this study are shown in Table 31.2.

TABLE 31.2

Statistical Results of Oxycodone Pharmacokinetic Metrics: Bioavailability Example 14.5 Formulation Relative to OxyContin ® 40 mg in the Fasted State (Population: Full Analysis)

| Metric | N | (Test)[b] | N | LS Mean[a] (Reference)[b] | Test/ Reference[c] | 90% Confidence Interval[d] |
|---|---|---|---|---|---|---|
| $C_{max}$ (ng/mL) | 85 | 46.1 | 83 | 47.7 | 96.6 | (92.80, 100.56) |
| $AUC_t$ (ng*hr/mL) | 85 | 442 | 83 | 463 | 95.5 | (92.93, 98.18) |
| $AUC_{inf}$ (ng*hr/mL) | 85 | 444 | 82 | 468 | 94.8 | (92.42, 97.24) |

[a]Least squares mean from ANOVA. Natural log (ln) metric means calculated by transforming the ln means back to the linear scale, i.e., geometric means.
[b]Test = Example 14.5 tablet; Reference = OxyContin ® 40 mg tablet.
[c]Ratio of metric means for ln-transformed metric (expressed as a percent). Ln-transformed ratio transformed back to linear scale.
[d]90% confidence interval for ratio of metric means (expressed as a percent). Ln-transformed confidence limits transformed back to linear scale.

The results show that Example 14.5 tablets are bioequivalent to OxyContin® 40 mg tablets in the fasted state.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference for all purposes.

The invention claimed is:

1. A method of treating pain comprising administering to a patient in need thereof a cured shaped tablet comprising an extended release matrix comprising a composition, wherein said tablet comprises:
   (1) an opioid or a pharmaceutically acceptable salt thereof,
   (2) at least one low molecular weight polyethylene oxide having, based on rheological measurements, an approximate molecular weight of less than 1,000,000, and
   (3) at least one high molecular weight polyethylene oxide having, based on rheological measurements, an approximate molecular weight of 7,000,000;
   wherein said tablet is prepared by a process comprising the steps of:
   (a) combining said opioid or pharmaceutically acceptable salt thereof with each of said low molecular weight polyethylene oxide and said high molecular weight polyethylene oxide to form at least one blend;
   (b) applying each said blend to form a shaped tablet; and
   (c) curing said shaped tablet by subjecting the shaped tablet to a temperature from about 60 to about 90° C. for a time of from about 15 minutes to about 10 hours,
   wherein said cured shaped tablet comprises a once-a-day dosage form having at least 79% by weight, based upon the total weight of said composition, of the total combined weight of said high and low molecular weight polyethylene oxides.

2. A method of treating pain comprising administering to a patient in need thereof a cured shaped tablet as defined in claim 1, wherein said opioid or pharmaceutically acceptable salt comprises at least 2.4% by weight, based upon the total weight of said composition.

3. A method of treating pain comprising administering to a patient in need thereof a cured shaped tablet as defined in claim 1, wherein said time in said curing step is 15 minutes to 60 minutes.

4. A method of treating pain comprising administering to a patient in need thereof a cured shaped tablet as defined in claim 1, wherein said temperature in said curing step is from 70 to 78° C.

5. A method of treating pain comprising administering to a patient in need thereof a cured shaped tablet as defined in claim 1, wherein said shaped tablet is coated before or after said curing step.

6. A method of treating pain comprising administering to a patient in need thereof a cured shaped tablet comprising an extended release matrix comprising a composition, wherein said tablet comprises:
   (1) hydrocodone or a pharmaceutically acceptable salt thereof,
   (2) at least one low molecular weight polyethylene oxide having, based on rheological measurements, an approximate molecular weight of less than 1,000,000, and
   (3) at least one high molecular weight polyethylene oxide having, based on rheological measurements, an approximate molecular weight of 7,000,000;
   wherein said tablet is prepared by a process comprising the steps of:
   (a) combining said hydrocodone or pharmaceutically acceptable salt thereof with each of said low molecular weight polyethylene oxide and said high molecular weight polyethylene oxide to form at least one blend;
   (b) applying each said blend to form a shaped tablet; and
   (c) curing said shaped tablet by subjecting the shaped tablet to a temperature from about 60 to about 90° C. for a time of from about 15 minutes to about 10 hours,
   wherein said cured shaped tablet comprises a once-a-day dosage form having at least 79% by weight, based upon the total weight of said composition, of the total combined weight of said high and low molecular weight polyethylene oxides, and wherein said low molecular weight polyethylene oxide comprises at least 20% by weight, based upon the total weight of said composition.

7. A method of treating pain comprising administering to a patient in need thereof a cured shaped tablet as defined in claim 6, wherein, said temperature in said curing step is from 70 to 78° C.

8. A method of treating pain comprising administering to a patient in need thereof a cured shaped tablet as defined in claim 6, wherein said at least one blend further comprises at least one additive.

9. A method of treating pain comprising administering to a patient in need thereof a cured shaped tablet as defined in claim 6, wherein said low molecular weight polyethylene oxide is at least 22% by weight and said high molecular weight polyethylene oxide is at least 50% by weight, based upon the total weight of said composition.

10. A method of treating pain comprising administering to a patient in need thereof a cured shaped tablet as defined in claim 6, wherein said hydrocodone or pharmaceutically acceptable salt thereof comprises at least 2.4% by weight, based upon the total weight of said composition.

11. A method of treating pain comprising administering to a patient in need thereof a cured shaped tablet as defined in claim 6, wherein said hydrocodone or pharmaceutically acceptable salt thereof comprises at least 5% by weight, based upon the total weight of said composition.

12. A method of treating pain comprising administering to a patient in need thereof a cured shaped tablet as defined in claim 6, wherein said hydrocodone or pharmaceutically acceptable salt thereof comprises at least 10% by weight, based upon the total weight of said composition.

13. A method of treating pain comprising administering to a patient in need thereof a cured shaped tablet as defined in claim 9, wherein said cured shaped tablet comprises at least 80% by weight, based upon the total weight of said composition, of said high and low molecular weight polyethylene oxides.

14. A method of treating pain comprising administering to a patient in need thereof a cured shaped tablet as defined in claim 10, wherein, said temperature in said curing step is from 70 to 78° C.

15. A method of treating pain comprising administering to a patient in need thereof a cured shaped tablet as defined in claim 6, wherein said time in said curing step is 15 minutes to 60 minutes.

16. A method of treating pain comprising administering to a patient in need thereof a cured shaped tablet as defined in claim 10, wherein said time in said curing step is 15 minutes to 60 minutes.

17. A method of treating pain comprising administering to a patient in need thereof a cured shaped tablet as defined in claim 6, wherein said temperature in said curing step is from 70 to 78° C. and said time in said curing step is 15 minutes to 60 minutes.

18. A method of treating pain comprising administering to a patient in need thereof a cured shaped tablet as defined in claim 10, wherein said temperature in said curing step is from 70 to 78° C. and said time in said curing step is 15 minutes to 60 minutes.

19. A method of treating pain comprising administering to a patient in need thereof a cured shaped tablet as defined in claim 10, wherein said cured shaped tablet comprises at least 54% high molecular weight polyethylene oxide.

20. A method of treating pain comprising administering to a patient in need thereof a cured shaped tablet as defined in claim 6, wherein said cured shaped tablet comprises at least 85% by weight, based upon the total weight of said composition, of said high and low molecular weight polyethylene oxides.

21. A method of treating pain comprising administering to a patient in need thereof a cured shaped tablet as defined in claim 6, wherein said cured shaped tablet comprises at least 90% by weight, based upon the total weight of said composition, of said high and low molecular weight polyethylene oxides.

22. A method of treating pain comprising administering to a patient in need thereof a cured shaped tablet as defined in claim 10, wherein said cured shaped tablet comprises at least about 80% by weight, based upon the total weight of said composition, of said high and low molecular weight polyethylene oxides.

23. A method of treating pain comprising administering to a patient in need thereof a cured shaped tablet as defined in claim 10, wherein said cured shaped tablet comprises at least about 85% by weight, based upon the total weight of said composition, of said high and low molecular weight polyethylene oxides.

24. A method of treating pain comprising administering to a patient in need thereof a cured shaped tablet as defined in claim 10, wherein said cured shaped tablet comprises at least about 90% by weight, based upon the total weight of said composition, of said high and low molecular weight polyethylene oxides.

25. A method of treating pain comprising administering to a patient in need thereof a cured shaped tablet as defined in claim 1, wherein said curing comprises convection curing in a convection curing device.

26. A method of treating pain comprising administering to a patient in need thereof a cured shaped tablet as defined in claim 8, wherein said at least one additive is selected from microcrystalline cellulose, hydroxypropyl cellulose, magnesium stearate, and combinations thereof, and said curing comprises convection curing in a convection curing device.

27. A method of treating pain comprising administering to a patient in need thereof a cured shaped tablet as defined in claim 17, wherein said curing comprises convection curing in a convection curing device.

28. A method of treating pain comprising administering to a patient in need thereof a cured shaped tablet as defined in claim 26, wherein said curing temperature is measured as a mean exhaust temperature of said convection curing device during said curing time.

29. A method of treating pain comprising administering to a patient in need thereof a cured shaped tablet as defined in claim 6, wherein said cured shaped tablet has a density that is at least about 1% lower than the density of said shaped tablet prior to curing.

30. A method of treating pain comprising administering to a patient in need thereof a cured shaped tablet as defined in claim 9, wherein said cured shaped tablet has a density that is at least about 1% lower than the density of said shaped tablet prior to curing.

* * * * *